(12) United States Patent
Allison et al.

(10) Patent No.: US 7,855,292 B2
(45) Date of Patent: Dec. 21, 2010

(54) SULFONAMIDE COMPOUNDS

(75) Inventors: Brett Allison, Del Mar, CA (US); Victor K. Phuong, San Diego, CA (US); Marna C. W. Pippel, Del Mar, CA (US); Michael H. Rabinowitz, San Diego, CA (US); Hariharan Venkatesan, San Diego, CA (US)

(73) Assignee: Janssen Pharmaceutica NV, Beerse (BE)

( * ) Notice: Subject to any disclaimer, the term of this patent is extended or adjusted under 35 U.S.C. 154(b) by 0 days.

(21) Appl. No.: 11/943,520

(22) Filed: Nov. 20, 2007

(65) Prior Publication Data
US 2008/0132511 A1 Jun. 5, 2008

Related U.S. Application Data

(62) Division of application No. 11/230,249, filed on Sep. 19, 2005, now Pat. No. 7,297,816.

(60) Provisional application No. 60/612,720, filed on Sep. 24, 2004.

(51) Int. Cl.
C07D 241/36 (2006.01)

(52) U.S. Cl. ............... 544/353; 514/361; 514/249; 548/127

(58) Field of Classification Search ........... 514/249, 514/361; 544/353; 548/127
See application file for complete search history.

(56) References Cited

U.S. PATENT DOCUMENTS

| | | | | |
|---|---|---|---|---|
| 4,507,315 A * | 3/1985 | Ashton et al. | ............... | 514/396 |
| 5,336,681 A * | 8/1994 | Imaki et al. | ............... | 514/347 |
| 5,397,798 A * | 3/1995 | Fitch et al. | ............... | 514/399 |
| 5,534,530 A | 7/1996 | Frehel et al. | | |
| 6,239,131 B1 | 5/2001 | Shinozaki et al. | | |
| 6,903,216 B2 * | 6/2005 | Brendel et al. | ............... | 546/172 |
| 7,235,664 B2 * | 6/2007 | Brendel et al. | ............... | 546/172 |
| 7,241,759 B2 | 7/2007 | Allison et al. | | |
| 7,268,115 B2 * | 9/2007 | Gour et al. | ............... | 514/12 |
| 7,297,816 B2 | 11/2007 | Allison et al. | | |
| 7,304,051 B2 | 12/2007 | Allison et al. | | |
| 7,332,608 B2 * | 2/2008 | Brendel et al. | ............... | 546/300 |
| 2002/0193422 A1 * | 12/2002 | Brendel et al. | ............... | 514/447 |
| 2005/0042283 A1 | 2/2005 | Wang | | |

FOREIGN PATENT DOCUMENTS

| | | |
|---|---|---|
| DE | 33 30 403 A1 | 8/1983 |
| EP | 0508796 B1 | 7/1998 |
| NZ | 542491 | 3/2004 |
| NZ | 545030 | 8/2004 |
| WO | WO 00 78145 A1 | 12/2000 |
| WO | WO 02 087568 A1 | 11/2002 |
| WO | WO 02 088073 A1 | 11/2002 |
| WO | WO 02 100825 A2 | 12/2002 |
| WO | WO 03 087304 A2 | 10/2003 |
| WO | WO 2004 013087 A1 | 2/2004 |
| WO | WO 2004 106306 A1 | 12/2004 |
| WO | WO 2004 106310 A1 | 12/2004 |
| WO | WO 2004 106315 A2 | 12/2004 |
| WO | WO 2005/012275 * | 2/2005 |
| WO | WO 2005/016896 * | 2/2005 |

OTHER PUBLICATIONS

Beaumont et al Current Drug Metab 2003 vol. 4 pp. 461-465.
Berge et al J Pharm Sci 1977 vol. 65 pp. 1-19.
Black et al Pharmacol Toxicol 2002 vol. 91 pp. 275-281.
Boechxstaens et al Am J. Gastroenterol 1998 vol. 93(10) pp. 10323-1828.
Boulant et al Gastroenterology 1994 vol. 107(4) pp. 1059-1828.
Boulant et al Gut 1997 vol. 40 pp. 547-581.
Bungaard et al. Design of Prodrugs Ed.H. Bungaard 1985.
Cheng et al Biochem Pharmacol 1973 vol. 22(23) pp. 3099-3108.
De Tullio et al Exp Opin Invest Drugs 2000 vol. 9(1) pp. 129-145.
Gavezzotti Accounts of Chemical Research 1994 vol. 27 pp. 309-314.
Greene T.W. & P.G.M. Wuts Protective Groups on Organic Synthesis 3rd Ed John Wiley & Sons 1999.
Harper et al Sr J. Pharmacol 1996 vol. 116(7) pp. 1717-1726.
Hawley's Condensed Chemical Dictionary 13th Ed Richard J. Lewis Sr. 1997 by Van Nostrand Reinhold p. 587.
Herranz et al Pharmacological and Therapeutic Potential Med Res Rev 2003 vol. 25(3) pp. 559-605.
Hirsch et al Dig Dis Sci 2002 vol. 47(11) pp. 2531-2537.
Holloway et al Br J. Pharmacol 1993 vol. 108 pp. 734-740.
Hull et al Br J Pharmacol 1993 vol. 106 pp. 734-740.
Mcomie Plenum J.F.W. Ed. Protective Groups in Organic Chemistry Plenum Press 1973.
Mizen et al Pharm Biotechnol 1998 vol. 11 pp. 345-365.
Parson et al Exp Opin Invest Drugs 2005 vol. 14(4) pp. 411-421.
Roberts et al Br J. Pharmacol 1996 vol. 118(7) pp. 1779-1789.
Stahl Handbook of Pharmaceutical Salts, Properties, Selections and Use Stahl P.H. Wermuth C.G. EDS Wiley-VCH and VHCA Zurich 2002.
Stark et al Pharm Unserer Zeit 2005 vol. 34(3) pp. 224-221.
Tabuchi et al Chem Pharm Bull 2000 vol. 48(1) pp. 1-15.
Tonini et al Drugs 2000 vol. 64(4) pp. 347-381.
Tracy et al Nature (London) 1964 vol. 204 pp. 935-938.
Trudgill et al Aliment Pharmacol Ther 2001 vol. 15(9) pp. 1357-1364.
Varnavas et al IL Farmaco 2000 vol. 55(5) pp. 359-375.
Varnavas et al Eur J Med Chem 2004 vol. 39 pp. 85-97.
Varnavas et al IL Farmaco 2001 vol. 56 pp. 555-554.
Varnavas et al Bioorg & Med Chem 2003 vol. 11(5) pp. 741-751.
Vippagunta et al Advanced Drug Delivery Reviews 2001 vol. 48 pp. 3-26.
Walsh et al Gastrointestinal Hormones Ed George B. Jerzy Glass Raven Press NJ 1960 pp. 769-795.

* cited by examiner

*Primary Examiner*—Daniel M Sullivan
*Assistant Examiner*—Chukwuma O Nwaonicha
(74) *Attorney, Agent, or Firm*—Samuel M. Kais

(57) ABSTRACT

Certain sulfonamide compounds are dual CCK1/CCK2 inhibitors useful in the treatment of CCK1/CCK2 mediated diseases.

29 Claims, No Drawings

SULFONAMIDE COMPOUNDS

This application is a division of parent application Ser. No. 11/230,249, filed on Sep. 19, 2005, which claims the benefit of priority of U.S. provisional application No. 60/612,720, filed Sep. 24, 2004. The complete disclosures of the aforementioned related U.S. patent applications are hereby incorporated by reference for all purposes.

FIELD OF THE INVENTION

There is provided by the present invention compounds that are dual CCK1/CCK2 receptor modulators. More particularly, there is provided by the present invention sulfonamides that are dual CCK1/CCK2 receptor antagonists useful for the treatment of disease states mediated by CCK1/CCK2 receptor activity.

BACKGROUND OF THE INVENTION

This invention relates to cholecystokinin (CCK) receptor ligands. The invention also relates to methods for preparing such ligands and to compounds that are useful intermediates in such methods. The invention further relates to pharmaceutical compositions comprising such ligands and methods for preparing such pharmaceutical compositions.

The gastrins and cholecystokinins are structurally related neuropeptides that exist in gastrointestinal tissue, gastrinomas and, in the case of the cholecystokinins, the central nervous system (J. H. Walsh, Gastrointestinal Hormones, L. R. Johnson, ed., Raven Press, New York, 1994, p. 1).

The actions of CCK are mediated by two G-protein coupled receptors: CCK-1 (formerly CCK-A) and CCK-2 (formerly CCK-B/gastrin). These CCK receptors are expressed throughout the gastrointestinal system and in different parts of the central nervous system including the cortex, the striatum, the hypothalamus, the hippocampus, the olfactory bulb, the vagal afferent neurones, in different enteric nerves, and in the genital tract.

Several forms of gastrin are found including 34-, 17- and 14-amino acid species with the minimum active fragment being the C-terminal tetrapeptide (TrpMetAspPhe-$NH_2$), which is reported in the literature to have full pharmacological activity (H. J. Tracy and R. A. Gregory, Nature (London), 1964, 204:935-938). Much effort has been devoted to the synthesis of analogs of this tetrapeptide (and the N-protected derivative Boc-TrpMetAspPhe-NH2) in an attempt to elucidate the relationship between structure and activity.

Natural cholecystokinin is a 33 amino acid peptide (CCK-33), the C-terminal 5 amino acids of which are identical to those of gastrin. Also found naturally is the C-terminal octapeptide (CCK-8) of CCK-33. A review of CCK receptors, ligands and the activities thereof may be found in P. de Tullio et al. (Exp. Opin. Invest. Drugs, 2000, 9(1):129-146).

Gastrin and cholecystokinin are key regulators of gastrointestinal function. In addition, cholecystokinin is a neurotransmitter in the brain. Gastrin is one of the three primary stimulants of gastric acid secretion. In addition to the acute stimulation of gastric acid, gastrin has a trophic effect on the gastrointestinal mucosa and is implicated as a trophic hormone of several adenocarcinomas, including pancreatic, colorectal, esophageal and small cell lung.

Cholecystokinin stimulates intestinal motility, gallbladder contraction, and biliary and pancreatic enzyme secretion, and is known to have trophic actions on the pancreas thus increasing, inter alia, pancreatic enzyme production. Cholecystokinin also inhibits gastric emptying and has various effects in the central nervous system, including regulation of appetite and pain. CCK regulates GI motility and specifically gut and colonic motility. CCK promotes protein synthesis and cell growth, especially in the GI system and in the pancreas. CCK is involved in mediating satiety after a meal. CCK is an important neuromodulator and neurotransmitter involved in anxiety and panic disorder. CCK modulates the release of dopamine. CCK is also known to antagonize morphine and beta-endorphine induced analgesia and the action on nociception.

Gastrin acts on CCK2 (otherwise known as gastrin/CCK-B receptors) whereas cholecystokinin acts on both CCK2 and CCK1 receptors (otherwise known as cholecystokinin/CCK-A receptors). Compounds that bind to cholecystokinin and/or gastrin receptors are important because of their potential pharmaceutical use as antagonists of the natural peptides or mimetics of the natural peptides acting as partial or full agonists at the cholecystokinin and/or gastrin receptors. A selective gastrin receptor antagonist has not yet been marketed. However, several are currently undergoing clinical evaluation. JB95008 (gastrazole) is being developed by The James Black Foundation and Johnson & Johnson Pharmaceutical Research & Development LLC for the potential treatment of advanced pancreatic cancer (pancreatic adenocarcinoma), and is currently in Phase II clinical trials. ML Laboratories and Panos are developing L-365,260 (Colycade), which is in Phase II clinical trials for pain. Other potential indications included eating disorders and cancer. YF-476 (formerly YM-220), under joint development by Yamanouchi and Ferring Research Institute, is in Phase I clinical trials for gastro-esophageal reflux disease (GERD). In Phase I trials, Zeria Pharmaceutical is investigating Z-360, an orally available 1,5-benzodiazepine derivative (WO-09825911), as a potential treatment for gastroduodenal ulcers and reflux esophagitis. CR 2945 (itriglumide), an orally active anthranilic acid derivative, has been investigated by Rotta in Phase I trials for anxiety disorders, cancer (particularly colon cancer) and peptic ulcer.

Gastrimmune, Aphton Corporation's anti-gastrin vaccine, which works by chemical neutralization of the hormone, is undergoing late stage clinical trials for cancer indications, in particular, pancreatic and gastric tumors.

In addition to those indications described above, gastrin (CCK2) antagonists have been proposed for the following gastrin-related disorders: gastrointestinal ulcers, Barrett's esophagus, antral G cell hyperplasia, pernicious anaemia, Zollinger-Ellison syndrome, and other conditions in which lower gastrin activity or lower acid secretion is desirable.

Cholecystokinin (CCK1) receptors have been shown to mediate cholecystokinin-stimulated gallbladder contraction, pancreatic enzyme secretion, satiety, gastric emptying inhibition and regulation of peristalsis, indicating a key role in the integrated physiological gastrointestinal response to a meal. In addition, there is evidence that cholecystokinin receptors mediate a mitogenic action of cholecystokinin on some adenocarcinomas. Consequently, selective cholecystokinin receptor antagonists, for example, tarazepide, devazepide (Merck), lorglumide (Rotta), 2-NAP (JBF), dexloxiglumide (Rotta), and lintitript (Sanofi) have been examined in the clinic for potential applications in, inter alia, irritable bowel syndrome, chronic constipation, non-ulcer dyspepsia, acute and chronic pancreatitis, biliary disease and pancreatic cancer. Also, Kaken Pharmaceuticals and Mitsubishi-Tokyo Pharmaceuticals are awaiting registration in Japan on loxiglumide, a CCK-1 receptor antagonist for the treatment of GI cancers and pancreatitis. Loxiglumide is the racemate of dexloxiglumide.

A number of CCK-1 receptor agonists are under preclinical investigation. Glaxo Smith Kline, Inc. is investigating GW 5823, GW 7854, GW 7178 and GW 8573, 1,5-benzodiazepines for the treatment of gallstones, gastrointestinal disease and obesity. Also, Pfizer is investigating the CCK-1 receptor agonist, PD 170292, for obesity.

Additional roles of cholecystokinin receptors include the regulation of appetite and metabolism, indicating potential therapeutic applications in the treatment of disorders such as obesity and anorexia nervosa. Other possible uses are in the potentiation of opiate (for example morphine) analgesia and in the treatment of cancers, especially of the pancreas. Moreover, ligands for cholecystokinin/gastrin receptors in the brain have been claimed to possess anxiolytic activity, and gastrin receptor antagonists would be expected to act as neurological agents towards the relief of anxiety and related neuroses and psychoses.

Non-selective compounds that act as antagonists of both CCK-1 and CCK-2 receptors are expected to offer the combined potential therapeutic applications the selective antagonists described above with the advantage of guaranteed synchronized action compared to the use of a combination of two selective compounds. These 'dual' or 'mixed' CCK receptor antagonists are important because of their potential pharmaceutical application for treatments of disorders where both cholecystokinin and gastrin stimulated effects are implicated. Thus, a combination of the inhibition of the number of transient lower esophageal sphincter relaxations, reported to be under the control of CCK-1 receptors (Boulant, J., et al. Gut, 1997, 40:575-581), together with inhibition of CCK-2 receptor mediated gastric acid secretion and gastric mucosal growth might be expected to be valuable for the treatment of gastrointestinal reflux disease. Similarly, the concurrent antagonism of cholecystokinin stimulated, CCK-1 receptor mediated, inhibition of gastric emptying together with inhibition of transient lower esophageal sphincter relaxations, gastric acid secretion and gastric mucosal growth might also be expected to be valuable for the treatment of gastrointestinal or gastroesophageal reflux disease. Moreover, it has been hypothesized that CCK-1/CCK-2 receptor dual antagonists, such as those described by Fujisawa Pharmaceutical Co. Ltd. (Tabuchi, S., et al. Chem. Pharm. Bull. 2000, 48(1):1-15), will be more efficacious for the treatment of pancreatitis than a selective CCK-1 receptor antagonist alone as a consequence of inhibiting acid secretion induced pancreatic enzyme release as well as cholecystokinin-stimulated pancreatic enzyme release.

The features and advantages of the invention are apparent to one of ordinary skill in the art. Based on this disclosure, including the summary, detailed description, background, examples, and claims, one of ordinary skill in the art will be able to make modifications and adaptations to various conditions and usages. Publications described herein are incorporated by reference in their entirety.

Described herein is a series of aryl sulfonamide compounds with the ability to modulate the activity of CCK1 and CCK2 receptors.

SUMMARY OF THE INVENTION

The invention features an aryl sulfonamide compound of formula (I):

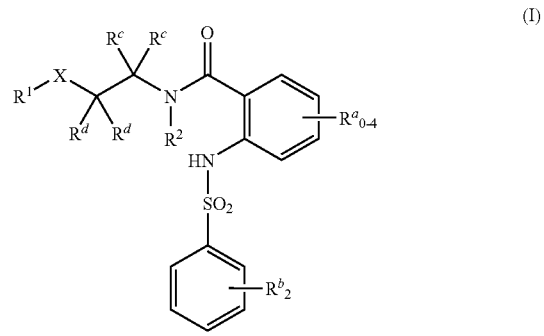

wherein
X is $C_{1-2}$alkyl or a bond;
$R^1$ is selected from the group consisting of
  a) naphthyl, phenyl, said phenyl optionally fused at two adjacent carbon atoms to $R^f$,
    $R^f$ is a linear 3- to 5-membered hydrocarbon moiety having 0 or 1 unsaturated bonds and having 0, 1 or 2 carbon members which is a carbonyl,
  b) $Ar^6$—, where $Ar^6$ is a 6-membered heteroaryl having carbon as a point of attachment, having 1 or 2 heteroatom members which are —N= and optionally benzo or pyrido fused,
  c) $Ar^5$—, where $Ar^5$ is a 5-membered heteroaryl having carbon as a point of attachment, having 1 heteroatom member selected from the group consisting of O, S, >NH, and >N$C_{1-4}$alkyl, having 0 or 1 additional heteroatom member which is —N= and optionally benzo or pyrido fused,
  d) $Ar^{6-6}$—, where $Ar^6$ is phenyl having the point of attachment and fused to a 6-membered heteroaryl having 1 or 2 heteroatom members which are —N=,
  e) $Ar^{6-5}$—, where $Ar^{6-5}$ is phenyl or pyridyl having the point of attachment and fused to a 5-membered heteroaryl having 1 heteroatom member selected from the group consisting of O, S, >NH, and >N$C_{1-4}$alkyl, and having 0 or 1 additional heteroatom member which is —N=,
  where each of a) to e) is substituted with 0, 1, 2, or 3 of $R^q$,
    $R^q$ is independently selected from the group consisting of —$C_{1-4}$alkyl, hydroxy, fluoro, chloro, bromo, iodo, trifluoromethyl, nitro, cyano, amino$C_{1-4}$alkyl, $C_{1-4}$alkylamino$C_{1-4}$alkyl, di$C_{1-4}$alkylamino$C_{1-4}$alkyl, HO—$C_{1-4}$alkyl, $C_{1-4}$alkylO—$C_{1-4}$alkyl, HS—$C_{1-4}$alkyl, $C_{1-4}$alkylS—$C_{1-4}$alkyl, $C_{1-4}$alkoxy, and $C_{1-4}$alkylS—;
$R^2$ is selected from the group consisting of —H, —$C_{1-6}$alkyl, —$C_{2-6}$alkenyl, —$C_{2-6}$alkynyl, —$C_{3-7}$cycloalkyl, and —$C_{3-7}$cycloalkenyl;
$R^a$ is, independently, selected from the group consisting of —$C_{1-6}$alkyl, —$C_{2-6}$alkenyl, —$C_{3-6}$cycloalkyl, phenyl, furanyl, thiophenyl, benzyl, pyrrol-1-yl, —OH, —O$C_{1-6}$alkyl, —O$C_{3-6}$cycloalkyl, —Ophenyl, —Obenzyl, —SH, —S$C_{1-6}$alkyl, —S$C_{3-6}$cycloalkyl, —Sphenyl, —Sbenzyl, cyano, nitro, —N($R^y$)$R^z$ (wherein $R^y$ and $R^z$ are independently —H, —$C_{1-4}$alkyl, or $C_{1-6}$cycloalkyl$C_{1-4}$alkyl), —(C=O)$C_{1-4}$alkyl, —SCF$_3$, halo, trifluoromethyl, —OCF$_3$, and —COOC$_{1-4}$alkyl, —COOH, or, alternatively, two adjacent R$^a$, may be taken together with the carbons of attachment to form a fused ring selected from the group consisting of phenyl, pyridyl, and pyrimidinyl; alternatively, R$^2$ and one of R$^a$ may be taken together as —CH$_2$— or >C═O to form a fused ring to the phenyl;

R$^b$ is selected from the group consisting of 2,4-difluoro, 2,6-difluoro, or alternatively, two adjacent R$^b$ substituents at 2- and 3-positions may be taken together to form a five- or six-membered heterocyclic ring selected from the group consisting of oxazole, thiazole, thiadiazole, [1,3]dioxole, and pyrazine;

R$^c$ is independently selected from the group consisting of hydrogen, —C$_{1-4}$alkyl, perhaloC$_{1-4}$alkyl, mono- or di-haloC$_{1-4}$alkyl, aminoC$_{1-4}$alkyl, C$_{1-4}$alkylaminoC$_{1-4}$alkyl, diC$_{1-4}$alkylaminoC$_{1-4}$alkyl, HO—C$_{1-4}$alkyl, HS—C$_{1-4}$alkyl, C$_{1-4}$alkylS—C$_{1-4}$alkyl, —C$_{0-2}$alkylCOOC$_{1-4}$alkyl, —C$_{0-2}$alkylCOOH, and —C$_{0-2}$alkylCON(R$^s$)R$^t$; —COO—C$_{0-2}$alkyl-ringA, and —COO—C$_{1-2}$alkyl-CON(R$^s$)R$^t$;

R$^s$ and R$^t$ are independently selected from the group consisting of —H, —C$_{1-4}$alkyl, C$_{1-6}$cycloalkylC$_{1-4}$alkyl, phenyl, phenyl substituted with halo, benzyl, benzyl substituted with halo,
or alternatively, R$^s$ and R$^t$ taken together with their nitrogen of attachment form pyrrolidine, piperidine, or morpholine;

ringA is selected from the group consisting of
i) a 6-membered heteroaryl having carbon as a point of attachment and having 1 or 2 heteroatom members which are —N═;
ii) a 5-membered heteroaryl having carbon as a point of attachment, having 1 heteroatom member selected from the group consisting of O, S, >NH, and >NC$_{1-4}$alkyl, and having 0 or 1 additional heteroatom member which is —N═; and
iii) a 5- or 6-membered non-aromatic heterocycle having a carbon or nitrogen as a point of attachment, having 1 or 2 heteroatoms selected from the group consisting of O, S, and N, having 0 or 1 double bonds, having 0 or 1 carbon member replaced by a carbonyl, and optionally substituted with —C$_{1-4}$alkyl, —OH, or halo;

R$^d$ is independently selected from the group consisting of hydrogen, —C$_{1-4}$alkyl, —OH, —OC$_{1-6}$alkyl, HO—C$_{1-4}$alkyl, perhaloC$_{1-4}$alkyl, mono- or di-haloC$_{1-4}$alkyl, aminoC$_{1-4}$alkyl, C$_{1-4}$alkylaminoC$_{1-4}$alkyl, diC$_{1-4}$alkylaminoC$_{1-4}$alkyl, HS—C$_{1-4}$alkyl, C$_{1-4}$alkylS—C$_{1-4}$alkyl, and optionally substituted phenyl; or two R$^d$ together can be ═O where at least one R$^c$ is selected from the group consisting of —COOC$_{1-4}$alkyl, —COO-ringA, —COOH, —CON(R$^s$)R$^t$, and —COOC$_{1-2}$alkylCON(R$^s$)R$^t$;

alternatively, one R$^c$ and one R$^d$ may be taken together to form a double bond;

and enantiomers, diastereomers, hydrates, solvates and pharmaceutically acceptable salts, esters and amides thereof.

Isomeric forms of the compounds of formula (I), and of their pharmaceutically acceptable salts, esters, and amides, are encompassed within the present invention, and reference herein to one of such isomeric forms is meant to refer to at least one of such isomeric forms. One of ordinary skill in the art will recognize that compounds according to this invention may exist, for example in a single isomeric form whereas other compounds may exist in the form of a regioisomeric or stereoisomeric mixture.

The present invention provides methods of treating or preventing diseases and conditions mediated by the CCK1 and CCK2 receptors. The invention also features pharmaceutical compositions containing such compounds and methods of using such compositions in the treatment or prevention of disease states mediated by dual CCK1/CCK2 receptor antagonist activity.

Additional features and advantages of the invention will become apparent from the detailed description and examples below, and the appended claims.

DETAILED DESCRIPTION OF THE INVENTION

Particular preferred compounds of the invention comprise a compound of Formula (I), or an enantiomer, diastereomer, hydrate, solvate thereof, or a pharmaceutically acceptable salt, amide or ester thereof, wherein R$^1$, R$^2$, R$^a$, R$^b$, R$^c$, and R$^d$ have any of the meanings defined hereinabove and equivalents thereof, or at least one of the following assignments and equivalents thereof. Such assignments may be used where appropriate with any of the definitions, claims or embodiments defined herein:

Preferably, X is a bond.
Preferably, R$^1$ is selected from the group consisting of
a) phenyl, naphthyl, 6,7,8,9-tetrahydro-5H-benzocyclohepten-1,2,3 or 4-yl, optionally 5,6,7,8 or 9 oxo substituted, 5,6,7,8-tetrahydro-naphthalen-1,2,3 or 4-yl, optionally 5,6,7 or 8 oxo substituted,
b) pyridyl, pyrazinyl, pyrimidinyl, pyridazinyl, quinolin-2,3 or 4-yl, isoquinolin-1,3 or 4-yl, quinazolin-2 or 4-yl, quinoxalin-2 or 3-yl, naphthyridinyl,
c) furanyl, thiophenyl, 1-(H or C$_{1-4}$alkyl)pyrrolyl, oxazolyl, thiazolyl, pyrazolyl, imidazolyl, isoxazolyl, isothiazolyl, benzofuran-2 or 3-yl, benzothiophen-2 or 3-yl, 1-(H or C$_{1-4}$alkyl)-1H-indol-2 or 3-yl, 1-(H or C$_{1-4}$alkyl)-1H-benzimidazol-2-yl, benzooxazol-2-yl, benzothiazol-2-yl, 1H-pyrrolopyridin-2 or 3-yl,
d) quinolin-5,6,7 or 8-yl, isoquinolin-5,6,7 or 8-yl, quinazolin-5,6,7 or 8-yl, quinoxalin-5,6,7 or 8-yl, and
e) benzofuran-4,5,6 or 7-yl, benzothiophen-4,5,6 or 7-yl, 1-(H or C$_{1-4}$alkyl)-1H-indol-4,5,6 or 7-yl, 1-(H or C$_{1-4}$alkyl)-1H-benzimidazol-4,5,6 or 7-yl, benzooxazol-4,5,6 or 7-yl, benzothiazol-4,5,6 or 7-yl, 1H-pyrrolopyridin-4,5,6 or 7-yl, where each of a) to e) is substituted with 0, 1, 2, or 3 of R$^q$.

Most preferably, R$^1$ is selected from the group consisting of phenyl, 6,7,8,9-tetrahydro-5H-benzocyclohepten-2-yl optionally 5,6,7,8 or 9 oxo substituted, naphthyl, pyridyl, furanyl, thiophenyl, and benzothiophenyl, where each member is substituted with 0, 1, 2, or 3 of R$^q$.

Specific R$^1$ are selected from the group consisting of phenyl, 2-bromophenyl, 3-bromophenyl, 4-bromophenyl, 2-chlorophenyl, 3-chlorophenyl, 4-chlorophenyl, 2,4-dichlorophenyl, 3,4-dichlorophenyl, 2,6-dichlorophenyl, 2,4,6-trichlorophenyl, 2-fluorophenyl, 4-fluorophenyl, 2,4-difluorophenyl, 3,4-difluorophenyl, 2,6-difluorophenyl, 2,4,6-trifluorophenyl, 2-chloro-4-fluorophenyl, 2-fluoro-4-bromophenyl, 2-fluoro-4-chlorophenyl, 3-bromo-4-chlorophenyl, 3-bromo-4-fluorophenyl, 4-chloro-3-iodophenyl, 2-methylphenyl, 4-methylphenyl, 4-methoxyphenyl, 4-dimethylaminophenyl, 2-methylsulfanylphenyl, 2-trifluoromethylphenyl, 4-trifluoromethylphenyl, 4-nitrophenyl, 3-cyanophenyl, 4-cyanophenyl, naphthyl, thiophen-3-yl, 5-bromothiophen-3-yl, and benzothiophen-3-yl.

Preferably, R$^f$ is selected from the group consisting of —CH$_2$CH$_2$CH$_2$—, —CH$_2$CH$_2$CH$_2$CH$_2$—, —CH$_2$CH$_2$CH$_2$CH$_2$CH$_2$— and —(C═O)CH$_2$CH$_2$CH$_2$—.

Preferably, R$^q$ is selected from the group consisting of methyl, ethyl, propyl, t-butyl, hydroxy, fluoro, chloro, bromo, iodo, trifluoromethyl, nitro, cyano, aminomethyl, methylaminomethyl, dimethylaminomethyl, hydroxymethyl, methoxymethyl, methylsulfanyl, methylsulfanylmethyl, methoxy, ethoxy, mercaptomethyl, and mercaptoethyl.

Most preferably, $R^a$ is selected from the group consisting of methyl, fluoro, chloro, bromo, iodo, trifluoromethyl, nitro, and cyano.

Preferably, $R^2$ is selected from the group consisting of —H, methyl, ethyl, i-propyl, t-butyl, allyl, propargyl, cyclopropyl, cyclohexyl, and cyclopentenyl.

Preferably, $R^2$ and one of $R^a$ are taken together as —CH$_2$— or >C═O to form a fused ring to the phenyl.

More preferably, $R^2$ is —H or methyl.

Preferably, each $R^a$ is independently selected from the group consisting of methyl, ethyl, propyl, i-propyl, ethenyl, propenyl, cyclopropyl, cyclobutyl, phenyl, furanyl, thiophenyl, pyrrol-1-yl, benzyl, methoxy, ethoxy, propoxy, cyclopropoxy, cyclobutoxy, cyclopentoxy, phenoxy, benzoxy, mercapto, methylsulfanyl, ethylsulfanyl, t-butylsulfanyl, cyclopropylsulfanyl, phenylsulfanyl, nitro, cyano, amino, dimethylamino, (cyclohexylmethyl)amino, acetyl, —SCF$_3$, iodo, fluoro, chloro, bromo, trifluoromethyl, —OCF$_3$, and methoxycarbonyl.

Preferably, there is one $R^a$. More preferably, there is one $R^a$ positioned on the ring para to the amide substituent. Preferably, there are two $R^a$ substituents.

Preferably, where two adjacent $R^a$ are taken together with the carbons of attachment to form a fused ring, the fused ring is phenyl.

Most preferably, each $R^a$ is independently selected from the group consisting of methyl, i-propyl, ethenyl, 2-propenyl, cyclopropyl, phenyl, thiophenyl, methoxy, ethoxy, propoxy, i-propoxy, nitro, cyano, dimethylamino, (cyclohexylmethyl)amino, acetyl, fluoro, chloro, bromo, iodo, —CF$_3$, and fused phenyl.

Preferably, two $R^b$ are 2,6-difluoro or 2,4-difluoro.

Preferably, two adjacent $R^b$ substituents at 2- and 3-positions are taken with the benzene ring of attachment to form benzothiazole, benzothiadiazole, or quinoxaline.

Preferably, $R^c$ is selected from the group consisting of hydrogen, methyl, ethyl, i-propyl, hydroxymethyl, methoxymethyl, dimethylaminomethyl, methylsulfanylmethyl, methoxycarbonyl, ethoxycarbonyl, tert-butoxycarbonyl, methoxycarbonylmethyl, carboxy, carboxymethyl, carbamoyl, carbamoylmethyl, dimethylcarbamoyl, piperidine-1-carbonyl, 5-methyl-2-oxo-[1,3]dioxol-4-yl-methoxycarbonyl, 3-pyridylmethoxycarbonyl, 3-chlorobenzylcarbamoyl, 4-fluorobenzylcarbamoyl, benzylcarbamoyl, phenylcarbamoyl, dimethylcarbamoylmethoxycarbonyl, and 2-morpholin-4-ylethoxycarbonyl.

More preferably, $R^c$ is selected from the group consisting of hydrogen, methyl, hydroxymethyl, methoxycarbonyl, methoxycarbonylmethyl, carboxy, carboxymethyl, carbamoyl, and carbamoylmethyl.

Preferably, the carbon to which the two $R^c$ groups are attached is in the (S) configuration.

Preferably, $R^d$ is selected from the group consisting of hydrogen, methyl, ethyl, i-propyl, hydroxy, hydroxymethyl, methoxymethyl, dimethylaminomethyl, phenyl, 4-chlorophenyl, and methylsulfanylmethyl.

Preferably, two $R^d$ together form ═O.

More preferably, $R^d$ is selected from the group consisting of hydrogen, methyl, phenyl, and hydroxy.

Compounds of Formula (I) comprise compounds that satisfy any one of the combinations of definitions given herein and equivalents thereof.

It is understood that some compounds referred to herein are chiral and/or have geometric isomeric centers, for example E- and Z-isomers. The present invention encompasses all such optical isomers, including diastereomers and racemic mixtures, atropisomers, and geometric isomers, and mixtures thereof, that possess the activity that characterizes the compounds of this invention. In addition, certain compounds referred to herein can exist in solvated as well as unsolvated forms. It is understood that this invention encompasses all such solvated and unsolvated forms that possess the activity that characterizes the compounds of this invention.

Compounds according to the present invention that have been modified to be detectable by some analytic technique are also within the scope of this invention. The compounds of the present invention may be labeled with radioactive elements such as $^{125}$I, $^{18}$F, $^{11}$C, $^{64}$Cu, $^{3}$H, $^{14}$C, and the like for use in imaging or for radioactive treatment of patients. An example of such compounds is an isotopically labeled compound, such as an $^{18}$F isotopically labeled compound that may be used as a probe in detection and/or imaging techniques, such as positron emission tomography (PET) and single-photon emission computed tomography (SPECT). Preferably, compounds of the present invention labeled with $^{18}$F or $^{11}$C may be used as a positron emission tomography (PET) molecular probe for studying CCK-mediated disorders. Alternatively, compounds of the present invention labeled with $^{14}$C may be used in metabolic studies. Another example of such compounds is an isotopically labeled compound, such as a deuterium and/or tritium labeled compound that may be used in reaction kinetic studies. The compounds described herein may be reacted with an appropriate functionalized radioactive reagents using conventional chemistry to provide radiolabeled compounds.

Preferred compounds of the present invention are selected from the group consisting of:

| EX | Chemical Name |
|---|---|
| 1 | (±)-2-(Benzo[1,2,5]thiadiazole-4-sulfonylamino)-4-chloro-N-[2-(4-chlorophenyl)-propyl]-benzamide; |
| 2 | (S)-2-[2-(Benzo[1,2,5]thiadiazole-4-sulfonylamino)-4-iodo-benzoylamino]-3-(3,4-dichloro-phenyl)-propionic acid; |
| 3 | 2-[2-(Benzo[1,2,5]thiadiazole-4-sulfonylamino)-4,5-dichloro-benzoylamino]-3-phenyl-propionic acid; |
| 4 | (S)-2-[2-(Benzo[1,2,5]thiadiazole-4-sulfonylamino)-4-iodo-benzoylamino]-3-(3-bromo-phenyl)-propionic acid; |
| 5 | 2-(Benzo[1,2,5]thiadiazole-4-sulfonylamino)-4-bromo-N-[2-(3,4-dichlorophenyl)-propyl]-benzamide; |
| 6 | 2-(Benzo[1,2,5]thiadiazole-4-sulfonylamino)-N-[2,2-bis-(4-chloro-phenyl)-ethyl]-4-chloro-benzamide; |

-continued

| EX | Chemical Name |
|---|---|
| 7 | 2-(Benzo[1,2,5]thiadiazole-4-sulfonylamino)-4-chloro-N-[2-(4-chloro-phenyl)-2-methyl-propyl]-benzamide; |
| 8 | (S)-3-(5-Bromo-thiophen-2-yl)-2-[4-chloro-2-(quinoxaline-5-sulfonylamino)-benzoylamino]-propionic acid methyl ester; |
| 9 | (S)-2-[4-Chloro-2-(quinoxaline-5-sulfonylamino)-benzoylamino]-3-naphthalen-2-yl-propionic acid; |
| 10 | (±)-4-Chloro-N-[2-(3,4-dichloro-phenyl)-propyl]-2-(2,4-difluorobenzenesulfonylamino)-benzamide; |
| 11 | (S)-2-(Benzo[1,2,5]thiadiazole-4-sulfonylamino)-N-[1-carbamoyl-2-(4-chloro-phenyl)-ethyl]-4,5-dichloro-benzamide; |
| 12 | (±)-2-(Benzo[1,2,5]thiadiazole-4-sulfonylamino)-N-[2-(4-chloro-phenyl)-1-hydroxymethyl-ethyl]-4-methyl-benzamide; |
| 13 | (S)-Benzo[1,2,5]thiadiazole-4-sulfonic acid [6-bromo-1,3-dioxo-2-(2-phenyl-propyl)-2,3-dihydro-1H-isoindol-4-yl]-amide; |
| 14 | (R)-2-[2-(Benzo[1,2,5]thiadiazole-4-sulfonylamino)-4,5-dichloro-benzoylamino]-3-(4-chloro-phenyl)-propionic acid; |
| 15 | (R)-3-(4-Chloro-phenyl)-2-[4-iodo-2-(quinoxaline-5-sulfonylamino)-benzoylamino]-propionic acid; |
| 16 | (±)-2-(Benzo[1,2,5]thiadiazole-4-sulfonylamino)-5-chloro-N-[2-(3,4-dichloro-phenyl)-propyl]-benzamide; |
| 17 | (R)-2-[2-(2,6-Difluoro-benzenesulfonylamino)-4-iodo-benzoylamino]-3-phenyl-propionic acid; |
| 18 | (±)-2-[4-Chloro-2-(quinoxaline-5-sulfonylamino)-benzoylamino]-3-(3,4-dichloro-phenyl)-3-oxo-propionic acid methyl ester; |
| 19 | 2-[2-(Benzo[1,2,5]thiadiazole-4-sulfonylamino)-4-chloro-benzoylamino]-3-(3,4-dichloro-phenyl)-3-hydroxy-propionic acid; |
| 20 | 2-(Benzo[1,2,5]thiadiazole-4-sulfonylamino)-4-bromo-N-methyl-N-phenethyl-benzamide; |
| 21 | 2-(Benzo[1,2,5]thiadiazole-4-sulfonylamino)-4-bromo-N-[2-(4-chloro-phenyl)-propyl]-benzamide; |
| 22 | 2-(Benzo[1,2,5]thiadiazole-4-sulfonylamino)-N-[2-(4-chloro-phenyl)-1-methyl-ethyl]-4-trifluoromethyl-benzamide; |
| 23 | 2-(Benzothiazole-4-sulfonylamino)-4-bromo-N-[2-(4-chloro-phenyl)-1-methyl-ethyl]-benzamide; |
| 24 | 4-Bromo-N-[2-(4-chloro-phenyl)-propyl]-2-(2,6-difluoro-benzenesulfonylamino)-benzamide; |
| 25 | 2-[2-(Benzo[1,2,5]thiadiazole-4-sulfonylamino)-4-bromo-benzoylamino]-3-phenyl-propionic acid; |
| 26 | 2-[2-(Benzo[1,2,5]thiadiazole-4-sulfonylamino)-4-trifluoromethyl-benzoylamino]-3-phenyl-propionic acid; |
| 27 | 2-[4-Iodo-2-(quinoxaline-5-sulfonylamino)-benzoylamino]-3-phenyl-propionic acid; |
| 28 | 2-[2-(Benzothiazole-4-sulfonylamino)-4-iodo-benzoylamino]-3-phenyl-propionic acid; |
| 29 | 2-[4,5-Dichloro-2-(quinoxaline-5-sulfonylamino)-benzoylamino]-3-phenyl-propionic acid; |
| 30 | 4-Bromo-N-[2-(3,4-dichloro-phenyl)-propyl]-2-(2,6-difluoro-benzenesulfonylamino)-benzamide; |
| 31 | 2-(Benzo[1,2,5]thiadiazole-4-sulfonylamino)-4-bromo-N-(2-phenyl-propyl)-benzamide; |
| 32 | 3-(3,4-Dichloro-phenyl)-2-[2-(2,6-difluoro-benzenesulfonylamino)-4-iodo-benzoylamino]-propionic acid; |
| 33 | 2-[2-(Benzo[1,2,5]thiadiazole-4-sulfonylamino)-4-iodo-benzoylamino]-3-(4-chloro-phenyl)-propionic acid; |
| 34 | 3-(4-Chloro-phenyl)-2-[2-(2,6-difluoro-benzenesulfonylamino)-4-iodo-benzoylamino]-propionic acid; |
| 35 | (S)-2-(Benzo[1,2,5]thiadiazole-4-sulfonylamino)-4-bromo-N-(2-phenyl-propyl)-benzamide; |
| 36 | (R)-2-(Benzo[1,2,5]thiadiazole-4-sulfonylamino)-4-bromo-N-(2-phenyl-propyl)-benzamide; |
| 37 | (S)-4-Bromo-2-(2,6-difluoro-benzenesulfonylamino)-N-(2-phenyl-propyl)-benzamide; |
| 38 | (R)-4-Bromo-2-(2,6-difluoro-benzenesulfonylamino)-N-(2-phenyl-propyl)-benzamide; |
| 39 | 2-(Benzo[1,2,5]thiadiazole-4-sulfonylamino)-N-[2-(3,4-dichloro-phenyl)-propyl]-4-iodo-benzamide; |

-continued

| EX | Chemical Name |
|---|---|
| 40 | N-[2-(3,4-Dichloro-phenyl)-propyl]-4-iodo-2-(quinoxaline-5-sulfonylamino)-benzamide; |
| 41 | 2-[4-Bromo-2-(2,6-difluoro-benzenesulfonylamino)-benzoylamino]-3-(2,4-dichloro-phenyl)-propionic acid; |
| 42 | N-[2-(3,4-Dichloro-phenyl)-propyl]-2-(2,6-difluoro-benzenesulfonylamino)-4-iodo-benzamide; |
| 43 | 4-Chloro-N-[2-(2,4-dichloro-phenyl)-propyl]-2-(2,6-difluoro-benzenesulfonylamino)-benzamide; |
| 44 | 4-Chloro-2-(2,6-difluoro-benzenesulfonylamino)-N-[2-(4-nitro-phenyl)-propyl]-benzamide; |
| 45 | 4-Chloro-2-(2,6-difluoro-benzenesulfonylamino)-N-[2-(4-trifluoromethyl-phenyl)-propyl]-benzamide; |
| 46 | 2-[4-Chloro-2-(2,6-difluoro-benzenesulfonylamino)-benzoylamino]-3-(2,4-dichloro-phenyl)-propionic acid; |
| 47 | N-[2-(2,4-Dichloro-phenyl)-propyl]-2-(2,6-difluoro-benzenesulfonylamino)-4-iodo-benzamide; |
| 48 | 2-(2,6-Difluoro-benzenesulfonylamino)-4-iodo-N-[2-(4-nitro-phenyl)-propyl]-benzamide; |
| 49 | 2-(Benzo[1,2,5]thiadiazole-4-sulfonylamino)-4-chloro-N-((2S,1R)-2-hydroxy-1-methyl-2-phenyl-ethyl)-benzamide; |
| 50 | 2-(Benzo[1,2,5]thiadiazole-4-sulfonylamino)-4-chloro-N-indan-2-yl-benzamide; |
| 51 | 2-(Benzo[1,2,5]thiadiazole-4-sulfonylamino)-4-chloro-N-methyl-N-(2-pyridin-2-yl-ethyl)-benzamide hydrochloride; |
| 52 | (±)-2-(Benzo[1,2,5]thiadiazole-4-sulfonylamino)-4-chloro-N-[2-(4-chloro-phenyl)-1-hydroxymethyl-ethyl]-benzamide; |
| 53 | (±)-2-(Benzo[1,2,5]thiadiazole-4-sulfonylamino)-4-bromo-N-[2-(4-chloro-phenyl)-1-methyl-ethyl]-benzamide; |
| 54 | (±)-2-(Benzo[1,2,5]thiadiazole-4-sulfonylamino)-N-[2-(4-chloro-phenyl)-propyl]-4-methyl-benzamide; |
| 55 | 2-(Benzo[1,2,5]thiadiazole-4-sulfonylamino)-4-chloro-N-[(1R,2S)-2-(4-chloro-phenyl)-2-hydroxy-1-methyl-ethyl]-benzamide; |
| 56 | (2S,3R)-2-[2-(Benzo[1,2,5]thiadiazole-4-sulfonylamino)-4-chloro-benzoylamino]-3-(3,4-dichloro-phenyl)-butyric acid; |
| 57 | (±)-2-(Benzo[1,2,5]thiadiazole-4-sulfonylamino)-4-chloro-N-[2-(3,4-dichloro-phenyl)-propyl]-benzamide; |
| 58 | (±)-2-(Benzo[1,2,5]thiadiazole-4-sulfonylamino)-4,5-dichloro-N-[2-(3,4-dichloro-phenyl)-propyl]-benzamide; |
| 59 | (±)-4-Chloro-N-[2-(3,4-dichloro-phenyl)-propyl]-2-(quinoxaline-5-sulfonylamino)-benzamide; |
| 60 | (R)-3-(3,4-Dichloro-phenyl)-2-[4-iodo-2-(quinoxaline-5-sulfonylamino)-benzoylamino]-propionic acid; |
| 61 | (±)-N-[2-(3,4-Dichloro-phenyl)-propyl]-4-iodo-2-(quinoxaline-5-sulfonylamino)-benzamide; |
| 62 | (R)-2-[2-(Benzo[1,2,5]thiadiazole-4-sulfonylamino)-5-chloro-benzoylamino]-3-(4-chloro-phenyl)-propionic acid; |
| 63 | (S)-2-[4-Chloro-2-(quinoxaline-5-sulfonylamino)-benzoylamino]-3-(3-cyano-phenyl)-propionic acid; |
| 64 | (S)-3-[4-Chloro-2-(quinoxaline-5-sulfonylamino)-benzoylamino]-4-(3,4-dichloro-phenyl)-butyric acid; |
| 65 | (S)-3-Benzo[b]thiophen-3-yl-2-[4-chloro-2-(quinoxaline-5-sulfonylamino)-benzoylamino]-propionic acid methyl ester; |
| 66 | (S)-3-Benzo[b]thiophen-3-yl-2-[4-chloro-2-(quinoxaline-5-sulfonylamino)-benzoylamino]-propionic acid; |
| 67 | (S)-2-[2-(Benzo[1,2,5]thiadiazole-4-sulfonylamino)-4,5-dichloro-benzoylamino]-3-(4-chloro-phenyl)-propionic acid methyl ester; |
| 68 | (S)-2-[2-(Benzo[1,2,5]thiadiazole-4-sulfonylamino)-4,5-dichloro-benzoylamino]-3-(4-chloro-phenyl)-propionic acid; |
| 69 | (R)-2-[4-Chloro-2-(2,4-difluoro-benzenesulfonylamino)-benzoylamino]-3-(4-chloro-phenyl)-propionic acid methyl ester; |
| 70 | 2-(Benzo[1,2,5]thiadiazole-4-sulfonylamino)-4-chloro-N-[2-(2,4-dichloro-phenyl)-ethyl]-benzamide; |
| 71 | (S)-2-[4-Chloro-2-(2,4-difluoro-benzenesulfonylamino)-benzoylamino]-3-(4-chloro-phenyl)-propionic acid methyl ester; |
| 72 | 2-(Benzo[1,2,5]thiadiazole-4-sulfonylamino)-N-[2-(4-chloro-phenyl)-propyl]-4-iodo-benzamide; |
| 73 | (R)-2-(Benzo[1,2,5]thiadiazole-4-sulfonylamino)-4-chloro-N-(2-hydroxy-1-methyl-2,2-diphenyl-ethyl)-benzamide; |

-continued

| EX | Chemical Name |
|---|---|
| 74 | (S)-2-(Benzo[1,2,5]thiadiazole-4-sulfonylamino)-4-chloro-N-(2-hydroxy-1-methyl-2,2-diphenyl-ethyl)-benzamide; |
| 75 | 2-(Benzo[1,2,5]thiadiazole-4-sulfonylamino)-N-[2-(2,4-dichloro-phenyl)-ethyl]-benzamide; |
| 76 | (S)-2-[2-(Benzo[1,2,5]thiadiazole-4-sulfonylamino)-4-chloro-benzoylamino]-3-(4-fluoro-phenyl)-propionic acid; |
| 77 | (S)-2-[2-(Benzo[1,2,5]thiadiazole-4-sulfonylamino)-4-chloro-benzoylamino]-3-thiophen-3-yl-propionic acid; |
| 78 | (S)-3-(3-Chloro-phenyl)-2-[4-chloro-2-(quinoxaline-5-sulfonylamino)-benzoylamino]-propionic acid; |
| 79 | (S)-2-[4-Iodo-2-(quinoxaline-5-sulfonylamino)-benzoylamino]-3-p-tolyl-propionic acid; |
| 80 | N-[2-(4-Bromo-phenyl)-ethyl]-4-chloro-2-(2,6-difluoro-benzenesulfonylamino)-benzamide; |
| 81 | 2-(Benzo[1,2,5]thiadiazole-4-sulfonylamino)-6-chloro-N-[2-(3,4-dichloro-phenyl)-propyl]-benzamide; |
| 82 | (R)-3-[4-Chloro-2-(quinoxaline-5-sulfonylamino)-benzoylamino]-4-(3,4-dichloro-phenyl)-butyric acid; |
| 83 | (S)-2-[2-(Benzo[1,2,5]thiadiazole-4-sulfonylamino)-5-chloro-benzoylamino]-3-(4-chloro-phenyl)-propionic acid; |
| 84 | (S)-2-[4-Chloro-2-(quinoxaline-5-sulfonylamino)-benzoylamino]-3-(3-nitro-phenyl)-propionic acid; |
| 85 | (S)-2-[4-Chloro-2-(quinoxaline-5-sulfonylamino)-benzoylamino]-3-(3,4-difluoro-phenyl)-propionic acid; |
| 86 | (S)-2-[4-Chloro-2-(quinoxaline-5-sulfonylamino)-benzoylamino]-3-(4-cyano-phenyl)-propionic acid; |
| 87 | (S)-2-[4-Chloro-2-(quinoxaline-5-sulfonylamino)-benzoylamino]-3-thiophen-3-yl-propionic acid; |
| 88 | (S)-4-(4-Chloro-phenyl)-3-[4-chloro-2-(quinoxaline-5-sulfonylamino)-benzoylamino]-butyric acid methyl ester; |
| 89 | (S)-4-(4-Chloro-phenyl)-3-[4-chloro-2-(quinoxaline-5-sulfonylamino)-benzoylamino]-butyric acid; |
| 90 | (S)-3-(4-Chloro-phenyl)-2-[4-iodo-2-(quinoxaline-5-sulfonylamino)-benzoylamino]-propionic acid; |
| 91 | (S)-2-[2-(Benzo[1,2,5]thiadiazole-4-sulfonylamino)-4-iodo-benzoylamino]-3-(3-bromo-4-chloro-phenyl)-propionic acid; |
| 92 | (S)-2-[2-(Benzo[1,2,5]thiadiazole-4-sulfonylamino)-4-iodo-benzoylamino]-3-(4-chloro-3-iodo-phenyl)-propionic acid; |
| 93 | (S)-2-[2-(Benzo[1,2,5]thiadiazole-4-sulfonylamino)-4-iodo-benzoylamino]-3-(3-bromo-4-fluoro-phenyl)-propionic acid; |
| 94 | (S)-2-[2-(Benzo[1,2,5]thiadiazole-4-sulfonylamino)-4-iodo-benzoylamino]-3,3-bis-(4-chloro-phenyl)-propionic acid; |
| 95 | (S)-2-[2-(Benzo[1,2,5]thiadiazole-4-sulfonylamino)-4-iodo-benzoylamino]-3-(4-chloro-phenyl)-3-methyl-butyric acid; |
| 96 | 2-[2-(Benzo[1,2,5]thiadiazole-4-sulfonylamino)-4-iodo-benzoylamino]-3-(4-chloro-phenyl)-2-methyl-propionic acid; |
| 97 | 2-[2-(Benzo[1,2,5]thiadiazole-4-sulfonylamino)-4-iodo-benzoylamino]-3-(3-bromo-phenyl)-propionic acid; |
| 98 | 2-[2-(Benzo[1,2,5]thiadiazole-4-sulfonylamino)-4-iodo-benzoylamino]-3-(4-chloro-phenyl)-3-hydroxy-propionic acid; |
| 99 | 2-(Benzo[1,2,5]thiadiazole-4-sulfonylamino)-N-[(2S,1R)-2-(4-chloro-phenyl)-2-hydroxy-1-methyl-ethyl]-4-iodo-benzamide; |
| 100 | 2-(Benzo[1,2,5]thiadiazole-4-sulfonylamino)-N-[2-(3,4-dichloro-phenyl)-2-hydroxy-1-methyl-ethyl]-4-iodo-benzamide; |
| 101 | 2-(Benzo[1,2,5]thiadiazole-4-sulfonylamino)-N-[(2S,1R)-2-(3-bromo-phenyl)-2-hydroxy-1-methyl-ethyl]-4-iodo-benzamide; |
| 102 | 2-[2-(Benzo[1,2,5]thiadiazole-4-sulfonylamino)-4-iodo-benzoylamino]-3-(3,4-dichloro-phenyl)-3-hydroxy-propionic acid; |
| 103 | 2-[2-(Benzo[1,2,5]thiadiazole-4-sulfonylamino)-4-iodo-benzoylamino]-3-(3-bromo-phenyl)-butyric acid; |
| 104 | 2-(Benzo[1,2,5]thiadiazole-4-sulfonylamino)-N-[2-(3-bromo-phenyl)-propyl]-4-iodo-benzamide; |
| 105 | 2-[2-(Benzo[1,2,5]thiadiazole-4-sulfonylamino)-4-iodo-benzoylamino]-3-(3,4-dichloro-phenyl)-acrylic acid; |
| 106 | (S)-2-[2-(Benzo[1,2,5]thiadiazole-4-sulfonylamino)-4-chloro-benzoylamino]-3,3-bis-(4-chloro-phenyl)-propionic acid; |
| 107 | (S)-2-[2-(Benzo[1,2,5]thiadiazole-4-sulfonylamino)-4-chloro-benzoylamino]-3-(4-chloro-phenyl)-3-methyl-butyric acid; |

-continued

| EX | Chemical Name |
|---|---|
| 108 | 2-(Benzo[1,2,5]thiadiazole-4-sulfonylamino)-N-[(2S,1R)-2-(3-bromo-phenyl)-2-hydroxy-1-methyl-ethyl]-4-chloro-benzamide; |
| 109 | 2-[2-(Benzooxazole-4-sulfonylamino)-4,5-dichloro-benzoylamino]-3-(4-chloro-phenyl)-propionic acid; |
| 110 | 2-[2-(Benzooxazole-4-sulfonylamino)-4-iodo-benzoylamino]-3-(3,4-dichloro-phenyl)-propionic acid; |
| 111 | 2-[2-(Benzo[1,3]dioxole-4-sulfonylamino)-4-iodo-benzoylamino]-3-(3,4-dichloro-phenyl)-propionic acid; |
| 112 | 2-(Benzo[1,3]dioxole-4-sulfonylamino)-4-chloro-N-[2-(4-chloro-phenyl)-2-hydroxy-1-methyl-ethyl]-benzamide; |
| 113 | 2-[2-(Benzo[1,2,5]thiadiazole-4-sulfonylamino)-4,5-dichloro-benzoylamino]-3-(3-bromo-4-fluoro-phenyl)-propionic acid 5-methyl-2-oxo-[1,3]dioxol-4-ylmethyl ester; |
| 114 | 2-[2-(Benzo[1,2,5]thiadiazole-4-sulfonylamino)-4,5-dichloro-benzoylamino]-3-(3-bromo-4-fluoro-phenyl)-propionic acid pyridin-3-ylmethyl ester; |
| 115 | (R)-2-[2-(Benzo[1,2,5]thiadiazole-4-sulfonylamino)-4-iodo-benzoylamino]-3-(3-bromo-phenyl)-propionic acid; |
| 116 | (2S,3R)-3-(3,4-Dichloro-phenyl)-2-[2-[2-(2,6-difluoro-benzenesulfonylamino)-4-iodo-benzoylamino]-butyric acid methyl ester; |
| 117 | (S)-2-[2-(Benzo[1,2,5]thiadiazole-4-sulfonylamino)-4-chloro-benzoylamino]-3-(3,4-dichloro-phenyl)-propionic acid; |
| 118 | (R)-2-[2-(Benzo[1,2,5]thiadiazole-4-sulfonylamino)-4-chloro-benzoylamino]-3-(3,4-dichloro-phenyl)-propionic acid; |
| 119 | (S)-2-[4-Chloro-2-(2,6-difluoro-benzenesulfonylamino)-benzoylamino]-3-(3,4-dichloro-phenyl)-propionic acid; |
| 120 | (R)-2-[4-Chloro-2-(2,6-difluoro-benzenesulfonylamino)-benzoylamino]-3-(3,4-dichloro-phenyl)-propionic acid; |
| 121 | anti-2-[2-(Benzo[1,2,5]thiadiazole-4-sulfonylamino)-4-chloro-benzoylamino]-3-(3,4-dichloro-phenyl)-3-hydroxy-propionic acid; |
| 122 | (S)-2-[2-(Benzo[1,2,5]thiadiazole-4-sulfonylamino)-4-iodo-benzoylamino]-3-(3-bromo-4-chloro-phenyl)-propionic acid methyl ester; |
| 123 | (S)-2-[2-(Benzo[1,2,5]thiadiazole-4-sulfonylamino)-4-iodo-benzoylamino]-3-(3-bromo-4-fluoro-phenyl)-propionic acid methyl ester; |
| 124 | (S)-3-(3-Bromo-4-fluoro-phenyl)-2-[4-iodo-2-(quinoxaline-5-sulfonylamino)-benzoylamino]-propionic acid methyl ester; |
| 125 | (S)-3-(3-Bromo-4-fluoro-phenyl)-2-[2-(2,6-difluoro-benzenesulfonylamino)-4-iodo-benzoylamino]-propionic acid methyl ester; |
| 126 | (S)-3-(3-Bromo-4-fluoro-phenyl)-2-[4-iodo-2-(quinoxaline-5-sulfonylamino)-benzoylamino]-propionic acid; |
| 127 | (S)-3-(3-Bromo-4-fluoro-phenyl)-2-[2-(2,6-difluoro-benzenesulfonylamino)-4-iodo-benzoylamino]-propionic acid; |
| 128 | (S)-2-(Benzo[1,2,5]thiadiazole-4-sulfonylamino)-4-chloro-N-[1-(3-chloro-benzylcarbamoyl)-2-(3,4-dichloro-phenyl)-ethyl]-benzamide; |
| 129 | (S)-2-(Benzo[1,2,5]thiadiazole-4-sulfonylamino)-N-[1-benzylcarbamoyl-2-(3,4-dichloro-phenyl)-ethyl]-4-chloro-benzamide; |
| 130 | (S)-2-(Benzo[1,2,5]thiadiazole-4-sulfonylamino)-4-chloro-N-[2-(3,4-dichloro-phenyl)-1-(4-fluoro-benzylcarbamoyl)-ethyl]-benzamide; |
| 131 | (S)-2-[2-(Benzo[1,2,5]thiadiazole-4-sulfonylamino)-4-bromo-benzoylamino]-3-(3,4-dichloro-phenyl)-propionic acid; |
| 132 | (S)-3-(3,4-Dichloro-phenyl)-2-[4-iodo-2-(quinoxaline-5-sulfonylamino)-benzoylamino]-propionic acid; |
| 133 | (S)-2-[2-(Benzo[1,2,5]thiadiazole-4-sulfonylamino)-4-iodo-benzoylamino]-3-(2,4-dichloro-phenyl)-propionic acid; |
| 134 | (S)-2-[2-(Benzo[1,2,5]thiadiazole-4-sulfonylamino)-4-iodo-benzoylamino]-3-(2,4-dichloro-5-fluoro-phenyl)-propionic acid; |
| 135 | (S)-2-[2-(Benzo[1,2,5]thiadiazole-4-sulfonylamino)-4-iodo-benzoylamino]-3-(3-iodo-phenyl)-propionic acid; |
| 136 | (S)-2-[2-(Benzo[1,2,5]thiadiazole-4-sulfonylamino)-4-iodo-benzoylamino]-3-(4-chloro-3-iodo-phenyl)-propionic acid methyl ester; |
| 137 | (S)-3-(4-Chloro-3-iodo-phenyl)-2-[4-iodo-2-(quinoxaline-5-sulfonylamino)-benzoylamino]-propionic acid methyl ester; |
| 138 | (S)-3-(4-Chloro-3-iodo-phenyl)-2-[4-iodo-2-(quinoxaline-5-sulfonylamino)-benzoylamino]-propionic acid; |
| 139 | (S)-2-(Benzo[1,2,5]thiadiazole-4-sulfonylamino)-4-chloro-N-[2-(3,4-dichloro-phenyl)-1-phenylcarbamoyl-ethyl]-benzamide; |
| 140 | (S)-2-(Benzo[1,2,5]thiadiazole-4-sulfonylamino)-4-chloro-N-[1-(3,4-dichloro-benzyl)-2-oxo-2-piperidin-1-yl-ethyl]-benzamide; |
| 141 | (S)-2-[2-(Benzo[1,2,5]thiadiazole-4-sulfonylamino)-4,5-dichloro-benzoylamino]-3-(3,4-dichloro-phenyl)-propionic acid; |
| 142 | (S)-2-[2-(Benzo[1,2,5]thiadiazole-4-sulfonylamino)-4-bromo-benzoylamino]-3-(3-bromo-4-chloro-phenyl)-propionic acid methyl ester; |
| 143 | (S)-2-[2-(Benzo[1,2,5]thiadiazole-4-sulfonylamino)-4-bromo-benzoylamino]-3-(3-bromo-4-fluoro-phenyl)-propionic acid methyl ester; |
| 144 | (Z)-2-[2-(Benzo[1,2,5]thiadiazole-4-sulfonylamino)-4,5-dichloro-benzoylamino]-3-(3,4-dichloro-phenyl)-acrylic acid; |
| 145 | (S)-2-[2-(Benzo[1,2,5]thiadiazole-4-sulfonylamino)-4-chloro-benzoylamino]-3-(3-bromo-4-chloro-phenyl)-propionic acid; |

-continued

| EX | Chemical Name |
|---|---|
| 146 | (S)-3-(3-Bromo-4-chloro-phenyl)-2-[4-chloro-2-(quinoxaline-5-sulfonylamino)-benzoylamino]-propionic acid; |
| 147 | (S)-2-[2-(Benzo[1,2,5]thiadiazole-4-sulfonylamino)-4,5-dichloro-benzoylamino]-3-(3-bromo-4-chloro-phenyl)-propionic acid; |
| 148 | (S)-3-(3-Bromo-4-chloro-phenyl)-2-[4,5-dichloro-2-(quinoxaline-5-sulfonylamino)-benzoylamino]-propionic acid; |
| 149 | (S)-2-[2-(Benzo[1,2,5]thiadiazole-4-sulfonylamino)-4-chloro-benzoylamino]-3-(3-bromo-4-fluoro-phenyl)-propionic acid methyl ester; |
| 150 | (S)-2-[2-(Benzo[1,2,5]thiadiazole-4-sulfonylamino)-4,5-dichloro-benzoylamino]-3-(3-bromo-4-fluoro-phenyl)-propionic acid methyl ester; |
| 151 | (S)-3-(3-Bromo-4-fluoro-phenyl)-2-[4-bromo-2-(quinoxaline-5-sulfonylamino)-benzoylamino]-propionic acid methyl ester; |
| 152 | (S)-3-(3-Bromo-4-fluoro-phenyl)-2-[4-chloro-2-(quinoxaline-5-sulfonylamino)-benzoylamino]-propionic acid methyl ester; |
| 153 | (S)-3-(3-Bromo-4-fluoro-phenyl)-2-[4,5-dichloro-2-(quinoxaline-5-sulfonylamino)-benzoylamino]-propionic acid methyl ester; |
| 154 | (S)-2-[2-(Benzo[1,2,5]thiadiazole-4-sulfonylamino)-4-iodo-benzoylamino]-3-(3,4-dichloro-phenyl)-propionic acid methyl ester; |
| 155 | (S)-3-(3-Bromo-4-chloro-phenyl)-2-[4-bromo-2-(quinoxaline-5-sulfonylamino)-benzoylamino]-propionic acid; |
| 156 | (S)-2-[2-(Benzo[1,2,5]thiadiazole-4-sulfonylamino)-4-chloro-benzoylamino]-3-(3-bromo-4-fluoro-phenyl)-propionic acid; |
| 157 | (S)-2-[2-(Benzo[1,2,5]thiadiazole-4-sulfonylamino)-4,5-dichloro-benzoylamino]-3-(3-bromo-4-fluoro-phenyl)-propionic acid; |
| 158 | (S)-3-(3-Bromo-4-fluoro-phenyl)-2-[4-bromo-2-(quinoxaline-5-sulfonylamino)-benzoylamino]-propionic acid; |
| 159 | (S)-3-(3-Bromo-4-fluoro-phenyl)-2-[4-chloro-2-(quinoxaline-5-sulfonylamino)-benzoylamino]-propionic acid; |
| 160 | (S)-3-(3-Bromo-4-fluoro-phenyl)-2-[4,5-dichloro-2-(quinoxaline-5-sulfonylamino)-benzoylamino]-propionic acid; |
| 161 | (S)-2-[2-(Benzo[1,2,5]thiadiazole-4-sulfonylamino)-4-bromo-benzoylamino]-3-(3-bromo-4-chloro-phenyl)-propionic acid; |
| 162 | (S)-2-[2-(Benzo[1,2,5]thiadiazole-4-sulfonylamino)-4-bromo-benzoylamino]-3-(3-bromo-4-fluoro-phenyl)-propionic acid; |
| 163 | (S)-2-[2-(Benzo[1,2,5]thiadiazole-4-sulfonylamino)-4,5-dichloro-benzoylamino]-3-(3-bromo-4-fluoro-phenyl)-propionic acid ethyl ester; |
| 164 | 2-[2-(Benzo[1,2,5]thiadiazole-4-sulfonylamino)-4-iodo-benzoylamino]-3-(3-bromo-4-chloro-phenyl)-propionic acid; |
| 165 | 2-[2-(Benzo[1,2,5]thiadiazole-4-sulfonylamino)-4-iodo-benzoylamino]-3-(4-chloro-3-iodo-phenyl)-propionic acid; |
| 166 | 2-[2-(Benzo[1,2,5]thiadiazole-4-sulfonylamino)-4-iodo-benzoylamino]-3-(3-bromo-4-fluoro-phenyl)-propionic acid; |
| 167 | 2-[2-(Benzo[1,2,5]thiadiazole-4-sulfonylamino)-4-iodo-benzoylamino]-3,3-bis-(4-chloro-phenyl)-propionic acid; |
| 168 | 2-[2-(Benzo[1,2,5]thiadiazole-4-sulfonylamino)-4-iodo-benzoylamino]-3-(4-chloro-phenyl)-3-methyl-butyric acid; |
| 169 | 2-(Benzo[1,2,5]thiadiazole-4-sulfonylamino)-N-[2-(4-chloro-phenyl)-2-hydroxy-1-methyl-ethyl]-4-iodo-benzamide; |
| 170 | 2-(Benzo[1,2,5]thiadiazole-4-sulfonylamino)-N-[2-(3-bromo-phenyl)-2-hydroxy-1-methyl-ethyl]-4-iodo-benzamide; |
| 171 | 2-[2-(Benzo[1,2,5]thiadiazole-4-sulfonylamino)-4-chloro-benzoylamino]-3,3-bis-(4-chloro-phenyl)-propionic acid; |
| 172 | 2-[2-(Benzo[1,2,5]thiadiazole-4-sulfonylamino)-4-chloro-benzoylamino]-3-(4-chloro-phenyl)-3-methyl-butyric acid; |
| 173 | 2-(Benzo[1,2,5]thiadiazole-4-sulfonylamino)-N-[2-(3-bromo-phenyl)-2-hydroxy-1-methyl-ethyl]-4-chloro-benzamide; |
| 174 | (S)-2-[2-(Benzo[1,2,5]thiadiazole-4-sulfonylamino)-4,5-dichloro-benzoylamino]-3-(3-bromo-4-fluoro-phenyl)-propionic acid tert-butyl ester; |
| 175 | (S)-2-[2-(Benzo[1,2,5]thiadiazole-4-sulfonylamino)-4,5-dichloro-benzoylamino]-3-(3-bromo-4-fluoro-phenyl)-propionic acid 2-morpholin-4-yl-ethyl ester; and |
| 176 | (S)-2-[2-(Benzo[1,2,5]thiadiazole-4-sulfonylamino)-4,5-dichloro-benzoylamino]-3-(3-bromo-4-fluoro-phenyl)-propionic acid dimethylcarbamoylmethyl ester. |

The compounds as described above may be made according to processes within the skill of the art and/or that are described in the schemes and examples that follow. To obtain the various compounds herein, starting materials may be employed that carry the ultimately desired substituents though the reaction scheme with or without protection as appropriate. This may be achieved by means of conventional protecting groups, such as those described in "Protective Groups in Organic Chemistry", ed. J. F. W. McOmie, Plenum Press, 1973; and T. W. Greene & P. G. M. Wuts, "Protective Groups in Organic Synthesis", 3$^{rd}$ ed., John Wiley & Sons, 1999. The protecting groups may be removed at a convenient subsequent stage using methods known from the art. Alternatively, it may be necessary to employ, in the place of the ultimately desired substituent, a suitable group that may be carried through the reaction scheme and replaced as appropriate with the desired substituent. Such compounds, precursors, or prodrugs are also within the scope of the invention. Reactions may be performed between the melting point and the reflux temperature of the solvent, and preferably between 0° C. and the reflux temperature of the solvent.

The compounds of Formula (I) may be prepared by a number of reaction schemes. Persons skilled in the art will recognize that certain compounds are more advantageously produced by one scheme as compared to another.

| Table of Acronyms | |
|---|---|
| Term | Acronym |
| Tetrahydrofuran | THF |
| N,N-Dimethylformamide | DMF |
| Dimethyl sulfoxide | DMSO |
| tert-Butylcarbamoyl | Boc |
| High-pressure liquid chromatography | HPLC |
| Acetyl | Ac |
| Ethyl acetate | EtOAc |
| Trifluoroacetic acid | TFA |
| Methanesulfonyl chloride | MsCl |
| Dichloromethane | DCM |
| O-(7-Azabenzotriazol-1-yl)-N,N,N',N'-tetramethyluronium hexafluorophosphate | HATU |
| 1,5,7-Triazabicyclo[4.4.0]dec-5-ene | TBD |
| 4-(Dimethylamino)pyridine | DMAP |

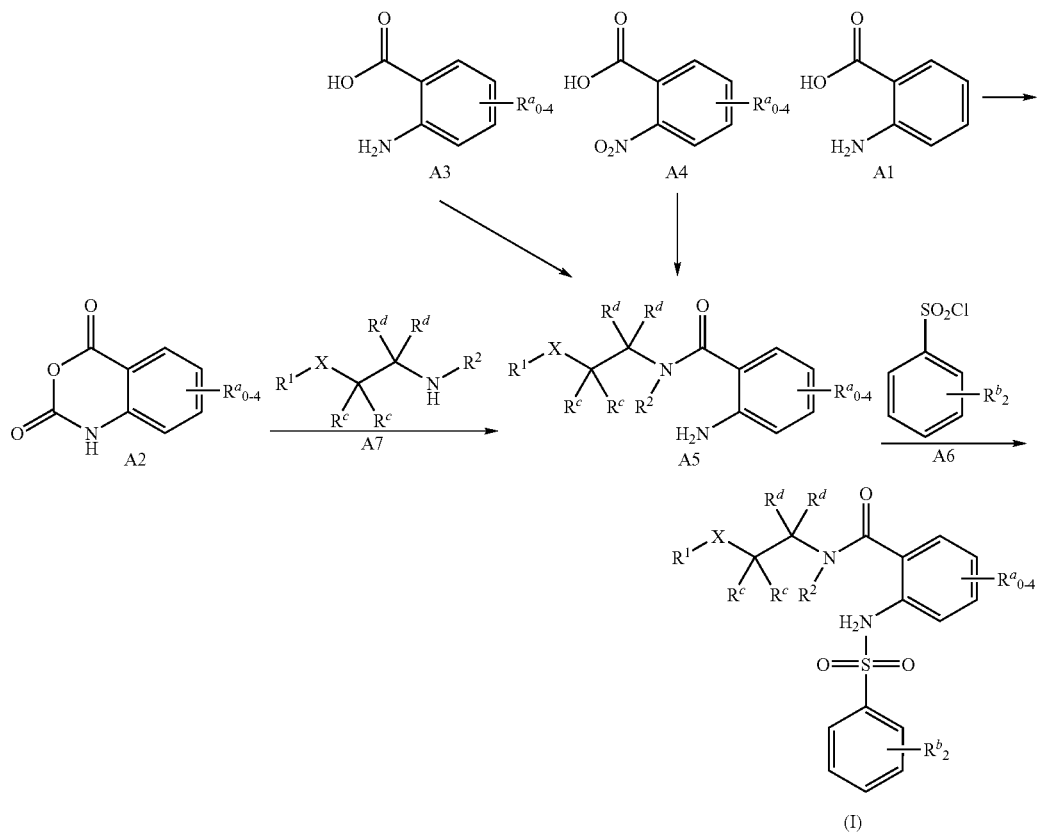

Scheme A

Referring to Scheme A, commercially available aminobenzoic acid A1 is reacted with triphosgene and Hünig's base to produce the benzofused isatoic anhydride species of the genus A2. Various isatoic anhydrides A2 are available commercially. An amine is acylated with the isatoic anhydride A2 to produce a benzamide A5. Benzamide A5 may also be obtained from commercially available anthranilic acid A3 through peptide coupling with amines A7. Benzamide A5 may additionally be obtained from commercially available nitrobenzoic acid A4 through peptide coupling with amines A7, followed by reduction of the nitro group. Benzamide A5 is sulfonylated with aryl sulfonyl chloride A6 to produce aryl sulfonamide compounds (I).

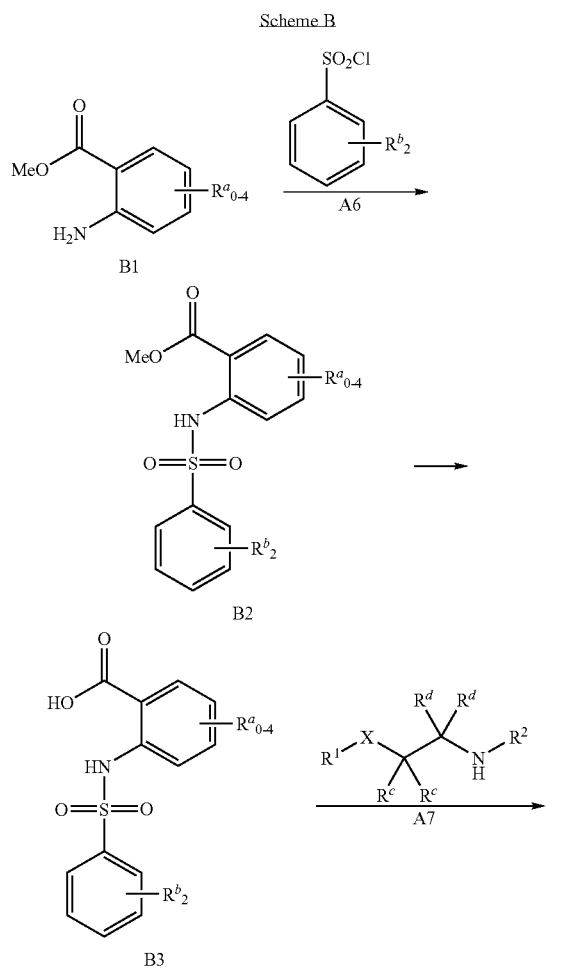

Referring to Scheme B, methyl anthranilate B1 is sulfonylated to sulfonamide B2. The methyl (or other alkyl) ester is hydrolyzed to the acid B3. Acid B3 undergoes peptide coupling with amine A7 under standard conditions to produce compounds of Formula (I).

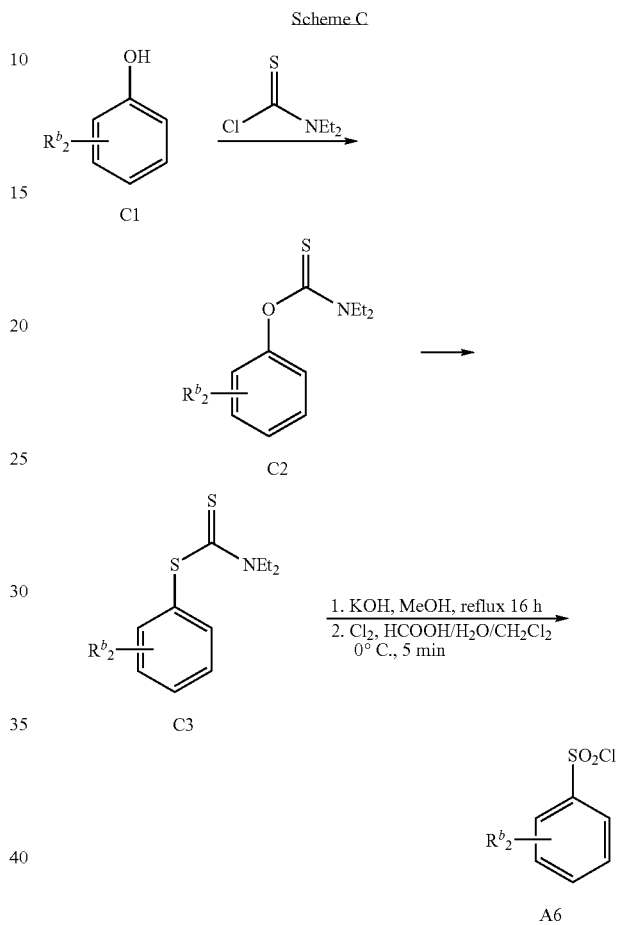

Referring to Scheme C, phenol C1 is acylated with thionocarbamoyl chloride producing a thionocarbamate. The thionocarbamate is isomerized by heating to thiocarbamate C3, where good yields are obtained with heating to 240 C for about 45 minutes. Finally, the thiocarbamate is saponified to the corresponding thiol and immediately thereafter oxidized to the sulfonylchloride A6. Additionally, some sulfonyl chlorides may be commercially available.

Amines of Formula A7 may be commercially available or may be prepared according to methods described in Schemes D-I.

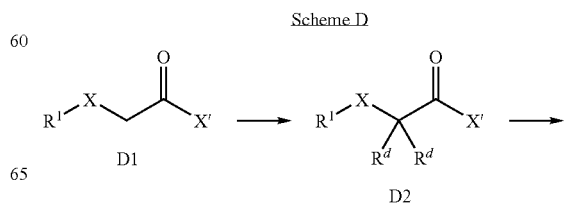

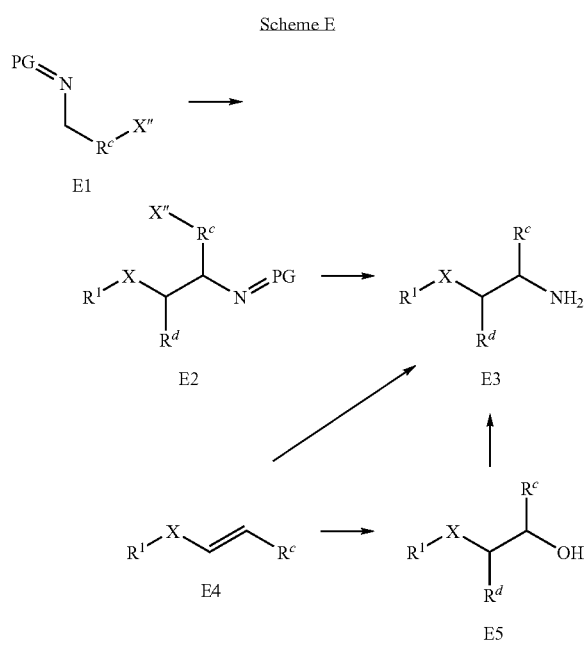

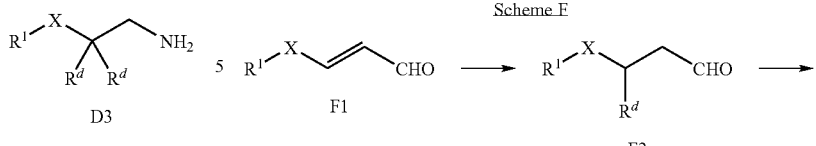

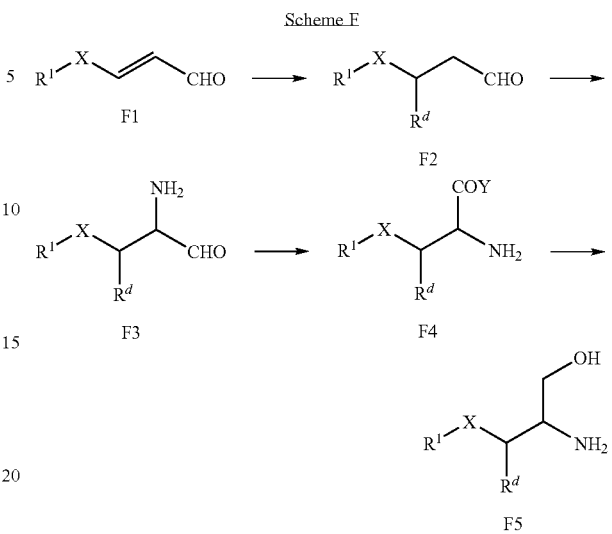

Referring to Scheme D, a carboxylic acid or derivative of type D1 (where X' is OH, $OC_{1-4}$alkyl, a protecting group, or a chiral auxiliary) is singly or multiply alkylated with an activated halide containing group $R^d$ and subsequently converted to an amine D3 by methods well known in the art. Where X' is a chiral auxiliary, and where the $R^d$ substituents differ from one another, particular non-racemic products are obtained.

Referring to Scheme F, $R^d$ is introduced to an unsaturated aldehyde (F1) by 1,4-addition to provide F2. An aldehyde of formula F2 is then electrophilically aminated to form an amino aldehyde F3. Oxidation and functionalization of the aldehyde produces a carboxylic acid or a carboxylate derivative such as F4, where Y is OH, $OC_{1-4}$alkyl, or $N(R^y)(R^z)$. A carboxylic acid analog of formula F4 may be subsequently reduced to the corresponding primary alcohol F5.

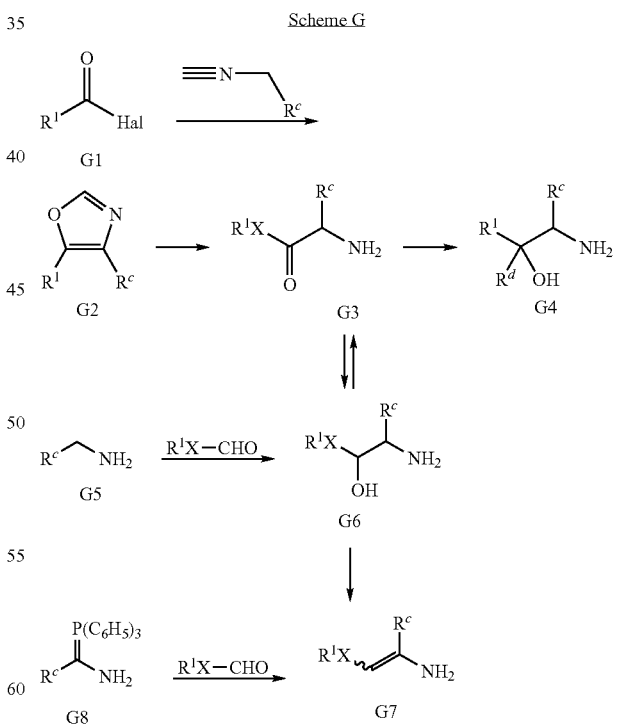

Referring to Scheme E, an amine of type E1 is converted to E3 via alkylation with an $R^d$-containing electrophile, followed by removal of X", if necessary. X" is absent or is a protecting group or a chiral auxiliary. The amine group "N=PG" may be a free amine, a suitably protected amine such as a Boc-protected amine or other carbamate, or an imine such as that derived from benzophenone. In the case where X" is a chiral directing group, non-racemic E2 and E3 may also be produced. Where $R^c$—X" is a t-butyl ester, alkylation may be performed in the presence of a chiral catalyst to produce non-racemic E2 and E3. A particular embodiment is described in Example 174. Preferably, said alkylation is performed in the presence of O-allyl-N-(9-anthracenylmethyl)-cinchonidinium bromide, at reduced temperature, and with a suitable base such as $CsOH.H_2O$. Alternatively, alkene E4 is converted directly to E3 via addition of the groups $R^d$ and ammonia or an ammonia equivalent across the double bond. Alternatively, alkene E4 is converted in a similar manner to alcohol E5, and subsequently to an amine E3 using methods known to those skilled in the art.

Referring to Scheme G, a carboxylic acid derivative such as an acid halide G1, where Hal is preferably chloride, reacts with an isonitrile to provide oxazole G2. Oxazole G2 is then hydrolyzed to an amino ketone of formula G3, where X is a bond. G3, in turn, is modified via addition of $R^d$ to the carbonyl to form G4, or reduced to G6 (where X is a bond) using methods well known in the art. Alternatively, the reduction of a ketone of type G3 to an alcohol of type G6 is performed after keto amine G3 is coupled to the anthranilic portion as described in Schemes A and B. An amine of type G5, or a nitrogen-protected analog, is condensed with a suitable aldehyde (where X is $C_{1-2}$alkyl or a bond) to form an amino alcohol G6. An alkene G7 may be prepared by dehydration of amine G6 or by condensation of an aldehyde with an appropriately derivatized amine, or nitrogen-protected analog, of the type G8 (preferably, where G8 is a phosphorous ylid).

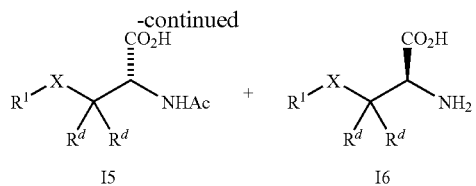

Referring to Scheme I, alkylation of a protected 2-amino malonic acid derivative I2 with an alkyl chloride or other

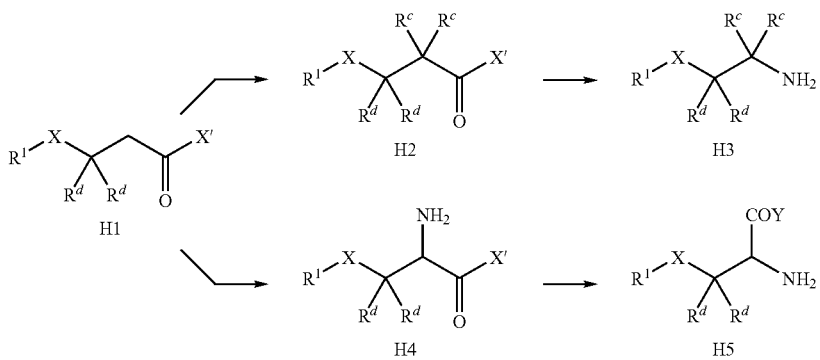

Referring to Scheme H, single or multiple alkylation of carboxylic acid derivative H1 provides H2, which is converted to amine H3 using methods known to those skilled in the art. Substituent X' is as defined above. Alternatively, carboxylic acid derivative H1 is aminated to provide amine H4 using methods well known in the art. Conversion of H4 to amino acid derivative H5 gives compounds of Formula (I) where Y is defined previously. Where X' is a chiral auxiliary, certain non-racemic products may be obtained.

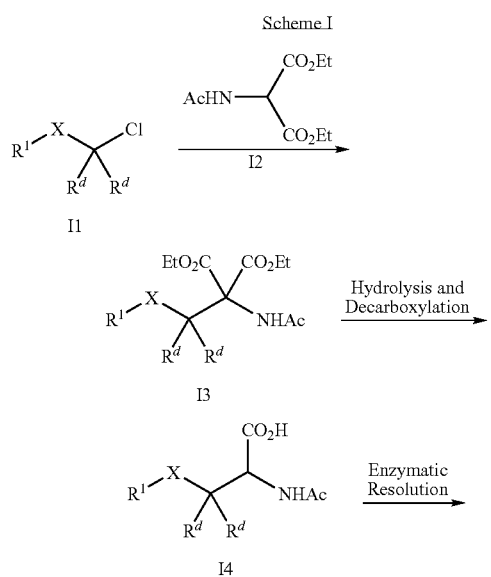

alkylating agent I1, in the presence of a base such as NaOEt, provides diesters I5. Hydrolysis and decarboxylation using standard methods gives amino acids I4. Selective deacetylization with a suitable enzyme, such as acylase from *Asperigillus* genus, allows for the isolation of non-racemic I5 and I6. The desired material may be further processed according to the preceding schemes to provide compounds of Formula (I). A particular embodiment is shown in Intermediate Example 1. Enzymatic resolution is preferably performed with the following conditions: in water, at a pH of approximately 8, in the presence of $CoCl_2$, and at 40° C. Preferably, the "L" enantiomer (I6) is obtained in greater than 90% ee. More preferably, the "L" enantiomer (I6) is obtained in greater than 95% ee. Even more preferably the "L" enantiomer (I6) is obtained in greater than 99% ee.

Compounds of Formula (I) may be converted to their corresponding salts using methods known to those skilled in the art. For example, amines of Formula (I) may be treated with trifluoroacetic acid, HCl, or citric acid in a solvent such as MeOH to provide the corresponding salt forms. Acids of Formula (I) may be treated with NaOH or KOH to provide the corresponding salt forms.

Compounds prepared according to the schemes described above may be obtained as single enantiomers, diastereomers, or regioisomers, or as racemic mixtures or mixtures of enantiomers, diastereomers, or regioisomers. Where regioisomeric or diastereomeric mixtures are obtained, isomers may be separated using conventional methods such as chromatography or crystallization. Where racemic (1:1) and non-racemic (not 1:1) mixtures of enantiomers are obtained, single enantiomers may be isolated using conventional separation methods known to one skilled in the art. Particularly useful separation methods may include chiral chromatography, recrystallization, resolution, diastereomeric salt formation, or derivatization into diastereomeric adducts followed by separation.

The present invention includes within its scope prodrugs of the compounds of this invention. In general, such prodrugs will be functional derivatives of the compounds that are readily convertible in vivo into the required compound. Thus, in the methods of treatment of the present invention, the term "administering" shall encompass the treatment of the various disorders described with a compound of Formula (I) or with a compound that converts to a compound of Formula (I) in vivo after administration to the patient. Conventional procedures for the selection and preparation of suitable prodrug derivatives are described, for example, in "Design of Prodrugs", ed. H. Bundgaard, Elsevier, 1985; Beaumont; K.; Webster, R.; Gardner, I.; Dack, K. *Curr. Drug Metab.* 2003, 4, 461-485; Mizen, L; Burton, G. *Pharm. Biotechnol.* 1998, 11, 345-365. In addition to prodrugs, the invention provides the salts, esters, amides, and other protected or derivatized forms of the described compounds.

For therapeutic use, salts of the compounds of the present invention are those that are pharmaceutically acceptable. However, salts of acids and bases that are non-pharmaceutically acceptable may also find use, for example, in the preparation or purification of a pharmaceutically acceptable compound. All salts, whether pharmaceutically acceptable or not are included within the ambit of the present invention.

Pharmaceutically acceptable salts, esters, and amides of compounds according to the present invention refer to those salt, ester, and amide forms of the compounds of the present invention which would be apparent to the pharmaceutical chemist, i.e., those that are non-toxic and that would favorably affect the pharmacokinetic properties of said compounds of the present invention. Those compounds having favorable pharmacokinetic properties would be apparent to the pharmaceutical chemist, i.e., those which are non-toxic and which possess such pharmacokinetic properties to provide sufficient palatability, absorption, distribution, metabolism and excretion. Other factors, more practical in nature, which are also important in the selection, are cost of raw materials, ease of crystallization, yield, stability, hygroscopicity and flowability of the resulting bulk drug.

Examples of acids that may be used in the preparation of pharmaceutically acceptable salts include the following: acetic acid, 2,2-dichloroacetic acid, acylated amino acids, adipic acid, alginic acid, ascorbic acid, L-aspartic acid, benzenesulfonic acid, benzoic acid, 4-acetamidobenzoic acid, boric acid, (+)-camphoric acid, camphorsulfonic acid, (+)-(1S)-camphor-10-sulfonic acid, capric acid, caproic acid, caprylic acid, cinnamic acid, citric acid, cyclamic acid, cyclohexanesulfamic acid, dodecylsulfuric acid, ethane-1,2-disulfonic acid, ethanesulfonic acid, 2-hydroxy-ethanesulfonic acid, formic acid, fumaric acid, galactaric acid, gentisic acid, glucoheptonic acid, D-gluconic acid, D-glucuronic acid, L-glutamic acid, α-oxo-glutaric acid, glycolic acid, hippuric acid, hydrobromic acid, hydrochloric acid, hydroiodic acid, (+)-L-lactic acid, (±)-DL-lactic acid, lactobionic acid, lauric acid, maleic acid, (−)-L-malic acid, malonic acid, (±)-DL-mandelic acid, methanesulfonic acid, naphthalene-2-sulfonic acid, naphthalene-1,5-disulfonic acid, 1-hydroxy-2-naphthoic acid, nicotinic acid, nitric acid, oleic acid, orotic acid, oxalic acid, palmitic acid, pamoic acid, perchloric acid, phosphoric acid, L-pyroglutamic acid, saccharic acid, salicylic acid, 4-amino-salicylic acid, sebacic acid, stearic acid, succinic acid, sulfuric acid, tannic acid, (+)-L-tartaric acid, thiocyanic acid, p-toluenesulfonic acid, undecylenic acid, and valeric acid.

Compounds of the present invention containing acidic protons may be converted into their therapeutically active non-toxic metal or amine addition salt forms by treatment with appropriate organic and inorganic bases. Appropriate base salt forms comprise, for example, the ammonium salts; the alkali and earth alkaline metal salts (e.g. lithium, sodium, potassium, magnesium, calcium salts, which may be prepared by treatment with, for example, magnesium hydroxide, calcium hydroxide, potassium hydroxide, zinc hydroxide, or sodium hydroxide); and amine salts made with organic bases (e.g. primary, secondary and tertiary aliphatic and aromatic amines such as L-arginine, benethamine, benzathine, choline, deanol, diethanolamine, diethylamine, dimethylamine, dipropylamine, diisopropylamine, 2-(diethylamino)-ethanol, ethanolamine, ethylamine, ethylenediamine, isopropylamine, N-methyl-glucamine, hydrabamine, 1H-imidazole, L-lysine, morpholine, 4-(2-hydroxyethyl)-morpholine, methylamine, piperidine, piperazine, propylamine, pyrrolidine, 1-(2-hydroxyethyl)-pyrrolidine, pyridine, quinuclidine, quinoline, isoquinoline, secondary amines, triethanolamine, trimethylamine, triethylamine, N-methyl-D-glucamine, 2-amino-2-(hydroxymethyl)-1,3-propanediol, and tromethamine). See, e.g., S. M. Berge, et al., "Pharmaceutical Salts", J. Pharm. Sci., 1977, 66:1-19, and *Handbook of Pharmaceutical Salts, Propertions, Selection, and Use*; Stahl, P. H., Wermuth, C. G., Eds.; Wiley-VCH and VHCA: Zurich, 2002, which are incorporated herein by reference.

Pharmaceutically acceptable esters and amides are those that are within a reasonable benefit/risk ratio, pharmacologically effective and suitable for contact with the tissues of patients without undue toxicity, irritation, or allergic response. Representative pharmaceutically acceptable amides of the invention include those derived from ammonia, primary $C_{1-6}$alkyl amines and secondary di($C_{1-6}$alkyl) amines. Secondary amines include 5- or 6-membered heterocyclic or heteroaromatic ring moieties containing at least one nitrogen atom and optionally between 1 and 2 additional heteroatoms. Preferred amides are derived from ammonia, $C_{1-3}$alkyl primary amines, and di($C_{1-2}$alkyl)amines.

Representative pharmaceutically acceptable esters of the invention include $C_{1-7}$alkyl, $C_{5-7}$cycloalkyl, phenyl, substituted phenyl, and phenyl$C_{1-6}$alkyl-esters. Preferred esters include methyl esters. Furthermore, examples of suitable esters include such esters where one or more carboxyl substituents is replaced with p-methoxybenzyloxy-carbonyl, 2,4,6-trimethylbenzyloxy-carbonyl, 9-anthryloxycarbonyl, $CH_3SCH_2COO$—, tetrahydrofur-2-yloxycarbonyl, tetrahydropyran-2-yloxy-carbonyl, fur-2-yloxycarbonyl, benzoylmethoxy-carbonyl, p-nitrobenzyloxy-carbonyl, 4-pyridylmethoxycarbonyl, 2,2,2-trichloro-ethoxycarbonyl, 2,2,2-tribromoethoxycarbonyl, t-butyloxycarbonyl, t-amyloxycarbonyl, diphenylmethoxycarbonyl, triphenylmethoxycarbonyl, adamantyloxy-carbonyl, 2-benzyloxyphenyloxycarbonyl, 4-methylthiophenyloxycarbonyl, or tetrahydropyran-2-yloxycarbonyl.

The compounds of the present invention are dual CCK1/CCK2 antagonists. A dual CCK1/CCK2 antagonist is useful in methods for treating a disorder mediated by the CCK1 or CCK2 receptor. Compounds of the present invention therefore may be useful in methods for treating or preventing pain, drug dependence, anxiety, panic attack, schizophrenia, pancreatic disorders, secretory disorders, gastrointestinal motility disorders, functional bowel disease, biliary colic, cancer, eating disorders (including, for example, anorexia), reflux diseases (including, for example, gastro-esophageal reflux disease and non-erosive reflux disease), gastroduodenal ulcers, reflux esophagitis, peptic ulcers, Barrett's esophagus, antral G cell hyperplasia, pernicious anaemia and Zollinger-Ellison syndrome. Cancer includes, for example, colon cancer, pancreatic adenocarcinoma, pancreatic tumors, and gastric tumors.

Particularly, dual CCK1/CCK2 antagonists are useful in methods for treating or preventing pancreatic adenocarcinoma, pain, gastro-esophageal reflux disease, non-erosive reflux disease, anorexia, pancreatitis, gastroduodenal ulcers, reflux esophagitis, anxiety, colon cancer, peptic ulcers, pancreatic tumors and gastric tumors.

Said methods of treating and preventing comprise the step of administering to a mammal suffering therefrom an effective amount of at least one compound of the present invention.

Compounds of the present invention may be administered in pharmaceutical compositions to treat patients (humans and other mammals) with disorders mediated by the CCK1 and CCK2 receptors. Thus, the invention features pharmaceutical compositions containing at least one compound of the present invention and a pharmaceutically acceptable carrier. A composition of the invention may further include at least one other therapeutic agent (for example, a combination formulation or combination of differently formulated active agents for use in a combination therapy method).

The present invention also features methods of using or preparing or formulating such pharmaceutical compositions. The pharmaceutical compositions can be prepared using conventional pharmaceutical excipients and compounding techniques known to those skilled in the art of preparing dosage forms. It is anticipated that the compounds of the invention can be administered by oral, parenteral, rectal, topical, or ocular routes, or by inhalation. Preparations may also be designed to give slow release of the active ingredient. The preparation may be in the form of tablets, capsules, sachets, vials, powders, granules, lozenges, powders for reconstitution, liquid preparations, or suppositories. Preferably, compounds may be administered by intravenous infusion or topical administration, but more preferably by oral administration.

For oral administration, the compounds of the invention can be provided in the form of tablets or capsules, or as a solution, emulsion, or suspension. Tablets for oral use may include the active ingredient mixed with pharmaceutically acceptable excipients such as inert diluents, disintegrating agents, binding agents, lubricating agents, sweetening agents, flavoring agents, coloring agents and preservatives. Suitable inert fillers include sodium and calcium carbonate, sodium and calcium phosphate, lactose, starch, sugar, glucose, methyl cellulose, magnesium stearate, mannitol, sorbitol, and the like; typical liquid oral excipients include ethanol, glycerol, water and the like. Starch, polyvinyl-pyrrolidone, sodium starch glycolate, microcrystalline cellulose, and alginic acid are suitable disintegrating agents. Binding agents may include starch and gelatin. The lubricating agent, if present, will generally be magnesium stearate, stearic acid or talc. If desired, the tablets may be coated with a material such as glyceryl monostearate or glyceryl distearate to delay absorption in the gastrointestinal tract, or may be coated with an enteric coating. Capsules for oral use include hard gelatin capsules in which the active ingredient is mixed with a solid, semi-solid, or liquid diluent, and soft gelatin capsules wherein the active ingredient is mixed with water, an oil such as peanut oil or olive oil, liquid paraffin, a mixture of mono and di-glycerides of short chain fatty acids, polyethylene glycol 400, or propylene glycol.

Liquids for oral administration may be suspensions, solutions, emulsions or syrups or may be presented as a dry product for reconstitution with water or other suitable vehicles before use. Compositions of such liquid may contain pharmaceutically-acceptable excipients such as suspending agents (for example, sorbitol, methyl cellulose, sodium alginate, gelatin, hydroxyethylcellulose, carboxymethylcellulose, aluminium stearate gel and the like); non-aqueous vehicles, which include oils (for example, almond oil or fractionated coconut oil), propylene glycol, ethyl alcohol or water; preservatives (for example, methyl or propyl p-hydroxybenzoate or sorbic acid); wetting agents such as lecithin; and, if needed, flavoring or coloring agents.

The compounds of this invention may also be administered by non-oral routes. The compositions may be formulated for rectal administration as a suppository. For parenteral use, including intravenous, intramuscular, intraperitoneal, or subcutaneous routes, the compounds of the invention will generally be provided in sterile aqueous solutions or suspensions, buffered to an appropriate pH and isotonicity or in parenterally acceptable oil. Suitable aqueous vehicles include Ringer's solution and isotonic sodium chloride. Such forms will be presented in unit dose form such as ampules or disposable injection devices, in multi-dose forms such as vials from which the appropriate dose may be withdrawn, or in a solid form or pre-concentrate that can be used to prepare an injectable formulation. Another mode of administration of the compounds of the invention may utilize a patch formulation to affect transdermal delivery. The compounds of this invention may also be administered by inhalation, via the nasal or oral routes using a spray formulation consisting of the compound of the invention and a suitable carrier.

Methods are known in the art for determining effective doses for therapeutic (treatment) and prophylactic (preventative) purposes for the pharmaceutical compositions or the drug combinations of the present invention, whether or not formulated in the same composition. The specific dosage level required for any particular patient will depend on a number of factors, including severity of the condition being treated, the route of administration, and the weight of the patient. For therapeutic purposes, "effective dose" or "effective amount" refers to that amount of each active compound or pharmaceutical agent, alone or in combination, that elicits the biological or medicinal response in a tissue system, animal, or human that is being sought by a researcher, veterinarian, medical doctor, or other clinician, which includes alleviation of the symptoms of the disease or disorder being treated. For prophylactic purposes (i.e., preventing or inhibiting the onset or progression of a disorder), the term "effective dose" or "effective amount" refers to that amount of each active compound or pharmaceutical agent, alone or in combination, that inhibits in a subject the onset or progression of a disorder as being sought by a researcher, veterinarian, medical doctor, or other clinician, the delaying of which disorder is mediated, at least in part, by the modulation of the CCK1 and CCK2 receptors. Methods of combination therapy include co-administration of a single formulation containing all active agents; essentially contemporaneous administration of more than one formulation; and administration of two or more active agents separately formulated.

It is anticipated that the daily dose (whether administered as a single dose or as divided doses) will be in the range 0.01 to 1000 mg per day, more usually from 1 to 500 mg per day, and most usually from 10 to 200 mg per day. Expressed as dosage per unit body weight, a typical dose will be expected to be between 0.0001 mg/kg and 15 mg/kg, especially between 0.01 mg/kg and 7 mg/kg, and most especially between 0.15 mg/kg and 2.5 mg/kg.

Preferably, oral doses range from about 0.05 to 200 mg/kg, daily, taken in 1 to 4 separate doses. Some compounds of the invention may be orally dosed in the range of about 0.05 to about 50 mg/kg daily, others may be dosed at 0.05 to about 20 mg/kg daily, while still others may be dosed at 0.1 to about 10 mg/kg daily. Infusion doses can range from about 1 to 1000 μg/kg/min of inhibitor, admixed with a pharmaceutical carrier over a period ranging from several minutes to several days. For topical administration compounds of the present invention may be mixed with a pharmaceutical carrier at a concentration of about 0.1% to about 10% of drug to vehicle.

EXAMPLES

In order to illustrate the invention, the following examples are included. These examples do not limit the invention. They are only meant to suggest a method of practicing the invention. Those skilled in the art may find other methods of practicing the invention, which are obvious to them. However, those methods are deemed to be within the scope of this invention.

Preparative reversed-phase HPLC was performed on a Gilson® instrument, using a YMC-Pack ODS-A, 5 μm, 75×30 mm column, with a flow rate of 10 mL/min, and detection at λ 220 and 254 nm. The gradient was 20 to 99% acetonitrile/water/0.05% TFA over 20 min.

For analytical reversed-phase HPLC, a Hewlett Packard Series 1100 was used, with an Agilent ZORBAX® C8, 5 μm, 4.6×150 mm column, a flow rate of 1 mL/min, and detection at λ 220 and 254 nm. The gradient was 1 to 99% acetonitrile/water/0.05% TFA over 8 min.

Mass spectra were obtained on an Agilent series 1100 MSD using electrospray ionization (ESI) in either positive or negative modes as indicated. The calculated (calcd.) mass corresponds to the exact mass.

NMR spectra were obtained on either a Bruker model DPX400 (400 MHz) or DPX500 (500 MHz) spectrometer. The format of the $^1$H NMR data below is: chemical shift in ppm down field of the tetramethylsilane reference (multiplicity, coupling constant J in Hz, integration).

Normal phase flash chromatography was performed using Isco® RediSep™ 4, 12, 40 or 120 g cartridges under medium pressure.

Elemental analyses were performed by NuMega Resonance Labs, Inc., San Diego, Calif.

Where solutions were "concentrated", they were concentrated under reduced pressure using a rotary evaporator.

Example 1

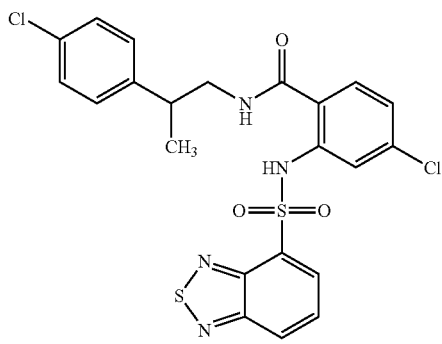

(±)-2-(Benzo[1,2,5]thiadiazole-4-sulfonylamino)-4-chloro-N-[2-(4-chloro-phenyl)-propyl]-benzamide A. 2-(Benzo[1,2,5]thiadiazole-4-sulfonylamino)-4-chlorobenzoic acid methyl ester To a solution of methyl 2-amino-4-chlorobenzoate (7.0 g, 37.7 mmol) in DCM (75 mL) at room temperature (rt) was added 4-chlorosulfonyl-2,1,3-benzothiadiazole (9.45 g, 39.6 mmol), pyridine (9.1 mL, 112 mmol), and DMAP (0.23 g, 1.88 mmol). The mixture was stirred at rt overnight, poured into 1 N HCl (200 mL), and extracted with DCM (2×100 mL). The combined organic layers were dried (Na$_2$SO$_4$) and concentrated. The crude residue was purified by flash chromatography (hexanes/EtOAc) to afford the title sulfonamide as a tan solid (11.65 g, 80%). MS (ESI-): mass calcd. for C$_{14}$H$_{10}$ClN$_3$O$_4$S$_2$, 383.8; m/z found, 382 [M−H]$^-$. $^1$H NMR (400 MHz, CDCl$_3$): 11.38 (s, 1H), 8.40 (dd, J=7.2, 1.2, 1H), 8.24 (dd, J=8.8, 1.2, 1H), 7.80 (d, J=8.4, 1H), 7.76 (d, J=2.0, 1H), 7.74 (dd, J=8.8, 7.2, 1H), 6.94 (dd, J=8.4, 2.0, 1H), 3.92 (s, 3H). Anal. calcd. for C$_{14}$H$_{10}$ClN$_3$O$_4$S$_2$: C, 43.81; H, 2.63; N, 10.95. Found: C, 44.19; H, 3.00; N, 11.23.

B. 2-(Benzo[1,2,5]thiadiazole-4-sulfonylamino)-4-chlorobenzoic acid

To a stirred suspension of 2-(benzo[1,2,5]thiadiazole-4-sulfonylamino)-4-chlorobenzoic acid methyl ester (2.0 g, 5.2 mmol) in THF (12 mL) at rt was added LiOH (2 M in water, 10 mL). The resulting orange mixture was stirred overnight at rt then poured into 0.5 M HCl (150 mL) causing precipitation of the desired benzoic acid. After stirring the mixture several minutes to complete precipitation, the product was collected by suction filtration and air-dried to afford the acid as a tan solid (1.87 g, 97%). MS (ESI-): mass calcd. for C$_{13}$H$_8$ClN$_3$O$_4$S$_2$, 369.8; m/z found, 368 [M−H]$^-$. $^1$H NMR (400 MHz, CDCl$_3$): 11.22 (br s, 1H), 8.43 (dd, J=7.2, 1.0, 1H), 8.26 (dd, J=8.8, 1.0, 1H), 7.90 (d, J=8.8, 1H), 7.80 (d, J=2.0, 1H), 7.75 (dd, J=8.8, 7.2, 1H), 6.99 (dd, J=8.8, 2.0, 1H). Anal. calcd. for C$_{13}$H$_8$ClN$_3$O$_4$S$_2$: C, 42.22; H, 2.18; N, 11.36. Found: C, 41.92; H, 2.50; N, 11.38.

C. (±)-2-(Benzo[1,2,5]thiadiazole-4-sulfonylamino)-4-chloro-N-[2-(4-chloro-phenyl)-propyl]-benzamide To a solution of 2-(benzo[1,2,5]thiadiazole-4-sulfonylamino)-4-chlorobenzoic acid (0.030 g, 0.081 mmol) in a mixture of THF (0.12 mL) and DMF (0.60 mL) at rt was added pyridine (0.020 mL, 0.25 mmol) followed by HATU (0.062 g, 0.17 mmol). The reaction mixture was agitated for 1 h on a shaker. (±)-2-(4-Chlorophenyl)-propylamine hydrochloride (0.035 g, 0.17 mmol) and N,N-diisopropylethylamine (Hünig's base; 0.030 mL, 0.17 mmol) were added. (Hünig's base may be omitted when using the free base form of the amine.) The reaction mixture was agitated for 1 h. TFA (0.050 mL) was added to quench the reaction. The mixture was diluted with DMF (1 mL), and the product amide was obtained by purification of the resulting mixture by preparative reverse-phase HPLC. The title amide was obtained as a solid (27 mg, 64%). HPLC: R$_T$=10.60 min. MS (ESI-): mass calcd. for C$_{22}$H$_{18}$Cl$_2$N$_4$O$_3$S, 520.02; m/z found, 519/521 [M−H]$^-$. $^1$H NMR (500 MHz, CDCl$_3$): 11.53 (s, 1H), 8.35 (dd, J=7.0, 1.0, 1H), 8.22 (dd, J=8.8, 1.0, 1H), 7.71 (dd, J=7.0, 1H), 7.70 (d, J=2.0, 1H), 7.32-7.27 (m, 2H), 7.16-7.09 (m, 2H), 6.95 (d, J=8.4, 1H), 6.88 (dd, J=8.4, 2.0, 1H), 5.79-

5.74 (br m, 1H), 3.76-3.68 (m, 1H), 3.33-3.25 (m, 1H), 3.05-2.95 (m, 1H), 1.31 (d, J=7.0, 3H).

Example 2

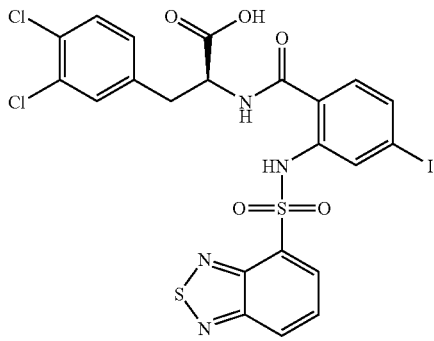

(S)-2-[2-(Benzo[1,2,5]thiadiazole-4-sulfonylamino)-4-iodo-benzoylamino]-3-(3,4-dichloro-phenyl)-propionic acid A. 2-Amino-3-(3,4-dichloro-phenyl)-propionic acid methyl ester hydrochloride To a stirred solution of (S)-2-tert-butoxycarbonylamino-3-(3,4-dichloro-phenyl)-propionic acid (0.67 g, 2.00 mmol) in MeOH (13 mL) at 0° C. was added $SOCl_2$ (0.29 mL, 4.00 mmol). The reaction mixture was allowed to stir and warm to rt overnight. The mixture was concentrated to provide the product as a white solid (0.56 g, 99%). $^1$H NMR (400 MHz, DMSO-$d_6$): 8.66 (br s, 2H), 7.65-7.60 (m, 2H), 7.26 (dd, J=8.2, 1.9, 1H), 4.37 (br s, 1H), 3.72 (s, 3H), 3.18-3.14 (m, 2H).

B. (S)-2-(2-Amino-4-iodo-benzoylamino)-3-(3,4-dichloro-phenyl)-propionic acid methyl ester A solution of 4-iodo-2-nitrobenzoic acid (0.35 g, 1.20 mmol) dissolved in $SOCl_2$ (5 mL) was heated at reflux for 2 h. The mixture was concentrated and the resulting liquid was dissolved in DMF (5 mL). DMAP (161 mg, 1.32 mmol) and 2-amino-3-(3,4-dichloro-phenyl)-propionic acid methyl ester hydrochloride (0.37 g, 1.32 mmol) were added and the solution was stirred overnight at rt. The mixture was poured into water and extracted with EtOAc (3×). The organic layers were combined, dried ($MgSO_4$), and concentrated to provide the crude product as a yellow oil. The oil was purified by flash chromatography (hexanes/EtOAc) to provide the product as a colorless oil (50%, 313 mg). $^1$H NMR (400 MHz, $CDCl_3$): 7.59 (d, J=8.1, 2H), 7.37 (d, J=8.2, 1H), 7.28 (d, J=2.0, 1H), 7.18 (d, J=8.0, 1H), 7.04 (dd, J=8.2, 2.0, 1H), 6.49 (d, J=7.4, 1H), 5.10-5.04 (m, 1H), 3.81 (s, 3H), 3.33-3.17 (m, 2H).

C. (S)-2-(2-Amino-4-iodo-benzoylamino)-3-(3,4-dichloro-phenyl)-propionic acid methyl ester (S)-2-(2-Amino-4-iodo-benzoylamino)-3-(3,4-dichloro-phenyl)-propionic acid methyl ester (313 mg, 0.60 mmol) was dissolved in 1:1 EtOAc/DCM (6 mL) and $SnCl_2.2H_2O$ (0.68 g, 2.99 mmol) was added. The mixture was stirred overnight at rt and then satd. aq. $NaHCO_3$ was added (10 mL). The mixture was filtered through a pad of diatomaceous earth and rinsed with copious water and DCM. The organic layer was separated, dried ($MgSO_4$), and concentrated to provide the desired product as a colorless oil (187 mg, 63%). MS (ESI-): mass calcd. for $C_{17}H_{15}Cl_2IN_2O_3$, 493.1; m/z found, 492 [M−H]$^-$, 531 [M+K]$^-$. $^1$H NMR (400 MHz, $CDCl_3$): 7.36 (d, J=8.2, 1H), 7.22 (d, J=1.9, 1H), 7.09-7.07 (m, 1H), 6.99-6.94 (m, 3H), 6.48 (d, J=7.1, 1H), 4.98 (q, J=5.6, 1H), 3.80 (s, 3H), 3.25-3.11 (m, 2H).

D. (S)-2-[2-(Benzo[1,2,5]thiadiazole-4-sulfonylamino)-4-iodo-benzoylamino]-3-(3,4-dichloro-phenyl)-propionic acid methyl ester To a solution of (S)-2-(2-amino-4-iodo-benzoylamino)-3-(3,4-dichloro-phenyl)-propionic acid methyl ester (39 mg, 0.079 mmol) in DCM (1 mL) was added 4-chlorosulfonyl-2,1,3-benzothiadiazole (37 mg, 0.158 mmol) and pyridine (30 μL, 0.371 mmol). The mixture was shaken overnight at rt, then polymer bound tris(2-aminoethyl)amine resin was added. The resulting mixture was shaken for 2 h, and the resin was removed by filtration and rinsed with DCM. TBD methyl polystyrene resin was then added and the mixture was shaken for 2 h. The liquid was drained and the resin was washed with DCM (3×). A solution of 10% TFA in DCM (3 mL) was added to the resin and the mixture was shaken for 1.5 h. The resin was removed by filtration, washed with 10% TFA in DCM and the filtrate was concentrated to provide the desired product as a white solid (55 mg, 99%). $^1$H NMR (400 MHz, $CDCl_3$): 11.10 (s, 1H), 8.36 (dd, J=7.0, 0.8, 1H), 8.24 (dd, J=8.8, 0.8, 1H), 8.02 (d, J=1.5, 1H), 7.75 (dd, J=8.8, 7.1, 1H), 7.37-7.32 (m, 2H), 7.16 (d, J=2.0, 1H), 6.96 (d, J=8.3, 1H), 6.92 (dd, J=8.2, 2.0, 1H), 6.67 (d, J=7.3, 1H), 4.96 (q, J=5.7, 1H), 3.83 (s, 3H), 3.20-3.12 (m, 2H).

E. (S)-2-[2-(Benzo[1,2,5]thiadiazole-4-sulfonylamino)-4-iodo-benzoylamino]-3-(3,4-dichloro-phenyl)-propionic acid.

To (S)-2-[2-(benzo[1,2,5]thiadiazole-4-sulfonylamino)-4-iodo-benzoylamino]-3-(3,4-dichloro-phenyl)-propionic acid methyl ester (55 mg, 0.079 mmol) in 2:1 water/THF (3 mL) was added LiOH-2$H_2O$ (7 mg, 0.158 mmol). The yellow solution was stirred for 2 h and then 20% aq. HCl (2 mL) was added. The mixture was extracted with EtOAc (3×). The organic layers were combined, dried ($MgSO_4$), and concentrated to provide the desired product as a white solid (41 mg, 76%). HPLC: $R_T$=9.77 min. MS (ESI-): mass calcd. for $C_{22}H_{15}Cl_2IN_4O_5S_2$, 677.3; m/z found, 676 [M−H]$^-$. $^1$H NMR (400 MHz, $CDCl_3$): 11.22 (s, 1H), 8.33 (d, J=7.0, 1H), 8.12 (d, J=8.8, 1H), 7.98 (d, J=0.8, 1H), 7.70 (dd, J=8.6, 7.3, 1H), 7.33 (d, J=8.2, 1H), 7.22 (d, J=8.2, 1H), 7.02 (dd, J=8.2, 1.6, 1H), 6.93 (d, J=8.3, 1H), 6.73 (d, J=7.3, 1H), 4.99 (q, J=6.3, 1H), 3.31 (dd, J=14.2, 5.7, 1H), 3.20 (dd, J=14.2, 5.7).

Example 3

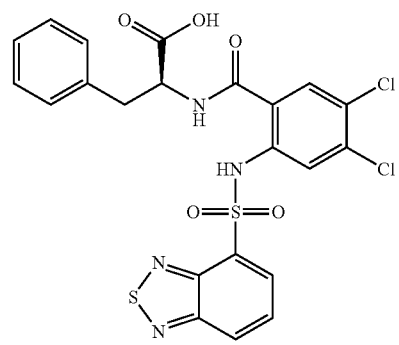

2-[2-(Benzo[1,2,5]thiadiazole-4-sulfonylamino)-4,5-dichloro-benzoylamino]-3-phenyl-propionic acid

A. 4,5-Dichlorophthalic acid monomethyl ester

To a stirred suspension of 4,5-dichlorophthalic anhydride (15.0 g, 69.1 mmol) in MeOH (1 L) was added NaOMe (5.40 g, 100 mmol). The mixture was heated at reflux for 12 h. The mixture was cooled to rt and concentrated to a volume of ~100 mL, and then was poured into 0.5 N HCl (1 L) causing precipitation of the product. The resulting white powder was collected by suction filtration, washed with water, and dried under vacuum to give 17.1 g (99.5%) of the monomethyl ester. $^1$H NMR (400 MHz, CDCl$_3$): 8.02 (s, 1H), 7.84 (s, 1H), 3.94 (s, 3H).

B. Methyl 2-amino-4,5-dichlorobenzoate

A suspension of 4,5-dichlorophthalic acid monomethyl ester (17 g, 69 mmol) in SOCl$_2$ (100 mL) was heated at reflux for 1 h. The resulting mixture was cooled and concentrated to give a yellow oil. The oil was azeotroped with toluene (5×5 mL), leaving the acid chloride as a yellow liquid. $^1$H NMR (400 MHz, CDCl$_3$): 7.96 (s, 1H), 7.82 (s, 1H), 3.95 (s, 3H). The crude acid chloride was stirred in dry acetone (400 mL) at 0° C. as a solution of NaN$_3$ (18.0 g, 277 mmol) in water (120 mL) was added dropwise, maintaining the temperature below 10° C. After addition was complete, the orange reaction mixture was stirred 1 h at 0° C. The mixture was concentrated with no external heating. The residue was partitioned between water and DCM (3×). The combined organic layers were dried (Na$_2$SO$_4$) and concentrated to give the crude acyl azide as a tan solid. $^1$H NMR indicated the acyl azide methyl ester was contaminated with 3 other minor unidentified components. $^1$H NMR (400 MHz, CDCl$_3$): 7.87 (s, 1H), 7.78 (s, 1H), 3.94 (s, 3H). The crude tan solid was suspended in a mixture of acetic acid (240 mL) and water (120 mL) and heated at reflux for 1 h. Rapid gas evolution occurred. The suspension was concentrated, and the resulting solid was collected by suction filtration and washed with water. The crude solid was stirred in toluene and filtered. The filtrate was concentrated to a white solid (9.10 g, ~54%, 91% pure by $^1$H NMR). The aminobenzoate was used without further purification. $^1$H NMR (400 MHz, CDCl$_3$): 7.92 (s, 1H), 6.78 (s, 1H), 5.77 (br s, 2H), 3.87 (s, 3H).

C. 2-Amino-4,5-dichloro-benzoic acid

Methyl 2-amino-4,5-dichlorobenzoate (2.1 g, 9.41 mmol) was dissolved in THF (15 mL) and water (30 mL) was added. LiOH (0.79 g, 18.8 mmol) was added the mixture was stirred overnight at rt. The product was precipitated by addition of 10% aq. HCl (30 mL) and isolated by suction filtration. The white solid was dried under vacuum (1.6 g, 81%). $^1$H NMR (400 MHz, DMSO-d$_6$): 7.78 (s, 1H), 7.01 (s, 1H).

D. 3,4-Dichloroisatoic anhydride

2-Amino-4,5-dichloro-benzoic acid (1.5 g, 7.28 mmol) was dissolved in 1:1 DCM/THF (20 mL) and cooled to 0° C. Phosgene (20% in toluene, 5.4 mL, 8.00 mmol) and Hünig's base (2.54 mL, 14.6 mmol) were added and the reaction was stirred overnight and warmed slowly to rt. The mixture was poured into water and extracted with DCM (3×) and EtOAc (2×). The combined organic layers were dried (MgSO$_4$), and concentrated to provide the product as a white solid (1.6 g, 92%). HPLC: R$_T$=8.10 min. MS (ESI−): mass calcd. for C$_8$H$_3$Cl$_2$NO$_3$, 232.0; m/z found, 231 [M−H]$^-$. $^1$H NMR (400 MHz, DMSO-d$_6$): 11.95 (s, 1H), 8.10 (s, 1H), 7.32 (s, 1H).

E. 2-(2-Amino-4,5-dichloro-benzoylamino)-3-phenyl-propionic acid methyl ester 3,4-Dichloroisatoic anhydride (147 mg, 0.634 mmol) was dissolved in DMF (2 mL). (L)-Phenylalanine methyl ester hydrochloride (150 mg, 0.697 mmol) and DMAP (85 mg, 0.697 mmol) were added and the mixture was stirred overnight at rt. The mixture was quenched with water and extracted with EtOAc (3×). The combined organic layers were washed with water, dried (MgSO$_4$), filtered and concentrated to provide the crude product. The crude solid was purified by flash chromatography (hexanes/EtOAc) to provide the desired product as a white solid (150 mg, 68%). $^1$H NMR (400 MHz, CDCl$_3$): 7.27-7.21 (m, 5H), 7.07-7.05 (m, 2H), 6.30 (d, J=7.2, 1H), 5.44 (br s, 2H), 4.95-4.90 (m, 1H), 3.71 (s, 3H), 3.22-3.09 (m, 2H).

F. 2-[2-(Benzo[1,2,5]thiadiazole-4-sulfonylamino)-4,5-dichloro-benzoylamino]-3-phenyl-propionic acid.

This compound was prepared from 2-(2-amino-4,5-dichloro-benzoylamino)-3-phenyl-propionic acid methyl ester and benzo[1,2,5]thiadiazole-4-sulfonyl chloride as in EXAMPLE 2, Parts D and E. HPLC: R$_T$=10.10 min. MS (ESI−): mass calcd. for C$_{22}$H$_{16}$Cl$_2$N$_4$O$_5$S$_2$, 551.4; m/z found, 550 [M−H]$^-$. $^1$H NMR (400 MHz, CDCl$_3$): 11.11 (s, 1H), 8.33 (dd, J=7.1, 0.9, 1H), 8.20 (dd, J=8.8, 0.8, 1H), 7.83 (s, 1H), 7.70 (dd, J=8.8, 7.1, 1H), 7.28 (m, 3H), 7.20 (s, 1H), 7.13 (dd, J=7.4, 1.7, 2H), 6.42 (d, J=7.5, 1H), 5.00 (dd, J=13.3, 6.0, 1H), 3.32 (dd, J=14.1, 5.7, 1H), 3.23 (dd, J=14.1, 6.1, 1H).

Example 4

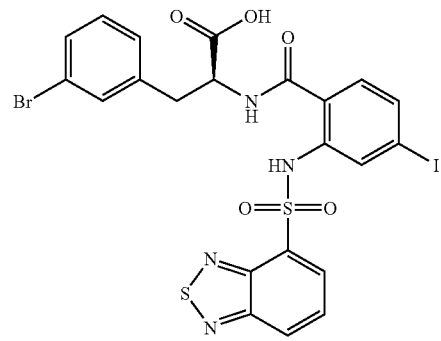

(S)-2-[2-(Benzo[1,2,5]thiadiazole-4-sulfonylamino)-4-iodo-benzoylamino]-3-(3-bromo-phenyl)-propionic acid

A. (1R,2R)-Pseudoephedrine glycinamide hydrate

To a flame-dried three-necked round bottom flask was added (1R,2R)-(−)-pseudoephedrine (10 g, 60.5 mmol), glycine methyl ester hydrochloride (9.9 g, 78.7 mmol), and THF (90 mL). The mixture was stirred for 15 min at rt and lithium t-butoxide (6.8 g, 84.7 mmol) was added. The resulting suspension was stirred at rt for 3 h. Water (150 mL) was added and the THF was removed in vacuo. The aqueous phase was extracted with DCM (3×). The combined organic layers were dried (K$_2$CO$_3$), filtered, and concentrated. Hot THF (50 mL) was added to dissolve the residue and water (2 mL) was added. The mixture was allowed to stand overnight. A white solid formed and was collected by suction filtration. The product was washed with Et$_2$O and dried (10.2 g, 70%). $^1$H NMR (400 MHz, CDCl$_3$; 1:1 ratio of rotamers): 7.42-7.28 (m, 5H), 4.65-4.52 (m, 1.5H), 3.95-3.83 (m, 0.5H), 3.71 (d, J=15.6, 0.5H), 3.45 (d, J=16.9, 1H), 3.37 (d, J=17.0, 0.5H), 2.97 (s, 1.5H), 2.79 (s, 1.5H), 1.85 (br s, 3H), 1.09 (d, J=6.8, 1.5H), 0.99 (d, J=6.8, 1.5H).

B. 2-Amino-3-(3-bromo-phenyl)-N-((2R)-hydroxy-(1R)-methyl-2-phenyl-ethyl)-N-methyl-propionamide A flame-dried flask was charged with LiCl (100 mg, 2.44 mmol). The flask was flushed with N$_2$ and (1R,2R)-pseudoephedrine glycinamide hydrate (1.0 g, 4.17 mmol) was added. The solid reagents were dissolved in THF (20 mL), cooled to 0° C., and lithium bis(trimethylsilyl)amide (LHMDS; 1 M in THF, 13.3 mL, 13.3 mmol) was added. The bright yellow solution was stirred for 1 h and then 3-bromobenzyl bromide (1.25, 5.00 mmol) was added. The mixture was stirred for 2 h at 0° C. and 1 M HCl (200 mL) was added. The solution was extracted with EtOAc (3×). The organic layers were combined and washed with 1 M HCl (3×). All aqueous layers were combined, cooled to 0° C., and basified to pH 14 with 40% aq. NaOH. The aqueous layers were extracted with DCM (4×). The organic layers were combined, dried (K$_2$CO$_3$), filtered and concentrated to provide the crude product. The crude product was purified by flash chromatography (DCM/MeOH) to provide the product as a colorless oil (232 mg, 14%). $^1$H NMR (400 MHz, CDCl$_3$): 8.39 (br s, 1H), 8.17 (br s, 2H), 7.30-7.16 (m, 7H), 7.08-6.97 (m, 2H), 4.88-4.81 (m, 1H), 4.39-4.36 (m, 1H), 4.25 (d, J=9.7, 1H), 3.16-3.13 (m, 1H), 2.96-2.89 (m, 1H), 2.16 (s, 3H), 0.48 (d, J=6.9, 3H).

C. (S)-3-(3-Bromo-phenyl)-2-tert-butoxycarbonylamino-propionic acid

A suspension of 2-amino-3-(3-bromo-phenyl)-N-((2R)-hydroxy-(1R)-methyl-2-phenyl-ethyl)-N-methyl-propionamide (232 mg, 0.593 mmol) in 1 M NaOH (1.2 mL) and water (1.2 mL) was heated at reflux for 2 h and then cooled to rt, whereupon the clear solution became cloudy. Water (10 mL) was added and the solution was extracted with DCM (2×). The combined organic layers were washed with water. The aqueous layers were back-extracted with DCM, then combined and concentrated to ~5 mL. NaHCO$_3$ (100 mg, 1.19 mmol) and dioxane (10 mL) were added. The mixture was cooled to 0° C. and di-tert-butyl dicarbonate (0.24 mL, 1.02 mmol) was added. The reaction mixture was stirred overnight and allowed to warm to rt. Water (20 mL) was added and the solution was extracted with EtOAc (3×). The organic layers were combined and washed with 2% aq. NaHCO$_3$. The combined aqueous layers were acidified to pH 3.5 with satd. aq. citric acid and extracted with EtOAc (3×). The organic layers were combined, washed with water, dried (Na$_2$SO$_4$), and concentrated to provide the product as a clear, colorless oil (38 mg, 17%). $^1$H NMR (400 MHz, CDCl$_3$; 1.7:1 ratio of rotamers): 7.40-7.33 (m, 3.2H), 7.12-7.20 (m, 3.2H), 6.69 (d, J=6.8, 0.6H), 5.00 (d, J=7.8, 1H), 4.62-4.54 (m, 1H), 4.48-4.34 (m, 0.6H), 3.26-3.12 (m, 1.6H), 3.10-2.84 (m, 1.6H), 1.43 (s, 9H), 1.29 (s, 5.4H).

D. (S)-2-Amino-3-(3-bromo-phenyl)-propionic acid methyl ester hydrochloride (S)-3-(3-Bromo-phenyl)-2-tert-butoxycarbonylamino-propionic acid was treated as in EXAMPLE 2, Part A, to provide a white solid. MS (ESI+): mass calcd. for C$_{10}$H$_{12}$BrNO$_2$, 258.1; m/z found, 259 [M+H]$^+$.

E. (S)-2-[2-(Benzo[1,2,5]thiadiazole-4-sulfonylamino)-4-iodo-benzoylamino]-3-(3-bromo-phenyl)-propionic acid 2-(Benzo[1,2,5]thiadiazole-4-sulfonylamino)-4-iodo-benzoic acid was coupled to (S)-2-amino-3-(3-bromo-phenyl)-propionic acid methyl ester hydrochloride as in EXAMPLE 1, Part C. The methyl ester was hydrolyzed as in EXAMPLE 2, Part E, to afford the title compound. HPLC: R$_T$=9.91 min. MS (ESI–): mass calcd. for C$_{22}$H$_{16}$BrIN$_4$O$_5$S$_2$, 687.3; m/z found, 686 [M–H]$^-$. $^1$H NMR (400 MHz, DMSO-d$_6$): 13.05 (s, 1H), 11.77 (s, 1H), 9.03 (d, J=7.8, 1H), 8.45-8.35 (m, 2H), 7.92-7.86 (m, 1H), 7.82 (d, J=1.5, 1H), 7.53-7.51 (br m, 1H), 7.47-7.38 (m, 2H), 7.36-7.34 (m, 1H), 7.31-7.19 (m, 2H), 4.65-4.54 (m, 1H), 3.19 (dd, J=14.0, 4.7, 1H), 3.00 (dd, J=13.7, 10.8, 1H).

Example 5

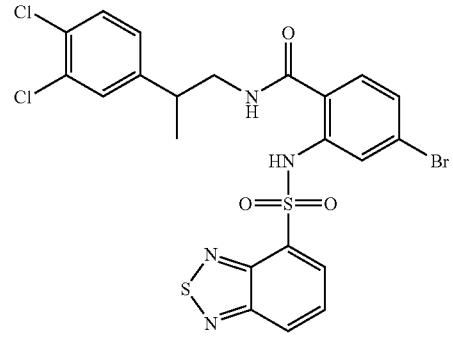

2-(Benzo[1,2,5]thiadiazole-4-sulfonylamino)-4-bromo-N-[2-(3,4-dichloro-phenyl)-propyl]-benzamide A. 2-(3,4-Dichloro-phenyl)-propionitrile To a –78° C. solution of (3,4-dichloro-phenyl)-acetonitrile (5.0 g, 26.9 mmol) in THF (60 mL) was added LHMDS (1 M in THF, 28.2 mL, 28.2 mmol). The reddish orange solution was stirred at –78° C. for 1 h and MeI (1.76 mL, 28.2 mmol) was added. The mixture was allowed to warm to rt overnight. The mixture was diluted with 1 M HCl (20 mL) and extracted with Et$_2$O (3×). The combined organic layers were dried (MgSO$_4$) and concentrated to provide a dark brown oil. The crude product was purified by flash chromatography (hexanes/EtOAc) to provide a colorless oil (5.0 g, 93%). $^1$H NMR (400 MHz, CDCl$_3$): 7.52-7.42 (m, 2H), 7.25-7.18 (m, 1H), 3.88 (q, J=7.3, 1H), 1.64 (d, J=7.3, 3H).

B. 2-(3,4-Dichloro-phenyl)-propylamine hydrochloride 2-(3,4-Dichloro-phenyl)-propionitrile (5.0 g, 25.0 mmol) was dissolved in THF (80 mL). BH$_3$.THF (1 M in THF, 27.5 mL, 27.5 mmol) was added and the mixture was stirred overnight at rt. EtOH (10 mL) was added, the mixture was stirred for 20 min, and HCl in Et$_2$O (2 M, 12.5 mL) was added. After stirring for 1 h, water was added, causing precipitation of the product. The product was collected by suction filtration and dried (4.2 g, 70%). MS (ESI+): mass calcd. for C$_9$H$_{11}$Cl$_2$N, 204.1; m/z found, 205 [M+H]$^+$. $^1$H NMR (400 MHz, CD$_3$OD): 7.45-7.42 (m, 2H), 7.17-7.15 (m, 1H), 3.05-3.02 (m, 2H), 2.98-2.96 (m, 1H), 1.24 (d, J=6.5, 3H).

C. 2-Amino-4-bromo-N-[2-(3,4-dichloro-phenyl)-propyl]-benzamide

The title compound (68 mg, 27%) was prepared from 4-bromo-2-nitrobenzoic acid as in Example 2, Parts B and C. MS (ESI–): mass calcd. for C$_{16}$H$_{15}$BrCl$_2$N$_2$O, 402.1; m/z found, 401 [M–H]$^-$, 440 [M+K]$^-$. $^1$H NMR (400 MHz, CDCl$_3$): 7.39 (d, J=8.2, 1H), 7.33 (d, J=2.0, 1H), 7.07 (dd, J=8.3, 2.0, 1H), 6.95 (d, J=8.4, 1H), 6.82 (d, J=1.8, 1H), 6.69 (dd, J=8.4, 1.9, 1H), 5.98-5.96 (br m, 1H), 5.58 (br s, 2H), 3.70-3.65 (m, 1H), 3.38-3.31 (m, 1H), 3.04 (sext, J=6.8, 1H), 1.30 (d, J=7.0, 3H).

D. 2-(Benzo[1,2,5]thiadiazole-4-sulfonylamino)-4-bromo-N-[2-(3,4-dichloro-phenyl)-propyl]-benzamide The title compound (45 mg, 99%) was prepared as in Example 2, Part D. HPLC: R$_T$=11.06 min. MS (ESI–): mass calcd. for C$_{22}$H$_{17}$BrCl$_2$N$_4$O$_3$S$_2$, 600.3; m/z found, 599 [M–H]$^-$. $^1$H NMR (400 MHz, CDCl$_3$): 11.47 (s, 1H), 8.36 (dd, J=7.0, 0.9, 1H), 8.23 (dd, J=8.8, 0.9, 1H), 7.86 (d, J=1.8, 1H), 7.72 (dd, J=8.8, 7.1, 1H), 7.40 (d, J=8.2, 1H), 7.29 (d, J=2.0, 1H), 7.05 (ddd, J=7.6, 5.6, 2.0, 2H), 6.93 (d, J=8.4, 1H), 5.85 (br m, 1H), 3.68 (td, J=13.2, 6.4, 1H), 3.31 (ddd, J=13.8, 8.7, 5.4, 1H), 3.00 (m, 1H), 1.31 (d, J=7.0, 3H).

Example 6

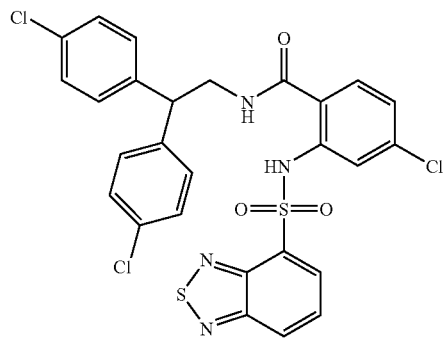

2-(Benzo[1,2,5]thiadiazole-4-sulfonylamino)-N-[2,2-bis-(4-chloro-phenyl)-ethyl]-4-chloro-benzamide

A. 2,2-Bis-(4-chloro-phenyl)-acetamide

A suspension of 2,2-bis-(4-chloro-phenyl)-acetic acid (0.50 g, 1.8 mmol) in SOCl$_2$ (5 mL) was heated at reflux for 1 h. The mixture was concentrated, and the residue was azeotroped with toluene (3×). The crude acid chloride was stirred in DCM (10 mL) at rt and treated with NH$_3$ (0.5 M in dioxane, 14 mL, 7.5 mmol). After 1 h, the reaction mixture was concentrated, and the residue was diluted with satd. aq. NaHCO$_3$ and extracted with DCM (3×). The combined organics were dried (Na$_2$SO$_4$) and concentrated to provide the amide as a white solid (0.50 g, 100%). The amide was used without further purification. $^1$H NMR (400 MHz, CDCl$_3$): 7.35-7.28 (m, 4H), 7.23-7.17 (m, 4H), 5.69 (br s, 1H), 5.53 (br s, 1H), 4.87 (s, 1H).

B. 2,2-Bis-(4-chloro-phenyl)-ethylamine

To a solution of 2,2-bis-(4-chloro-phenyl)-acetamide (0.50 g, 1.8 mmol) in THF (10 mL) at rt was added BH$_3$-THF (1.0 M in THF, 4.5 mL, 4.5 mmol). The solution was heated at reflux for 2 h. The mixture was cooled in an ice bath, and the excess BH$_3$ was quenched by careful addition of 10 mL of MeOH. HCl (2.0 M in MeOH, 5 mL) was added, and the resulting mixture was heated at reflux for 1 h. After cooling, the mixture was concentrated, and the residue was partitioned between 1 N HCl and Et$_2$O. The acidic aqueous layer was basified with 10 N NaOH and extracted with Et$_2$O (3×). The combined organic extracts were dried (MgSO$_4$) and concentrated to provide the desired amine (181 mg, 38%). The amine was used without further purification. $^1$H NMR (400 MHz, CDCl$_3$): 7.30-7.26 (m, 4H), 7.18-7.12 (m, 4H), 3.94 (t, J=7.5, 1H), 3.28 (d, J=7.6, 2H), 1.06 (br s, 2H).

C. 2-(Benzo[1,2,5]thiadiazole-4-sulfonylamino)-N-[2,2-bis-(4-chloro-Phenyl)-ethyl]-4-chloro-benzamide 2-(Benzo[1,2,5]thiadiazole-4-sulfonylamino)-4-chlorobenzoic acid was coupled with 2,2-bis-(4-chloro-phenyl)-ethylamine as in EXAMPLE 1, Part C. HPLC: R$_T$=11.40 min. MS (ESI–): mass calcd. for C$_{27}$H$_{19}$Cl$_3$N$_4$O$_3$S$_2$, 616.00; m/z found, 615/617 [M–H]$^-$. $^1$H NMR (400 MHz, CDCl$_3$): 11.49 (s, 1H), 8.36 (dd, J=7.1, 1.0, 1H), 8.23 (dd, J=8.8, 1.0, 1H), 7.72 (dd, J=8.8, 7.0, 1H), 7.68 (d, J=1.8, 1H), 7.34-7.30 (m, 4H), 7.18-7.13 (m, 4H), 6.89 (d, J=8.4, 1H), 6.86 (dd, J=8.4, 1.8, 1H), 5.87 (br t, J=5.6, 1H), 4.24 (t, J=8.0, 1H), 3.95 (dd, J=7.9, 5.9, 2H).

Example 7

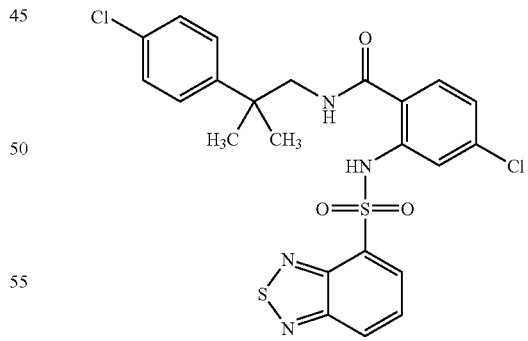

2-(Benzo[1,2,5]thiadiazole-4-sulfonylamino)-4-chloro-N-[2-(4-chloro-phenyl)-2-methyl-propyl]-benzamide

A. 2-(4-Chloro-phenyl)-isobutyramide

Prepared from 2-(4-chloro-phenyl)-2-methyl-propionic acid (0.50 g, 2.5 mmol), as in EXAMPLE 6, Step A (0.45 g, 92%). ¹H NMR (400 MHz, CDCl₃): 7.34 (s, 4H), 5.26 (br s, 1H), 5.15 (br s, 1H), 1.57 (s, 6H).

B. 2-(4-Chloro-phenyl)-2-methyl-propylamine

Prepared from 2-(4-chloro-phenyl)-isobutyramide (0.45 g, 2.3 mmol), as in EXAMPLE 6, Step B (310 mg, 73%). ¹H NMR (400 MHz, CDCl₃): 7.32-7.24 (m, 4H), 2.78 (s, 2H), 1.29 (s, 6H), 0.97 (br s, 2H).

C. 2-(Benzo[1,2,5]thiadiazole-4-sulfonylamino)-4-chloro-N-[2-(4-chloro-phenyl)-2-methyl-propyl]-benzamide 2-(Benzo[1,2,5]thiadiazole-4-sulfonylamino)-4-chlorobenzoic acid was coupled with 2-(4-chloro-phenyl)-2-methyl-propylamine as in EXAMPLE 1, Part C. HPLC: $R_T$=11.08 min. MS (ESI−): mass calcd. for $C_{23}H_{20}Cl_2N_4O_3S_2$, 534.04; m/z found, 533/535 [M−H]⁻. ¹H NMR (400 MHz, CDCl₃): 11.53 (s, 1H), 8.35 (dd, J=7.0, 1.0, 1H), 8.22 (dd, J=8.8, 1.0, 1H), 7.71 (dd, J=8.8, 7.0, 1H), 7.70 (d, J=1.8, 1H), 7.35-7.31 (m, 2H), 7.30-7.26 (m, 2H), 6.89 (d, J=8.3, 1H), 6.86 (dd, J=8.4, 1.8, 1H), 5.58-5.52 (m, 1H), 3.56 (d, J=6.1, 2H), 1.36 (s, 6H).

Example 8

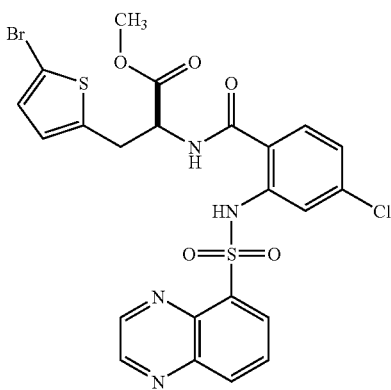

(S)-3-(5-Bromo-thiophen-2-yl)-2-[4-chloro-2-(quinoxaline-5-sulfonylamino)-benzoylamino]-propionic acid methyl ester A. Diethylthiocarbamic acid O-quinoxalin-5-yl ester A mixture of 5-hydroxyquinoxaline (2.13 g, 14.6 mmol), finely ground K₂CO₃ (4.0 g, 29 mmol), and DMF (50 mL) was stirred at 23° C. for 1 h. Solid diethylthiocarbamoyl chloride (2.43 g, 16.1 mmol) was then added. The resulting mixture was stirred for 2 h, then was diluted with water (150 mL) and extracted with Et₂O (2×100 mL). The combined organic extracts were washed with water (100 mL) and brine (100 mL), then dried and concentrated to a viscous orange oil, which was used without purification (3.63 g, 95%). MS (ESI+): mass calcd. for $C_{13}H_{15}N_3OS$, 261.1; m/z found, 262 [M+H]⁺. ¹H NMR (500 MHz, CDCl₃): 8.85-8.65 (m, 2H), 7.96 (dd, J=8.5, 1.1, 1H), 7.71 (t, J=7.9, 1H), 7.46 (dd, J=7.6, 1.2, 1H), 3.87 (q, J=7.1, 2H), 3.78 (q, J=7.1, 2H), 1.38 (t, J=7.1, 3H), 1.28 (t, J=7.1, 3H). ¹³C NMR (125 MHz, CDCl₃): 186.6, 149.4, 144.9, 144.5, 143.4, 137.0, 128.9, 127.0, 123.1, 48.2, 44.5, 13.1, 11.5.

B. Diethylthiocarbamic acid S-quinoxalin-5-yl ester

Neat diethylthiocarbamic acid O-quinoxalin-5-yl ester (0.52 g, 2.0 mmol) was heated at 240° C. for 1 h. The resulting brown oil was chromatographed (EtOAc/hexanes), providing a pale yellow oil (0.49 g, 94%). MS (ESI+): mass calcd. for $C_{13}H_{15}N_3OS$, 261.1; m/z found, 262 [M+H]⁺. ¹H NMR (500 MHz, CDCl₃): 8.93 (d, J=1.8, 1H), 8.87 (d, J=1.8, 1H), 8.18 (dd, J=8.4, 1.2, 1H), 8.13 (dd, J=7.3, 1.2, 1H), 7.81 (dd, J=7.3, 1.0, 1H), 3.61 (br s, 2H), 3.43 (br s, 2H), 1.38 (br s, 3H), 1.16 (br s, 3H).

C. Quinoxaline-5-sulfonyl chloride

A solution of diethylthiocarbamic acid S-quinoxalin-5-yl ester (3.20 g, 12.3 mmol), KOH (6.89 g, 123 mmol) and MeOH (100 mL) was heated at reflux for 16 h. The solution was allowed to cool to rt, and then acetic acid (7 mL) was added. The mixture was diluted with water (100 mL) and extracted with EtOAc (2×100 mL). The combined extracts were washed with water (100 mL) and brine (100 mL), then dried and concentrated to a tan solid (1.90 g). A portion of this thiol (0.22 g, 1.4 mmol) was combined with DCM (50 mL), formic acid (25 mL), and water (25 mL), and the resulting biphasic mixture was cooled to 0° C. Chlorine gas was bubbled through this mixture with rapid stirring for 5 min. The mixture was transferred to a separatory funnel, and the organic phase was collected. The aqueous phase was extracted with DCM (50 mL), and the combined organic phases were washed with 1 M NaOH (50 mL) and brine (50 mL), and then dried. The solution was concentrated to afford the title compound as a light yellow crystalline solid (0.28 g, 86%). ¹H NMR (500 MHz, CDCl₃): 9.17 (d, J=1.8, 1H), 9.07 (d, J=1.8, 1H), 8.60 (dd, J=7.5, 1.4, 1H), 8.53 (dd, J=8.4, 1.4, 1H), 7.96 (dd, J=8.6, 0.8, 1H). ¹³C NMR (125 MHz, CDCl₃): 146.9, 146.8, 143.7, 140.4, 139.0, 138.4, 132.4, 128.8.

D. 4-Chloro-2-(quinoxaline-5-sulfonylamino)benzoic acid methyl ester

A solution of methyl 2-amino-4-chlorobenzoate (0.33 g, 1.8 mmol), quinoxaline-5-sulfonyl chloride (0.40 g, 1.8 mmol), pyridine (0.71 mL, 8.8 mmol), and DCM (10 mL) was stirred at rt for 16 h. EtOAc (75 mL) was added and the solution was washed with satd. aq. NaHCO₃ (50 mL), then dried and concentrated. Chromatographic purification of this residue (EtOAc/hexanes) gave the title compound as a white solid (0.60 mg, 90%). MS (ESI+): mass calcd. for $C_{16}H_{12}ClN_3O_4S$, 377.0; m/z found, 378 [M+H]⁺. ¹H NMR (400 MHz, CDCl₃): 11.44 (s, 1H), 8.97 (d, J=1.8, 1H), 8.95 (d, J=1.8, 1H), 8.61 (dd, J=7.4, 1.4, 1H), 8.33 (dd, J=8.5, 1.4, 1H), 7.89 (dd, J=8.4, 1.0, 1H), 7.84 (d, J=2.0, 1H), 7.77 (d, J=8.6, 1H), 6.89 (dd, J=8.6, 2.0, 1H), 3.90 (s, 3H).

E. 4-Chloro-2-(quinoxaline-5-sulfonylamino)benzoic acid

A solution of LiOH.H₂O (0.32 g, 7.7 mmol) in water (5 mL) was added to a solution of 4-chloro-2-(quinoxaline-5-sulfonylamino)benzoic acid methyl ester (0.58 g, 1.5 mmol) and THF (10 mL). The biphasic mixture was stirred rapidly at rt for 16 h, then adjusted to pH 5 with 1 M HCl. The resulting precipitate was collected by filtration to afford the acid as a white solid (0.51 g, 92%). MS (ESI+): calcd. for $C_{15}H_{10}ClN_3O_4S$, 363.0; m/z found, 364 [M+H]⁺. ¹H NMR (500 MHz, DMSO-d₆): 14.20 (br s, 1H), 11.73 (s, 1H), 9.12

(d, J=1.6, 1H), 9.00 (d, J=1.5, 1H), 8.65 (d, J=7.3, 1H), 8.42 (d, J=8.3, 1H), 8.06 (t, J=7.8, 1H), 7.80 (d, J=8.5, 1H), 7.63 (d, J=2.0, 1H), 7.07 (dd, J=8.4, 1.9, 1H).

F. (S)-2-Amino-3-(5-bromo-thiophen-2-yl)-propionic acid methyl ester hydrochloride (S)-2-tert-Butoxycarbonylamino-3-(5-bromo-thiophen-2-yl)-propionic acid was treated as in EXAMPLE 2, Part A. $^1$H NMR (400 MHz, CD$_3$OD): 7.02 (d, J=3.6, 1H), 6.79 (d, J=3.6, 1H), 4.35 (t, J=5.9, 1H), 3.87 (s, 3H), 3.42 (d, J=5.7, 2H).

G. (S)-3-(5-Bromo-thiophen-2-yl)-2-[4-chloro-2-(quinoxaline-5-sulfonylamino)-benzoylamino]-propionic acid methyl ester 4-Chloro-2-(quinoxaline-5-sulfonylamino)benzoic acid was coupled with (S)-2-amino-3-(5-bromo-thiophen-2-yl)-propionic acid methyl ester hydrochloride as in EXAMPLE 1, Part C. HPLC: R$_T$=10.34 min. MS (ESI−): mass calcd. for C$_{23}$H$_{18}$BrClN$_4$O$_5$S$_2$, 607.96; m/z found, 607/609 [M−H]$^-$. $^1$H NMR (500 MHz, CDCl$_3$): 11.31 (s, 1H), 8.94 (d, J=1.8, 1H), 8.91 (d, J=1.8, 1H), 8.59 (dd, J=7.4, 1.4, 1H), 8.32 (dd, J=8.4, 1.3, 1H), 7.89 (dd, J=8.4, 7.4, 1H), 7.80 (d, J=2.0, 1H), 7.27 (d, J=8.4, 1H), 6.96 (dd, J=8.4, 2.0, 1H), 6.86 (d, J=3.7, 1H), 6.57 (br d, J=6.8, 1H), 6.48 (d, J=3.6, 1H), 4.92 (dt, J=7.0, 4.6, 1H), 3.83 (s, 3H), 3.40 (d, J=4.6, 2H).

Example 9

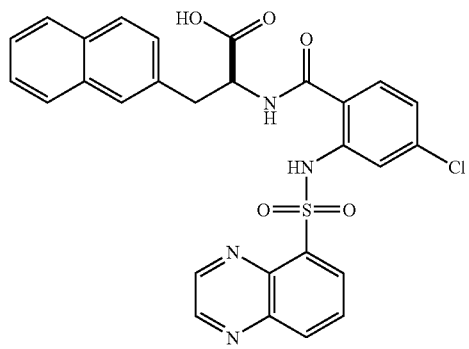

(S)-2-[4-Chloro-2-(quinoxaline-5-sulfonylamino)-benzoylamino]-3-naphthalen-2-yl-propionic acid

A. (S)-2-Amino-3-naphthalen-2-yl-propionic acid methyl ester hydrochloride (S)-2-(tert-Butoxycarbonylamino)-3-naphthalen-2-yl-propionic acid was treated as in EXAMPLE 2, Part A, to give a white solid. $^1$H NMR (400 MHz, CD$_3$OD): 7.91-7.82 (m, 3H), 7.75 (br s, 1H), 7.54-7.47 (m, 2H), 7.38 (dd J=8.4, 1.7, 1H), 4.43 (dd, J=7.7, 6.0, 1H), 3.82 (s, 3H), 3.45 (dd, J=14.4, 5.9, 1H), 3.32 (dd, J=14.4, 7.7, 1H).

B. (S)-3-Naphthalene-2-yl-2-[4-chloro-2-(quinoxaline-5-sulfonylamino)-benzoylamino]-propionic acid methyl ester 4-Chloro-2-(quinoxaline-5-sulfonylamino)benzoic acid was coupled with (S)-2-amino-3-naphthalen-2-yl-propionic acid methyl ester hydrochloride as in EXAMPLE 1, Part C.

C. (S)-2-[4-Chloro-2-(quinoxaline-5-sulfonylamino)-benzoylamino]-3-naphthalen-2-yl-propionic acid (S)-3-Naphthalen-2-yl-2-[4-chloro-2-(quinoxaline-5-sulfonylamino)-benzoylamino]-propionic acid methyl ester was hydrolyzed as in EXAMPLE 2, Part E, to provide the title acid as a solid. HPLC: R$_T$=9.60 min. MS (ESI−): mass calcd. for C$_{28}$H$_{21}$ClN$_4$O$_5$S, 560.09; m/z found, 559 [M−H]$^-$. $^1$H NMR (400 MHz, CD$_3$OD): 8.66 (d, J=1.8, 1H), 8.58 (d, J=1.7, 1H), 8.51 (dd, J=7.4, 1.3, 1H), 8.26 (dd, J=8.5, 1.3, 1H), 7.90 (dd, J=8.4, 7.4, 1H), 7.85-7.73 (m, 3H), 7.70 (br s, 1H), 7.67 (d, J=2.0, 1H), 7.47-7.38 (m, 3H), 7.35 (d, J=8.5, 1H), 6.89 (dd, J=8.5, 2.0, 1H), 4.97-4.85 (m, 1H), 3.46 (dd, J=13.9, 4.8, 1H), 3.19 (dd, J=13.9, 9.8, 1H).

Example 10

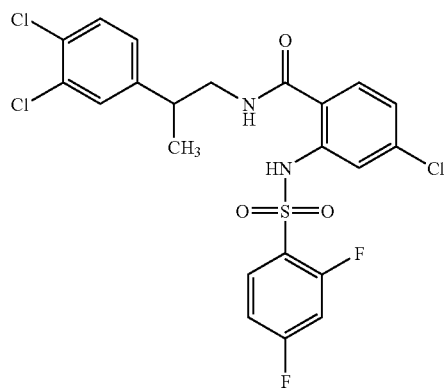

(±)-4-Chloro-N-[2-(3,4-dichloro-phenyl)-propyl]-2-(2,4-difluorobenzenesulfonylamino)-benzamide

A. 4-Chloro-2-(2,4-difluoro-benzenesulfonylamino)-benzoic acid methyl ester

To a solution of methyl 4-chloroanthranilate (0.50 g, 2.7 mmol) and pyridine (0.87 mL, 10.8 mmol) in DCM (10 mL) at rt was added 2,4-difluorobenzenesulfonyl chloride (0.64 g, 3.0 mmol). The mixture was stirred overnight at rt, poured into 1 N HCl, and extracted with DCM (3×). The combined organic extracts were dried (Na$_2$SO$_4$) and concentrated. The residue was purified by flash chromatography (EtOAc/hexanes) to provide 0.69 g (70%) of the desired sulfonamide as a solid. $^1$H NMR (400 MHz, CDCl$_3$): 11.02 (s, 1H), 8.07-8.00 (m, 1H), 7.91 (d, J=8.6, 1H), 7.64 (d, J=2.0, 1H), 7.04-6.98 (m, 1H), 7.02 (dd, J=8.6, 2.0, 1H), 6.93-6.86 (m, 1H), 3.94 (s, 3H).

B. 4-Chloro-2-(2,4-difluoro-benzenesulfonylamino)-benzoic acid

The title compound (0.65 g, 98%) was prepared from 4-chloro-2-(2,4-difluoro-benzenesulfonylamino)-benzoic acid methyl ester as in Example 1, Part B. $^1$H NMR (500 MHz, CD$_3$OD): 8.08-8.02 (m, 1H), 7.98 (d, J=8.5, 1H), 7.60 (d, J=2.0, 1H), 7.20-7.14 (m, 2H), 7.10 (dd, J=8.5, 2.1, 1H).

C. (±)-4-Chloro-N-[2-(3,4-dichloro-Phenyl)-propyl]-2-(2,4-difluorobenzenesulfonylamino)-benzamide 4-Chloro-2-(2,4-difluoro-benzenesulfonylamino)-benzoic acid was coupled with (±)-2-(3,4-dichloro-phenyl)-propylamine hydrochloride as in EXAMPLE 1, Part C. HPLC: $R_T$=12.04 min. MS (ESI–): mass calcd. for $C_{22}H_{17}Cl_3FN_2O_3S_2$, 532.00; m/z found, 531/533 [M–H]⁻. ¹H NMR (400 MHz, CDCl₃): 11.41 (s, 1H), 8.00 (ddd, J=8.6, 8.6, 6.0, 1H), 7.61 (d, J=2.0, 1H), 7.42 (d, J=8.2, 1H), 7.32 (d, J=2.1, 1H), 7.11 (d, J=8.4, 1H), 7.08 (dd, J=8.2, 2.1, 1H), 7.03-6.97 (m, 1H), 6.97 (dd, J=8.4, 2.0, 1H), 6.92-6.86 (m, 1H), 6.02-5.95 (br m, 1H), 3.76-3.68 (m, 1H), 3.41-3.31 (m, 1H), 3.11-3.01 (m, 1H), 1.32 (d, J=7.0, 3H).

Example 11

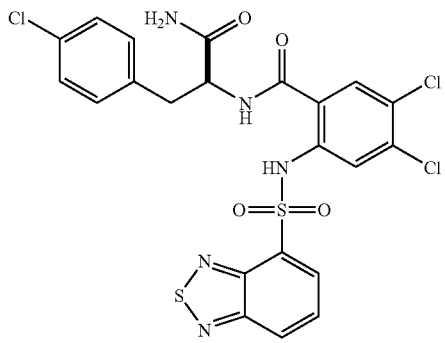

(S)-2-(Benzo[1,2,5]thiadiazole-4-sulfonylamino)-N-[1-carbamoyl-2-(4-chloro-phenyl)-ethyl]-4,5-dichloro-benzamide The title compound (3 mg, 20%) was prepared from (S)-2-[2-(benzo[1,2,5]thiadiazole-4-sulfonylamino)-4,5-dichloro-benzoylamino]-3-(4-chloro-phenyl)-propionic acid and NH₃ (0.5 M in dioxane) as in Example 1, Part C. HPLC: $R_T$=10.08 min. MS (ESI–): mass calcd. for $C_{22}H_{16}Cl_3N_5O_4S_2$, 582.97; m/z found, 582/584 [M–H]⁻. ¹H NMR (400 MHz, CDCl₃): 11.34 (s, 1H), 8.37 (dd, J=7.1, 1.0, 1H), 8.24 (dd, J=8.8, 1.0, 1H), 7.84 (s, 1H), 7.73 (dd, J=8.8, 7.1, 1H), 7.36 (s, 1H), 7.36-7.32 (m, 2H), 7.24-7.20 (m, 2H), 6.84 (br d, J=6.9, 1H), 5.47 (br s, 1H), 5.41 (br s, 1H), 4.68 (ddd, J=8.6, 7.0, 5.0, 1H), 3.18 (dd, J=13.7, 4.9, 1H), 3.01 (dd, J=13.6, 8.6, 1H).

Example 12

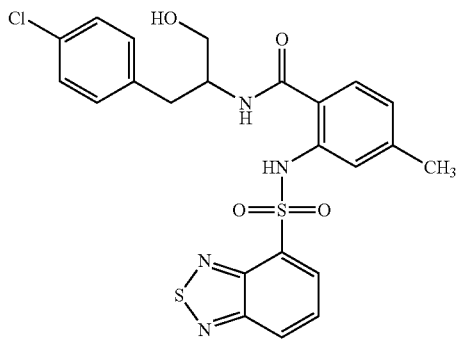

(±)-2-(Benzo[1,2,5]thiadiazole-4-sulfonylamino)-N-[2-(4-chloro-phenyl)-1-hydroxymethyl-ethyl]-4-methyl-benzamide A. 2-(Benzo[1,2,5]thiadiazole-4-sulfonylamino)-4-methylbenzoic acid methyl ester The title compound (1.22 g, 53%) was prepared from benzo[1,2,5]thiadiazole-4-sulfonyl chloride and 2-amino-4-methyl-benzoic acid methyl ester as in Example 10, Part A. ¹H NMR (500 MHz, CDCl₃): 11.28 (s, 1H), 8.36 (dd, J=7.1, 1.0, 1H), 8.19 (dd, J=8.8, 1.0, 1H), 7.73 (d, J=8.1, 1H), 7.68 (dd, J=8.8, 7.1, 1H), 7.51 (br s, 1H), 6.77 (dd, J=8.1, 0.9, 1H), 3.89 (s, 3H), 2.28 (s, 3H).

B. 2-(Benzo[1,2,5]thiadiazole-4-sulfonylamino)-4-methylbenzoic acid

A solution of 2-(benzo[1,2,5]thiadiazole-4-sulfonylamino)-4-methylbenzoic acid methyl ester (1.22 g, 3.36 mmol) in 3:1 THF/water (10 mL) was treated with LiOH.H₂O (1.41 g, 33.6 mmol) and was stirred at rt for 16 h. The mixture was acidified with 1 N HCl, and the resulting precipitate was collected by filtration, washing with water. Drying in air provided the title acid as a tan solid (0.89 g, 2.5 mmol, 74%). ¹H NMR (500 MHz, CDCl₃): 11.16 (s, 1H), 8.38 (dd, J=7.0, 1.0, 1H), 8.22 (dd, J=8.8, 1.0, 1H), 7.84 (d, J=8.1, 1H), 7.71 (dd, J=8.8, 7.1, 1H), 7.56 (br s, 1H), 6.83 (br d, J=8.4, 1H), 2.32 (s, 3H).

C. (±)-2-(Benzo[1,2,5]thiadiazole-4-sulfonylamino)-N-[2-(4-chloro-phenyl)-1-hydroxymethyl-ethyl]-4-methyl-benzamide 2-(Benzo[1,2,5]thiadiazole-4-sulfonylamino)-4-methylbenzoic acid was coupled with (±)-2-amino-3-(4-chloro-phenyl)-propan-1-ol as in EXAMPLE 1, Part C. HPLC: $R_T$=9.31 min. MS (ESI–): mass calcd. for $C_{23}H_{21}ClN_4O_4S_2$, 516.07; m/z found, 515 [M–H]⁻. ¹H NMR (400 MHz, CDCl₃): 11.52 (s, 1H), 8.33 (dd, J=7.0, 1.0, 1H), 8.19 (dd, J=8.8, 1.0, 1H), 7.68 (dd, J=8.8, 7.0, 1H), 7.48 (s, 1H), 7.32-7.27 (m, 2H), 7.21-7.17 (m, 2H), 7.09 (d, J=8.0, 1H), 6.75 (d, J=8.0, 1H), 6.28 (br d, J=7.4, 1H), 4.32-4.23 (m, 1H), 3.72 (dd, J=10.8, 3.6, 1H), 3.65 (dd, J=10.8, 4.5, 1H), 2.91 (d, J=7.4, 2H), 2.75 (br s, 1H), 2.27 (s, 3H).

Example 13

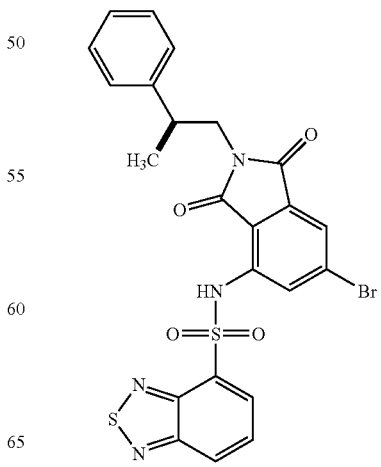

(S)-Benzo[1,2,5]thiadiazole-4-sulfonic acid [6-bromo-1,3-dioxo-2-(2-phenyl-propyl)-2,3-dihydro-1H-isoindol-4-yl]-amide

A. Methyl 4,5-dibromo-2-furoate

Neat methyl 2-furoate (20.0 g, 158 mmol), in a 500 mL round bottom three-necked flask fitted with a mechanical stirrer, was stirred as $AlCl_3$ (45.0 g, 337 mmol) was carefully added in several portions. A mild exotherm was observed. $Br_2$ (54.0 g, 338 mmol) was then added via dropping funnel over 30 min. The resulting thick mixture was stirred for 30 min. The mixture was cooled in an ice bath and treated slowly with crushed ice. The resulting mixture was extracted with $Et_2O$ (3×). The combined organic extracts were washed with 10% aq. $Na_2S_2O_3$, dried ($MgSO_4$), and concentrated to give a yellow solid. The crude product was purified by flash chromatography ($Et_2O$/hexanes) to provide 26.19 g (58%) of the desired dibromofuroate as a pale yellow solid. $^1H$ NMR (400 MHz, $CDCl_3$): 7.18 (s, 1H), 3.90 (s, 3H).

B. 4,5-Dibromo-2-furoic acid

To a suspension of methyl 4,5-dibromo-2-furoate (26.19 g, 92.2 mmol) in THF (60 mL) at rt was added LiOH (3 M in water, 60 mL, 180 mmol). The biphasic mixture was stirred for 4 h. The mixture was poured into 1 N HCl (500 mL) and extracted with DCM (3×). The combined organic layers were dried ($Na_2SO_4$) and concentrated to provide 24.59 g (99%) of the acid as an off-white solid. $^1H$ NMR (400 MHz, $CD_3OD$): 7.30 (s, 1H).

C. 4-Bromo-2-furoic acid 4,5-Dibromo-2-furoic acid (24.51 g, 90.8 mmol) was dissolved in a mixture of water (280 mL) and aq. $NH_4OH$ (33% $NH_3$; 80 mL) and cooled in an ice bath. The mixture was stirred rapidly as zinc dust (6.23 g, 95.3 mmol) was added in portions while keeping the internal temperature below 7° C. The mixture was stirred at 0° C. for 30 min. HPLC analysis of an aliquot of the reaction mixture indicated some starting material remaining. An additional portion of zinc dust (0.5 g, 7.6 mmol) was added and the mixture was stirred at 0° C. for 30 min. HPLC analysis of an aliquot indicated only a trace of starting material as well as formation of a small amount of 2-furoic acid from over-reduction. The mixture was acidified to pH 1 with conc. HCl causing precipitation of the product. The mixture was cooled to 10° C., and the product was collected by suction filtration, washed with water, and air dried to provide 8.0 g (46%) of the desired acid. Additional product could be obtained by extraction of the filtrate with DCM and recrystallization of the crude extract from water. $^1H$ NMR (400 MHz, $CDCl_3$): 7.76 (d, J=0.8, 1H), 7.14 (d, J=0.8, 1H).

D. 4-Bromo-furan-2-carbonyl azide

A suspension of 4-bromo-2-furoic acid (1.87 g, 9.8 mmol) was heated at reflux in $SOCl_2$ (5 mL) for 1 h. The mixture was concentrated, and the residue was azeotroped with toluene (3×). The crude acid chloride was stirred in acetone (15 mL) at 0° C., and a solution of $NaN_3$ (702 mg, 10.8 mmol) in water (5 mL) was added dropwise via pipette. The mixture was stirred for 1 h at 0° C. then was concentrated without external heating. The residue was diluted with satd. aq. $NaHCO_3$ and extracted with DCM (3×). The combined organic layers were dried ($Na_2SO_4$) and concentrated without heating to give 1.85 g (87%) of the acyl azide as a white solid. $^1H$ NMR (400 MHz, $CDCl_3$): 7.65 (d, J=0.9, 1H), 7.26 (d, J=0.9, 1H).

E. (S)-E-3-(2-Phenyl-propylcarbamoyl)-acrylic acid

To a solution of maleic anhydride (765 mg, 7.8 mmol) in acetic acid (20 mL) at rt was added (S)-2-phenylpropylamine. The mixture was stirred overnight then was partially concentrated. Water (50 mL) was added causing precipitation of the product acid. The white solid was collected by suction filtration, washed with water, and dried to provide 1.44 g (79%) of the pure acid. $^1H$ NMR (400 MHz, $CDCl_3$): 7.38-7.32 (m, 2H), 7.29-7.24 (m, 1H), 7.24-7.20 (m, 2H), 6.68 (br m, 1H), 6.29 (d J=12.7, 1H), 6.18 (d, J=12.7, 1H), 3.78-3.69 (m, 1H), 3.47-3.38 (m, 1H), 3.11-3.00 (m, 1H), 1.33 (d, J=7.0, 3H).

F. (S)—N-2-Phenylpropyl maleimide

A mixture of (S)-E-3-(2-phenyl-propylcarbamoyl)-acrylic acid (1.44 g, 6.2 mmol), NaOAc (305 mg, 3.7 mmol), and $Ac_2O$ (6 mL) was heated at 120° C. for 5 h. The mixture was concentrated, and the residue was stirred vigorously with satd. aq. $NaHCO_3$. The resulting mixture was extracted with DCM (3×). The combined organic layers were dried ($Na_2SO_4$) and concentrated. The crude product was purified by flash chromatography (EtOAc/hexanes) to provide 340 mg (26%) of the desired maleimide as a white solid. $^1H$ NMR (400 MHz, $CDCl_3$): 7.32-7.26 (m, 2H), 7.24-7.17 (m, 3H), 6.60 (s, 2H), 3.70 (dd, J=13.7, 8.2, 1H), 3.61 (dd, J=13.7, 7.8, 1H), 3.23 (app. sextet, J=7.7, 1H), 1.26 (d, J=7.0, 3H).

G. (S)-[6-Bromo-1,3-dioxo-2-(2-phenyl-propyl)-2,3-dihydro-1H-isoindol-4-yl]-carbamic acid tert-butyl ester A solution of 4-bromo-furan-2-carbonyl azide (444 mg, 2.06 mmol) and (S)—N-2-phenylpropyl maleimide (340 mg, 1.58 mmol) in degassed tert-butanol (3 mL) was heated under $N_2$ at 70° C. for 24 h. The resulting dark red solution was concentrated, and the residue was adsorbed onto $SiO_2$ and purified by flash chromatography (EtOAc/hexanes) to give a pale yellow foam (160 mg, 22%). $^1H$ NMR (400 MHz, $CDCl_3$): 8.72 (d, J=1.3, 1H), 8.69 (br s, 1H), 7.51 (d, J=1.5, 1H), 7.33-7.18 (m, 5H), 3.81 (dd, J=13.6, 7.8, 1H), 3.73 (dd, J=13.6, 8.1, 1H), 3.36-3.24 (m, 1H), 1.54 (s, 9H), 1.26 (d, J=7.0, 3H).

H. (S)-4-Amino-6-bromo-2-(2-phenyl-propyl)-isoindole-1,3-dione (S)-[6-Bromo-1,3-dioxo-2-(2-phenyl-propyl)-2,3-dihydro-1H-isoindol-4-yl]-carbamic acid tert-butyl ester (160 mg, 0.35 mmol) was stirred in a mixture of DCM (2 mL) and TFA (1 mL) for 3 h at rt. The mixture was concentrated, and the residue was diluted with satd. aq. $NaHCO_3$ and extracted with DCM (3×). The combined organic layers were dried ($Na_2SO_4$) and concentrated to give a yellow oil. Purification by flash chromatography (EtOAc/hexanes) gave 110 mg (87%) of the desired amine as a yellow foam. $^1H$ NMR (500 MHz, $CDCl_3$): 7.31-7.23 (m, 4H), 7.22-7.17 (m, 2H), 6.81 (d, J=1.5, 1H), 5.19 (br s, 2H), 3.78 (dd, J=13.6, 7.6, 1H), 3.71 (dd, J=13.6, 8.2, 1H), 3.30 (app sextet, $J_{app}$=7.5, 1H), 1.29 (d, J=7.0, 3H).

I. (S)-Benzo[1,2,5]thiadiazole-4-sulfonic acid [6-bromo-1,3-dioxo-2-(2-phenyl-propyl)-2,3-dihydro-1H-isoindol-4-yl]-amide A mixture of (S)-4-amino-6-bromo-2-(2-phenyl-propyl)-isoindole-1,3-dione (30 mg, 0.08 mmol) and benzo[1,2,5]thiadiazole-4-sulfonyl chloride (150 mg, 0.64 mmol) was heated to 170° C. forming a melt and stirred for 2 h. The mixture was allowed to cool, and the solidified residue was dissolved in EtOAc, and the solution was washed with satd. aq. NaHCO$_3$, dried (Na$_2$SO$_4$), and concentrated. Purification by flash chromatography (EtOAc/hexanes) gave the desired sulfonamide as a tan solid (30 mg, 64%). HPLC: R$_T$=11.01 min. MS (ESI−): mass calcd. for C$_{23}$H$_{17}$BrN$_4$O$_4$S$_2$, 555.99; m/z found, 555/557 [M−H]$^-$. $^1$H NMR (400 MHz, CDCl$_3$): 9.59 (br s, 1H), 8.39 (dd, J=7.0, 1.0, 1H), 8.27 (dd, J=8.8, 1.0, 1H), 8.08 (d, J=1.4, 1H), 7.75 (dd, J=8.8, 7.1, 1H), 7.47 (d, J=1.3, 1H), 7.27-7.22 (m, 2H), 7.21-7.17 (m, 3H), 3.78 (dd, J=13.6, 8.1, 1H), 3.68 (dd, J=13.6, 7.81, 1H), 3.26 (sextet, J=7.4, 1H), 1.26 (d, J=7.0, 3H).

Example 14

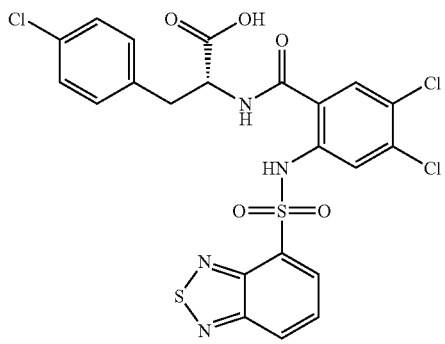

(R)-2-[2-(Benzo[1,2,5]thiadiazole-4-sulfonylamino)-4,5-dichloro-benzoylamino]-3-(4-chloro-phenyl)-propionic acid A. 2-(Benzo[1,2,5]thiadiazole-4-sulfonylamino)-4,5-dichloro-benzoic acid methyl ester The title compound (0.95 g, 50%) was prepared from methyl 2-amino-4,5-dichlorobenzoate and 4-chlorosulfonyl-2,1,3-benzothiadiazole as in Example 1, Part A (without DMAP). $^1$H NMR (500 MHz, CDCl$_3$): 11.21 (s, 1H), 8.39 (dd, J=7.1, 1.0, 1H), 8.25 (dd, J=8.8, 1.0, 1H), 7.94 (s, 1H), 7.91 (s, 1H), 7.74 (dd, J=8.8, 7.1, 1H), 3.93 (s, 3H).

B. 2-(Benzo[1,2,5]thiadiazole-4-sulfonylamino)-4,5-dichloro-benzoic acid

To a solution of 2-(benzo[1,2,5]thiadiazole-4-sulfonylamino)-4,5-dichloro-benzoic acid methyl ester (0.95 g, 2.3 mmol) in THF (21 mL) and water (7 mL) was added LiOH.H$_2$O (0.38 g, 9.1 mmol). The biphasic mixture was stirred overnight at rt. The mixture was acidified with conc. HCl and extracted with DCM (3×). The combined organic layers were dried (MgSO$_4$) and concentrated to provide 0.80 g (88%) of the pure acid as a white solid. $^1$H NMR (500 MHz, CDCl$_3$): 11.07 (s, 1H), 8.41 (dd, J=7.0, 1.0, 1H), 8.27 (dd, J=8.8, 1.0, 1H), 8.01 (s, 1H), 7.94 (s, 1H), 7.75 (dd, J=8.8, 7.0, 1H).

C. (R)-2-[2-(Benzo[1,2,5]thiadiazole-4-sulfonylamino)-4,5-dichloro-benzoylamino]-3-(4-chloro-phenyl)-propionic acid (R)-2-(tert-Butoxycarbonylamino)-3-(4-chloro-phenyl)-propionic acid was treated as in EXAMPLE 2, Part A, to produce (R)-2-amino-3-(4-chloro-phenyl)-propionic acid methyl ester hydrochloride as a white solid. This salt was then coupled with 2-(benzo[1,2,5]thiadiazole-4-sulfonylamino)-4,5-dichloro-benzoic acid as in EXAMPLE 1, Part C. The resulting methyl ester was hydrolyzed as in EXAMPLE 2, Part E, to afford the title compound. HPLC: R$_T$=10.35 min. MS (ESI−): mass calcd. for C$_{22}$H$_{15}$Cl$_3$N$_4$O$_5$S$_2$, 583.95; m/z found, 583/585 [M−H]. $^1$H NMR (500 MHz, CDCl$_3$): 11.07 (s, 1H), 8.34 (d, J=7.1, 1H), 8.23 (d, J=8.8, 1H), 7.84 (s, 1H), 7.74-7.70 (m, 1H), 7.30-7.26 (m, 2H), 7.24 (s, 1H), 7.07 (d, J=8.3, 2H), 6.38 (d, J=7.4, 1H), 5.00-4.97 (m, 1H), 3.30 (dd, J=14.1, 5.9, 1H), 3.21 (dd, J=14.1, 5.9, 1H).

Example 15

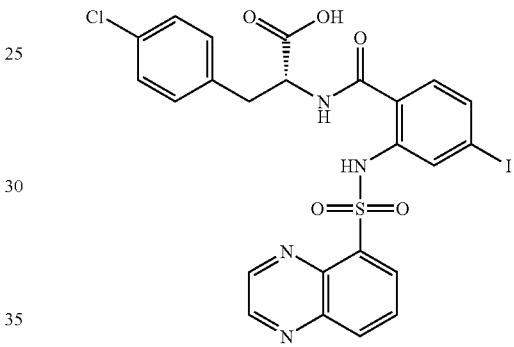

(R)-3-(4-Chloro-phenyl)-2-[4-iodo-2-(quinoxaline-5-sulfonylamino)-benzoylamino]-propionic acid A. 4-Iodo-2-nitro-benzoic acid In a 1 L three-neck round-bottom flask equipped with an internal thermometer, a reflux condenser, and an addition funnel, Bu$_4$N$^+$MnO$_4$$^-$ (124 g, 343 mmol) was dissolved in pyridine (200 mL). The solution was heated to 60° C., and then the heating source was removed. A solution of 4-iodo-2-nitrotoluene (43.0 g, 163 mmol) in pyridine (60 mL) was added through the additional funnel over 2 h. The reaction temperature was maintained at 60° C. by adjusting the addition rate. When the addition was complete, the reaction mixture was cooled to rt. The solution was concentrated, diluted with EtOAc (300 mL) and water (200 mL), and stirred at rt for 30 min. The precipitated brown solid was filtered off and washed with EtOAc. The clear organic layer was washed with 5% aq. H$_2$SO$_4$ (200 mL) and brine (200 mL), dried (MgSO$_4$), and concentrated to afford a thick, brown oil. The crude product was dissolved in EtOAc (200 mL) and then a solution of KOH (9.1 g, 163 mmol) in MeOH (ca. 30 mL) was added dropwise. The mixture was stirred at rt for 1 h, and the precipitated solid was collected by filtration and washed with EtOAc. The filtrate was concentrated and the precipitation was repeated with KOH in MeOH. The two crops were combined and dissolved in water (ca. 250 mL) and acidified with conc. HCl to pH<2. The precipitated white solid was collected by filtration and dried under vacuum to give the desired product (40 g, 136 mmol, 83%, >98% purity by HPLC). $^1$H NMR (400 MHz, CD$_3$OD): 8.13 (d, J=1.6, 1H), 8.01 (dd, J=8.1, 1.6, 1H), 7.50 (d, J=8.1, 1H).

B. 2-Amino-4-iodo-benzoic acid

4-Iodo-2-nitro-benzoic acid (20 g, 68 mmol, 1.0 equiv.) was dissolved in 200 mL of EtOAc and then SnCl$_2$.2H$_2$O (46 g, 204 mmol, 3.0 equiv.) was added in three portions. The reaction mixture was stirred at rt for 16 h. Satd. aq. NaHCO$_3$ was carefully added to adjust the mixture to pH=9. The precipitated solid was removed by filtration through diatomaceous earth, washing with water. The aqueous layer in the filtrate was separated and acidified with conc. HCl to pH=2. The precipitated solid was collected by filtration and dried to afford the title compound as white solid (19 g, 68 mmol, 100%). $^1$H NMR (400 MHz, CD$_3$OD): $^1$H NMR (500 MHz, CDCl$_3$): 7.56 (d, J=8.5, 1H), 7.08 (s, 1H), 6.99 (d, J=8.5, 1H), 5.71 (br s, 2H).

C. 4-Iodo-2-(quinoxaline-5-sulfonylamino)-benzoic acid

A mixture of 2-amino-4-iodo-benzoic acid (10 g, 38 mmol, 1.0 equiv.) and quinoxaline-5-sulfonyl chloride (8.7 g, 38 mmol) in 100 mL of water was basified with satd. aq. Na$_2$CO$_3$, with stirring, to adjust the pH to 8.0. As the reaction progressed, the pH was maintained at 8.0±0.2 by adding satd. aq. Na$_2$CO$_3$. After 3 h, no further pH changes were observed. The reaction mixture was stirred at rt for another 16 h. Conc. HCl was added to adjust the pH to <2. The precipitated solid was collected by filtration, washed with water and dried to afford the title compound as white solid (17 g, 37.4 mmol, 98%). MS (ESI+): calcd. for C$_{15}$H$_{10}$IN$_3$O$_4$S, 455.0; m/z found, 456 [M+H]$^+$. $^1$H NMR (500 MHz, DMSO-d$_6$): 14.0 (br s, 1H), 11.6 (s, 1H), 9.10 (d, J=1.5, 1H), 9.97 (d, J=1.5, 1H), 8.60 (d, J=7.4, 1H), 8.42 (d, J=8.4, 1H), 8.06 (t, J=7.5, 1H), 7.95 (d, J=1.2, 1H), 7.51 (d, J=8.3, 1H), 7.37 (dd, J=8.3, 1.2, 1H).

D. (R)-3-(4-Chloro-phenyl)-2-[4-iodo-2-(quinoxaline-5-sulfonylamino)-benzoylamino]-propionic acid (R)-2-(tert-Butoxycarbonylamino)-3-(4-chloro-phenyl)-propionic acid was treated as in EXAMPLE 2, Part A, to produce (R)-2-amino-3-(4-chloro-phenyl)-propionic acid methyl ester hydrochloride as a white solid. This ester was coupled with 4-iodo-2-(quinoxaline-5-sulfonylamino)-benzoic acid as in EXAMPLE 1, Part C. The resulting methyl ester was hydrolyzed as in EXAMPLE 2, Part E. HPLC: R$_T$=9.74 min. MS (ESI−): mass calcd. for C$_{24}$H$_{18}$ClIN$_4$O$_5$S, 635.97; m/z found, 635/637 [M−H]$^−$. $^1$H NMR (500 MHz, CDCl$_3$): 10.93 (d, J=12.8, 1H), 8.99 (d, J=1.6, 1H), 8.92 (s, 1H), 8.54 (d, J=7.4, 1H), 8.31 (d, J=8.5, 1H), 8.10 (s, 1H), 7.90-7.87 (m, 1H), 7.30-7.22 (m, 3H), 7.05 (d, J=8.4, 2H), 6.84 (d, J=8.2, 1H), 6.29 (d, J=7.9, 1H), 4.93-4.80 (m, 1H), 3.24 (dd, J=14.3, 5.8, 1H), 3.16 (dd, J=14.2, 5.9, 1H).

Example 16

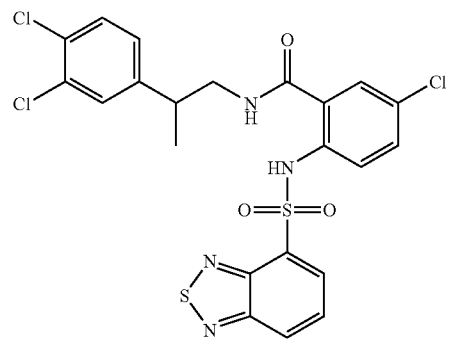

(±)-2-(Benzo[1,2,5]thiadiazole-4-sulfonylamino)-5-chloro-N-[2-(3,4-dichloro-phenyl)-propyl]-benzamide

A. 2-(Benzo[1,2,5]thiadiazole-4-sulfonylamino)-5-chloro-benzoic acid methyl ester The title compound (1.56 g, 75%) was prepared from benzo[1,2,5]thiadiazole-4-sulfonyl chloride and 2-amino-5-chloro-benzoic acid methyl ester as in Example 1, Part A. HPLC: R$_T$=10.77 min. MS (ESI+): mass calcd. for C$_{14}$H$_{10}$ClN$_3$O$_4$S$_2$, 382.98; m/z found, 406 [M+Na]$^+$. $^1$H NMR (500 MHz, CDCl$_3$): 11.16 (s, 1H), 8.35 (dd, J=7.0, 1.0, 1H), 8.22 (dd, J=8.8, 1.0, 1H), 7.82 (d, J=2.5, 1H), 7.72-7.68 (m, 2H), 7.34 (dd, J=9.0, 2.5, 1H), 3.92 (s, 3H).

B. 2-(Benzo[1,2,5]thiadiazole-4-sulfonylamino)-5-chloro-benzoic acid

LiOH.H$_2$O (0.68 g, 16.2 mmol) was added to a stirred solution of 2-(benzo[1,2,5]thiadiazole-4-sulfonylamino)-5-chloro-benzoic acid methyl ester (1.56 g, 4.06 mmol) in THF (15 mL) and water (5 mL). After 18 h, the solution was acidified to pH 2 with conc. HCl, diluted with water, and extracted with DCM (3×). The combined organic layers were dried (MgSO$_4$), and concentrated to provide the title compound (1.50 g, 100%). HPLC: R$_T$=9.48 min. MS (ESI−): mass calcd. for C$_{13}$H$_8$ClN$_3$O$_4$S$_2$, 368.96; m/z found, 368/370 [M−H]$^-$. $^1$H NMR (500 MHz, CDCl$_3$): 11.07 (s, 1H), 8.38 (dd, J=7.0, 1.0, 1H), 8.24 (dd, J=8.8, 1.0, 1H), 7.92 (d, J=2.5, 1H), 7.75 (d, J=9.0, 1H), 7.71-7.69 (m, 1H), 7.40 (dd, J=9.0, 2.6, 1H).

C. (±)-2-(Benzo[1,2,5]thiadiazole-4-sulfonylamino)-5-chloro-N-[2-(3,4-dichloro-Phenyl-propyl]-benzamide The title compound was prepared from 2-(benzo[1,2,5]thiadiazole-4-sulfonylamino)-5-chloro-benzoic acid and (±)-2-(3,4-dichloro-phenyl)-propylamine hydrochloride as in EXAMPLE 1, Part C. HPLC: R$_T$=11.76 min. MS (ESI−): mass calcd. for C$_{22}$H$_{17}$Cl$_3$N$_4$O$_3$S$_2$, 553.98; m/z found, 553/555 [M−H]$^-$. $^1$H NMR (400 MHz, CDCl$_3$): 11.05 (s, 1H), 8.30 (dd, J=7.0, 1.0, 1H), 8.21 (d, J=8.0, 1H), 7.70-7.66 (m, 1H), 7.65-7.63 (m, 1H), 7.41 (d, J=8.2, 1H), 7.29 (dd, J=4.6, 2.1, 2H), 7.05 (dd, J=9.6, 2.1, 2H), 5.80 (s, 1H), 3.67-3.60 (m, 1H), 3.32-3.26 (m, 1H), 3.02-2.97 (m, 1H), 1.30 (d, J=7.0, 3H).

Example 17

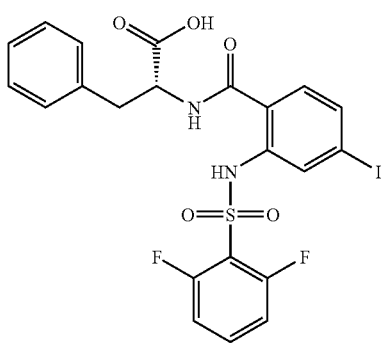

(R)-2-[2-(2,6-Difluoro-benzenesulfonylamino)-4-iodo-benzoylamino]-3-phenyl-propionic acid

A. 2-(2,6-Difluoro-benzenesulfonylamino)-4-iodo-benzoic acid

2-Amino-4-iodo-benzoic acid was sulfonylated with 2,6-difluorobenzenesulfonyl chloride as in EXAMPLE 1, Part A. $^1$H NMR (500 MHz, CD$_3$OD): 8.05 (d, J=1.6, 1H), 7.72 (d, J=8.4, 1H), 7.68-7.60 (m, 1H), 7.48 (dd, J=8.4, 1.6, 1H), 7.16-7.09 (m, 2H).

B. (R)-2-[2-(2,6-Difluoro-benzenesulfonylamino)-4-iodo-benzoylamino]-3-phenyl-propionic acid (R)-2-(tert-Butoxycarbonylamino)-3-phenyl-propionic acid was treated as in EXAMPLE 2, Part A, to produce (R)-2-amino-3-phenyl-propionic acid methyl ester hydrochloride as a white solid. This ester was coupled with 2-(2,6-difluoro-benzenesulfonylamino)-4-iodo-benzoic acid as in EXAMPLE 1, Part C. The resulting methyl ester was hydrolyzed as in EXAMPLE 2, Part E, to afford the title compound. HPLC: R$_T$=9.27 min. MS (ESI−): mass calcd. for C$_{22}$H$_{17}$F$_2$IN$_2$O$_5$S, 585.99; m/z found, 584/586 [M−H]. $^1$H NMR (500 MHz, CDCl$_3$): 11.32 (s, 1H), 8.11 (s, 1H), 7.50-7.46 (m, 1H), 7.38-7.28 (m, 4H), 7.16-7.15 (m, 2H), 7.00-6.96 (m, 3H), 6.51 (d, J=7.6, 1H), 5.07-5.03 (m, 1H), 3.34 (dd, J=14.0, 5.6, 1H), 3.25 (dd, J=14.3, 5.3, 1H).

Example 18

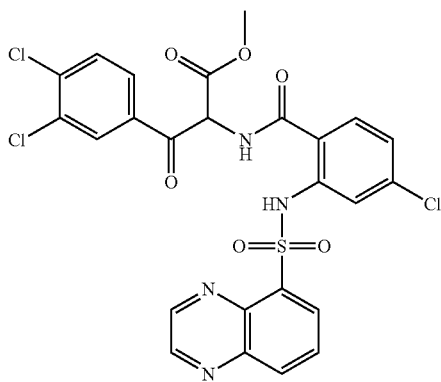

(±)-2-[4-Chloro-2-(quinoxaline-5-sulfonylamino)-benzoylamino]-3-(3,4-dichloro-phenyl)-3-oxo-propionic acid methyl ester

A. 5-(3,4-Dichloro-phenyl)-oxazole-4-carboxylic acid methyl ester

A solution of methyl isocyanoacetate (5.0 g, 50.0 mmol), 3,4-dichlorobenzoyl chloride (10.6 g, 50.0 mmol), and Et$_3$N (20.9 mL, 150 mmol) was stirred in THF (20 mL) for 48 h at rt. The solution was concentrated, diluted with EtOAc, washed with water, dried (MgSO$_4$), and concentrated to afford a solid. The solid was washed with hexanes and collected by filtration to provide 8.7 g (64%) of the desired product. HPLC: R$_T$=9.68 min. MS (ESI+): mass calcd. for C$_{11}$H$_7$Cl$_2$NO$_3$, 270.98; m/z found, 272/274 [M+H]$^+$. $^1$H NMR (400 MHz, CDCl$_3$): 8.29 (d, J=2.1, 1H), 8.03 (dd, J=8.5, 2.1, 1H), 7.94 (s, 1H), 7.56 (d, J=8.5, 1H), 3.98 (s, 3H).

B. (±)-2-Amino-3-(3,4-dichloro-phenyl)-3-oxo-propionic acid methyl ester hydrochloride A suspension of 5-(3,4-dichloro-phenyl)-oxazole-4-carboxylic acid methyl ester (1.5 g, 5.51 mmol), 3 N HCl (10 mL), and MeOH (15 mL) was heated at 50° C. for 4 h. The mixture was concentrated, diluted with water, and washed with Et$_2$O. The aqueous layer was concentrated and Et$_2$O was added, causing precipitation of a white solid. The precipitate was collected by filtration to provide 1.0 g (63%) of the desired product as an apparent 10:1 mixture of keto-enol tautomers. MS (ESI+): mass calcd. for C$_{10}$H$_9$Cl$_2$NO$_3$, 261.00; m/z found, 262/264 [M+H]$^+$. Major tautomer: $^1$H NMR (500 MHz, CDCl$_3$): 8.32 (d, J=2.1, 1H), 8.09 (dd, J=8.4, 2.1, 1H), 7.79 (d, J=8.5, 1H), 3.80 (s, 3H). Minor tautomer: $^1$H NMR (500 MHz, CDCl$_3$): 8.19 (d, J=2.0, 1H), 7.96 (dd, J=8.4, 2.1, 1H), 7.76 (d, J=8.4, 1H), 6.18 (s, 1H).

C. (±)-2-[4-Chloro-2-(quinoxaline-5-sulfonylamino)-benzoylamino]-3-(3,4-dichloro-phenyl)-3-oxo-propionic acid methyl ester 4-Chloro-2-(quinoxaline-5-sulfonylamino)-benzoic acid was coupled to (±)-2-amino-3-(3,4-dichloro-phenyl)-3-oxo-propionic acid methyl ester hydrochloride as in EXAMPLE 1, Part C. HPLC: R$_T$=10.65 min. MS (ESI+): mass calcd. for C$_{25}$H$_{17}$Cl$_3$N$_4$O$_6$S, 605.99; m/z found, 607/609 [M+H]$^+$. $^1$H NMR (500 MHz, CDCl$_3$): 11.23 (s, 1H), 8.88 (d, J=1.8, 1H), 8.85 (d, J=1.8, 1H), 8.58 (dd, J=7.4, 1.4, 1H), 8.32 (d, J=8.5, 1.4, 1H), 8.24 (d, J=2.1, 1H), 8.03 (dd, J=8.4, 2.1, 1H), 7.89-7.86 (m, 1H), 7.79 (d, J=2.0, 1H), 7.69 (d, J=8.4, 1H), 7.45 (d, J=8.5, 1H), 7.30 (d, J=6.9, 1H), 6.97 (dd, J=8.4, 2.0, 1H), 6.19 (d, J=6.9, 1H), 3.78 (s, 3H).

Example 19

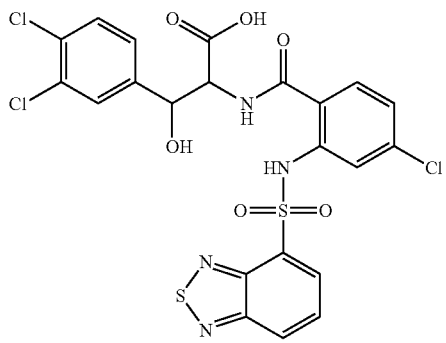

2-[2-(Benzo[1,2,5]thiadiazole-4-sulfonylamino)-4-chloro-benzoylamino]-3-(3,4-dichloro-phenyl)-3-hydroxy-propionic acid 2-[2-(Benzo[1,2,5]thiadiazole-4-sulfonylamino)-4-chloro-benzoylamino]-3-(3,4-dichloro-phenyl)-3-oxo-propionic acid methyl ester was prepared as in EXAMPLE 18, substituting 2-(benzo[1,2,5]thiadiazole-4-sulfonylamino)-4-chloro-benzoic acid in Part C. A suspension of the methyl ester (34 mg, 0.055 mmol) in EtOH (0.6 mL) was treated with $NH_4Cl$ (59 mg, 1.11 mmol), water (0.2 mL), and $NaBH_4$ (10 mg, 0.277 mmol). The resulting yellow, homogenous suspension was stirred at rt for 1 h. The mixture was diluted with water and extracted with DCM (3×). The combined organic layers were dried ($MgSO_4$) and concentrated to provide the crude product. The crude product was dissolved in DMF (~1 mL) and purified by preparative reversed-phase HPLC to provide the desired product as a white solid as a 9:1 mixture of diastereomers (11 mg, 33%). HPLC: $R_T$=10.16 min (major diastereomer) and 10.26 min (minor diastereomer). MS (ESI−): mass calcd. for $C_{22}H_{15}Cl_3N_4O_6S_2$, 601.9; m/z found, 601 [M−H]−. $^1$H NMR (400 MHz, $CDCl_3$): Major diastereomer: 11.41 (s, 1H), 8.33 (d, J=6.9, 1H), 8.18 (d, J=8.8, 1H), 7.73-7.68 (m, 1H), 7.58 (br s, 1H), 7.44 (br s, 1H), 7.38-7.34 (m, 1H), 7.23-7.16 (m, 2H), 7.03 (br d, J=6.6, 1H), 6.83 (br d, J=7.9, 1H), 5.83 (br d, J=3.9, 1H), 5.16-5.09 (br m, 1H); Minor diastereomer: 11.01 (s, 1H), 8.29 (d, J=6.9, 1H), 8.14 (d, J=9.4, 1H), 7.70-7.63 (m, 1H), 7.53-7.49 (br m, 2H), 7.34-7.30 (m, 1H), 7.18-7.10 (m, 2H), 7.02-7.00 (m, 1H), 6.82-6.78 (m, 1H), 5.61-5.56 (br m, 1H), 5.06-5.02 (br m, 1H).

Example 20

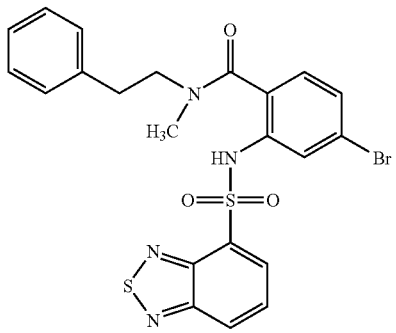

2-(Benzo[1,2,5]thiadiazole-4-sulfonylamino)-4-bromo-N-methyl-N-phenethyl-benzamide

A. 4-Bromo-2-nitrobenzoic acid

A mixture of 4-bromo-2-nitrotoluene (5.0 g, 23 mmol), $KMnO_4$ (10.9 g, 69 mmol), and water (250 mL) was heated at reflux overnight. The mixture was filtered through a pad of diatomaceous earth, washing with water. The basic filtrate was acidified to pH~1 with conc. HCl and extracted with EtOAc (3×300 mL). The combined organic layers were dried ($MgSO_4$) and concentrated to provide the desired benzoic acid (1.22 g, 22%). MS (ESI−): mass calcd. for $C_7H_4BrNO_4$, 244.9; m/z found, 244 [M−H]−. $^1$H NMR (400 MHz, $CD_3OD$): 8.07 (d, J=1.9, 1H), 7.85 (dd, J=8.2, 1.9, 1H), 7.65 (d, J=8.2, 1H).

B. Methyl 2-amino-4-bromobenzoate

To a stirred solution of 4-bromo-2-nitrobenzoic acid (3.81 g, 15 mmol) in DMF (30 mL) at 0° C. was added 1,8-diazabicycloundecane (DBU; 10.3 mL, 75 mmol) followed by MeI (4.67 mL, 75 mmol). The mixture was stirred for 15 min at 0° C., then was allowed to warm to rt and was stirred overnight. The mixture was poured into water and extracted with EtOAc (2×). The combined organic extracts were washed with water (2×), dried ($MgSO_4$), and concentrated. The residue was purified by flash chromatography (hexanes/EtOAc) to afford methyl 4-bromo-2-nitrobenzoate as a pale yellow solid (3.52 g, 90%). To a solution of the nitrobenzoate (3.52 g, 13.5 mmol) in 1:1 EtOAc/DCM (30 mL) at rt was added $SnCl_2 \cdot 2H_2O$ (15.27 g, 67 mmol). After 18 h, the mixture was concentrated, diluted with satd. aq. $NaHCO_3$, and extracted with DCM (3×). The combined organic layers were dried ($MgSO_4$) and concentrated to provide the desired aminobenzoate as a white solid (2.89 g, 93%). $^1$H NMR (400 MHz, $CDCl_3$): 7.70 (d, J=8.6, 1H), 6.84 (d, J=1.9, 1H), 6.75 (dd, J=8.6, 1.9, 1H), 5.78 (br s, 2H), 3.86 (s, 3H).

C. 2-(Benzo[1,2,5]thiadiazole-4-sulfonylamino)-4-bromo-benzoic acid methyl ester The title compound (3.95 g, 75%) was prepared from methyl 2-amino-4-bromobenzoate and 4-chlorosulfonyl-2,1,3-benzothiadiazole as in Example 1, Part A. MS (ESI−): mass calcd. for $C_{14}H_{10}BrN_3O_4S_2$, 426.9; m/z found, 426 [M−H]−. $^1$H NMR (400 MHz, $CDCl_3$): 11.34 (br s, 1H), 8.40 (dd, J=7.0, 0.9, 1H), 8.24 (dd, J=8.8, 0.9, 1H), 7.92 (d, J=1.8, 1H), 7.74 (dd, J=8.8, 7.0, 1H), 7.72 (d, J=8.5, 1H), 7.10 (dd, J=8.5, 1.8, 1H), 3.92 (s, 3H).

D. 2-(Benzo[1,2,5]thiadiazole-4-sulfonylamino)-4-bromobenzoic acid

The title compound (2.79 g, 98%) was prepared as in Example 1, Part B. $^1$H NMR (500 MHz, $CDCl_3$): 11.14 (br s, 1H), 8.42 (dd, J=7.2, 1.1, 1H), 8.26 (dd, J=8.8, 1.1, 1H), 7.98 (d, J=1.6, 1H), 7.82 (d, J=8.5, 1H), 7.75 (dd, J=8.8, 7.2, 1H), 7.16 (dd, J=8.5, 1.6, 1H).

E. 2-(Benzo[1,2,5]thiadiazole-4-sulfonylamino)-4-bromo-N-methyl-N-Phenethyl-benzamide 2-(Benzo[1,2,5]thiadiazole-4-sulfonylamino)-4-bromobenzoic acid was coupled with N-methylphenethylamine as in EXAMPLE 1, Part C. HPLC: $R_T$=9.90 min. MS (ESI−): mass calcd. for $C_{22}H_{19}BrN_4O_3S_2$, 530.01; m/z found, 529/531 [M−H]−. $^1$H NMR (400 MHz, $CDCl_3$; rotameric broadening): 8.95-8.80 (br s, 0.6H), 8.57-8.43 (br s, 0.4H), 8.27 (dd, J=7.0, 0.9, 1H), 8.23 (br d, J=8.8, 1H), 7.80-7.64 (m, 2H), 7.37-6.85 (br m, 6H), 6.73-6.62 (br m, 0.6H), 6.55-6.40 (br m, 0.4H), 3.68-3.35 (br m, 1.3H), 3.35-3.07 (br m, 0.7H), 3.07-2.25 (br m, 5H).

Example 21

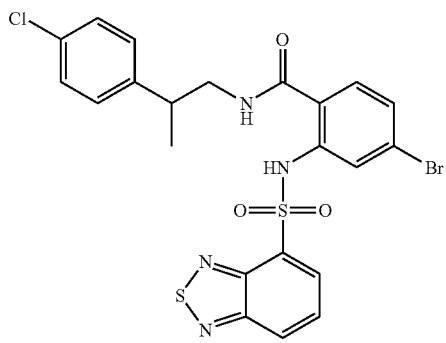

2-(Benzo[1,2,5]thiadiazole-4-sulfonylamino)-4-bromo-N-[2-(4-chloro-phenyl)-propyl]-benzamide This compound was prepared as in EXAMPLE 5, Parts C and D, substituting 4-chloro-β-methyl phenethylamine hydrochloride in Part C. HPLC: $R_T$=10.82 min. MS (ESI−): mass calcd. for $C_{22}H_{18}BrClN_4O_3S_2$, 565.9; m/z found, 565 [M−H]⁻. ¹H NMR (400 MHz, CDCl₃): 11.49 (s, 1H), 8.34 (dd, J=7.0, 0.6, 1H), 8.22 (dd, J=8.8, 0.7, 1H), 7.86 (d, J=1.7, 1H), 7.72 (dd, J=8.8, 7.0, 1H), 7.31-7.29 (m, 2H), 7.14-7.11 (m, 2H), 7.03 (dd, J=8.4, 1.8, 1H), 6.88 (d, J=8.4, 1H), 5.82-5.79 (br m, 1H), 3.72 (td, J=13.1, 6.4, 1H), 3.30 (ddd, J=13.7, 8.9, 5.2, 1H), 3.03-2.98 (m, 1H), 1.30 (d, J=7.0, 3H).

Example 22

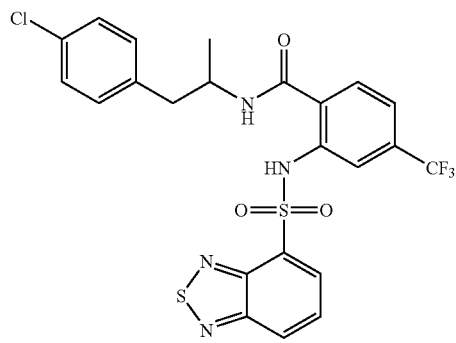

2-(Benzo[1,2,5]thiadiazole-4-sulfonylamino)-N-[2-(4-chloro-phenyl)-1-methyl-ethyl]-4-trifluoromethyl-benzamide This compound was prepared as in EXAMPLE 3, Parts A and B, and EXAMPLE 5, Part D. HPLC (reversed-phase): $R_T$=11.00 min. MS (ESI−): mass calcd. for $C_{23}H_{18}ClF_3N_4O_3S_2$, 555.0; m/z found, 554 [M−H]⁻. ¹H NMR (400 MHz, CDCl₃): 11.25 (s, 1H), 8.37 (dd, J=7.0, 0.8, 1H), 8.23 (dd, J=8.8, 0.9, 1H), 7.94 (s, 1H), 7.72 (dd, J=8.8, 7.1, 1H), 7.30-7.28 (m, 3H), 7.20 (d, J=8.2, 1H), 7.13 (d, J=8.3, 2H), 5.95 (d, J=7.9, 1H), 4.40-4.35 (m, 1H), 2.84 (ddd, J=20.7, 13.6, 6.5, 2H), 1.21 (d, J=6.7, 3H).

Example 23

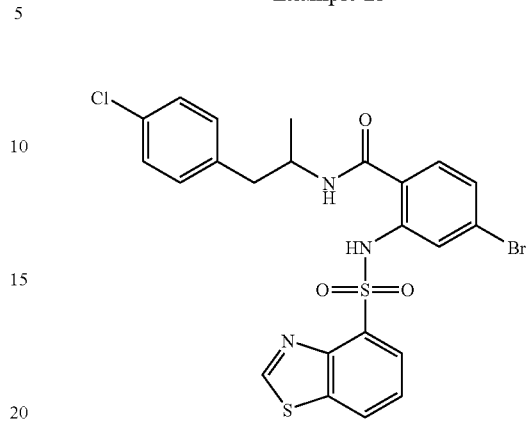

2-(Benzothiazole-4-sulfonylamino)-4-bromo-N-[2-(4-chloro-phenyl)-1-methyl-ethyl]-benzamide This compound was prepared as in EXAMPLE 5, Parts C and D, substituting 4-chloro-β-methyl phenethylamine hydrochloride in Part C. HPLC: $R_T$=10.62 min. MS (ESI−): mass calcd. for $C_{23}H_{19}BrClN_3O_3S_2$, 564.9; m/z found, 564 [M−H]⁻. ¹H NMR (400 mHz, CDCl₃): 11.19 (s, 1H), 9.16 (s, 1H), 8.93 (d, J=4.1, 1H), 8.20 (dd, J=17.0, 7.3, 2H), 7.91-7.89 (m, 1H), 7.81 (s, 1H), 7.60-7.56 (m, 1H), 7.11 (d, J=7.6, 2H), 7.04 (s, 1H), 5.79-5.82 (m, 1H), 4.37-4.34 (m, 1H), 2.78-2.73 (m, 1H), 2.89-2.86 (m, 1H), 1.17 (d, J=6.1, 3H).

Example 24

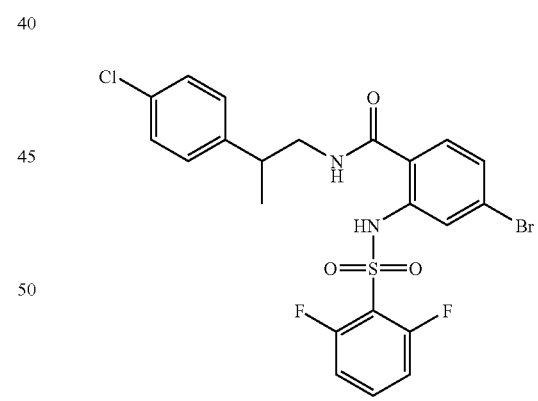

4-Bromo-N-[2-(4-chloro-phenyl)-propyl]-2-(2,6-difluoro-benzenesulfonylamino)-benzamide This compound was prepared as in EXAMPLE 5, Parts C and D, substituting 4-chloro-β-methyl phenethylamine hydrochloride in Part C. HPLC: $R_T$=10.85 min. MS (ESI−): mass calcd. for $C_{22}H_{18}BrClF_2N_2O_3S$, 543.8; m/z found, 543 [M−H]⁻. ¹H NMR (400 MHz, CDCl₃): 11.59 (s, 1H), 7.85 (d, J=1.7, 1H), 7.52-7.44 (m, 1H), 7.32-7.28 (m, 2H), 7.19-7.14 (m, 2H), 7.13-7.10 (m, 1H), 7.05-6.96 (m, 3H), 6.14-6.12 (m, 1H), 3.73 (td, J=13.1, 6.4, 1H), 3.38 (ddd, J=13.8, 8.8, 5.3, 1H), 3.07 (m, 1H), 1.31 (d, J=6.98, 3H).

Example 25

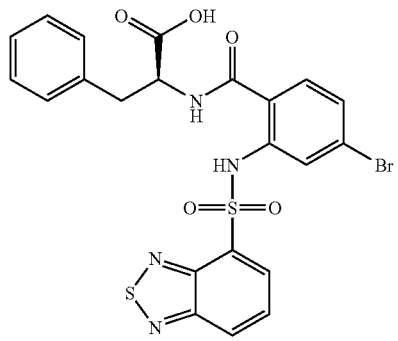

2-[2-(Benzo[1,2,5]thiadiazole-4-sulfonylamino)-4-bromo-benzoylamino]-3-phenyl-propionic acid This compound was prepared as in EXAMPLE 2, Parts B-E, substituting 4-bromo-2-nitrobenzoic acid and (L)-phenylalanine methyl ester hydrochloride in Part B. HPLC: $R_T$=9.55 min. MS (ESI−): mass calcd. for $C_{22}H_{17}BrN_4O_5S_2$, 561.4; m/z found, 560 [M−H]⁻. ¹H NMR (400 MHz, CDCl₃): 11.35 (s, 1H), 8.35 (dd, J=7.1, 0.9, 1H), 8.20 (dd, J=8.8, 0.9, 1H), 7.89 (d, J=1.7, 1H), 7.71 (dd, J=8.8, 7.1, 1H), 7.31-7.26 (m, 3H), 7.14-7.11 (m, 2H), 7.06-7.04 (m, 1H), 7.03-6.98 (m, 1H), 6.34 (d, J=7.3, 1H), 5.01 (dd, J=13.1, 5.8, 1H), 3.32 (dd, J=14.1, 5.8, 1H), 3.24 (dd, J=14.1, 5.8, 1H).

Example 26

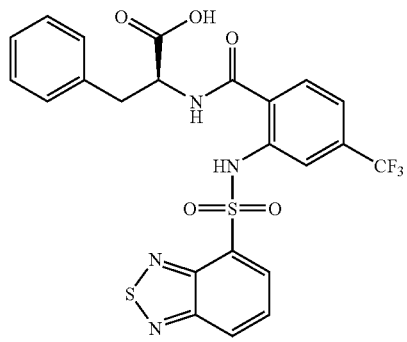

2-[2-(Benzo[1,2,5]thiadiazole-4-sulfonylamino)-4-trifluoromethyl-benzoylamino]-3-phenyl-propionic acid This compound was prepared as in EXAMPLE 3, Parts C-F, substituting 2-amino-4-trifluoromethyl-benzoic acid in Part B. HPLC: $R_T$=9.70 min. MS (ESI−): mass calcd. for $C_{23}H_{17}F_3N_4O_5S_2$, 550.5; m/z found, 550 [M−H]⁻. ¹H NMR (400 MHz, CDCl₃): 11.21 (s, 1H), 8.36 (dd, J=7.1, 1.0), 8.19 (dd, J=8.8, 0.9, 1H), 7.99 (s, 1H), 7.70 (dd, J=8.8, 7.1, 1H), 7.29 (m, 4H), 7.15 (dt, J=7.3, 1.3, 3H), 6.44 (d, J=7.4, 1H), 5.04 (dd, J=13.2, 5.8, 1H), 3.35 (dd, J=14.2, 5.7, 1H), 3.26 (dd, J=14.1, 5.9, 1H).

Example 27

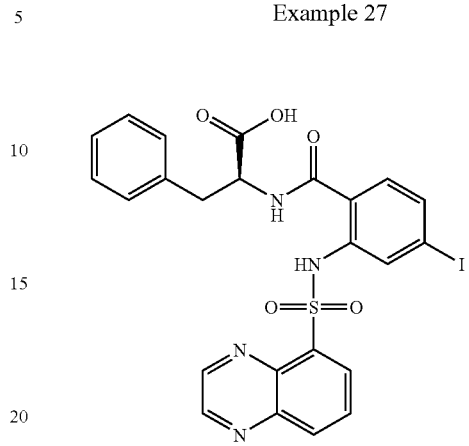

2-[4-Iodo-2-(quinoxaline-5-sulfonylamino)-benzoylamino]-3-phenyl-propionic acid

This compound was prepared as in EXAMPLE 2, Parts B-E, substituting (L)-phenylalanine methyl ester hydrochloride in Part B. HPLC: $R_T$=9.33 min. MS (ESI−): mass calcd. for $C_{24}H_{19}IN_4O_5S$, 602.4; m/z found, 601 [M−H]⁻. ¹H NMR (400 MHz, CDCl₃): 11.00 (s, 1H), 8.99 (d, J=1.7, 1H), 8.89 (d, J=1.7, 1H), 8.54 (dd, J=7.4, 1.3, 1H), 8.30 (dd, J=8.5, 1.3, 1H), 8.13 (d, J=1.5, 1H), 7.87 (dd, J=8.4, 7.5, 1H), 7.29 (m, 2H), 7.11 (dd, J=7.3, 2.0, 1H), 6.80 (d, J=8.3, 1H), 6.24 (d, J=7.4, 1H), 4.92 (dd, J=13.4, 5.9, 1H), 3.26 (dd, J=14.1, 5.8, 1H), 3.19 (dd, J=14.1, 6.0, 1H).

Example 28

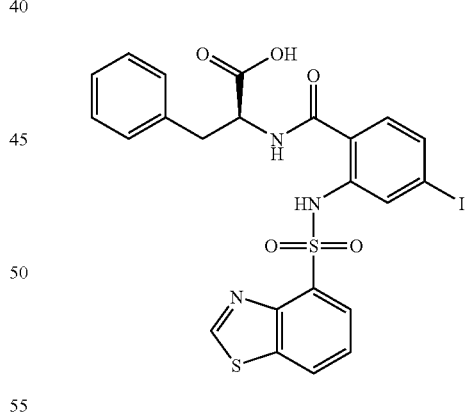

2-[2-(Benzothiazole-4-sulfonylamino)-4-iodo-benzoylamino]-3-phenyl-propionic acid This compound was prepared as in EXAMPLE 2, Parts B-E, substituting (L)-phenylalanine methyl ester hydrochloride in Part B, benzothiazole-4-sulfonyl chloride in Part D. HPLC: $R_T$=9.42 min. MS (ESI−): mass calcd. for $C_{23}H_{18}IN_3O_5S_2$, 607.4; m/z found, 606 [M−H]⁻. ¹H NMR (400 MHz, CDCl₃): 11.01 (s, 1H), 9.20 (s, 1H), 8.23 (d, J=7.6, 1H), 8.17 (d, J=8.0, 1H), 8.01 (d, J=1.2, 1H), 7.58 (t, J=7.9, 1H), 7.25 (m, 2H), 7.15 (m, 2H), 6.85 (d, J=8.2, 1H), 6.47 (d, J=6.8, 1H), 5.04 (dd, J=12.7, 6.0, 1H), 3.33 (dd, J=14.2, 5.5, 1H), 3.25 (dd, J=14.0, 6.0, 1H).

Example 29

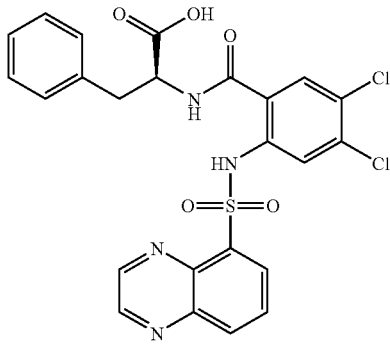

2-[4,5-Dichloro-2-(quinoxaline-5-sulfonylamino)-benzoylamino]-3-phenyl-propionic acid This compound was prepared as in EXAMPLE 3, substituting quinoxaline-5-sulfonyl chloride in Part F. HPLC: $R_T$=9.46 min. MS (ESI−): mass calcd. for $C_{24}H_{18}Cl_2N_4O_5S$, 545.4; m/z found, 544 [M−H]$^-$. $^1$H NMR (400 MHz, CDCl$_3$): 10.90 (s, 1H), 8.99 (d, J=1.2, 1H), 8.90 (d, J=1.0, 1H), 8.52 (dd, J=7.3, 0.9, 1H), 8.30 (dd, J=8.5, 0.8, 1H), 7.86 (m, 2H), 7.28 (m, 1H), 7.21 (m, 1H), 7.12 (dd, J=7.6, 1.8, 2H), 6.36 (d, J=7.4, 1H), 4.90 (dd, J=13.5, 6.1, 1H), 3.25 (dd, J=14.0, 5.6, 1H), 3.17 (dd, J=14.0, 6.3, 1H).

Example 30

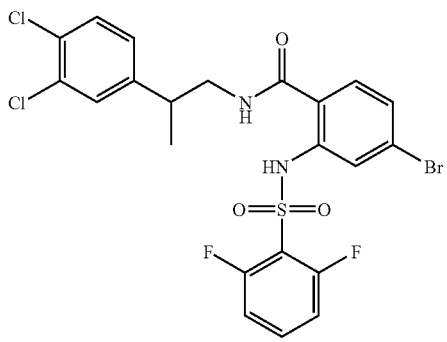

4-Bromo-N-[2-(3,4-dichloro-phenyl)-propyl]-2-(2,6-difluoro-benzenesulfonylamino)-benzamide This compound was prepared as in EXAMPLE 5, substituting 2,6-difluoro-benzenesulfonyl chloride in Part D. HPLC: $R_T$=11.05 min. MS (ESI−): mass calcd. for $C_{22}H_{17}BrCl_2F_2N_2O_3S$, 578.3; m/z found, 577 [M−H]$^-$. $^1$H NMR (400 MHz, CDCl$_3$): 11.58 (s, 1H), 7.88 (d, J=1.8, 1H), 7.54-7.46 (m, 1H), 7.41 (d, J=8.3, 1H), 7.32 (d, J=2.1, 1H), 7.15-7.12 (m, 1H), 7.10-7.05 (m, 1H), 7-02-6.96 (m, 2H), 6.07 (br m, 1H), 3.73 (td, J=13.1, 6.4, 1H), 3.38 (ddd, J=13.8, 8.7, 5.5, 1H), 3.12-3.01 (m, 1H), 1.32 (d, J=7.0, 3H).

Example 31

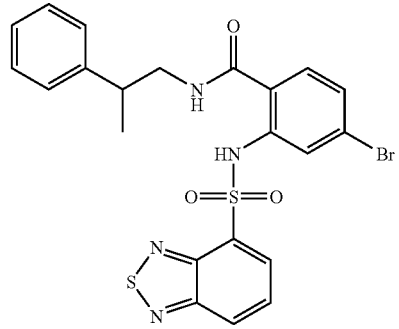

2-(Benzo[1,2,5]thiadiazole-4-sulfonylamino)-4-bromo-N-(2-phenyl-propyl)-benzamide This compound was prepared as in EXAMPLE 5, Parts C and D, substituting (±)-β-methylphenethylamine hydrochloride in Part C. HPLC: $R_T$=10.17 min. MS (ESI−): mass calcd. for $C_{22}H_{19}BrN_4O_3S_2$, 531.5; m/z found, 530 [M−H]$^-$. $^1$H NMR (400 MHz, CDCl$_3$): 11.51 (s, 1H), 8.32 (dd, J=7.0, 0.8, 1H), 8.20 (dd, J=8.8, 0.8, 1H), 7.83 (d, J=1.8, 1H), 7.70 (dd, J=8.8, 7.1, 1H), 7.34-7.31 (m, 2H), 7.26-7.18 (m, 3H), 7.00 (dd, J=8.4, 1.8, 1H), 6.85 (d, J=8.4, 1H), 5.90 (br m, 1H), 3.77-3.70 (m, 1H), 3.30 (ddd, J=13.6, 9.0, 4.9, 1H), 3.04-2.96 (m, 1H), 1.32 (d, J=7.0, 3H).

Example 32

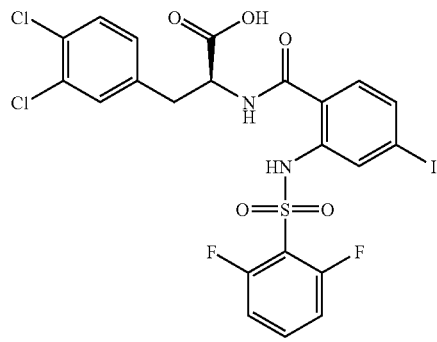

3-(3,4-Dichloro-phenyl)-2-[2-(2,6-difluoro-benzenesulfonylamino)-4-iodo-benzoylamino]-propionic acid This compound was prepared as in EXAMPLE 2, substituting 2,6-difluoro-benzenesulfonyl chloride in Part D. HPLC: $R_T$=9.94 min. MS (ESI−): mass calcd. for $C_{22}H_{15}Cl_2F_2IN_2O_5S$, 655.2; m/z found, 654 [M−H]$^-$. $^1$H NMR (400 MHz, CDCl$_3$): 11.29 (s, 1H), 8.05 (d, J=1.4, 1H), 7.53-7.45 (m, 1H), 7.39-7.36 (m, 2H), 7.27-7.26 (m, 1H), 7.07-6.96 (m, 3H), 6.77 (d, J=7.3, 1H), 5.00 (q, J=6.0, 1H), 3.32 (dd, J=14.2, 5.7, 1H), 3.19 (dd, J=14.2, 6.2, 1H).

Example 33

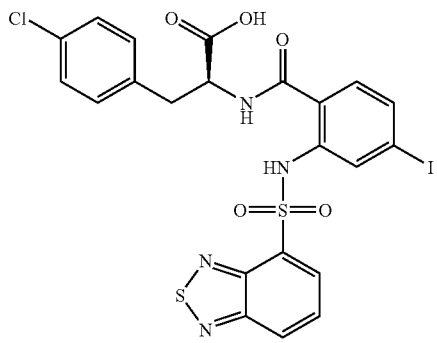

2-[2-(Benzo[1,2,5]thiadiazole-4-sulfonylamino)-4-iodo-benzoylamino]-3-(4-chloro-phenyl)-propionic acid This compound was prepared as in EXAMPLE 2, substituting (S)-2-tert-butoxycarbonylamino-3-(4-chloro-phenyl)-propionic acid in Part A. HPLC: $R_T$=9.72 min. MS (ESI−): mass calcd. for $C_{22}H_{16}ClIN_4O_5S_2$, 642.9; m/z found, 642 [M−H]$^−$. $^1$H NMR (400 MHz, CDCl$_3$): 11.31 (s, 1H), 8.37 (dd, J=6.9, 0.6, 1H), 8.22 (d, J=8.8, 1H), 8.08 (d, J=1.4, 1H), 7.73 (dd, J=8.8, 7.1, 1H), 7.33-7.19 (m, 3H), 7.05 (d, J=8.4, 2H), 6.88 (d, J=8.3, 1H), 6.40 (d, J=7.3, 1H), 4.99 (q, J=5.7, 1H), 3.30 (dd, J=14.2, 5.6), 3.21 (dd, J=14.3, 5.4, 1H).

Example 34

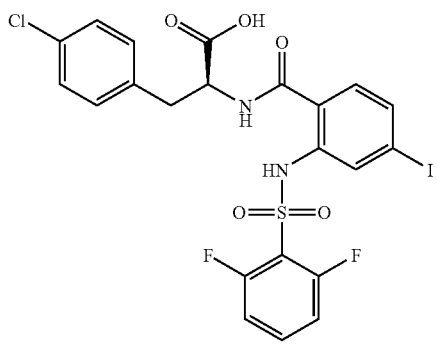

3-(4-Chloro-phenyl)-2-[2-(2,6-difluoro-benzenesulfonylamino)-4-iodo-benzoylamino]-propionic acid This compound was prepared as in EXAMPLE 2, substituting (S)-2-tert-butoxycarbonylamino-3-(4-chloro-phenyl)-propionic acid in Part A and 2,6-difluoro-benzenesulfonyl chloride in Part D. HPLC: $R_T$=9.71 min. MS (ESI−): mass calcd. for $C_{22}H_{16}ClF_2IN_2O_5S$, 620.8; m/z found, 620 [M−H]$^−$. $^1$H NMR (400 MHz, CDCl$_3$): 11.33 (s, 1H), 8.06 (d, J=1.4, 1H), 7.53-7.46 (m, 1H), 7.36 (dd, J=8.3, 1.4, 1H), 7.27-7.25 (m, 2H), 7.10 (d, J=8.4, 2H), 7.05-6.96 (m, 2H), 6.72 (d, J=7.4, 1H), 6.32 (br s, 1H), 4.99 (q, J=6.0, 1H), 3.31 (dd, J=14.2, 5.7, 1H), 3.19 (dd, J=14.2, 6.2, 1H).

Example 35

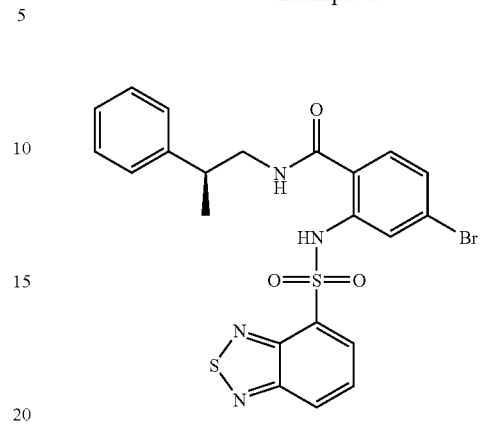

(S)-2-(Benzo[1,2,5]thiadiazole-4-sulfonylamino)-4-bromo-N-(2-phenyl-propyl)-benzamide This compound was prepared as in EXAMPLE 5, Parts C and D, substituting (R)-1-methyl phenethylamine in Part C. HPLC: $R_T$=11.06 min. MS (ESI−): mass calcd. for $C_{22}H_{19}BrN_4O_3S_2$, 531.5; m/z found, 530 [M−H]$^−$. $^1$H NMR (400 MHz, CDCl$_3$): 11.43 (s, 1H), 8.33 (dd, J=7.1, 0.9, 1H), 8.21 (dd, J=8.8, 0.9, 1H), 7.84 (d, J=1.8, 1H), 7.70 (dd, J=8.8, 7.1, 1H), 7.35-7.31 (m, 2H), 7.26-7.23 (m, 1H), 7.20-7.18 (m, 2H), 7.00 (dd, J=8.4, 1.8, 1H), 6.84 (d, J=8.4, 1H), 5.85 (br m, 1H), 4.50 (br s, 1H), 3.78-3.72 (m, 1H), 3.30 (ddd, J=13.7, 9.1, 4.9, 1H), 3.06-2.95 (m, 1H), 1.33 (d, J=7.0, 3H).

Example 36

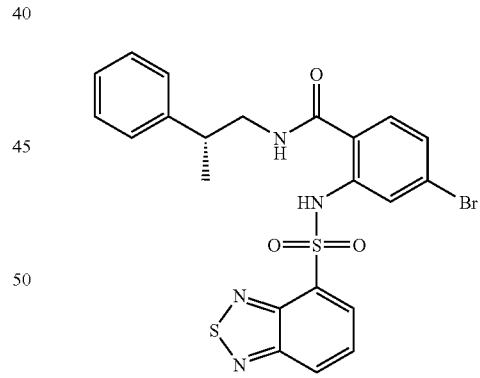

(R)-2-(Benzo[1,2,5]thiadiazole-4-sulfonylamino)-4-bromo-N-(2-phenyl-propyl)-benzamide This compound was prepared as in EXAMPLE 5, Parts C and D, substituting (S)-β-methyl phenethylamine in Part C. HPLC: $R_T$=11.05 min. MS (ESI−): mass calcd. for $C_{22}H_{19}BrN_4O_3S_2$, 531.5; m/z found, 530 [M−H]$^−$. $^1$H NMR (400 MHz, CDCl$_3$): 11.41 (s, 1H), 8.33 (dd, J=7.1, 0.9, 1H), 8.21 (dd, J=8.8, 0.9, 1H), 7.84 (d, J=1.8, 1H), 7.70 (dd, J=8.8, 7.1, 1H), 7.35-7.31 (m, 2H), 7.26-7.23 (m, 1H), 7.20-7.18 (m, 2H), 7.01 (dd, J=8.4, 1.8, 1H), 6.83 (d, J=8.4, 1H), 5.86 (br m, 1H), 4.68 (br s, 1H), 3.72-3.78 (m, 1H), 3.30 (ddd, J=13.6, 9.1, 4.9, 1H), 3.04-2.95 (m, 1H), 1.33 (d, J=7.0, 3H).

Example 37

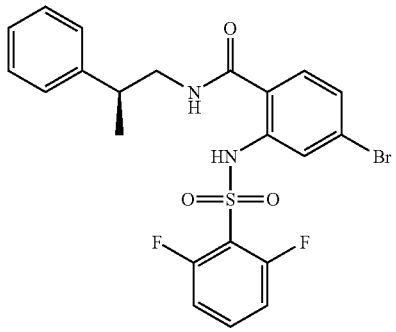

(S)-4-Bromo-2-(2,6-difluoro-benzenesulfony-lamino)-N-(2-phenyl-propyl)-benzamide This compound was prepared as in EXAMPLE 5, Parts C and D, substituting (R)-1-methyl phenethylamine in Part C, 2,6-difluoro-benzenesulfonyl chloride in Part D. HPLC: $R_T$=11.11 min. MS (ESI−): mass calcd. for $C_{22}H_{19}BrF_2N_2O_3S$, 509.4; m/z found, 508 [M−H]$^−$. $^1$H NMR (400 MHz, CDCl$_3$): 11.44 (s, 1H), 7.86 (d, J=1.8, 1H), 7.53-7.45 (m, 1H), 7.37-7.34 (m, 2H), 7.29-7.22 (m, 3H), 7.10 (dd, J=8.4, 1.8, 1H), 7.01-6.95 (m, 3H), 6.06-6.04 (br m, 1H), 5.50 (br s, 1H), 3.84-3.77 (m, 1H), 3.40-3.33 (m, 1H), 3.13-3.02 (m, 1H), 1.34 (d, J=7.0, 3H).

Example 38

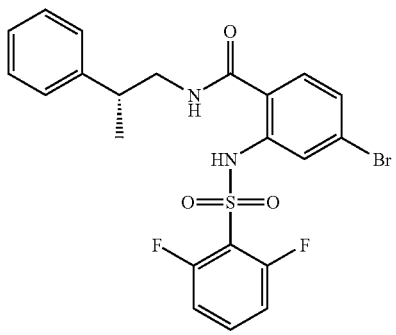

(R)-4-Bromo-2-(2,6-difluoro-benzenesulfony-lamino)-N-(2-phenyl-propyl)-benzamide This compound was prepared as in EXAMPLE 5, Parts C and D, substituting (S)-β-methyl phenethylamine in Part C, 2,6-difluoro-benzenesulfonyl chloride in Part D. HPLC: $R_T$=11.11 min. MS (ESI−): mass calcd. for $C_{22}H_{19}BrF_2N_2O_3S$, 509.4; m/z found, 508 [M−H]$^−$. $^1$H NMR (400 MHz, CDCl$_3$): 11.49 (s, 1H), 7.86 (d, J=1.8, 1H), 7.45-7.52 (m, 1H), 7.40-7.33 (m, 2H), 7.28-7.22 (m, 3H), 7.10 (dd, J=8.4, 1.8, 1H), 7.01-6.96 (m, 3H), 6.05 (br m, 1H), 5.21 (br s, 1H), 3.84-3.77 (m, 1H), 3.37 (ddd, J=13.7, 9.1, 5.0, 1H), 3.08-3.04 (m, 1H), 1.34 (d, J=7.0, 3H).

Example 39

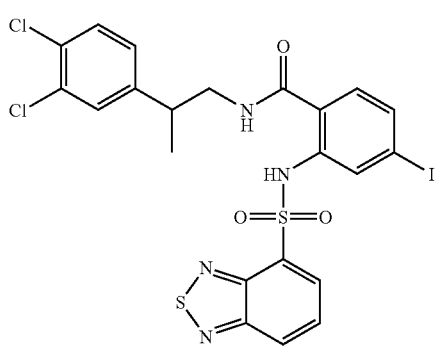

2-(Benzo[1,2,5]thiadiazole-4-sulfonylamino)-N-[2-(3,4-dichloro-phenyl)-propyl]-4-iodo-benzamide This compound was prepared as in EXAMPLE 5, substituting 4-iodo-2-nitrobenzoic acid in Part C. HPLC: $R_T$=11.97 min. MS (ESI−): mass calcd. for $C_{22}H_{17}Cl_2IN_4O_3S_2$, 647.3; m/z found, 646 [M−H]$^−$. $^1$H NMR (400 MHz, CDCl$_3$): 11.40 (s, 1H), 8.34 (dd, J=7.0, 0.9, 1H), 8.23 (dd, J=8.8, 0.9, 1H), 8.04 (d, J=1.6, 1H), 7.73 (dd, J=8.8, 7.1, 1H), 7.39 (d, J=8.2, 1H), 7.29-7.25 (m, 2H), 7.04 (dd, J=8.3, 2.1, 1H), 6.77 (d, J=8.3, 1H), 5.92-5.90 (br m, 1H), 3.71-3.64 (m, 1H), 3.30 (ddd, J=13.7, 8.6, 5.4, 1H), 3.04-2.98 (m, 1H), 1.30 (d, J=7.0, 3H).

Example 40

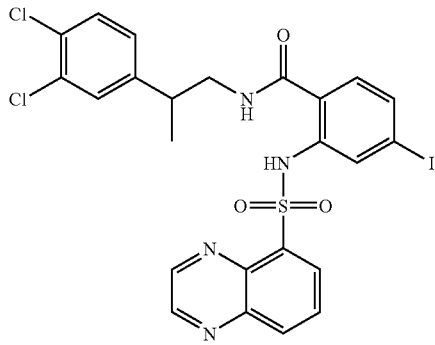

N-[2-(3,4-Dichloro-phenyl)-propyl]-4-iodo-2-(quinoxaline-5-sulfonylamino)-benzamide This compound was prepared as in EXAMPLE 5, substituting quinoxaline-5-sulfonyl chloride in Part D. HPLC: $R_T$=11.49 min. MS (ESI–): mass calcd. for $C_{24}H_{19}Cl_2IN_4O_3S$, 641.3; m/z found, 640 [M–H]$^-$. $^1$H NMR (400 MHz, CDCl$_3$): 11.13 (s, 1H), 9.01 (d, J=1.7, 1H), 8.95 (d, J=1.7, 1H), 8.54 (dd, J=7.4, 1.3, 1H), 8.33 (dd, J=8.5, 1.3, 1H), 8.03 (d, J=1.6, 1H), 7.89 (dd, J=8.4, 7.5, 1H), 7.38 (d, J=8.23, 1H), 7.28 (d, J=2.0, 1H), 7.23 (dd, J=8.2, 1.6, 1H), 7.03 (dd, J=8.3, 2.1, 1H), 6.77 (d, J=8.3, 1H), 5.96-5.94 (br m, 1H), 3.60-3.56 (m, 1H), 3.29 (ddd, J=13.7, 8.5, 5.5, 1H), 3.01-2.95 (m, 1H), 1.29 (d, J=7.0, 1H).

Example 41

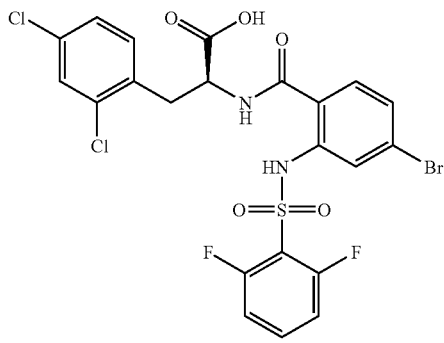

2-[4-Bromo-2-(2,6-difluoro-benzenesulfonylamino)-benzoylamino]-3-(2,4-dichloro-phenyl)-propionic acid A. 2-(2,6-Difluoro-benzenesulfonylamino)-4-bromo-benzoic acid Methyl 2-amino-4-bromobenzoate was sulfonylated with 2,6-difluorobenzenesulfonyl chloride and hydrolyzed as in EXAMPLE 1, Part B. $^1$H NMR (400 MHz, acetone-d$_6$): 11.65 (s, 1H), 8.02 (d, J=8.5, 1H), 7.93 (d, J=1.8, 1H), 7.74-7.82 (m, 1H), 7.38 (dd, J=8.5, 1.9, 1H), 7.28-7.23 (m, 2H).

B. 2-[4-Bromo-2-(2,6-difluoro-benzenesulfonylamino)-benzoylamino]-3-(2,4-dichloro-phenyl)-propionic acid (S)-2-Amino-3-(2,4-dichloro-phenyl)-propionic acid was treated as in EXAMPLE 2, Part A, to produce (S)-2-amino-3-(2,4-dichloro-phenyl)-propionic acid methyl ester hydrochloride as a white solid. This ester was coupled with 4-bromo-2-(2,6-difluoro-benzenesulfonylamino)-benzoic acid as in EXAMPLE 1, Part C. The resulting methyl ester was hydrolyzed as in EXAMPLE 2, Part E, to afford title compound. HPLC: $R_T$=10.26 min. MS (ESI–): mass calcd. for $C_{22}H_{15}BrCl_2F_2N_2O_5S$, 608.2; m/z found, 607 [M–H]$^-$. $^1$H NMR (400 MHz, CDCl$_3$): 11.36 (s, 1H), 7.87 (d, J=1.8, 1H), 7.52-7.44 (m, 1H), 7.39 (d, J=1.6, 1H), 7.27-7.25 (m, 1H), 7.25-7.22 (m, 1H), 7.18-7.15 (m, 1H), 6.97 (t, J=8.7, 2H), 6.79 (d, J=7.7, 1H), 5.05-5.00 (m, 1H), 3.50 (dd, J=14.2, 5.5, 1H), 3.29 (dd, J=14.2, 8.1, 1H).

Example 42

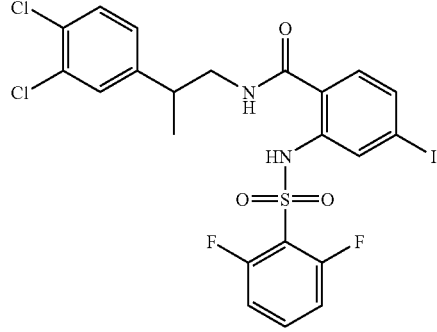

N-[2-(3,4-Dichloro-phenyl)-propyl]-2-(2,6-difluoro-benzenesulfonylamino)-4-iodo-benzamide This compound was prepared from 2-(2,6-difluorobenzenesulfonylamino)-4-iodo-benzoic acid and 2-(3,4-dichloro-phenyl)-propylamine as in EXAMPLE 1, Part C. HPLC: $R_T$=11.98 min. MS (ESI–): mass calcd. for $C_{22}H_{17}Cl_2F_2IN_2O_3S$, 625.3; m/z found, 624 [M–H]$^-$. $^1$H NMR (400 MHz, CDCl$_3$): 11.63 (s, 1H), 8.02 (d, J=1.5, 1H), 7.54-7.45 (m, 1H), 7.39 (d, J=8.2, 1H), 7.34 (d, J=1.6, 1H), 7.32 (d, J=1.8, 1H), 7.09 (dd, J=8.3, 2.1, 1H), 7.02-6.94 (m, 3H), 6.34-6.32 (br m, 1H), 3.74-3.65 (m, 1H), 3.40 (ddd, J=13.7, 8.5, 5.6, 1H), 3.14-3.04 (m, 1H), 1.30 (d, J=7.0, 3H).

Example 43

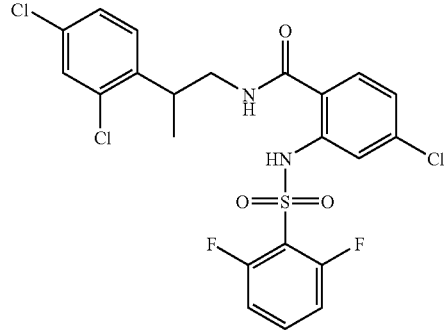

4-Chloro-N-[2-(2,4-dichloro-phenyl)-propyl]-2-(2,6-difluoro-benzenesulfonylamino)-benzamide A. 2-(2,6-Difluoro-benzenesulfonylamino)-4-chloro-benzoic acid Methyl 2-amino-4-chlorobenzoate was sulfonylated with 2,6-difluorobenzenesulfonyl chloride and hydrolyzed as in EXAMPLE 1, Parts A and B.

B. 4-Chloro-N-[2-(2,4-dichloro-phenyl)-propyl]-2-(2,6-difluoro-benzenesulfonylamino)-benzamide The title compound was prepared from 2-(2,6-difluoro-benzenesulfonylamino)-4-chloro-benzoic acid and 2-(2,4-dichloro-phenyl)-propylamine hydrochloride (prepared as in EXAMPLE 5, substituting 2,4-dichlorophenyl-acetonitrile in Part A) as in Example 1, Part C. HPLC: $R_T$=11.20 min. MS (ESI−): mass calcd. for $C_{22}H_{17}Cl_3F_2N_2O_3S$, 533.8; m/z found, 533 [M−H]⁻. ¹H NMR (400 MHz, CDCl₃): 11.62 (s, 1H), 7.73 (d, J=1.9, 1H), 7.52-7.45 (m, 1H), 7.40 (d, J=1.8, 1H), 7.28-7.25 (m, 2H), 7.18 (d, J=8.5, 1H), 7.01-6.96 (m, 3H), 6.05 (br m, 1H), 3.76-3.70 (m, 1H), 3.68-3.57 (m, 1H), 3.57-3.49 (m, 1H), 1.32 (d, J=6.8, 3H).

Example 44

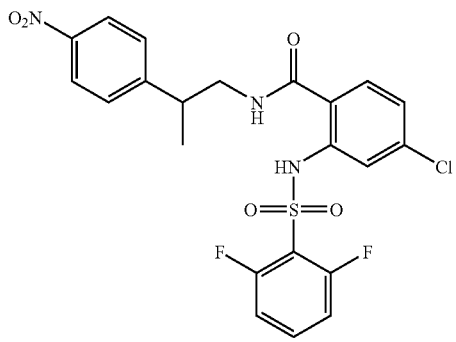

4-Chloro-2-(2,6-difluoro-benzenesulfonylamino)-N-[2-(4-nitro-phenyl)-propyl]-benzamide This compound was prepared from 4-chloro-2-(2,6-difluoro-benzenesulfonylamino)-benzoic acid and 2-(4-nitrophenyl)-propylamine hydrochloride (prepared as in EXAMPLE 5, substituting 4-nitrophenylacetonitrile in Part A) as in Example 1, Part C. HPLC: $R_T$=10.37 min. MS (ESI−): mass calcd. for $C_{22}H_{18}ClF_2N_3O_5S$, 509.9; m/z found, 509 [M−H]⁻. ¹H NMR (400 MHz, CDCl₃): 11.63 (s, 1H), 8.18 (d, J=8.6, 1H), 7.69 (d, J=1.7, 1H), 7.56-7.46 (m, 1H), 7.42 (d, J=8.6, 2H), 7.15 (d, J=8.5, 1H), 7.02-6.94 (m, 1H), 6.19-6.17 (br m, 1H), 3.79-3.70 (m, 1H), 3.57-3.49 (m, 1H), 3.33-3.23 (m, 1H), 1.38 (d, J=6.9, 3H).

Example 45

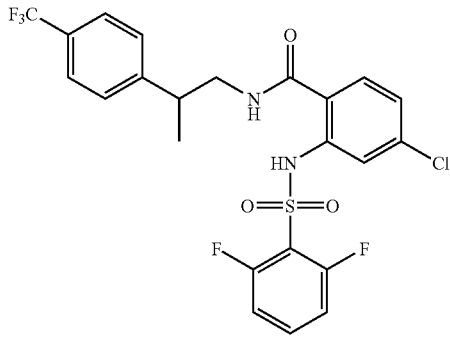

4-Chloro-2-(2,6-difluoro-benzenesulfonylamino)-N-[2-(4-trifluoromethyl-phenyl)-propyl]-benzamide This compound was prepared from 4-chloro-2-(2,6-difluoro-benzenesulfonylamino)-benzoic acid and 2-(4-trifluoro-phenyl)-propylamine hydrochloride (prepared as in EXAMPLE 5, substituting 4-trifluorophenyl-acetonitrile in Part A) as in Example 1, Part C. HPLC: $R_T$=10.93 min. MS (ESI−): mass calcd. for $C_{23}H_{18}ClF_5N_2O_3S$, 532.9; m/z found, 532 [M−H]⁻. ¹H NMR (400 MHz, CDCl₃): 11.64 (s, 1H), 7.72 (d, J=2.0, 1H), 7.61 (d, J=8.1, 2H), 7.53-7.46 (m, 1H), 7.36 (d, J=8.1, 2H), 7.10 (d, J=8.5, 1H), 7.01-6.94 (m, 3H), 6.02 (br m, 1H), 3.83-3.74 (m, 1H), 3.45 (ddd, J=13.8, 8.7, 5.4, 1H), 3.23-3.13 (m, 1H), 1.36 (d, J=7.0, 1H).

Example 46

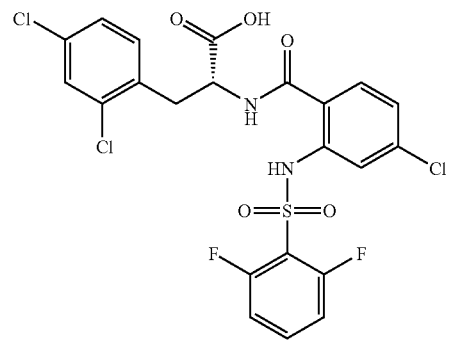

2-[4-Chloro-2-(2,6-difluoro-benzenesulfonylamino)-benzoylamino]-3-(2,4-dichloro-phenyl)-propionic acid (R)-2-Amino-3-(2,4-dichloro-phenyl)-propionic acid was treated as in EXAMPLE 2, Part A, to produce (R)-2-amino-3-(2,4-dichloro-phenyl)-propionic acid methyl ester hydrochloride as a white solid. This ester was coupled with 4-chloro-2-(2,6-difluoro-benzenesulfonylamino)-benzoic acid as in EXAMPLE 1, Part C. The resulting methyl ester was hydrolyzed as in EXAMPLE 2, Part E, to afford title compound. HPLC: $R_T$=10.20 min. MS (ESI−): mass calcd. for $C_{22}H_{15}Cl_3F_2N_2O_5S$, 563.8; m/z found, 563 [M−H]⁻. ¹H NMR (400 MHz, acetone-$d_6$): 8.56 (d, J=8.1, 1H), 7.82 (d, J=8.6, 1H), 7.77-7.71 (m, 1H), 7.70 (d, J=2.0, 1H), 7.50-7.48 (m, 2H), 7.31 (dd, J=8.3, 2.1, 1H), 7.22-7.14 (m, 3H), 5.08-5.00 (m, 1H), 3.62-3.51 (m, 1H), 3.34-3.21 (m, 1H).

Example 47

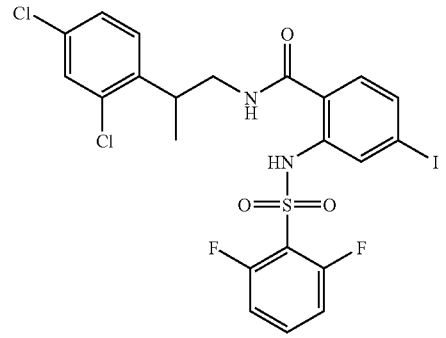

N-[2-(2,4-Dichloro-phenyl)-propyl]-2-(2,6-difluoro-benzenesulfonylamino)-4-iodo-benzamide This compound was prepared from 2-(2,6-difluoro-benzenesulfonylamino)-4-iodo-benzoic acid and 2-(2,4-dichloro-phenyl)-propylamine hydrochloride (prepared as in EXAMPLE 5, substituting 2,4-dichloro-phenyl)-acetonitrile in Part A) as in Example 1, Part C. HPLC: $R_T$=11.10 min. MS (ESI−): mass calcd. for $C_{22}H_{17}Cl_2F_2IN_2O_3S$, 625.3; m/z found, 624 [M−H]−. $^1$H NMR (400 MHz, CDCl$_3$): 11.51 (s, 1H), 8.06 (d, J=1.6, 1H), 7.52-7.45 (m, 1H), 7.39 (d, J=1.8, 1H), 7.35 (dd, J=8.3, 1.6, 1H), 7.27 (d, J=1.9, 2H), 7.04-6.93 (m, 3H), 6.09 (br m, 1H), 3.77-3.69 (m, 1H), 3.69-3.58 (m, 1H), 3.57-3.47 (m, 1H), 1.31 (d, J=6.8, 3H).

Example 48

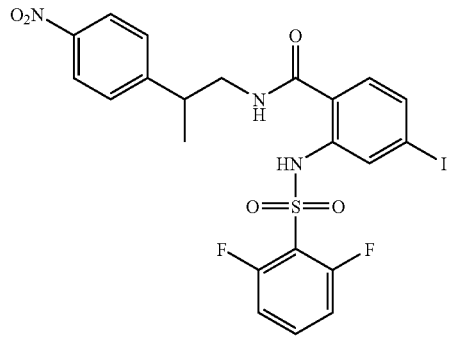

2-(2,6-Difluoro-benzenesulfonylamino)-4-iodo-N-[2-(4-nitro-phenyl)-propyl]-benzamide This compound was prepared from 2-(2,6-difluorobenzenesulfonylamino)-4-iodo-benzoic acid and 2-(4-nitrophenyl)-propylamine hydrochloride (prepared as in EXAMPLE 5, substituting 4-nitro-phenyl)-acetonitrile in Part A) as in Example 1, Part C. HPLC: $R_T$=10.30 min. MS (ESI−): mass calcd. for $C_{22}H_{18}F_2IN_3O_5S$, 601.4; m/z found, 600 [M−H]−. $^1$H NMR (400 MHz, CDCl$_3$): 8.19 (d, J=8.7, 2H), 8.05 (d, J=1.5, 1H), 7.56-7.46 (m, 1H), 7.41 (d, J=8.7, 2H), 7.33 (dd, J=8.3, 1.5, 1H), 7.00 (t, J=8.6, 2H), 6.89 (d, J=8.3, 1H), 6.13 (br m, 1H), 3.74 (td, J=12.9, 6.3, 1H), 3.51 (ddd, J=14.0, 8.5, 5.9, 1H), 3.26 (m, 1H), 1.38 (d, J=7.0, 3H).

Example 49

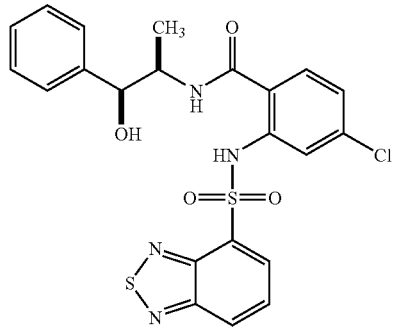

2-(Benzo[1,2,5]thiadiazole-4-sulfonylamino)-4-chloro-N-((2S,1R)-2-hydroxy-1-methyl-2-phenyl-ethyl)-benzamide 2-(Benzo[1,2,5]thiadiazole-4-sulfonylamino)-4-chlorobenzoic acid was coupled with (1S,2R)-(+)-norephedrine as in EXAMPLE 1, Part C. HPLC: $R_T$=10.13 min. MS (ESI−): mass calcd. for $C_{22}H_{19}ClN_4O_4S_2$, 502.05; m/z found, 501 [M−H]−. $^1$H NMR (400 MHz, CDCl$_3$): 11.69 (s, 1H), 8.37 (dd, J=7.0, 1.0, 1H), 8.22 (dd, J=8.8, 1.0, 1H), 7.73 (d, J=2.0, 1H), 7.72 (dd, J=8.8, 7.0, 1H), 7.41-7.29 (m, 5H), 7.24 (d, J=8.4, 1H), 6.93 (dd, J=8.4, 2.0, 1H), 6.28 (br d, J=8.3, 1H), 4.98 (d, J=3.0, 1H), 4.45 (dd q, J=8.3, 6.9, 3.0, 1H), 2.60 (br s, 1H), 1.05 (d, J=6.9, 3H).

Example 50

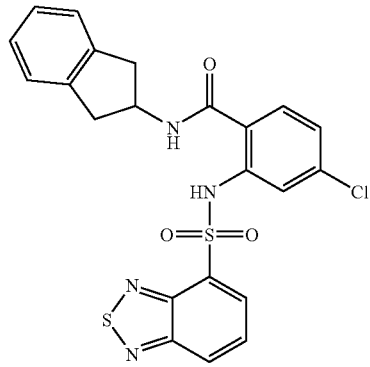

2-(Benzo[1,2,5]thiadiazole-4-sulfonylamino)-4-chloro-N-indan-2-yl-benzamide 2-(Benzo[1,2,5]thiadiazole-4-sulfonylamino)-4-chlorobenzoic acid was coupled with 2-aminoindane as in EXAMPLE 1, Part C. HPLC: $R_T$=10.24 min. MS (ESI−): mass calcd. for $C_{22}H_{17}ClN_4O_3S_2$, 484.04; m/z found, 483 [M−H]−. $^1$H NMR (400 MHz, CDCl$_3$): 11.64 (s, 1H), 8.37 (dd, J=7.0, 1.0, 1H), 8.23 (dd, J=8.8, 1.0, 1H), 7.72 (dd, J=8.8, 7.0, 1H), 7.72 (d, J=2.0, 1H), 7.28-7.19 (m, 4H), 7.14 (d, J=8.4, 1H), 6.89 (dd, J=8.4, 2.0, 1H), 6.12 (br d, J=7.5, 1H), 4.87-4.80 (m, 1H), 3.41 (dd, J=16.3, 7.0, 2H), 2.83 (dd, J=16.3, 3.9, 2H).

Example 51

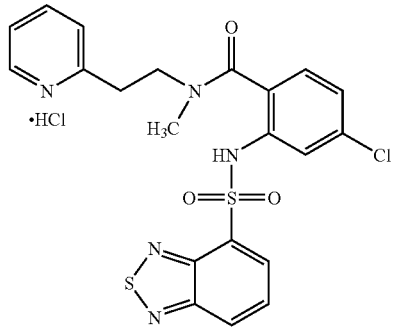

2-(Benzo[1,2,5]thiadiazole-4-sulfonylamino)-4-chloro-N-methyl-N-(2-pyridin-2-yl-ethyl)-benzamide hydrochloride 2-(Benzo[1,2,5]thiadiazole-4-sulfonylamino)-4-chlorobenzoic acid was coupled with N-methyl-2-pyridin-2-yl-ethylamine as in EXAMPLE 1, Part C. The hydrochloride salt was isolated as a white solid after repeated concentration from methanolic HCl. HPLC: $R_T$=7.10 min. MS (ESI−): mass calcd. for $C_{21}H_{18}ClN_5O_3S_2$, 487.05; m/z found, 486 [M−H]−. $^1$H NMR (500 MHz, $CD_3OD$): rotameric broadening, 8.79 (br d, J=4.7, 1H), 8.61-8.52 (br m, 1H), 8.33 (br d, J=8.8, 1H), 8.24-8.16 (br m, 1H), 8.16-8.10 (br m, 1H), 7.98-7.90 (br m, 1H), 7.82-7.75 (br m, 1H), 7.23-7.15 (br m, 1H), 7.00-6.90 (br m, 1H), 3.95-3.83 (br m, 2H), 3.49-3.38 (br m, 2H), 2.92 (br s, 3H).

Example 52

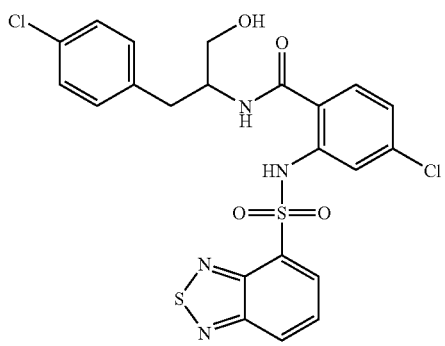

(±)-2-(Benzo[1,2,5]thiadiazole-4-sulfonylamino)-4-chloro-N-[2-(4-chloro-phenyl)-1-hydroxymethyl-ethyl]-benzamide 2-(Benzo[1,2,5]thiadiazole-4-sulfonylamino)-4-chlorobenzoic acid was coupled with (±)-2-amino-3-(4-chlorophenyl)-propan-1-ol as in EXAMPLE 1, Part C. HPLC: $R_T$=9.71 min. MS (ESI−): mass calcd. for $C_{22}H_{18}Cl_2N_4O_4S_2$, 536.01; m/z found, 535/537 [M−H]−. $^1$H NMR (500 MHz, $CDCl_3$): 11.57 (s, 1H), 8.38 (br d, J=6.2, 1H), 8.22 (br d, J=8.4, 1H), 7.71 (br m, 2H), 7.35-7.10 (br m, 5H), 6.92 (br d, J=6.0, 1H), 6.30 (br m, 1H), 4.36-4.27 (br m, 1H), 3.76-3.62 (br m, 2H), 2.98-2.85 (br m, 2H), 1.92 (br s, 1H).

Example 53

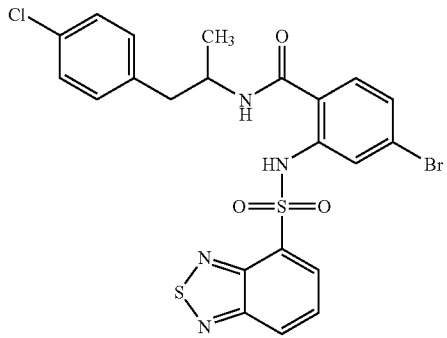

(±)-2-(Benzo[1,2,5]thiadiazole-4-sulfonylamino)-4-bromo-N-[2-(4-chloro-phenyl)-1-methyl-ethyl]-benzamide 2-(Benzo[1,2,5]thiadiazole-4-sulfonylamino)-4-bromobenzoic acid was coupled with (±)-2-(4-chlorophenyl)-1-methylethylamine as in EXAMPLE 1, Part C. HPLC: $R_T$=10.50 min. MS (ESI−): mass calcd. for $C_{22}H_{18}BrClN_4O_3S_2$, 563.97; m/z found, 563/565 [M−H]−. $^1$H NMR (400 MHz, $CDCl_3$): 11.61 (s, 1H), 8.37 (dd, J=7.0, 1.2, 1H), 8.22 (dd, J=8.8, 1.0, 1H), 7.88 (d, J=1.8, 1H), 7.72 (dd, J=8.8, 7.0, 1H), 7.32-7.25 (m, 2H), 7.13-7.05 (m, 2H), 7.07 (dd, J=8.4, 1.8, 1H), 7.01 (d, J=8.4, 1H), 5.74 (br d, J=7.8, 1H), 4.40-4.28 (m, 1H), 2.88 (dd, J=13.6, 5.6, 1H), 2.75 (dd, J=13.6, 7.1, 1H), 1.17 (d, J=6.7, 3H).

Example 54

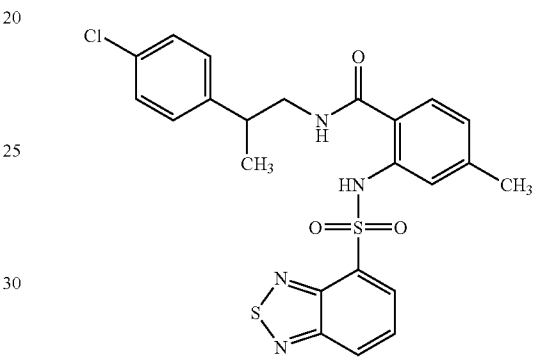

(±)-2-(Benzo[1,2,5]thiadiazole-4-sulfonylamino)-N-[2-(4-chloro-phenyl)-propyl]-4-methyl-benzamide 2-(Benzo[1,2,5]thiadiazole-4-sulfonylamino)-4-methylbenzoic acid was coupled with (±)-2-(4-chloro-phenyl)-propylamine as in EXAMPLE 1, Part C. HPLC: $R_T$=10.22 min. MS (ESI−): mass calcd. for $C_{23}H_{21}ClN_4O_3S_2$, 500.07; m/z found, 499 [M−H]−. $^1$H NMR (400 MHz, $CDCl_3$): 11.48 (s, 1H), 8.31 (dd, J=7.0, 1.0, 1H), 8.18 (dd, J=8.8, 1.0, 1H), 7.67 (dd, J=8.8, 7.0, 1H), 7.47 (s, 1H), 7.33-7.27 (m, 2H), 7.16-7.10 (m, 2H), 6.90 (d, J=8.0, 1H), 6.71 (d, J=8.0, 1H), 5.75-5.70 (m, 1H), 3.73-3.64 (m, 1H), 3.30-3.21 (m, 1H), 3.05-2.94 (m, 1H), 2.26 (s, 3H), 1.30 (d, J=7.0, 3H).

Example 55

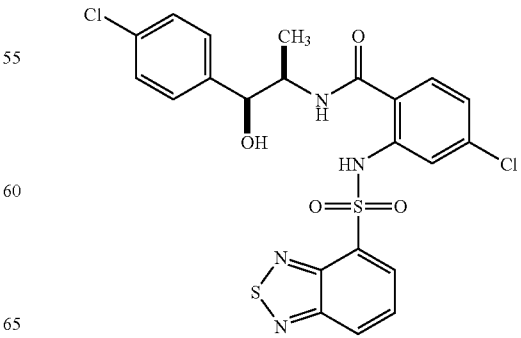

2-(Benzo[1,2,5]thiadiazole-4-sulfonylamino)-4-chloro-N-[(1R,2S)-2-(4-chloro-phenyl)-2-hydroxy-1-methyl-ethyl]-benzamide

A. (R)-4-Benzyl-3-propionyl-oxazolidin-2-one

To a solution of (R)-4-benzyl-oxazolidin-2-one (3.0 g, 16.9 mmol) in THF (100 mL) at −78° C. was added n-BuLi (2.5 M hexanes, 7.1 mL, 17.8 mmol) in rapid drops via syringe. The solution was stirred for 20 min at −78° C. Propionyl chloride (1.6 mL, 18.4 mmol) was added rapidly via syringe. The reaction solution was allowed to warm slowly to rt overnight then was quenched by the addition of satd. aq. $NH_4Cl$. The mixture was concentrated, diluted with water, and extracted with DCM (3×). The combined organic layers were dried ($Na_2SO_4$) and concentrated to give the crude product, which was purified by flash chromatography (EtOAc/hexanes) to afford the title compound as a white solid (3.70 g, 94%). $^1H$ NMR (500 MHz, $CDCl_3$): 7.36-7.31 (m, 2H), 7.30-7.25 (m, 1H), 7.23-7.19 (m, 2H), 4.71-4.64 (m, 1H), 4.20 (dd, J=9.1, 7.5, 1H), 4.17 (dd, J=9.1, 3.1, 1H), 3.31 (dd, J=13.4, 3.3, 1H), 2.99 (dq, J=17.9, 7.4, 1H), 2.93 (dq, J=17.9, 7.3, 1H), 2.77 (dd, J=13.4, 9.6, 1H), 1.21 (t, J=7.3, 3H).

B. (4R)-4-Benzyl-3-[(2R,3R)-3-(4-chloro-phenyl)-3-hydroxy-2-methyl-propionyl]-oxazolidin-2-one To a solution of (R)-4-benzyl-3-propionyl-oxazolidin-2-one (1.0 g, 4.3 mmol) in dry DCM (10 mL) at 0° C. under an inert atmosphere was added n-$Bu_2BOTf$ (1.32 mL, 5.2 mmol) followed by $Et_3N$ (0.78 mL, 5.6 mmol) both in a dropwise manner via syringe while keeping the internal temperature below 4° C. After 30 min at 0° C., the mixture was cooled to −65° C., and a solution of p-chlorobenzaldehyde (661 mg, 4.7 mmol) in DCM (2 mL) was added dropwise via syringe. The resulting mixture was stirred for 1 h at −65° C., then was allowed to warm to 0° C. slowly and was held at 0° C. for 1 h. The reaction was quenched by the addition of 3:1 MeOH/pH 7 phosphate buffer (20 mL). A 2:1 solution of MeOH/30% $H_2O_2$ (15 mL) was carefully added by pipette while keeping the internal temperature below 10° C. After addition was complete, the mixture was concentrated, and the residue was poured into water and extracted with DCM (3×). The combined organic layers were dried ($Na_2SO_4$) and concentrated to give the crude product, which was purified by flash chromatography (0 to 30% $Et_2O$ in 1:1 hexanes/DCM) to afford the aldol adduct as a white foam (1.32 g, 82%). $^1H$ NMR (400 MHz, $CDCl_3$): 7.37-7.26 (m, 7H), 7.23-7.17 (m, 2H), 5.12-5.08 (m, 1H), 4.69-4.62 (m, 1H), 4.22-4.13 (m, 2H), 4.03 (dq, J=7.0, 3.6, 1H), 3.25 (dd, J=13.4, 3.3, 1H), 3.20 (d, J=2.5, 1H), 2.79 (dd, J=13.4, 9.4, 1H), 1.18 (d, J=7.0, 3H).

C. (2R,3R)-3-(4-Chloro-phenyl)-3-hydroxy-2-methyl-propionic acid

A solution of (4R)-4-benzyl-3-[(2R,3R)-3-(4-chloro-phenyl)-3-hydroxy-2-methyl-propionyl]-oxazolidin-2-one (1.32 g, 3.53 mmol) in 4:1 THF/water (20 mL) was cooled to 0° C. and treated with 30% aq. $H_2O_2$ (1.5 mL, 13.2 mmol) and LiOH (1 M in water, 5.6 mL, 5.6 mmol). The reaction mixture was stirred for 1 h at 0° C., and then a solution of $Na_2SO_3$ (1.76 g, 14 mmol) in water (10 mL) was added. The mixture was concentrated at a temperature<30° C. The aqueous layer was extracted with DCM (3×), then was acidified with conc. HCl and extracted with EtOAc (4×). The combined EtOAc layers were dried ($Na_2SO_4$) and concentrated to give the crude acid, which was used without further purification (0.76 g, quant.). $^1H$ NMR (500 MHz, $CDCl_3$): 7.36-7.32 (m, 2H), 7.32-7.28 (m, 2H), 5.16 (d, J=3.9, 1H), 2.81 (dq, J=7.2, 3.9, 1H), 1.15 (d, J=7.2, 3H).

D. (2R,3R)-3-(tert-Butyl-dimethyl-silyloxy)-3-(4-chloro-phenyl)-2-methyl-propionic acid A solution of (2R,3R)-3-(4-chloro-phenyl)-3-hydroxy-2-methyl-propionic acid (0.76 g, 3.5 mmol) in DCM (20 mL) was cooled to 0° C. and treated with 2,6-lutidine (1.24 mL, 10.6 mmol) and tert-butyldimethylsilyl trifluoromethanesulfonate (1.9 mL, 8.27 mmol). The reaction solution was stirred at 0° C. for 30 min then allowed to warm to rt and stir 1 h. The reaction was quenched with 1 M HCl and the mixture was extracted with DCM (3×). The combined organic layers were dried ($Na_2SO_4$) and concentrated to give the crude bis-silylated ester. The silyl ester was stirred in MeOH (10 mL) at rt and treated with 5% aq. $K_2CO_3$ (5 mL). The mixture was stirred 3 h, then was concentrated, diluted with 1 N HCl, and extracted with DCM (4×). The combined organic layers were dried ($Na_2SO_4$) and concentrated to give the crude acid, which was used without further purification (1.06 g, 91%). $^1H$ NMR (400 MHz, $CDCl_3$): 7.32-7.27 (m, 2H), 7.27-7.22 (m, 2H), 5.01 (d, J=5.3, 1H), 2.70 (dq, J=7.2, 5.6, 1H), 1.11 (d, J=6.8, 3H), 0.88 (s, 9H), 0.03 (s, 3H), −0.18 (s, 3H).

E. (1R,2S)-[2-(tert-Butyl-dimethyl-silyloxy)-2-(4-chloro-phenyl)-1-methyl-ethyl]-carbamic acid tert-butyl ester To a solution of (2R,3R)-3-(tert-butyl-dimethyl-silyloxy)-3-(4-chloro-phenyl)-2-methyl-propionic acid (0.93 g, 2.8 mmol) in THF (30 mL) at 0° C. was added $Et_3N$ (0.438 mL, 3.1 mmol) followed by ethyl chloroformate (0.30 mL, 3.1 mmol). The solution was stirred for 1 h at 0° C., and a solution of $NaN_3$ (552 mg, 8.5 mmol) in water (10 mL) was added. The reaction solution was stirred for 4 h with warming to rt. The mixture was poured into water and extracted with $Et_2O$ (3×). The combined organic extracts were dried ($MgSO_4$) and concentrated to afford the crude acyl azide. A mixture of the acyl azide, tert-butanol (10 mL), and toluene (20 mL) was heated at reflux for 12 h. The reaction mixture was cooled and concentrated, and the residue was purified by flash chromatography (EtOAc/hexanes) to provide the desired product as a colorless oil (354 mg, 31%). $^1H$ NMR (400 MHz, $CDCl_3$): 7.28 (s, 4H), 4.90 (br s, 1H), 4.60 (br d, J=8.0, 1H), 3.77-3.65 (m, 1H), 1.46 (s, 9H), 0.94 (s, 9H), 0.88 (d, J=6.8, 3H), 0.06 (s, 3H), −0.13 (s, 3H).

F. (1S,2R)-2-Amino-1-(4-chloro-phenyl)-propan-1-ol hydrochloride

A solution of (1R,2S)-[2-(tert-butyl-dimethyl-silyloxy)-2-(4-chloro-phenyl)-1-methyl-ethyl]-carbamic acid tert-butyl ester (354 mg, 0.88 mmol) in MeOH (10 mL) at rt was treated with HCl (4 M in dioxane, 3 mL). After 1 h, the mixture was concentrated to provide the desired amine as the hydrochloride salt (200 mg, quant.). $^1H$ NMR (400 MHz, $CD_3OD$): 7.43-7.37 (m, 4H), 4.91 (d, J=3.4, 1H), 3.50 (dq, J=6.8, 3.5, 1H), 1.07 (d, J=6.8, 3H).

G. 2-(Benzo[1,2,5]thiadiazole-4-sulfonylamino)-4-chloro-N-[(1R,2S)-2-(4-chloro-phenyl)-2-hydroxy-1-methyl-ethyl]-benzamide 2-(Benzo[1,2,5]-thiadiazole-4-sulfonylamino)-4-chlorobenzoic acid was coupled with (1S,2R)-2-amino-1-(4- chloro-phenyl)-propan-1-ol hydrochloride as in EXAMPLE 1, Part C. HPLC: R$_t$=10.17 min. MS (ESI–): mass calcd. for C$_{22}$H$_{18}$Cl$_2$N$_4$O$_4$S$_2$, 536.01; m/z found, 535/537 [M–H]$^-$. $^1$H NMR (400 MHz, CDCl$_3$): 11.64 (s, 1H), 8.39 (dd, J=7.0, 1.0, 1H), 8.23 (dd, J=8.8, 1.0, 1H), 7.73 (dd, J=8.8, 7.0, 1H), 7.72 (d, J=2.0, 1H), 7.38-7.33 (m, 2H), 7.33-7.28 (m, 2H), 7.24 (d, J=8.5, 1H), 6.95 (dd, J=8.4, 2.0, 1H), 6.22 (br d, J=8.1, 1H), 4.97 (d, J=2.9, 1H), 4.42 (ddq, J=8.3, 7.0, 2.9, 1H), 1.04 (d, J=6.9, 3H).

Example 56

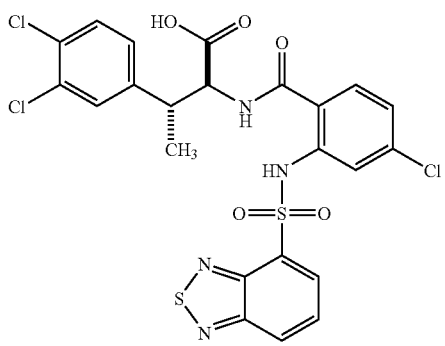

(2S,3R)-2-[2-(Benzo[1,2,5]thiadiazole-4-sulfonylamino)-4-chloro-benzoylamino]-3-(3,4-dichloro-phenyl)-butyric acid A. 3,4-Dichlorocinnamyl alcohol To a stirred suspension of 3,4-dichlorocinnamic acid (25.39 g, 117 mmol) in THF (117 mL) at rt was added Et$_3$N (16.7 mL, 120 mmol). The resulting mixture was cooled in an ice bath and treated with ethyl chloroformate (11.5 mL, 120 mmol) while keeping the internal temperature below 10° C. The resulting thick suspension was stirred rapidly for 1 h in an ice bath. The mixture was filtered through a sintered glass funnel, washing with THF. The filtrate was concentrated to afford the mixed carbonate. The crude carbonate was stirred in MeOH (71 mL) at rt as NaBH$_4$ (16.82 g, 445 mmol) was added in portions while maintaining the internal temperature below 45° C. The mixture was stirred overnight. The mixture was concentrated, diluted with DCM, and washed with 1 N NaOH (2×). The organic layer was dried (Na$_2$SO$_4$) and concentrated to afford a white solid, which was recrystallized (EtOAc/hexanes) to afford 3 crops of the desired cinnamyl alcohol totaling 15.9 g (67%, 96% purity by $^1$H NMR). $^1$H NMR (400 MHz, CDCl$_3$): 7.46 (d, J=2.1, 1H), 7.38 (d, J=8.3, 1H), 7.20 (dd, J=8.4, 2.1, 1H), 6.54 (dt, J=15.9, 1.5, 1H), 6.36 (dt, J=15.9, 5.3, 1H), 4.34 (ddd, J=5.8, 5.3, 1.5, 2H), 1.51 (t, J=5.8, 1H).

B. (2S-trans)-[3-(3,4-Dichloro-phenyl)-oxiranyl]-methanol

To a suspension of powdered 4 Å molecular sieves (3.2 g) in DCM (144 mL) was added Ti(O-iPr)$_4$ (0.864 mL, 2.93 mmol), (+)-L-diisopropyl tartrate (0.924 mL, 4.39 mmol), and t-BuOOH (5.5 M in decane, 10.8 mL, 59.4 mmol). The mixture was cooled to –20° C. stirred for 1 h. A solution of 3,4-dichlorocinnamyl alcohol (6.0 g, 29.5 mmol) in DCM (30 mL) was added via cannula. After 18 h at –20° C., the reaction was quenched by addition of 10% aq. NaOH and brine (10%, 4 mL). The cooling bath was removed, and after stirring for 20 min, Et$_2$O (30 mL) was added followed by MgSO$_4$ (8 g) and diatomaceous earth (8 g). The mixture was stirred rapidly for 15 min then was filtered through a pad of diatomaceous earth, washing with excess Et$_2$O. The filtrate was concentrated, and the desired epoxide was crystallized from the yellow residue with a warm DCM/hexanes mixture to afford 4.22 g (65%) of pale yellow crystals. The epoxide was determined to be >95% ee by $^1$H NMR analysis of both the R- and S-Mosher ester derivatives. $^1$H NMR (400 MHz, CDCl$_3$): 7.42 (d, J=8.3, 1H), 7.37 (d, J=2.0, 1H), 7.13 (dd, J=8.3, 2.0, 1H), 4.04 (dd, J=12.9, 2.2, 1H), 3.91 (d, J=2.0, 1H), 3.82 (dd, J=12.9, 3.4, 1H), 3.18-3.11 (m, 1H), 1.80 (br s, 1H).

C. (2R,3R)-3-(3,4-Dichloro-phenyl)-butane-1,2-diol

To a slurry of CuCN (5.20 g, 58.1 mmol) in dry Et$_2$O (300 mL) under an inert atmosphere at –78° C. was added MeLi (1.6 M in Et$_2$O, 73 mL, 117 mmol). A yellow precipitate formed, and the mixture was allowed to stir until homogeneous (1 h). A solution of (2S-trans)-[3-(3,4-dichloro-phenyl)-oxiranyl]-methanol (4.22 g, 19.3 mmol) in Et$_2$O (80 mL) was added dropwise via cannula over 40 min. The mixture was stirred for 1 h at –78° C., then was allowed to warm to 0° C. over 2 h. The reaction was quenched by careful addition of satd. aq. NH$_4$Cl (160 mL) causing vigorous gas evolution and precipitation of a white and yellow solid. Concentrated NH$_4$OH (33% NH$_3$, 20 mL) was added, and the mixture was stirred vigorously for 10 min. The biphasic mixture was separated, and the aqueous layer was extracted with Et$_2$O (3×). The combined organic layers were dried (MgSO$_4$) and concentrated. The residue was purified by flash chromatography (EtOAc/hexanes) to afford the diol as a colorless viscous liquid (3.40 g, 75%). $^1$H NMR (400 MHz, CDCl$_3$): 7.40 (d, J=8.3, 1H), 7.36 (d, J=2.1, 1H), 7.10 (dd, J=8.4, 2.2, 1H), 3.81-3.71 (m, 2H), 3.57-3.47 (m, 1H), 2.84 (quint, J=7.2, 1H), 3.18-3.11 (m, 1H), 1.96 (br s, 1H), 1.89 (br s, 1H), 1.26 (d, J=7.1, 3H).

D. (2R,3R)-1-(tert-Butyl-dimethyl-silyloxy)-3-(3,4-dichloro-phenyl)-butan-2-ol

To a stirred solution of (2R,3R)-3-(3,4-dichloro-phenyl)-butane-1,2-diol (3.20 g, 13.6 mmol) and imidazole (1.39 g, 20.4 mmol) in DCM (28 mL) at rt was added tert-butyldimethylsilyl chloride (TBSCl; 2.15 g, 14.3 mmol). The solution was stirred for 1 h then quenched by addition of satd. aq. NH$_4$Cl (100 mL). The mixture was stirred for 5 min, the layers were separated, and the aqueous layer was extracted with DCM (3×). The combined organic layers were dried (Na$_2$SO$_4$) and concentrated to yield a viscous yellow liquid. The product was purified by flash chromatography (EtOAc/hexanes) to afford 4.52 g (95%) of the desired product as a colorless viscous liquid. $^1$H NMR (400 MHz, CDCl$_3$): 7.37 (d, J=8.3, 1H), 7.36 (d, J=2.1, 1H), 7.10 (dd, J=8.2, 2.1, 1H), 3.75-3.68 (m, 1H), 3.65 (dd, J=9.9, 3.8, 1H), 3.45 (dd, J=9.9, 7.1, 1H), 2.81 (quint, J=7.0, 1H), 2.37 (d, J=4.0, 1H), 1.25 (d, J=7.2, 3H), 0.89 (s, 9H), 0.07 (s, 3H), 0.06 (s, 3H).

E. (2R,3R)-1-(tert-Butyl-dimethyl-silyloxy)-3-(3,4-dichloro-phenyl)-2-methanesulfonyloxy-butane To a solution of (2R,3R)-1-(tert-butyl-dimethyl-silyloxy)-3-(3,4-dichloro-phenyl)-butan-2-ol (4.63 g, 13.2 mmol) in DCM (44 mL) at 0° C. were added Et$_3$N (4.6 mL, 33.0 mmol), DMAP (81.0 mg, 0.7 mmol), and MsCl (2.2 ml, 28.4 mmol).

The mixture was stirred overnight at rt. The reaction was quenched with water (100 mL) and extracted with DCM (3×). The combined organic layers were dried (Na$_2$SO$_4$) and concentrated to yield an orange oil. The product was purified by flash chromatography (Et$_2$O/hexanes) to afford 4.99 g (88%) of the desired product as a colorless liquid. $^1$H NMR (400 MHz, CDCl$_3$): 7.39 (d, J=8.3, 1H), 7.35 (d, J=2.1, 1H), 7.12 (dd, J=8.3, 2.1, 1H), 4.72-4.69 (m, 1H), 3.71 (dd, J=11.4, 5.7, 1H), 3.64 (dd, J=11.4, 4.3, 1H), 3.24-3.18 (m, 1H), 2.81 (s, 3H), 1.36 (d, J=7.2, 3H), 0.90 (s, 9H), 0.06 (s, 3H), 0.06 (s, 3H).

F. (2R,3R)-3-(3,4-Dichloro-phenyl)-2-methanesulfonyloxy-butan-1-ol

To a solution of (2R,3R)-1-(tert-butyl-dimethyl-silyloxy)-3-(3,4-dichloro-phenyl)-2-methanesulfonyloxy-butane (4.99 g, 11.7 mmol) in THF (117 mL) at 0° C. was added tetrabutylammonium fluoride (TBAF; 1.0 M in THF, 23.4 mL). The solution was stirred at 0° C. for 15 min, then was diluted with 1 N HCl (100 ml) and extracted with DCM (3×). The combined organic layers were dried (Na$_2$SO$_4$) and concentrated to yield a yellow oil. The product was purified by flash chromatography (EtOAc/hexanes) to give 3.45 g (94%) of the desired product. $^1$H NMR (400 MHz, CDCl$_3$): 7.41 (d, J=8.0, 1H), 7.35 (d, J=2.0, 1H), 7.12 (dd, J=8.2, 2.4, 1H), 4.82-4.78 (m, 1H), 3.88-3.84 (m, 1H), 3.74-3.69 (m, 1H), 3.17 (q, J=7.1, 1H), 2.78 (s, 3H), 1.98 (br s, 1H), 1.36 (d, J=7.2, 3H).

G. (2R,3R)-3-(3,4-Dichloro-phenyl)-2-methanesulfonyloxy-butyric acid methyl ester Jones reagent was prepared by mixing chromium (VI) oxide (2.87 g, 28.7 mmol), sulfuric acid (2.44 mL), and water (9.5 mL) for 10 min. The solution was used directly, and was added dropwise to a solution of (2R,3R)-3-(3,4-dichloro-phenyl)-2-methanesulfonyloxy-butan-1-ol (1.50 g, 4.79 mmol) in acetone (100 mL). After 4 h, isopropanol (9 mL) was added and the mixture was concentrated. Water was added, and the aqueous layer was extracted with DCM (3×). The combined organic layers were washed with brine, dried (MgSO$_4$), and concentrated to give the crude acid. To a solution of (2R,3R)-3-(3,4-dichloro-phenyl)-2-methanesulfonyloxy-butyric acid (1.57 g, 4.80 mmol) in DMF (20 mL) were added KHCO$_3$ (1.44 g, 14.4 mmol) and MeI (0.90 mL, 14.4 mmol). After 12 h, the mixture was diluted with water and extracted with EtOAc (2×), and the combined organic phases were washed with brine, dried (MgSO$_4$) and concentrated. The product was purified by flash chromatography to give 1.13 g (69% over 2 steps) of the desired product. $^1$H NMR (400 MHz, CDCl$_3$): 7.38 (d, J=8.3, 1H), 7.31 (d, J=2.1, 1H), 7.08 (dd, J=8.3, 2.1, 1H), 5.14 (d, J=4.7, 1H), 3.73 (s, 3H), 3.47-3.43 (m, 1H), 3.07 (s, 3H), 1.43 (d, J=7.2, 3H).

H. (2S,3R)-2-Azido-3-(3,4-dichloro-phenyl)-butyric acid methyl ester

To a solution of (2R,3R)-3-(3,4-dichloro-phenyl)-2-methanesulfonyloxy-butyric acid methyl ester (0.70 g, 2.05 mmol) in DMF (10 mL) was added NaN$_3$ (0.27 g, 4.10 mmol). The reaction was heated at 55° C. overnight. The mixture was quenched with water and extracted with EtOAc. The organic phase was washed with water (2×), dried (MgSO$_4$), and concentrated. The product was purified by flash chromatography to give 0.42 g (71%) of product. $^1$H NMR (500 MHz, CDCl$_3$): 7.39 (d, J=8.3, 1H), 7.35 (d, J=2.1, 1H), 7.10 (dd, J=8.3, 2.1, 1H), 3.96 (d, J=6.4, 1H), 3.71 (s, 3H), 3.29 (m, 1H), 1.33 (d, J=7.0, 3H).

I. (2S,3R)-2-Amino-3-(3,4-dichloro-phenyl)-butyric acid methyl ester

To a solution of (2S,3R)-2-azido-3-(3,4-dichloro-phenyl)-butyric acid methyl ester (0.42 g, 1.46 mmol) in EtOAc (30 mL) was added Lindlar's catalyst. The mixture was hydrogenated at 50 psi. After 16 h, the reaction mixture was filtered through SiO$_2$ and concentrated to afford 0.28 g (74%) of the desired product. $^1$H NMR (500 MHz, CDCl$_3$): 7.39 (d, J=8.3, 1H), 7.35 (d, J=2.1, 1H), 7.10 (dd, J=8.3, 2.1, 1H), 3.96 (d, J=6.4, 1H), 3.71 (s, 3H), 3.31-3.27 (m, 1H), 1.33 (d, J=7.0, 3H).

J. (2S,3R)-2-[2-(Benzo[1,2,5]thiadiazole-4-sulfonylamino)-4-chloro-benzoylamino]-3-(3,4-dichloro-phenyl)-butyric acid 2-(Benzo[1,2,5]thiadiazole-4-sulfonylamino)-4-chloro-benzoic acid was coupled to (2S,3R)-2-amino-3-(3,4-dichloro-phenyl)-butyric acid methyl ester as in EXAMPLE 1, Part C. The resulting methyl ester was hydrolyzed as in EXAMPLE 2, Part E, to afford the title compound. HPLC: R$_T$=10.22 min. MS (ESI−): mass calcd. for C$_{23}$H$_{17}$Cl$_3$N$_4$O$_5$S$_2$, 597.97; m/z found, 597/599 [M−H]$^−$. $^1$H NMR (500 MHz, CDCl$_3$): 11.26 (s, 1H), 8.36 (d, J=7.0, 1H), 8.21 (d, J=8.8, 1H), 7.73-7.70 (m, 2H), 7.37 (d, J=8.3, 1H), 7.27 (m, 1H), 7.23 (d, J=6.4, 1H), 7.04 (dd, J=8.2, 2.0, 1H), 6.96 (dd, J=8.4, 2.0, 1H), 6.44 (d, J=8.6, 1H), 4.97-4.94 (m, 1H), 3.38-3.36 (m, 1H), 1.46 (d, J=7.2, 3H).

Example 57

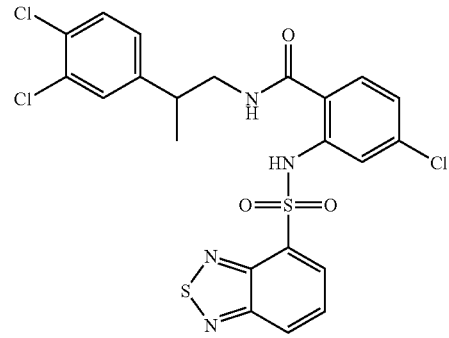

(±)-2-(Benzo[1,2,5]thiadiazole-4-sulfonylamino)-4-chloro-N-[2-(3,4-dichloro-phenyl)-propyl]-benzamide The title compound was prepared from 2-(benzo[1,2,5]thiadiazole-4-sulfonylamino)-4-chloro-benzoic acid and (±)-2-(3,4-dichloro-phenyl)-propylamine hydrochloride as in EXAMPLE 1, Part C. HPLC: R$_T$=11.97 min. MS (ESI−): mass calcd. for C$_{22}$H$_{17}$Cl$_3$N$_4$O$_3$S$_2$, 553.98; m/z found, 553/555/557 [M−H]. $^1$H NMR (400 MHz, CDCl$_3$): 11.51 (s, 1H), 8.36 (dd, J=7.0, 1.1, 1H), 8.22 (dd, J=8.8, 1.0, 1H), 7.74-7.70 (m, 2H), 7.40 (d, J=8.2, 1H), 7.29 (d, J=2.1, 1H), 7.04 (dd, J=8.3, 2.1, 1H), 7.01-6.99 (m, 1H), 6.89 (dd, J=8.4, 2.0, 1H), 5.81 (s, 1H), 3.74-3.67 (m, 1H), 3.34-3.28 (m, 1H), 3.06-2.98 (m, 1H), 1.30 (d, J=7.0, 3H).

Example 58

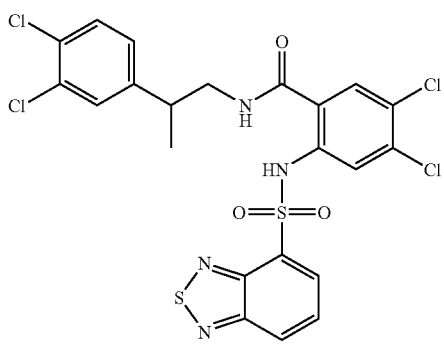

(±)-2-(Benzo[1,2,5]thiadiazole-4-sulfonylamino)-4,5-dichloro-N-[2-(3,4-dichloro-phenyl)-propyl]-benzamide The title compound was prepared from 2-(benzo[1,2,5]thiadiazole-4-sulfonylamino)-4,5-dichloro-benzoic acid and (±)-2-(3,4-dichloro-phenyl)-propylamine hydrochloride as in EXAMPLE 1, Part C. HPLC: $R_T$=12.51 min. MS (ESI−): mass calcd. for $C_{22}H_{16}Cl_4N_4O_3S_2$, 587.94; m/z found, 587/589/591 [M−H]. $^1$H NMR (500 MHz, CDCl$_3$): 11.22 (s, 1H), 8.35 (d, J=7.0, 1H), 8.24 (d, J=8.8, 1H), 7.89 (s, 1H), 7.74-7.71 (m, 1H), 7.41 (d, J=8.2, 1H), 7.29 (d, J=2.0, 1H), 7.14 (s, 1H), 7.05 (dd, J=8.2, 2.0, 1H), 5.79 (s, 1H), 3.69-3.63 (m, 1H), 3.34-3.29 (m, 1H), 3.03-2.99 (m, 1H), 1.31 (d, J=7.0, 3H).

Example 59

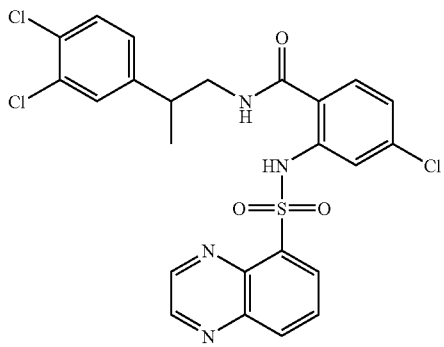

(±)-4-Chloro-N-[2-(3,4-dichloro-phenyl)-propyl]-2-(quinoxaline-5-sulfonylamino)-benzamide The title compound was prepared from 4-chloro-2-(quinoxaline-5-sulfonylamino)-benzoic acid and (±)-2-(3,4-dichloro-phenyl)-propylamine hydrochloride as in EXAMPLE 1, Part C. HPLC: $R_T$=10.78 min. MS (ESI+): mass calcd. for $C_{24}H_{19}Cl_3N_4O_3S$, 548.02; m/z found, 551/553 [M+H]$^+$, m/z found, 571/575 [M+Na]$^+$. $^1$H NMR (400 MHz, CDCl$_3$): 11.21 (s, 1H), 9.04 (d, J=1.7, 1H), 8.96 (d, J=1.7, 1H), 8.57 (dd, J=7.3, 1.3, 1H), 8.33 (dd, J=8.5, 1.2, 1H), 7.91-7.87 (m, 1H), 7.71 (d, J=1.9, 1H), 7.39 (d, J=8.2, 1H), 7.29 (d, J=2.0, 1H), 7.04 (dd, J=8.2, 2.0, 1H), 6.99 (d, J=8.4, 1H), 6.88 (dd, J=8.4, 2.0, 1H), 5.82 (s, 1H), 3.70-3.63 (m, 1H), 3.33-3.26 (m, 1H), 3.02-2.98 (m, 1H), 1.30 (d, J=7.0, 3H).

Example 60

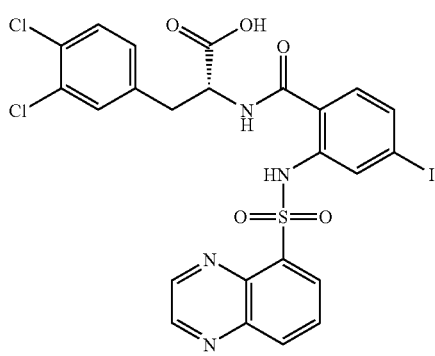

(R)-3-(3,4-Dichloro-phenyl)-2-[4-iodo-2-(quinoxaline-5-sulfonylamino)-benzoylamino]-propionic acid (R)-2-(tert-Butoxycarbonylamino)-3-(3,4-dichloro-phenyl)-propionic acid was treated as in EXAMPLE 2, Part A, to produce (R)-2-amino-3-(3,4-dichloro-phenyl)-propionic acid methyl ester hydrochloride as a white solid. This ester was coupled to 4-iodo-2-(quinoxaline-5-sulfonylamino)-benzoic acid as in EXAMPLE 1, Part C. The resulting methyl ester was hydrolyzed as in EXAMPLE 2, Part E, to afford the title compound. HPLC: $R_T$=10.06 min. MS (ESI−): mass calcd. for $C_{24}H_{17}Cl_2IN_4O_5S$, 669.93; m/z found, 669/671 [M−H]$^−$. $^1$H NMR (500 MHz, CDCl$_3$): 10.85 (s, 1H), 9.00 (d, J=1.8, 1H), 8.92 (d, J=1.7, 1H), 8.54 (dd, J=7.4, 1.2, 1H), 8.33-8.31 (m, 1H), 8.07 (d, J=1.5, 1H), 7.91-7.87 (m, 1H), 7.47-7.22 (m, 3H), 6.98 (dd, J=8.2, 2.0, 1H), 6.87 (d, J=8.3, 1H), 6.37 (d, J=7.7, 1H), 4.92-4.88 (m, 1H), 3.23 (dd, J=14.2, 5.9, 1H), 3.14 (dd, J=14.1, 6.1, 1H).

Example 61

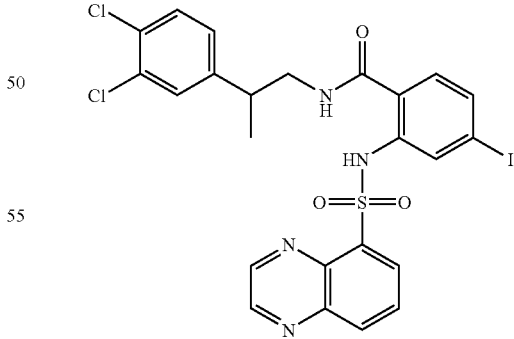

(±)-N-[2-(3,4-Dichloro-phenyl)-propyl]-4-iodo-2-(quinoxaline-5-sulfonylamino)-benzamide The title compound was prepared from 4-iodo-2-(quinoxaline-5-sulfonylamino)-benzoic acid and (±)-2-(3,4-dichlorophenyl)-propylamine hydrochloride as in EXAMPLE 1, Part C. HPLC: $R_T$=10.97 min. MS (ESI+): mass calcd. for $C_{24}H_{19}Cl_2IN_4O_3S$, 639.96; m/z found, 641/643 [M+H]+, m/z found, 663/665 [M+Na]+. $^1$H NMR (400 MHz, CDCl$_3$): 11.07 (s, 1H), 9.03 (d, J=1.8, 1H), 8.95 (d, J=1.8, 1H), 8.56 (dd, J=7.4, 1.4, 1H), 8.33 (dd, J=8.5, 1.4, 1H), 8.05 (d, J=1.6, 1H), 7.91-7.87 (m, 1H), 7.39 (d, J=8.2, 1H), 7.28-7.24 (m, 2H), 7.02 (dd, J=8.3, 2.1, 1H), 6.75 (d, J=8.2, 1H), 5.81 (s, 1H), 3.68-3.61 (m, 1H), 3.31-3.24 (m, 1H), 3.00-2.95 (m, 1H), 1.29 (d, J=7.0, 3H).

Example 62

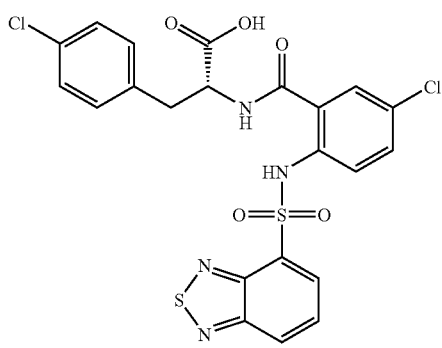

(R)-2-[2-(Benzo[1,2,5]thiadiazole-4-sulfonylamino)-5-chloro-benzoylamino]-3-(4-chloro-phenyl)-propionic acid (R)-2-(tert-Butoxycarbonylamino)-3-(4-chloro-phenyl)-propionic acid was treated as in EXAMPLE 2, Part A, to produce (R)-2-amino-3-(4-chloro-phenyl)-propionic acid methyl ester hydrochloride as a white solid. This ester was coupled with 2-(benzo[1,2,5]thiadiazole-4-sulfonylamino)-5-chloro-benzoic acid as in EXAMPLE 1, Part C. The resulting methyl ester was hydrolyzed as in EXAMPLE 2, Part E, to afford the title compound. HPLC: $R_T$=10.28 min. MS (ESI-): mass calcd. for $C_{22}H_{16}Cl_2N_4O_5S_2$, 549.99; m/z found, 549/551 [M-H]-. $^1$H NMR (500 MHz, CDCl$_3$): 10.92 (s, 1H), 8.30 (d, J=7.0, 1H), 8.19 (d, J=8.8, 1H), 7.70-7.66 (m, 1H), 7.64 (d, J=9.0, 1H), 7.31-7.26 (m, 3H), 7.14 (d, J=2.3, 1H), 7.08 (d, J=8.3, 2H), 6.38 (d, J=7.3, 1H), 5.00-4.96 (m, 1H), 3.29 (dd, J=14.3, 5.7, 1H), 3.20 (dd, J=14.2, 5.8, 1H).

Example 63

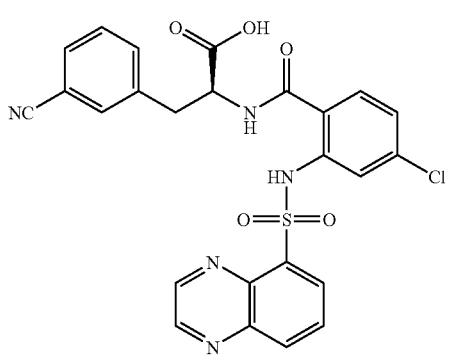

(S)-2-[4-Chloro-2-(quinoxaline-5-sulfonylamino)-benzoylamino]-3-(3-cyano-phenyl)-propionic acid (S)-2-(tert-Butoxycarbonylamino)-3-(3-cyano-phenyl)-propionic acid was treated as in EXAMPLE 2, Part A, to produce (S)-2-amino-3-(3-cyano-phenyl)-propionic acid methyl ester hydrochloride as a white solid. This ester was coupled to 4-chloro-2-(quinoxaline-5-sulfonylamino)-benzoic acid as in EXAMPLE 1, Part C. The resulting methyl ester was hydrolyzed as in EXAMPLE 2, Part E, to afford the title compound. HPLC: $R_T$=8.94 min. MS (ESI-): mass calcd. for $C_{25}H_{18}ClN_5O_5S$, 535.07; m/z found, 534/536 [M-H]-. $^1$H NMR (500 MHz, CDCl$_3$): 11.01 (s, 1H), 9.03 (d, J=1.7, 1H), 8.94 (d, J=1.7, 1H), 8.57 (d, J=7.4, 1H), 8.33 (d, J=8.5, 1H), 7.90 (t, 7.5, 1H), 7.74 (d, J=1.9, 1H), 7.57-7.55 (m, 1H), 7.47-7.41 (m, 3H), 7.12 (d, J=8.4, 1H), 6.93 (dd, J=5.6, 1.9, 1H), 6.40 (d, J=7.3, 1H), 5.02-4.98 (m, 1H), 3.36 (dd, J=14.1, 6.0, 1H), 3.25 (dd, J=14.2, 5.6, 1H).

Example 64

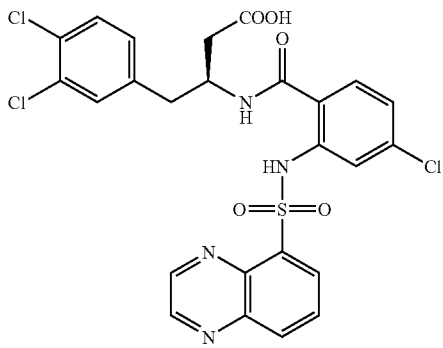

(S)-3-[4-Chloro-2-(quinoxaline-5-sulfonylamino)-benzoylamino]-4-(3,4-dichloro-phenyl)-butyric acid (S)-3-(tert-Butoxycarbonylamino)-4-(3,4-dichloro-phenyl)-butyric acid was treated as in EXAMPLE 2, Part A, to produce (S)-3-amino-4-(3,4-dichloro-phenyl)-butyric acid methyl ester hydrochloride as a white solid. This ester was coupled to 4-chloro-2-(quinoxaline-5-sulfonylamino)-benzoic acid as in EXAMPLE 1, Part C. The resulting methyl ester was hydrolyzed as in EXAMPLE 2, Part E. HPLC: $R_T$=9.78 min. MS (ESI-): mass calcd. for $C_{25}H_{19}Cl_3N_4O_5S$, 592.01; m/z found, 593/595 [M-H]-. $^1$H NMR (500 MHz, CD$_3$OD): 8.97 (d, J=1.8, 1H), 8.93 (d, J=1.8, 1H), 8.55 (dd, J=7.4, 1.3, 1H), 8.33 (dd, J=8.5, 1.3, 1H), 7.97-7.94 (m, 1H), 7.69 (d, J=2.0, 1H), 7.42 (d, J=8.2, 1H), 7.38-7.36 (m, 2H), 7.16 (dd, J=8.2, 2.0, 1H), 6.97 (dd, J=8.6, 2.0, 1H), 4.56-4.50 (m, 1H), 2.90 (dd, J=13.7, 6.1, 1H), 2.81 (dd, J=13.7, 7.7, 1H), 2.54 (dd, J=15.9, 6.2, 1H), 2.45 (dd, J=15.9, 7.4, 1H).

Example 65

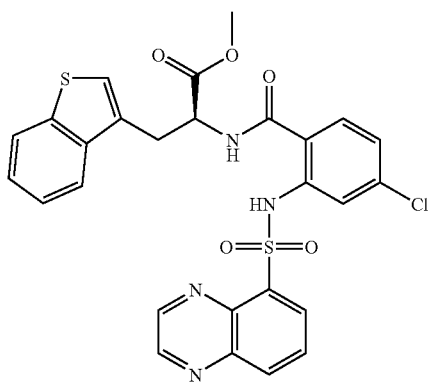

(S)-3-Benzo[b]thiophen-3-yl-2-[4-chloro-2-(quinoxaline-5-sulfonylamino)-benzoylamino]-propionic acid methyl ester 3-Benzo[b]thiophen-3-yl-2-(tert-butoxycarbonylamino)-propionic acid was treated as in EXAMPLE 2, Part A, to produce (S)-2-amino-3-benzo[b]thiophen-3-yl-propionic acid methyl ester hydrochloride as a white solid. This ester was coupled to 4-chloro-2-(quinoxaline-5-sulfonylamino)-benzoic acid as in EXAMPLE 1, Part C, to afford the title compound. HPLC: $R_T$=10.33 min. MS (ESI−): mass calcd. for $C_{27}H_{21}ClN_4O_5S_2$, 580.06; m/z found, 579/581 [M−H]−. $^1$H NMR (400 MHz, CDCl$_3$): 11.35 (s, 1H), 8.94 (d, J=1.8, 1H), 8.85 (d, J=1.8, 1H), 8.58 (dd, J=7.3, 1.4, 1H), 8.31 (dd, J=8.5, 1.3, 1H), 7.90-7.86 (m, 2H), 7.77 (d, J=2.0, 1H), 7.72-7.70 (m, 1H), 7.37-7.26 (m, 2H), 7.09 (s, 1H), 7.00 (d, J=8.4, 1H), 6.83 (dd, J=8.4, 2.0, 1H), 6.45 (d, J=7.1, 1H), 5.09-5.05 (m, 1H), 3.77 (s, 3H), 3.53 (dd, J=14.7, 5.8, 1H), 3.45 (dd, J=14.8, 5.2, 1H).

Example 66

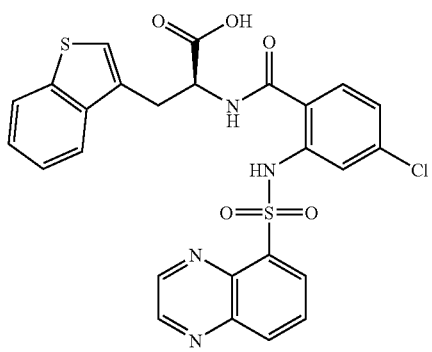

(S)-3-Benzo[b]thiophen-3-yl-2-[4-chloro-2-(quinoxaline-5-sulfonylamino)-benzoylamino]-propionic acid (S)-3-Benzo[b]thiophen-3-yl-2-[4-chloro-2-(quinoxaline-5-sulfonylamino)-benzoylamino]-propionic acid methyl ester was hydrolyzed as in EXAMPLE 2, Part E. HPLC: $R_T$=9.67 min. MS (ESI−): mass calcd. for $C_{26}H_{19}ClN_4O_5S_2$, 566.05; m/z found, 565/567 [M−H]−. $^1$H NMR (500 MHz, CDCl$_3$): 11.09 (s, 1H), 8.96 (d, J=1.8, 1H), 8.84 (d, J=1.8, 1H), 8.54 (dd, J=7.4, 1.3, 1H), 8.28 (dd, J=8.5, 1.3, 1H), 7.87-7.84 (m, 2H), 7.75-7.74 (m, 2H), 7.36-7.33 (m, 2H), 7.21 (s, 1H), 6.89 (d, J=8.4, 1H), 6.80 (dd, J=8.4, 2.0, 1H), 6.35 (d, J=7.2, 1H), 5.06 (m, 1H), 3.58 (dd, J=15.0, 5.5, 1H), 3.47 (dd, J=15.0, 6.0, 1H).

Example 67

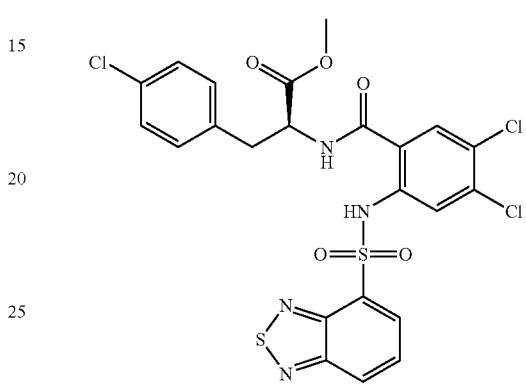

(S)-2-[2-(Benzo[1,2,5]thiadiazole-4-sulfonylamino)-4,5-dichloro-benzoylamino]-3-(4-chloro-phenyl)-propionic acid methyl ester (S)-2-(tert-Butoxycarbonylamino)-3-(4-chloro-phenyl)-propionic acid was treated as in EXAMPLE 2, Part A, to produce (S)-2-amino-3-(4-chloro-phenyl)-propionic acid methyl ester hydrochloride as a white solid. This ester was coupled to 2-(benzo[1,2,5]thiadiazole-4-sulfonylamino)-4,5-dichloro-benzoic acid as in EXAMPLE 1, Part C, to afford the title compound. HPLC: $R_T$=11.61 min. MS (ESI−): mass calcd. for $C_{23}H_{17}Cl_3N_4O_5S_2$, 597.97; m/z found, 597/599 [M−H]−. $^1$H NMR (500 MHz, CDCl$_3$): 11.20 (s, 1H), 8.36 (d, J=6.3, 1H), 8.23 (d, J=8.7, 1H), 7.87 (s, 1H), 7.74-7.71 (m, 1H), 7.27-7.25 (m, 3H), 6.98 (d, J=8.3, 2H), 6.38 (d, J=7.3, 1H), 4.96-4.92 (m, 1H), 3.82 (s, 3H), 3.23-3.14 (m, 2H).

Example 68

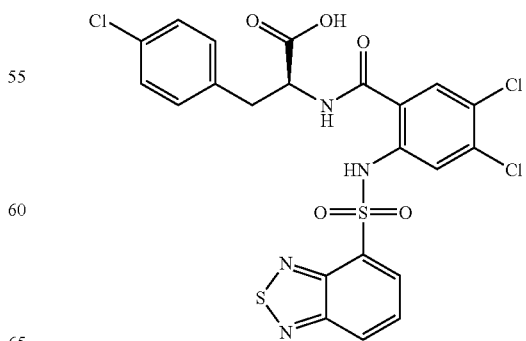

(S)-2-[2-(Benzo[1,2,5]thiadiazole-4-sulfonylamino)-4,5-dichloro-benzoylamino]-3-(4-chloro-phenyl)-propionic acid (S)-2-[2-(Benzo[1,2,5]thiadiazole-4-sulfonylamino)-4,5-dichloro-benzoylamino]-3-(4-chloro-phenyl)-propionic acid methyl ester was hydrolyzed as in EXAMPLE 2, Part E, to afford the title compound. HPLC: $R_T$=10.34 min. MS (ESI−): mass calcd. for $C_{22}H_{15}Cl_3N_4O_5S_2$, 583.95; m/z found, 583/585 [M−H]$^−$. $^1$H NMR (500 MHz, CDCl$_3$): 11.07 (s, 1H), 8.34 (d, J=7.9, 1H), 8.22 (d, J=8.8, 1H), 7.83 (s, 1H), 7.74-7.71 (m, 1H), 7.28-7.24 (m, 3H), 7.07 (d, J=8.3, 2H), 6.38 (d, J=7.2, 1H), 5.01-4.97 (m, 1H), 3.30 (dd, J=14.2, 5.7, 1H), 3.21 (dd, J=14.2, 5.8, 1H).

Examples 69-93 were prepared as described in the preceding examples. Satisfactory analytical data was obtained for each compound.

Example 69

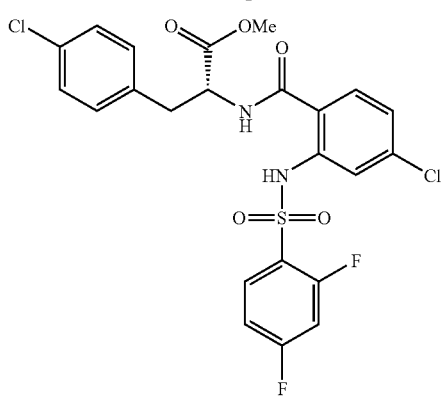

(R)-2-[4-Chloro-2-(2,4-difluoro-benzenesulfonylamino)-benzoylamino]-3-(4-chloro-phenyl)-propionic acid methyl ester MS (ESI−): mass calcd. for $C_{23}H_{18}Cl_2F_2N_2O_5S$, 542.03; m/z found, 541/543 [M−H]$^−$.

Example 70

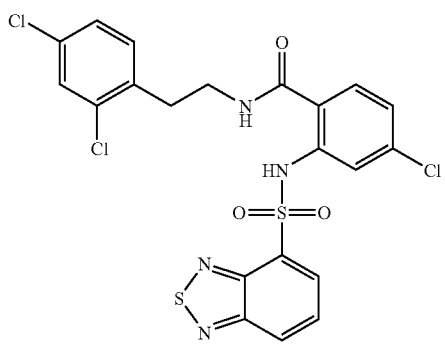

2-(Benzo[1,2,5]thiadiazole-4-sulfonylamino)-4-chloro-N-[2-(2,4-dichloro-phenyl)-ethyl]-benzamide MS (ESI−): mass calcd. for $C_{21}H_{15}Cl_3N_4O_3S_2$, 539.97; m/z found, 539/541 [M−H]$^−$.

Example 71

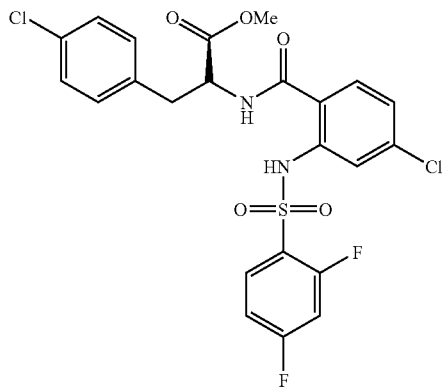

(S)-2-[4-Chloro-2-(2,4-difluoro-benzenesulfonylamino)-benzoylamino]-3-(4-chloro-phenyl)-propionic acid methyl ester MS (ESI−): mass calcd. for $C_{23}H_{18}Cl_2F_2N_2O_5S$, 542.03; m/z found, 541/543 [M−H]$^−$.

Example 72

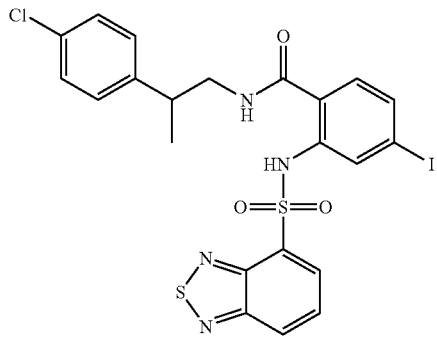

2-(Benzo[1,2,5]thiadiazole-4-sulfonylamino)-N-[2-(4-chloro-phenyl)-propyl]-4-iodo-benzamide MS (ESI−): mass calcd. for $C_{22}H_{18}ClIN_4O_3S_2$, 611.96; m/z found, 611/613 [M−H]$^−$.

Example 73

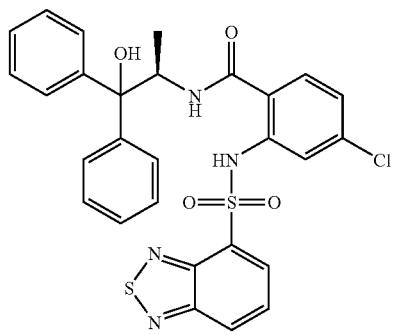

(R)-2-(Benzo[1,2,5]thiadiazole-4-sulfonylamino)-4-chloro-N-(2-hydroxy-1-methyl-2,2-diphenyl-ethyl)-benzamide MS (ESI−): mass calcd. for $C_{28}H_{23}ClN_4O_4S_2$, 578.08; m/z found, 577/579 [M−H]−.

Example 74

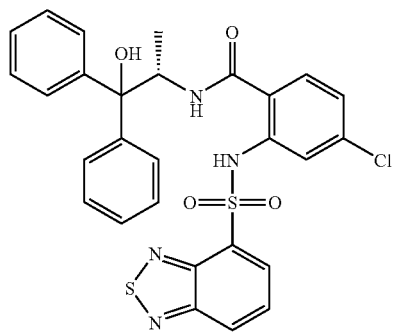

(S)-2-(Benzo[1,2,5]thiadiazole-4-sulfonylamino)-4-chloro-N-(2-hydroxy-1-methyl-2,2-diphenyl-ethyl)-benzamide MS (ESI−): mass calcd. for $C_{28}H_{23}ClN_4O_4S_2$, 578.08; m/z found, 577/579 [M−H]−.

Example 75

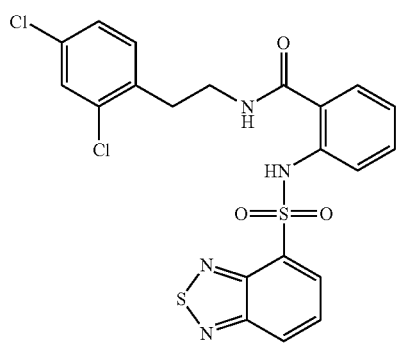

2-(Benzo[1,2,5]thiadiazole-4-sulfonylamino)-N-[2-(2,4-dichloro-phenyl)-ethyl]-benzamide MS (ESI−): mass calcd. for $C_{21}H_{16}Cl_2N_4O_3S_2$, 506.00; m/z found, 505/507 [M−H]−.

Exmple 76

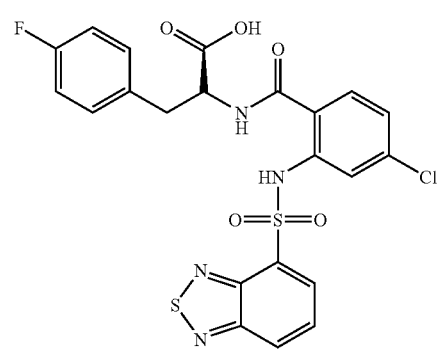

(S)-2-[2-(Benzo[1,2,5]thiadiazole-4-sulfonylamino)-4-chloro-benzoylamino]-3-(4-fluoro-phenyl)-propionic acid MS (ESI−): mass calcd. for $C_{22}H_{16}ClFN_4O_5S_2$, 534.02; m/z found, 533/535 [M−H]−.

Example 77

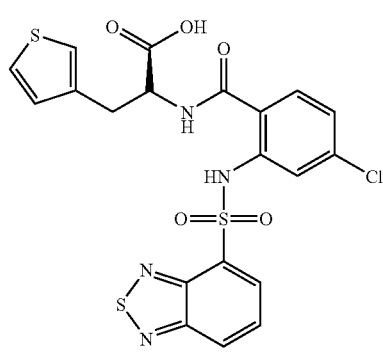

91

(S)-2-[2-(Benzo[1,2,5]thiadiazole-4-sulfonylamino)-4-chloro-benzoylamino]-3-thiophen-3-yl-propionic acid MS (ESI−): mass calcd. for $C_{20}H_{15}ClN_4O_5S_3$, 521.99; m/z found, 521/523 [M−H]−.

Example 78

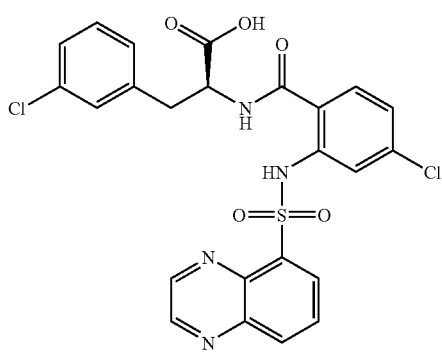

(S)-3-(3-Chloro-phenyl)-2-[4-chloro-2-(quinoxaline-5-sulfonylamino)-benzoylamino]-propionic acid MS (ESI−): mass calcd. for $C_{24}H_{18}Cl_2N_4O_5S$, 544.04; m/z found, 543/545 [M−H]−.

Example 79

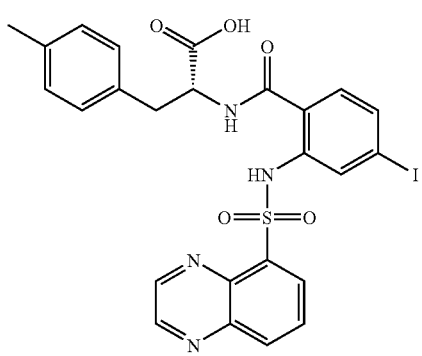

92

(S)-2-[4-Iodo-2-(quinoxaline-5-sulfonylamino)-benzoylamino]-3-p-tolyl-propionic acid MS (ESI−): mass calcd. for $C_{25}H_{21}IN_4O_5S$, 616.03; m/z found, 615 [M−H]−.

Example 80

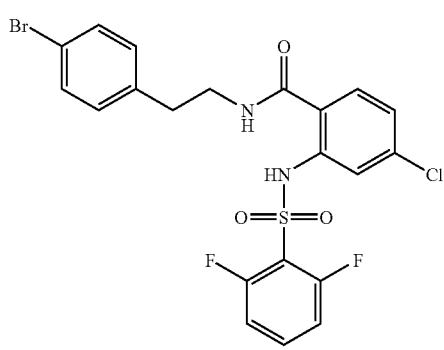

N-[2-(4-Bromo-phenyl)-ethyl]-4-chloro-2-(2,6-difluoro-benzenesulfonylamino)-benzamide MS (ESI−): mass calcd. for $C_{21}H_{16}BrClF_2N_2O_3S$, 527.97; m/z found, 527/529 [M−H]−.

Example 81

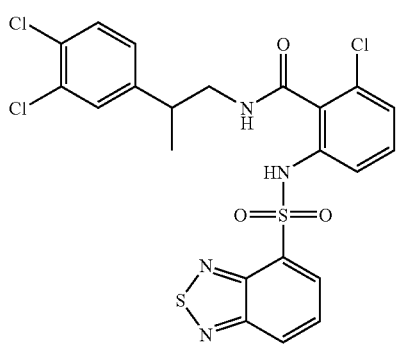

2-(Benzo[1,2,5]thiadiazole-4-sulfonylamino)-6-chloro-N-[2-(3,4-dichloro-phenyl)-propyl]-benzamide MS (ESI−): mass calcd. for $C_{22}H_{17}Cl_3N_4O_3S_2$, 553.98; m/z found, 553/555 [M−H]$^-$.

Example 82

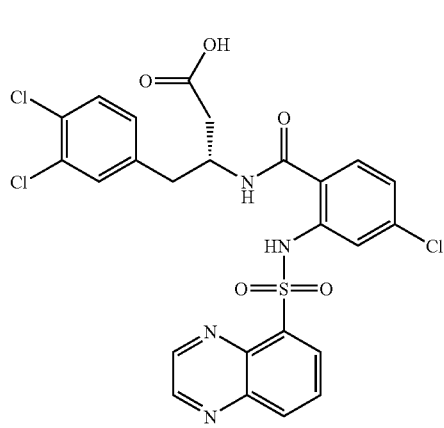

(R)-3-[4-Chloro-2-(quinoxaline-5-sulfonylamino)-benzoylamino]-4-(3,4-dichloro-phenyl)-butyric acid MS (ESI−): mass calcd. for $C_{25}H_{19}Cl_3N_4O_5S$, 592.01; m/z found, 591/593 [M−H]$^-$.

Example 83

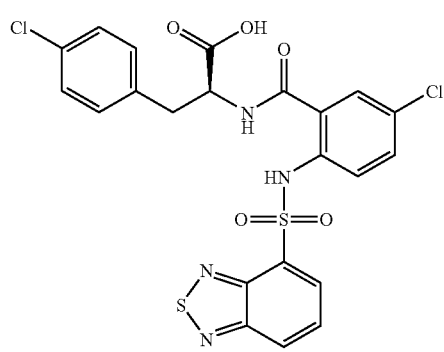

(S)-2-[2-(Benzo[1,2,5]thiadiazole-4-sulfonylamino)-5-chloro-benzoylamino]-3-(4-chloro-phenyl)-propionic acid MS (ESI−): mass calcd. for $C_{22}H_{16}Cl_2N_4O_5S_2$, 549.99; m/z found, 549/551 [M−H]$^-$.

Example 84

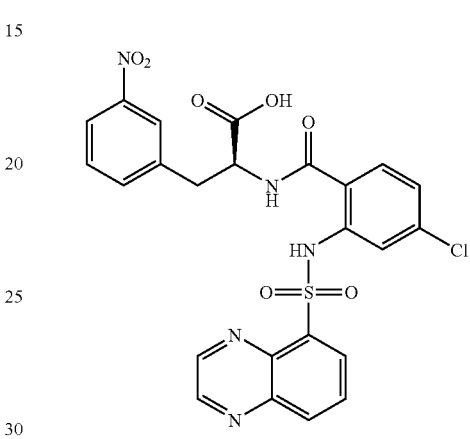

(S)-2-[4-Chloro-2-(quinoxaline-5-sulfonylamino)-benzoylamino]-3-(3-nitro-phenyl)-propionic acid MS (ESI−): mass calcd. for $C_{24}H_{18}ClN_5O_7S$, 555.06; m/z found, 554/556 [M−H]$^-$.

Example 85

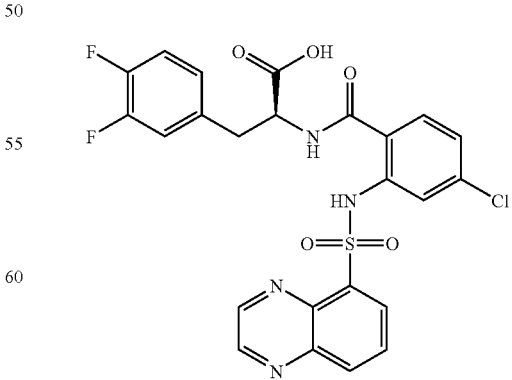

(S)-2-[4-Chloro-2-(quinoxaline-5-sulfonylamino)-benzoylamino]-3-(3,4-difluoro-phenyl)-propionic acid MS (ESI−): mass calcd. for $C_{24}H_{17}ClF_2N_4O_5S$, 546.06; m/z found, 545/547 [M−H]−.

Example 86

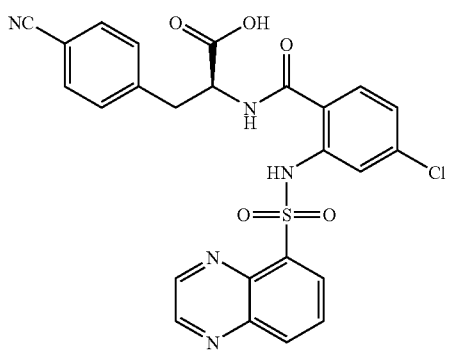

(S)-2-[4-Chloro-2-(quinoxaline-5-sulfonylamino)-benzoylamino]-3-(4-cyano-phenyl)-propionic acid MS (ESI−): mass calcd. for $C_{25}H_{18}ClN_5O_5S$, 535.07; m/z found, 534/536 [M−H]−.

Example 87

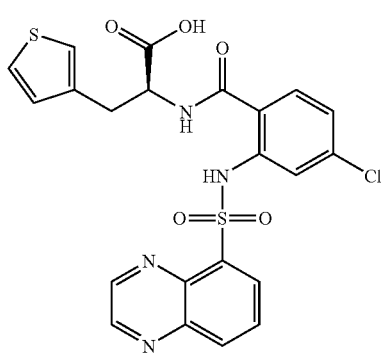

(S)-2-[4-Chloro-2-(quinoxaline-5-sulfonylamino)-benzoylamino]-3-thiophen-3-yl-propionic acid MS (ESI−): mass calcd. for $C_{22}H_{17}ClN_4O_5S_2$, 516.03; m/z found, 515/517 [M−H]−.

Example 88

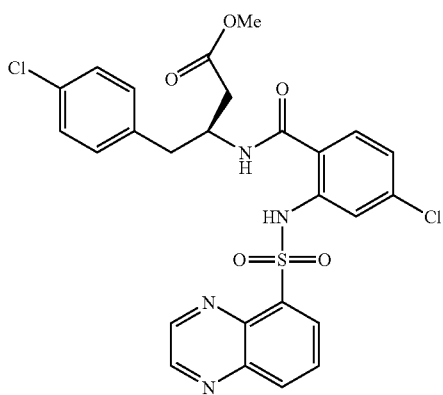

(S)-4-(4-Chloro-phenyl)-3-[4-chloro-2-(quinoxaline-5-sulfonylamino)-benzoylamino]-butyric acid methyl ester MS (ESI+): mass calcd. for $C_{26}H_{22}Cl_2N_4O_5S$, 572.07; m/z found, 573/575 [M+H]+, 595/597 [M+Na]+.

Example 89

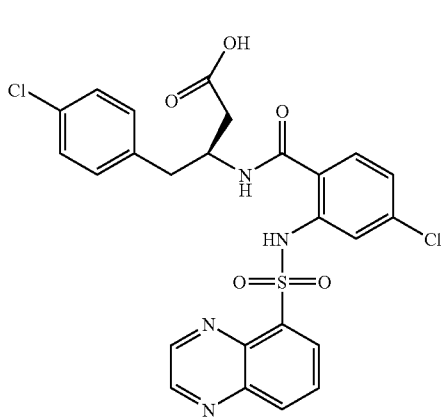

(S)-4-(4-Chloro-phenyl)-3-[4-chloro-2-(quinoxaline-5-sulfonylamino)-benzoylamino]-butyric acid MS (ESI−): mass calcd. for $C_{25}H_{20}Cl_2N_4O_5S$, 558.05; m/z found, 557/559 [M−H]$^-$.

Example 90

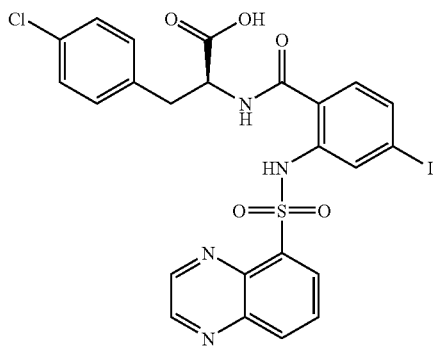

(S)-3-(4-Chloro-phenyl)-2-[4-iodo-2-(quinoxaline-5-sulfonylamino)-benzoylamino]-propionic acid MS (ESI−): mass calcd. for $C_{24}H_{18}ClIN_4O_5S$, 635.97; m/z found, 635/637 [M−H]$^-$.

Example 91

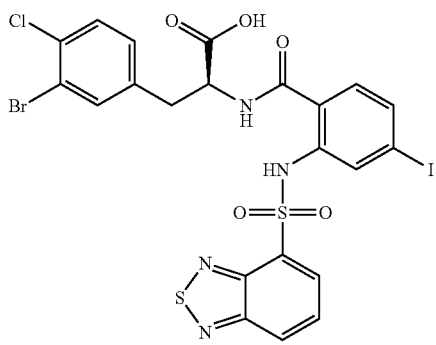

(S)-2-[2-(Benzo[1,2,5]thiadiazole-4-sulfonylamino)-4-iodo-benzoylamino]-3-(3-bromo-4-chloro-phenyl)-propionic acid HPLC: $R_T$=10.22 min. MS (ESI−): mass calcd. for $C_{22}H_{15}BrClIN_4O_5S_2$, 721.77; m/z found, 719/721 [M−H]$^-$. $^1$H NMR (500 MHz, CDCl$_3$): 11.09 (s, 1H), 8.31 (d, J=7.0, 1H), 8.19 (d, J=8.8, 1H), 8.02 (s, 1H), 7.71 (dd, J=8.7, 7.1, 1H), 7.39 (d, J=1.7, 1H), 7.34 (d, J=8.2, 1H), 7.31-7.25 (m, 1H), 7.02 (dd, J=8.2, 1.5, 1H), 6.89 (d, J=8.3, 1H), 6.50 (br s, 1H), 4.95 (q, J=5.8, 1H), 3.32-3.13 (m, 2H).

Example 92

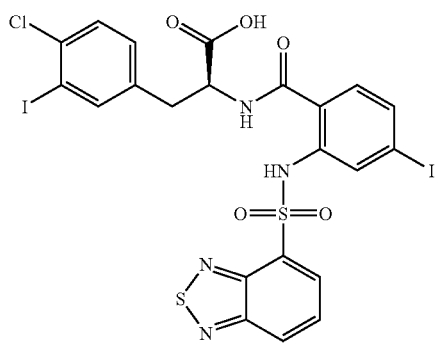

(S)-2-[2-(Benzo[1,2,5]thiadiazole-4-sulfonylamino)-4-iodo-benzoylamino]-3-(4-chloro-3-iodo-phenyl)-propionic acid HPLC: $R_T$=10.24 min. MS (ESI−): mass calcd. for $C_{22}H_{15}ClI_2N_4O_5S_2$, 768.77; m/z found, 767/769 [M−H]$^-$. $^1$H NMR (400 MHz, CDCl$_3$): 11.16 (s, 1H), 8.35 (d, J=6.9, 1H), 8.22 (d, J=8.8, 1H), 8.10-8.06 (m, 1H), 7.73 (dd, J=8.6, 7.3, 1H), 7.65-7.63 (m, 1H), 7.38-7.30 (m, 2H), 7.10-7.05 (m, 1H), 6.92 (d, J=8.3, 1H), 6.43 (d, J=7.2, 1H), 4.95 (q, J=5.5, 1H), 3.30-3.12 (m, 2H).

Example 93

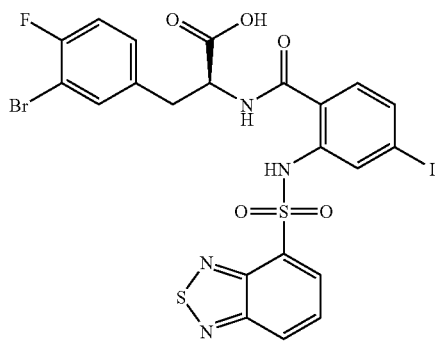

(S)-2-[2-(Benzo[1,2,5]thiadiazole-4-sulfonylamino)-4-iodo-benzoylamino]-3-(3-bromo-4-fluoro-phenyl)-propionic acid HPLC: $R_T$=10.92 min. MS (ESI−): mass calcd. for $C_{22}H_{15}BrFIN_4O_5S_2$, 705.32; m/z found, 703/705 [M−H]$^-$. $^1$H NMR (500 MHz, CDCl$_3$): 11.16 (s, 1H), 8.34 (dd, J=7.0, 0.9, 1H), 8.20 (dd, J=8.8, 0.9, 1H), 8.04 (d, J=1.5, 1H), 7.72 (dd, J=8.8, 7.1, 1H), 7.32 (dd, J=6.5, 1.8, 1H), 7.29 (dd, J=8.2, 1.6, 1H), 7.09-6.99 (m, 2H), 6.89 (d, J=8.3, 1H), 6.45 (d, J=7.1, 1H), 4.96 (q, J=5.7, 1H), 3.31-3.14 (m, 2H).

Example 94

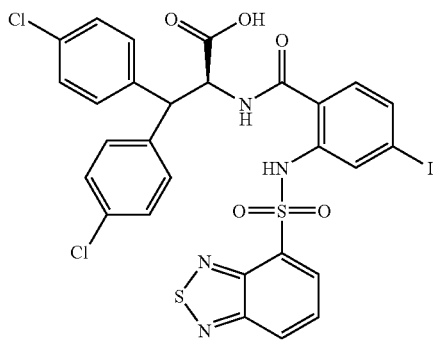

(S)-2-[2-(Benzo[1,2,5]thiadiazole-4-sulfonylamino)-4-iodo-benzoylamino]-3,3-bis-(4-chloro-phenyl)-propionic acid A. (S)-2-[2-(Benzo[1,2,5]thiadiazole-4-sulfonylamino)-4-iodo-benzoylamino]-3,3-bis-(4-chloro-phenyl)-propionic acid methyl ester The title compound (49 mg, 84%) was prepared from 2-(benzo[1,2,5]thiadiazole-4-sulfonylamino)-4-iodobenzoic acid (EXAMPLE 101, Part D) and (S)-2-amino-3,3-bis-(4-chloro-phenyl)-propionic acid methyl ester (EXAMPLE 106, Part H) as in Example 1, Part C. $^1$H NMR (500 MHz, CDCl$_3$): 11.16 (s, 1H), 8.36 (dd, J=7.0, 1.0, 1H), 8.23 (dd, J=8.8, 1.0, 1H), 8.03 (d, J=1.6, 1H), 7.72 (dd, J=8.8, 7.1, 1H), 7.32-7.27 (m, 4H), 7.24 (dd, J=8.2, 1.6, 1H), 7.21-7.15 (m, 4H), 6.71 (d, J=8.3, 1H), 6.22 (br d, J=8.8, 1H), 5.48 (t, J=8.5, 1H), 4.48 (d, J=8.3, 1H), 3.62 (s, 3H).

B. (S)-2-[2-(Benzo[1,2,5]thiadiazole-4-sulfonylamino)-4-iodo-benzoylamino]-3,3-bis-(4-chloro-phenyl)-propionic acid A mixture of (S)-2-[2-(benzo[1,2,5]thiadiazole-4-sulfonylamino)-4-iodo-benzoylamino]-3,3-bis-(4-chloro-phenyl)-propionic acid methyl ester (49 mg, 0.064 mmol), THF (2 mL), and LiOH (1 M in water, 1 mL) was stirred vigorously overnight at rt. The mixture was acidified with conc. HCl (4 drops), diluted with THF to 3.5 mL, and purified by preparative reverse phase HPLC to provide 37 mg (77%) of the acid as a white solid. HPLC: $R_T$=10.62 min. MS (ESI−): mass calcd. for $C_{28}H_{19}Cl_2IN_4O_5S_2$, 753.42; m/z found, 751/753 [M−H]$^-$. $^1$H NMR (500 MHz, MeOD): 8.32 (dd, J=7.1, 0.9, 1H), 8.24 (dd, J=8.8, 0.8, 1H), 7.95 (d, J=1.5, 1H), 7.76 (dd, J=8.8, 7.1, 1H), 7.38-7.21 (m, 9H), 6.72 (d, J=8.3, 1H), 5.37 (d, J=11.5, 1H), 4.50 (d, J=11.5, 1H).

Example 95

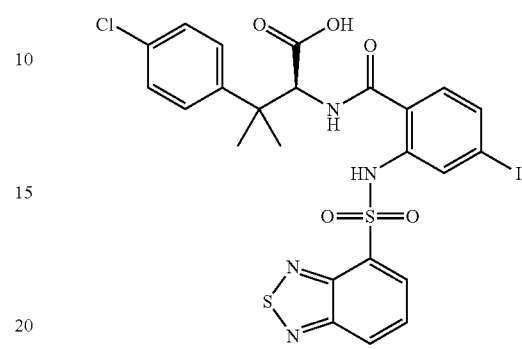

(S)-2-[2-(Benzo[1,2,5]thiadiazole-4-sulfonylamino)-4-iodo-benzoylamino]-3-(4-chloro-phenyl)-3-methyl-butyric acid A. (S)-2-[2-(Benzo[1,2,5]thiadiazole-4-sulfonylamino)-4-iodo-benzoylamino]-3-(4-chloro-phenyl)-3-methyl-butyric acid methyl ester The title compound (61 mg, 90%) was prepared from 2-(benzo[1,2,5]thiadiazole-4-sulfonylamino)-4-iodobenzoic acid (EXAMPLE 101, Part D) and (S)-2-amino-3-(4-chloro-phenyl)-3-methyl-butyric acid methyl ester (EXAMPLE 107, Part F) as in Example 94, Part A. $^1$H NMR (500 MHz, CDCl$_3$): 11.26 (s, 1H), 8.36 (dd, J=7.0, 1.0, 1H), 8.21 (dd, J=8.8, 1.0, 1H), 8.07 (d, J=1.6, 1H), 7.72 (dd, J=8.8, 7.0, 1H), 7.35-7.25 (m, 5H), 6.89 (d, J=8.3, 1H), 6.32 (br d, J=9.2, 1H), 4.97 (d, J=9.0, 1H), 3.64 (s, 3H), 1.45 (s, 3H), 1.40 (s, 3H).

B. (S)-2-[2-(Benzo[1,2,5]thiadiazole-4-sulfonylamino)-4-iodo-benzoylamino]-3-(4-chloro-phenyl)-3-methyl-butyric acid The title compound (22 mg, 37%) was prepared as in Example 94, Part B, along with 27 mg (44%) of the starting methyl ester. HPLC: $R_T$=10.30 min. MS (ESI−): mass calcd. for $C_{24}H_{20}ClIN_4O_5S_2$, 670.93; m/z found, 669/671 [M−H]$^-$. $^1$H NMR (500 MHz, MeOD): 8.27 (dd, J=7.1, 0.7, 1H), 8.23 (dd, J=8.8, 0.7, 1H), 7.96 (d, J=1.5, 1H), 7.75 (dd, J=8.8, 7.1, 1H), 7.41-7.37 (m, 2H), 7.31 (dd, J=8.2, 1.6, 1H), 7.29-7.27 (m, 2H), 6.89 (d, J=8.2, 1H), 4.94 (s, 1H), 1.48 (s, 3H), 1.41 (s, 3H).

The compounds in Examples 96-98 may be prepared using methods analogous to those described in the preceding and subsequent examples.

Example 96

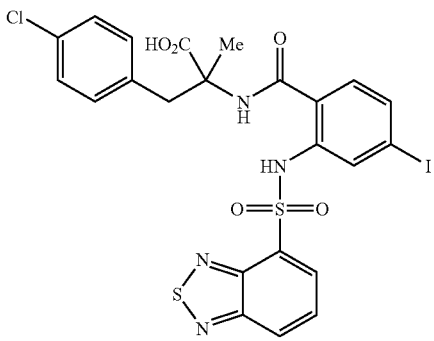

2-[2-(Benzo[1,2,5]thiadiazole-4-sulfonylamino)-4-iodo-benzoylamino]-3-(4-chloro-phenyl)-2-methyl-propionic acid

Example 97

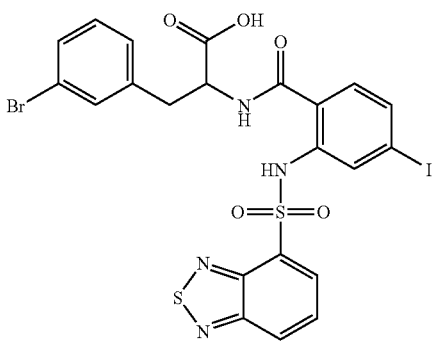

2-[2-(Benzo[1,2,5]thiadiazole-4-sulfonylamino)-4-iodo-benzoylamino]-3-(3-bromo-phenyl)-propionic acid

Example 98

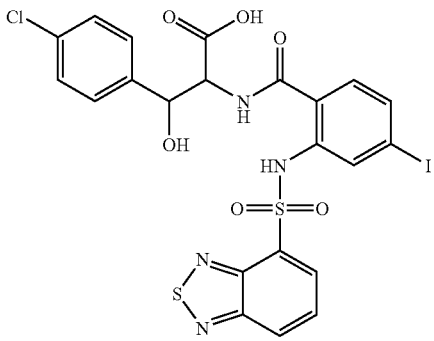

2-[2-(Benzo[1,2,5]thiadiazole-4-sulfonylamino)-4-iodo-benzoylamino]-3-(4-chloro-phenyl)-3-hydroxy-propionic acid

Example 99

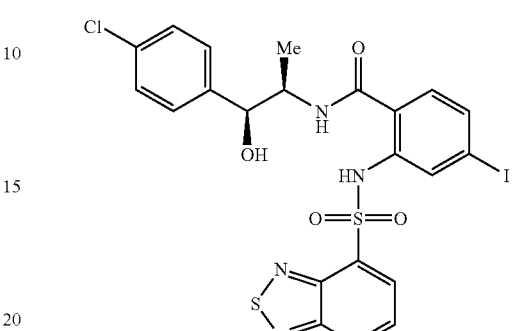

2-(Benzo[1,2,5]thiadiazole-4-sulfonylamino)-N-[(2S,1R)-2-(4-chloro-phenyl)-2-hydroxy-1-methyl-ethyl]-4-iodo-benzamide

A. 4-(S)-Benzyl-3-[(2R,3R)-3-(4-chloro-phenyl)-3-hydroxy-2-methyl-propionyl]-oxazolidin-2-one The title compound (1.32 g, 80%) was prepared from 4-(S)-benzyl-3-propionyl-oxazolidin-2-one and 4-chlorobenzaldehyde as in Example 55, Part B. $^1$H NMR (400 MHz, CDCl$_3$): 7.37-7.26 (m, 7H), 7.23-7.17 (m, 2H), 5.12-5.08 (m, 1H), 4.69-4.62 (m, 1H), 4.22-4.13 (m, 2H), 4.03 (dq, J=7.0, 3.6, 1H), 3.25 (dd, J=13.4, 3.3, 1H), 3.20 (d, J=2.5, 1H), 2.79 (dd, J=13.4, 9.4, 1H), 1.18 (d, J=7.0, 3H).

B. (2R,3R)-3-(4-Chloro-phenyl)-3-hydroxy-2-methyl-propionic acid

The title compound (0.76 g, 100%) was prepared as in Example 55, Part C. $^1$H NMR (400 MHz, CDCl$_3$): 7.36-7.32 (m, 2H), 7.32-7.28 (m, 2H), 5.16 (d, J=3.9, 1H), 2.81 (dq, J=7.2, 3.9, 1H), 1.15 (d, J=7.2, 3H).

C. (2R,3R)-3-(4-Chloro-phenyl)-3-(tert-butyl-dimethyl-silanyloxy)-2-methyl-propionic acid The title compound was prepared as in Example 55, Part D. Purification by flash chromatography (EtOAc/hexanes) provided 1.06 g (91%) of the desired silylated acid as a colorless oil. $^1$H NMR (400 MHz, CDCl$_3$): 7.32-7.27 (m, 2H), 7.27-7.22 (m, 2H), 5.01 (d, J=5.3, 1H), 2.70 (dq, J=7.2, 5.6, 1H), 1.11 (d, J=7.2, 3H), 0.88 (s, 9H), 0.03 (s, 3H), −0.18 (s, 3H).

D. (1R,2S)-[2-(4-Chloro-phenyl)-2-(tert-butyl-dimethyl-silanyloxy)-1-methyl-ethyl]-carbamic acid tert-butyl ester The title compound (354 mg, 31%) was prepared as in Example 55, Part E. $^1$H NMR (400 MHz, CDCl$_3$; rotameric broadening): 7.28 (s, 4H), 4.90 (br s, 1H), 4.60 (br d, J=8.0, 1H), 3.77-3.65 (m, 1H), 1.46 (s, 9H), 0.94 (s, 9H), 0.88 (d, J=6.8, 3H), 0.06 (s, 3H), −0.13 (s, 3H).

E. (1S,2R)-2-Amino-1-(4-chloro-phenyl)-propan-1-ol hydrochloride salt

The title compound (195 mg, 100%) was prepared as in Example 55, Part F. MS (ESI+): mass calcd. for $C_9H_{12}BrNO$, 229.01; m/z found, 230, 232 [M+H]$^+$. $^1$H NMR (400 MHz, CD$_3$OD): 7.43-7.37 (m, 4H), 4.91 (d, J=3.4, 1H), 3.50 (dq, J=6.8, 3.5, 1H), 1.07 (d, J=6.8, 3H).

F. 2-(Benzo[1,2,5]thiadiazole-4-sulfonylamino)-N-[(2S,1R)-2-(4-chloro-phenyl)-2-hydroxy-1-methyl-ethyl]-4-iodo-benzamide.

The title compound (42 mg, 67%) was obtained from 2-(benzo[1,2,5]thiadiazole-4-sulfonylamino)-4-iodobenzoic acid (EXAMPLE 101, Part D) and (1S,2R)-2-amino-1-(4-chloro-phenyl)-propan-1-ol hydrochloride salt as in Example 1, Part C. HPLC: R$_T$=10.13 min. MS (ESI–): mass calcd. for $C_{22}H_{18}ClIN_4O_4S_2$, 628.89; m/z found, 627/629 [M–H]$^-$. $^1$H NMR (500 MHz, CDCl$_3$): 11.49 (s, 1H), 8.37 (dd, J=7.0, 0.8, 1H), 8.23 (dd, J=8.8, 0.8, 1H), 8.07 (d, J=1.5, 1H), 7.73 (dd, J=8.8, 7.1, 1H), 7.37-7.27 (m, 5H), 6.98 (d, J=8.3, 1H), 6.20 (d, J=8.1, 1H), 4.95 (d, J=2.7, 1H), 4.42-4.38 (m, 1H), 2.65 (s, 1H), 1.03 (d, J=6.9, 1H).

Example 100

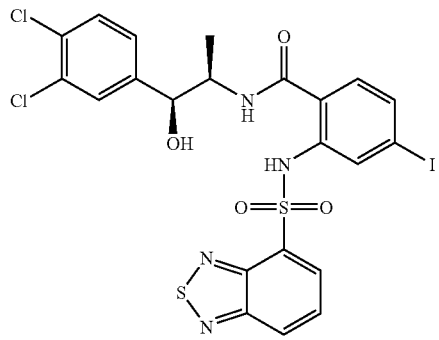

2-(Benzo[1,2,5]thiadiazole-4-sulfonylamino)-N-[2-(3,4-dichloro-phenyl)-2-hydroxy-1-methyl-ethyl]-4-iodo-benzamide The title compound may be prepared using methods described in the preceding and subsequent examples.

Example 101

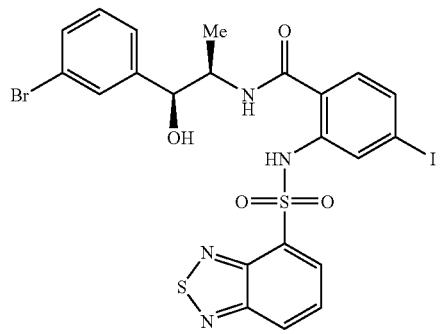

2-(Benzo[1,2,5]thiadiazole-4-sulfonylamino)-N-[(2S,1R)-2-(3-bromo-phenyl)-2-hydroxy-1-methyl-ethyl]-4-iodo-benzamide

A. 4-Iodo-2-nitrobenzoic acid

4-Iodo-2-nitrotoluene (9.0 g, 34.2 mmol), KMnO$_4$ (22.0 g, 139 mmol) and water (340 mL) were heated at reflux for 5 h. The resulting brown suspension was filtered through a pad of diatomaceous earth, washing with water. The basic filtrate was acidified with conc. HCl. The resulting solids were collected by suction filtration and dried to afford 1.86 g of the acid. The mother liquor was extracted with DCM (3×), and the combined extracts were dried (Na$_2$SO$_4$) and concentrated to afford an additional 0.16 g of the benzoic acid. Total yield=2.02 g (20%). $^1$H NMR (400 MHz, CD$_3$OD): 8.13 (d, J=1.6, 1H), 8.01 (dd, J=8.1, 1.6, 1H), 7.50 (d, J=8.1, 1H).

B. Methyl 2-amino-4-iodobenzoate

The title compound (1.87 g, 91%) was prepared as in Example 20, Part B. $^1$H NMR (500 MHz, CDCl$_3$): 7.52 (d, J=8.5, 1H), 7.07 (d, J=1.6, 1H), 6.96 (dd, J=8.5, 1.6, 1H), 5.72 (br s, 2H), 3.86 (s, 3H).

C. 2-(Benzo[1,2,5]thiadiazole-4-sulfonylamino)-4-iodo-benzoic acid methyl ester The title compound (1.87 g, 68%) was prepared as in Example 20, Part C (without DMAP). MS (ESI–): mass calcd. for $C_{14}H_{10}IN_3O_4S_2$, 474.92; m/z found, 474 [M–H]$^-$. $^1$H NMR (400 MHz, CDCl$_3$): 11.26 (br s, 1H), 8.40 (dd, J=7.0, 1.0, 1H), 8.24 (dd, J=8.8, 1.0, 1H), 8.12 (d, J=1.5, 1H), 7.74 (dd, J=8.8, 7.0, 1H), 7.53 (d, J=8.5, 1H), 7.32 (dd, J=8.5, 1.5, 1H), 3.91 (s, 3H).

D. 2-(Benzo[1,2,5]thiadiazole-4-sulfonylamino)-4-iodobenzoic acid

The title compound (1.24 g, 69%) was prepared as in Example 20, Part D. $^1$H NMR (500 MHz, CDCl$_3$): 11.03 (br s, 1H), 8.34 (dd, J=7.2, 1.1, 1H), 8.19 (dd, J=8.8, 1.1, 1H), 8.09 (d, J=1.6, 1H), 7.69 (dd, J=8.8, 7.2, 1H), 7.56 (d, J=8.5, 1H), 7.30 (dd, J=8.5, 1.6, 1H).

E. 2-(Benzo[1,2,5]thiadiazole-4-sulfonylamino)-N-[(2S,1R)-2-(3-bromo-phenyl)-2-hydroxy-1-methyl-ethyl]-4-iodo-benzamide.

2-(Benzo[1,2,5]thiadiazole-4-sulfonylamino)-4-iodobenzoic acid was coupled with (1S,2R)-2-amino-1-(3-bromo-phenyl)-propan-1-ol hydrochloride salt (EXAMPLE 108, Part E) as in Example 1, Part C (11 mg, 16%). HPLC: R$_T$=10.19 min. MS (ESI–): mass calcd. for $C_{22}H_{18}BrIN_4O_4S_2$, 673.34; m/z found, 671/673 [M–H]$^-$. $^1$H NMR (500 MHz, CDCl$_3$): 11.45 (s, 1H), 8.37 (d, J=7.0, 1H), 8.23 (d, J=8.8, 1H), 8.08 (d, J=1.5, 1H), 7.73 (dd, J=8.8, 7.1, 1H), 7.55-7.53 (m, 1H), 7.47-7.43 (m, 1H), 7.33 (dd, J=8.2, 1.5, 1H), 7.31-7.21 (m, 3H), 6.99 (d, J=8.3, 1H), 6.19 (d, J=8.6, 1H), 4.95-4.94 (m, 1H), 4.44-4.40 (m, 1H), 2.60 (s, 1H), 1.03 (d, J=6.9, 3H).

The compounds in Examples 102-105 may be prepared using methods analogous to those described in the preceding and subsequent examples.

Example 102

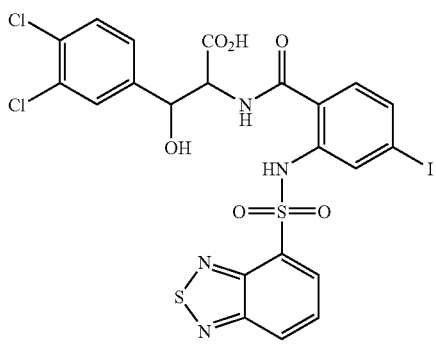

2-[2-(Benzo[1,2,5]thiadiazole-4-sulfonylamino)-4-iodo-benzoylamino]-3-(3,4-dichloro-phenyl)-3-hydroxy-propionic acid

Example 103

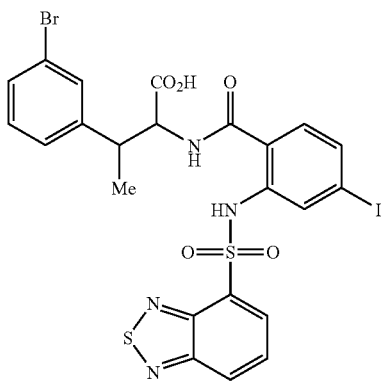

2-[2-(Benzo[1,2,5]thiadiazole-4-sulfonylamino)-4-iodo-benzoylamino]-3-(3-bromo-phenyl)-butyric acid

Example 104

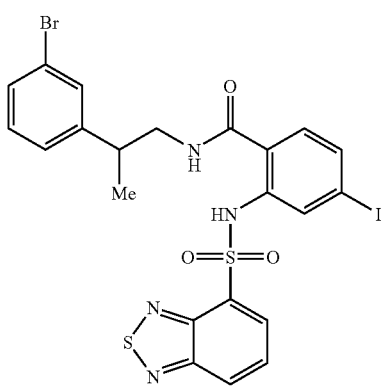

2-(Benzo[1,2,5]thiadiazole-4-sulfonylamino)-N-[2-(3-bromo-phenyl)-propyl]-4-iodo-benzamide

Example 105

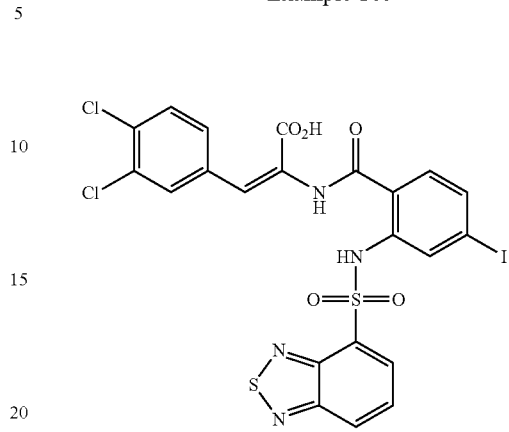

2-[2-(Benzo[1,2,5]thiadiazole-4-sulfonylamino)-4-iodo-benzoylamino]-3-(3,4-dichloro-phenyl)-acrylic acid

Example 106

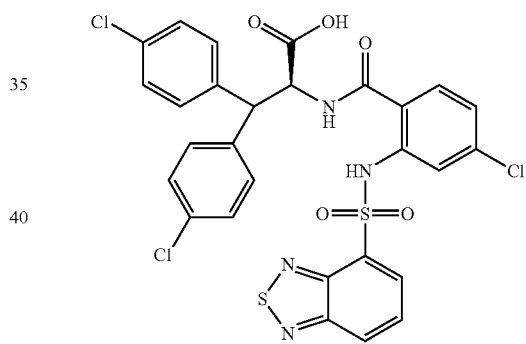

(S)-2-[2-(Benzo[1,2,5]thiadiazole-4-sulfonylamino)-4-chloro-benzoylamino]-3,3-bis-(4-chloro-phenyl)-propionic acid A. 3,3-Bis-(4-chloro-phenyl)-propionic acid To a suspension of 4-chlorocinnamic acid (10.0 g, 54.8 mmol) in chlorobenzene (75 mL) at 0° C. was added AlCl$_3$ (12.0 g, 90 mmol) in 4 portions. The mixture was stirred for 10 min at 0° C. then was warmed to 40° C. and stirred for 1 h. Crushed ice (75 g) was added carefully, followed by water (75 mL). The aqueous layer was extracted with DCM (3×). The combined organic extracts were dried (Na$_2$SO$_4$) and concentrated to provide the crude acid as a tan solid. Recrystallization from EtOH provided 7.81 g (48%) of the desired acid as a pale yellow solid. $^1$H NMR (400 MHz, CDCl$_3$): 7.31-7.22 (m, 4H), 7.14-7.07 (m, 4H), 4.47 (t, J=8.0, 1H), 3.03 (d, J=7.9, 2H).

B. 4-(S)-Benzyl-3-[3,3-bis-(4-chloro-phenyl)-propionyl]-oxazolidin-2-one

A suspension of 3,3-bis-(4-chloro-phenyl)-propionic acid (3.0 g, 10.2 mmol) in $SOCl_2$ (10 mL) was heated at reflux for 30 min. The mixture was cooled and concentrated, and the residue was azeotroped with toluene (3×) to give the acid chloride as a yellow liquid. $^1$H NMR (400 MHz, $CDCl_3$): 7.32-7.26 (m, 4H), 7.15-7.10 (m, 4H), 4.55 (t, J=7.8, 1H), 3.57 (d, J=7.8, 2H). To a stirred solution of 4-(S)-benzyl-oxazolidin-2-one (1.65 g, 9.3 mmol) in THF (46 mL) at −78° C. was added n-BuLi (1.6 M in hexanes, 6.1 mL, 9.8 mmol). After stirring 20 min at −78° C., a solution of the acid chloride (10.2 mmol) in THF (7 mL) was added rapidly via cannula. The mixture was stirred overnight with slow warming to rt and was quenched by addition of satd. aq. $NH_4Cl$. The mixture was concentrated, and the residue was diluted with water and extracted with DCM (3×). The combined organic extracts were dried ($Na_2SO_4$) and concentrated. The residue was purified by flash chromatography (EtOAc/hexanes) to give 3.83 g (91%) of the title acyl imide as a white solid. $^1$H NMR (400 MHz, $CDCl_3$): 7.33-7.25 (m, 7H), 7.25-7.19 (m, 4H), 7.10-7.05 (m, 2H), 4.66 (t, J=7.7, 1H), 4.62-4.54 (m, 1H), 4.18-4.10 (m, 2H), 3.76 (dd, J=17.0, 7.4, 1H), 3.65 (dd, J=17.0, 8.0, 1H), 3.10 (dd, J=13.5, 3.3, 1H), 2.64 (dd, J=13.4, 9.4, 1H).

C. 2,4,6-Triisopropylbenzenesulfonyl azide

To a solution of triisopropylbenzenesulfonyl chloride (6.94 g, 22.9 mmol) in acetone (115 mL) at 0° C. was added a solution of $NaN_3$ (1.64 g, 25.2 mmol) in water (10 mL). The mixture was stirred for 30 min at 0° C. and then was warmed to rt and stirred for 1 h. The mixture was concentrated, diluted with water, and extracted with DCM (3×). The combined organic extracts were dried ($Na_2SO_4$) and concentrated. The residue was purified by flash chromatography (EtOAc/hexanes) to provide 6.71 g (95%) of the desired sulfonyl azide as a white solid. $^1$H NMR (400 MHz, $CDCl_3$): 7.22 (s, 2H), 4.05 (sept, J=6.7, 2H), 2.93 (sept, J=6.9, 1H), 1.29 (d, J=6.8, 12H), 1.27 (d, J=6.9, 6H).

D. 3-[2-(S)-Azido-3,3-bis-(4-chloro-phenyl)-propionyl]-4-(S)-benzyl-oxazolidin-2-one A solution of 4-(S)-benzyl-3-[3,3-bis-(4-chloro-phenyl)-propionyl]-oxazolidin-2-one (2.0 g, 4.4 mmol) in THF (25 mL) was cooled to −78° C. and added via cannula to a solution of potassium bis(trimethylsilyl)amide (0.5 M in toluene, 9.7 mL, 4.8 mmol) in THF (15 mL) at −78° C. After 30 min at −78° C., a solution of 2,4,6-triisopropylbenzenesulfonyl azide (1.77 g, 5.7 mmol) in THF (15 mL) was cooled to −78° C. and added via cannula. After 1 min, the reaction was quenched by addition of AcOH (1.2 mL, 21 mmol). The cooling bath was removed, and the mixture was allowed to warm to rt and stir overnight. The reaction mixture was diluted with water and extracted with DCM (3×). The combined organic extracts were dried ($Na_2SO_4$) and concentrated. The residue was purified by flash chromatography (EtOAc/hexanes) to provide 1.58 g (72%) of the desired azide as a white foam. $^1$H NMR (400 MHz, $CDCl_3$): 7.38-7.15 (m, 13H), 5.94 (d, J=11.0, 1H), 4.50 (d, J=11.0, 1H), 4.34-4.25 (m, 1H), 4.08 (dd, J=9.2, 2.4, 1H), 3.76 (dd, J=8.8, 8.1, 1H), 3.22 (dd, J=13.5, 3.3, 1H), 2.77 (dd, J=13.5, 9.5, 1H).

E. (S)-2-Azido-3,3-bis-(4-chloro-phenyl)-propionic acid

To a solution of 3-[2-(S)-azido-3,3-bis-(4-chloro-phenyl)-propionyl]-4-(S)-benzyl-oxazolidin-2-one (1.53 g, 3.1 mmol) in 3:1 THF/water (60 mL) at 0° C. was added 30% aq. $H_2O_2$ (1.4 mL, 12.3 mmol) and $LiOH \cdot H_2O$ (259 mg, 6.2 mmol). The mixture was stirred for 1 h at 0° C. $Na_2SO_3$ (2.52 g, 20 mmol) was added, and the mixture was stirred for 30 min at 0° C., then warmed to rt, and stirred for 1 h. The mixture was concentrated without external heating, and the residue was diluted with water and extracted with DCM (3×). The aqueous layer was acidified with conc. HCl and extracted with EtOAc (4×). The combined EtOAc extracts were dried ($Na_2SO_4$) and concentrated to provide the desired azidoacid as a colorless solid (0.98 g, 94%). $^1$H NMR (500 MHz, $CDCl_3$): 7.33-7.24 (m, 6H), 7.21-7.18 (m, 2H), 4.52 (d, J=8.3, 1H), 4.49 (d, J=8.3, 1H).

F. (S)-2-Amino-3,3-bis-(4-chloro-phenyl)-propionic acid (S)-2-Azido-3,3-bis-(4-chloro-phenyl)-propionic acid (0.98 g, 2.9 mmol), Lindlar's catalyst (307 mg, 5 mol % Pd), and EtOAc (29 mL) was placed in a 500 mL Parr bottle. The bottle was pressurized with 50 psi of $H_2$ and shaken overnight in a Parr shaker apparatus. The mixture was diluted with MeOH, and the catalyst was removed by filtration through diatomaceous earth, rinsing with MeOH. The filtrate was concentrated to provide 0.90 g (100%) of the desired amino acid as a white solid. MS (ESI−): mass calcd. for $C_{15}H_{13}Cl_2NO_2$, 309; m/z found, 308 [M−H]$^-$. $^1$H NMR (400 MHz, $CD_3OD$): 7.41-7.22 (m, 8H), 4.46 (d, J=9.1, 1H), 4.26 (d, J=9.1, 1H).

G. (S)-2-tert-Butoxycarbonylamino-3,3-bis-(4-chloro-phenyl)-propionic acid methyl ester To a solution of (S)-2-amino-3,3-bis-(4-chloro-phenyl)-propionic acid (0.90 g, 2.9 mmol) in MeOH (20 mL) at rt was added $SOCl_2$ (2 mL) carefully via pipette. The mixture was allowed to stand for 1 h at rt and was then concentrated. $^1$H NMR indicated only partial conversion to the methyl ester. A mixture of the crude methyl ester, $Boc_2O$ (0.77 g, 3.52 mmol), and 1 M NaOH (10 mL) was stirred rapidly for 2 h. The reaction mixture was extracted with DCM (3×), and the combined organic extracts were dried ($Na_2SO_4$) and concentrated. The residue was purified by flash chromatography (EtOAc/hexanes) to provide 0.24 g (19%) of the desired N-Boc methyl ester. MS (ESI+): mass calcd. for $C_{21}H_{23}Cl_2NO_4$, 423.10; m/z found, 446 [M+Na]$^+$. $^1$H NMR (400 MHz, $CDCl_3$): 7.38-7.10 (m, 8H), 5.10-5.00 (br m, 1H), 4.81 (br d, J=9.3, 1H), 4.34 (br d, J=8.4, 1H), 3.54 (s, 3H), 1.37 (s, 9H).

H. (S)-2-Amino-3,3-bis-(4-chloro-phenyl)-propionic acid methyl ester

To a solution of (S)-2-tert-butoxycarbonylamino-3,3-bis-(4-chloro-phenyl)-propionic acid methyl ester (0.23 g, 0.54 mmol) in DCM (3 mL) at rt was added TFA (1 mL). After 2 h, the mixture was concentrated, diluted with water, and extracted with DCM (3×). The combined organic extracts were dried ($Na_2SO_4$) and concentrated to provide 100 mg (57%) of the amine as a tan viscous oil. MS (ESI+): mass calcd. for $C_{16}H_{15}Cl_2NO_2$, 323.05; m/z found, 324 [M+H]$^+$. $^1$H NMR (500 MHz, $CDCl_3$): 7.32-7.19 (m, 8H), 4.26 (d, J=8.0, 1H), 4.15 (app q, J=7.4, 1H), 3.57 (s, 3H), 1.46 (br d, J=6.6, 2H).

I. (S)-2-[2-(Benzo[1,2,5]thiadiazole-4-sulfonylamino)-4-chloro-benzoylamino]-3,3-bis-(4-chlorophenyl)-propionic acid methyl ester The title compound (48 mg, 94%) was obtained from 2-(benzo[1,2,5]thiadiazole-4-sulfonylamino)-4-chlorobenzoic acid and (S)-2-amino-3,3-bis-(4-chloro-phenyl)-propionic acid methyl ester as in Example 1, Part C. $^1$H NMR (500 MHz, CDCl$_3$): 11.28 (s, 1H), 8.37 (dd, J=7.0, 1.0, 1H), 8.22 (dd, J=8.8, 1.0, 1H), 7.72 (dd, J=8.8, 7.1, 1H), 7.68 (d, J=1.9, 1H), 7.32-7.28 (m, 4H), 7.20-7.15 (m, 4H), 6.96 (d, J=8.5, 1H), 6.87 (dd, J=8.4, 2.0, 1H), 6.21 (br d, J=8.8, 1H), 5.50 (t, J=8.5, 1H), 4.48 (d, J=8.3, 1H), 3.63 (s, 3H).

J. (S)-2-[2-(Benzo[1,2,5]thiadiazole-4-sulfonylamino)-4-chloro-benzoylamino]-3,3-bis-(4-chlorophenyl)-propionic acid.

The title compound (35 mg, 74%) was prepared as in Example 94, Part B. HPLC: R$_T$=10.54 min. MS (ESI–): mass calcd. for C$_{28}$H$_{19}$Cl$_3$N$_4$O$_5$S$_2$, 661.96; m/z found, 659/661 [M–H]$^-$. $^1$H NMR (500 MHz, MeOD): 8.36-8.34 (m, 1H), 8.26-8.23 (m, 1H), 7.79-7.75 (m, 1H), 7.62-7.61 (m, 1H), 7.39-7.26 (m, 8H), 7.00-6.98 (m, 1H), 6.88-6.86 (m, 1H), 5.41-5.38 (m, 1H), 4.53-4.50 (m, 1H).

Example 107

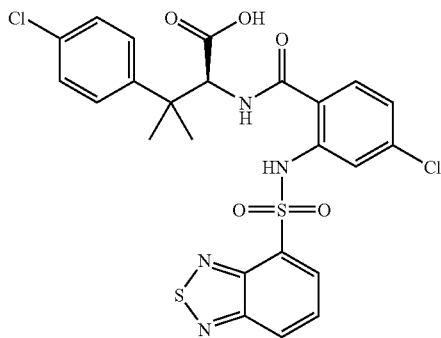

(S)-2-[2-(Benzo[1,2,5]thiadiazole-4-sulfonylamino)-4-chloro-benzoylamino]-3-(4-chloro-phenyl)-3-methyl-butyric acid A. 3-(4-Chloro-phenyl)-3-methyl-butyric acid The title compound was prepared from 3-methyl-2-butenoic acid as in Example 106, Part A. Recrystallization from EtOAc/hexanes provided 9.80 g (84%) of the desired acid as a white solid. $^1$H NMR (500 MHz, CDCl$_3$): 7.30-7.25 (m, 4H), 2.63 (s, 2H), 1.43 (s, 6H).

B. (S)-4-Benzyl-3-[3-(4-chloro-phenyl)-3-methyl-butyryl]-oxazolidin-2-one

The title compound (3.72 g, 78%) was prepared as in Example 106, Part B. $^1$H NMR (400 MHz, CDCl$_3$): 7.38-7.22 (m, 7H), 7.15-7.09 (m, 2H), 4.52-4.45 (m, 1H), 4.09-3.97 (m, 2H), 3.38 (d, J=16.0, 1H), 3.33 (d, J=16.0, 1H), 3.12 (dd, J=13.4, 3.3, 1H), 2.55 (dd, J=13.4, 9.8, 1H), 1.50 (s, 3H), 1.49 (s, 3H).

C. 3-[2-(S)-Azido-3-(4-chloro-phenyl)-3-methyl-butyryl]-4-(S)-benzyl-oxazolidin-2-one The title compound (1.60 g, 72%) was prepared as in Example 106, Part D. $^1$H NMR (400 MHz, CDCl$_3$): 7.38-7.25 (m, 7H), 7.19-7.14 (m, 2H), 5.64 (s, 1H), 4.27-4.19 (m, 1H), 4.03 (dd, J=9.0, 2.0, 1H), 3.66 (ddd, J=8.9, 7.6, 0.6, 1H), 3.22 (dd, J=13.4, 3.2, 1H), 2.73 (dd, J=13.4, 9.6, 1H), 1.55 (s, 3H), 1.53 (s, 3H).

D. (S)-2-Azido-3-(4-chloro-phenyl)-3-methyl-butyric acid

The title compound (0.89 g, 99%) was prepared as in Example 106, Part E. $^1$H NMR (400 MHz, CDCl$_3$): 7.35-7.29 (m, 4H), 4.18 (s, 1H), 1.48 (s, 6H).

E. (S)-2-Azido-3-(4-chloro-phenyl)-3-methyl-butyric acid methyl ester

A mixture of (S)-2-azido-3-(4-chloro-phenyl)-3-methyl-butyric acid (0.89 g, 3.5 mmol), powdered KHCO$_3$ (780 mg, 7.8 mmol), MeI (0.44 mL, 7.1 mmol), and DMF (7 mL) was stirred rapidly at rt overnight. The mixture was poured into water and extracted with Et$_2$O (3×). The combined organic layers were washed with water (4×), dried (MgSO$_4$), and concentrated to provide 0.90 g (96%) of the desired methyl ester as a colorless liquid. $^1$H NMR (400 MHz, CDCl$_3$): 7.34-7.28 (m, 4H), 4.10 (s, 1H), 3.64 (s, 3H), 1.46 (s, 3H), 1.43 (s, 3H).

F. (S)-2-Amino-3-(4-chloro-phenyl)-3-methyl-butyric acid methyl ester

The title compound was prepared as in Example 106, Part F. The crude residue was purified by flash chromatography (EtOAc/hexanes) to give the starting azide (0.39 g, 43%) and the desired amine as a colorless oil (0.39 g, 48%). MS (ESI+): mass calcd. for C$_{12}$H$_{16}$ClNO$_2$, 241.09; m/z found, 242 [M+H]$^+$. $^1$H NMR (400 MHz, CDCl$_3$): 7.29 (br s, 4H), 3.60 (s, 3H), 3.59 (s, 1H), 1.38 (s, 3H), 1.37 (s, 3H).

G. (S)-2-[2-(Benzo[1,2,5]thiadiazole-4-sulfonylamino)-4-chloro-benzoylamino]-3-(4-chloro-phenyl)-3-methyl-butyric acid methyl ester.

The title compound (57 mg, 97%) was obtained from 2-(benzo[1,2,5]thiadiazole-4-sulfonylamino)-4-chlorobenzoic acid (37 mg, 0.1 mmol) and (S)-2-amino-3-(4-chloro-phenyl)-3-methyl-butyric acid methyl ester (0.048 g, 0.20 mmol) as in Example 1, Part C. $^1$H NMR (500 MHz, CDCl$_3$): 11.39 (s, 1H), 8.36 (dd, J=7.1, 1.0, 1H), 8.21 (dd, J=8.8, 1.0, 1H), 7.72 (d, J=2.0, 1H), 7.71 (dd, J=8.8, 7.1, 1H), 7.34-7.26 (m, 4H), 7.14 (d, J=8.4, 1H), 6.94 (dd, J=8.4, 2.0, 1H), 6.32 (br d, J=9.0, 1H), 4.99 (d, J=9.0, 1H), 3.64 (s, 3H), 1.46 (s, 3H), 1.41 (s, 3H).

H. (S)-2-[2-(Benzo[1,2,5]thiadiazole-4-sulfonylamino)-4-chloro-benzoylamino]-3-(4-chloro-phenyl)-3-methyl-butyric acid The title compound (21 mg, 38%) was prepared as in Example 94, Part B. HPLC: R$_T$=10.19 min. MS (ESI–): mass calcd. for C$_{24}$H$_{20}$Cl$_2$N$_4$O$_5$S$_2$, 579.48; m/z found, 577/579 [M–H]$^-$. $^1$H NMR (500 MHz, MeOD): 8.29 (dd, J=7.0, 0.9, 1H), 8.23 (dd, J=8.8, 0.9, 1H), 7.74 (dd, J=8.8, 7.1, 1H), 7.62

(d, J=2.0, 1H), 7.45-7.40 (m, 2H), 7.32-7.24 (m, 2H), 7.15 (d, J=8.4, 1H), 6.95 (dd, J=8.4, 2.0, 1H), 4.96 (s, 1H), 1.49 (s, 3H), 1.42 (s, 3H).

Example 108

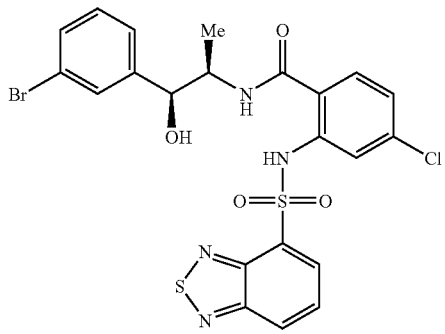

2-(Benzo[1,2,5]thiadiazole-4-sulfonylamino)-N-[(2S,1R)-2-(3-bromo-phenyl)-2-hydroxy-1-methyl-ethyl]-4-chloro-benzamide A. 4-(S)-Benzyl-3-[(2R,3R)-3-(3-bromo-phenyl)-3-hydroxy-2-methyl-propionyl]-oxazolidin-2-one The title compound (2.73 g, 76%) was prepared from 4-(S)-benzyl-3-propionyl-oxazolidin-2-one and 3-bromobenzaldehyde as in Example 55, Part B. $^1$H NMR (400 MHz, CDCl$_3$): 7.59-7.56 (m, 1H), 7.42-7.38 (m, 1H), 7.37-7.28 (m, 4H), 7.25-7.18 (m, 3H), 5.11 (app t, J=2.8, 1H), 4.73-4.64 (m, 1H), 4.22-4.16 (m, 2H), 4.02 (dq, J=7.0, 3.3, 1H), 3.27 (d, J=2.6, 1H), 3.25 (dd, J=13.4, 3.4, 1H), 2.80 (dd, J=13.4, 9.4, 1H), 1.18 (d, J=7.0, 3H).

B. (2R,3R)-3-(3-Bromo-phenyl)-3-hydroxy-2-methyl-propionic acid

The title compound (1.54 g, 91%) was prepared as in Example 55, Part C. $^1$H NMR (400 MHz, CDCl$_3$): 7.56-7.52 (m, 1H), 7.45-7.39 (m, 1H), 7.31-7.26 (m, 1H), 7.23 (dd, J=7.7, 7.7, 1H), 5.17 (d, J=3.6, 1H), 2.83 (dq, J=7.2, 3.6, 1H), 1.15 (d, J=7.2, 3H).

C. (2R,3R)-3-(3-Bromo-phenyl)-3-(tert-butyl-dimethyl-silanyloxy)-2-methyl-propionic acid The title compound (1.88 g, 85%) was prepared as in Example 55, Part D. MS (ESI−): mass calcd. for C$_{16}$H$_{25}$BrO$_3$Si, 372.08; m/z found, 371, 373 [M−H]$^−$. $^1$H NMR (400 MHz, CDCl$_3$): 7.48-7.45 (m, 1H), 7.42-7.37 (m, 1H), 7.27-7.23 (m, 1H), 7.19 (dd, J=7.8, 7.8, 1H), 5.03 (d, J=5.0, 1H), 2.73 (dq, J=7.2, 4.8, 1H), 1.11 (d, J=7.2, 3H), 0.89 (s, 9H), 0.05 (s, 3H), −0.16 (s, 3H).

D. (1R,2S)-[2-(3-Bromo-phenyl)-2-(tert-butyl-dimethyl-silanyloxy)-1-methyl-ethyl]-carbamic acid tert-butyl ester.

The title compound (0.71 g, 32%) was prepared as in Example 55, Part E. MS (ESI+): mass calcd. for C$_{20}$H$_{34}$BrNO$_3$Si, 443.15; m/z found, 466, 468 [M+Na]$^+$. $^1$H NMR (400 MHz, CDCl$_3$; rotameric broadening): 7.53-7.49 (m, 1H), 7.38-7.34 (m, 1H), 7.31-7.26 (m, 1H), 7.18 (dd, J=7.8, 7.7, 1H), 4.90 (br s, 1H), 4.61 (br d, J=8.4, 1H), 3.80-3.69 (m, 1H), 1.46 (s, 9H), 0.95 (s, 9H), 0.89 (d, J=6.0, 3H), 0.06 (s, 3H), −0.11 (s, 3H).

E. (1S,2R)-2-Amino-1-(3-bromo-phenyl)-propan-1-ol hydrochloride salt

To a solution of (1R,2S)-[2-(3-bromo-phenyl)-2-(tert-butyl-dimethyl-silanyloxy)-1-methyl-ethyl]-carbamic acid tert-butyl ester (0.71 g, 1.6 mmol) in MeOH (10 mL) was added 4 M HCl in dioxane (3 mL). After 1 h, the mixture was diluted with basic brine (prepared by dissolving a quantity of NaOH in brine), and extracted with DCM (4×). The combined organic layers were dried (Na$_2$SO$_4$) and concentrated. The residue was purified by preparative reverse phase HPLC. The TFA salt thus obtained was diluted with basic brine and extracted with DCM (4×). The combined organic layers were dried (Na$_2$SO$_4$) and concentrated. The residue was diluted with MeOH and treated with 4 M HCl in dioxane. The mixture was concentrated to provide the desired HCl salt. MS (ESI+): mass calcd. for C$_9$H$_{12}$BrNO, 229.01; m/z found, 230, 232 [M+H]$^+$. $^1$H NMR (400 MHz, CDCl$_3$; free base): 7.53-7.50 (m, 1H), 7.43-7.38 (m, 1H), 7.27-7.24 (m, 1H), 7.21 (dd, J=7.7, 7.6, 1H), 4.53 (d, J=4.0, 1H), 3.30-3.18 (m, 1H), 0.93 (d, J=6.5, 3H).

F. 2-(Benzo[1,2,5]thiadiazole-4-sulfonylamino)-N-[(2S,1R)-2-(3-bromo-phenyl)-2-hydroxy-1-methyl-ethyl]-4-chloro-benzamide.

The title compound (7 mg, 12%) was obtained from 2-(benzo[1,2,5]thiadiazole-4-sulfonylamino)-4-chlorobenzoic acid and (1S,2R)-2-amino-1-(3-bromo-phenyl)-propan-1-ol hydrochloride salt as in Example 1, Part C. HPLC: R$_T$=10.08 min. MS (ESI−): mass calcd. for C$_{22}$H$_{18}$BrClN$_4$O$_4$S$_2$, 581.89; m/z found, 579/581 [M−H]$^−$. $^1$H NMR (500 MHz, CDCl$_3$): 11.58 (s, 1H), 8.38 (dd, J=7.0, 0.9, 1H), 8.22 (dd, J=8.8, 0.9, 1H), 7.74-7.71 (m, 2H), 7.55-7.53 (m, 1H), 7.47-7.43 (m, 1H), 7.31-7.22 (m, 2H), 6.95 (dd, J=8.4, 2.0, 1H), 6.19 (d, J=8.5, 1H), 4.95 (d, J=2.7, 1H), 4.48-4.39 (m, 1H), 2.61 (s, 1H), 1.04 (d, J=6.9, 3H).

The compounds in Examples 109-114 may be prepared using methods analogous to those described in the preceding and subsequent examples.

Example 109

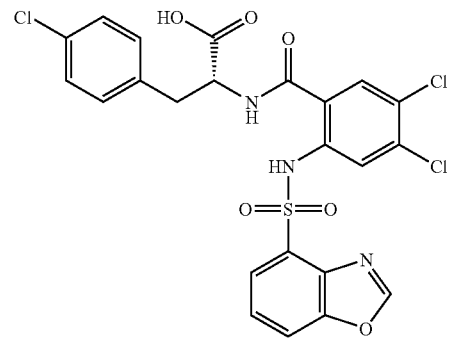

113

2-[2-(Benzooxazole-4-sulfonylamino)-4,5-dichloro-benzoylamino]-3-(4-chloro-phenyl)-propionic acid Example 110

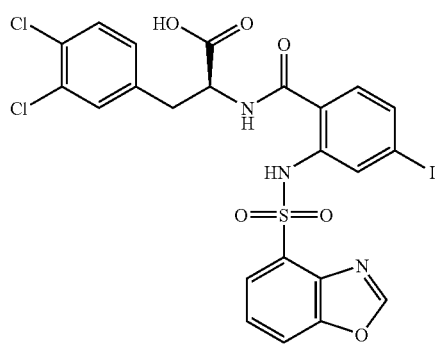

2-[2-(Benzooxazole-4-sulfonylamino)-4-iodo-benzoylamino]-3-(3,4-dichloro-phenyl)-propionic acid Example 111

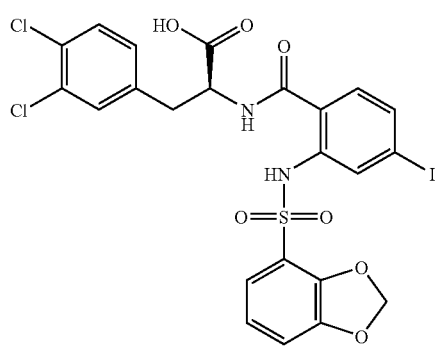

2-[2-(Benzo[1,3]dioxole-4-sulfonylamino)-4-iodo-benzoylamino]-3-(3,4-dichloro-phenyl)-propionic acid Example 112

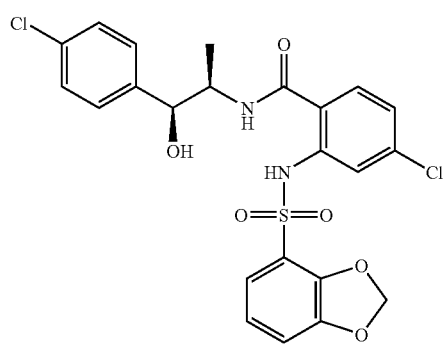

114

2-(Benzo[1,3]dioxole-4-sulfonylamino)-4-chloro-N-[2-(4-chloro-phenyl)-2-hydroxy-1-methyl-ethyl]-benzamide Example 113

2-[2-(Benzo[1,2,5]thiadiazole-4-sulfonylamino)-4,5-dichloro-benzoylamino]-3-(3-bromo-4-fluoro-phenyl)-propionic acid 5-methyl-2-oxo-[1,3]dioxol-4-ylmethyl ester Example 114

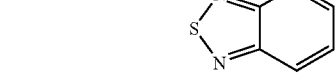

2-[2-(Benzo[1,2,5]thiadiazole-4-sulfonylamino)-4,5-dichloro-benzoylamino]-3-(3-bromo-4-fluoro-phenyl)-propionic acid pyridin-3-ylmethyl ester Example 115

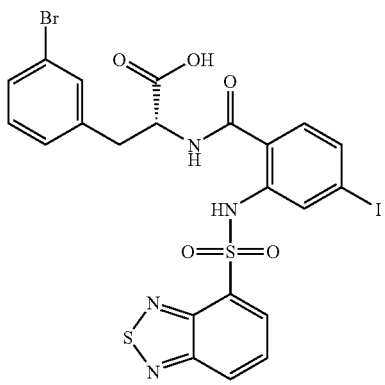

(R)-2-[2-(Benzo[1,2,5]thiadiazole-4-sulfonylamino)-4-iodo-benzoylamino]-3-(3-bromo-phenyl)-propionic acid (R)-2-[2-(Benzo[1,2,5]thiadiazole-4-sulfonylamino)-4-iodo-benzoylamino]-3-(3-bromo-phenyl)-propionic acid was prepared as in EXAMPLE 4, substituting (1S,2S)-pseudoephedrine glycinamide hydrate in Part A. HPLC: $R_T$=9.93 min. MS (ESI−): mass calcd. for $C_{22}H_{16}BrIN_4O_5S_2$, 687.33; m/z found, 685/687 [M−H]−. $^1$H NMR (400 MHz, CDCl$_3$): 11.23 (s, 1H), 8.33 (dd, J=7.1, 0.8, 1H), 8.15 (dd, J=8.8, 0.8, 1H), 8.01 (d, J=1.5, 1H), 7.70 (dd, J=8.8, 7.1, 1H), 7.37-7.35 (m, 1H), 7.30 (s, 1H), 7.23 (dd, J=8.3, 1.5, 1H), 7.16-7.06 (m, 2H), 6.92 (d, J=8.3, 1H), 6.66 (d, J=7.4, 1H), 4.99 (q, J=6.1, 1H), 3.36-3.17 (m, 2H).

Example 116

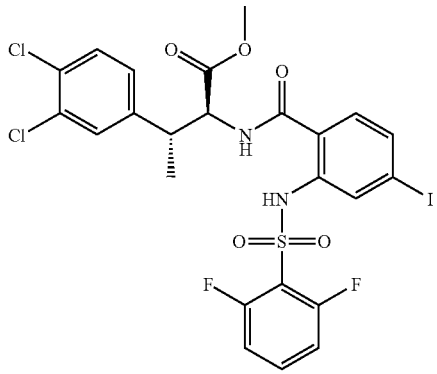

(2S,3R)-3-(3,4-Dichloro-phenyl)-2-[2-(2,6-difluoro-benzenesulfonylamino)-4-iodo-benzoylamino]-butyric acid methyl ester 2-(2,6-Difluoro-benzenesulfonylamino)-4-iodo-benzoic acid was coupled to (2S,3R)-2-amino-3-(3,4-dichloro-phenyl)-butyric acid methyl ester as in EXAMPLE 1, Part C, to afford the title compound. HPLC: $R_T$=12.39 min. MS (ESI+): mass calcd. for $C_{24}H_{19}Cl_2F_2IN_2O_5S$, 683.29; m/z found, 683/685 [M+H]+. $^1$H NMR (400 MHz, CDCl$_3$): 11.29 (s, 1H), 8.11 (d, J=1.6, 1H), 7.52-7.47 (m, 1H), 7.42 (dd, J=8.3, 1.6, 1H), 7.37 (d, J=13.9, 1H), 7.24 (d, J=2.1, 2H), 7.11 (d, J=8.3, 1H), 7.02-6.98 (m, 3H), 6.65 (d, J=8.3, 1H), 4.95-4.91 (m, 1H), 3.26 (s, 3H), 3.31 (quin, J=7.2, 1H), 1.43 (d, J=7.2, 3H).

Example 117

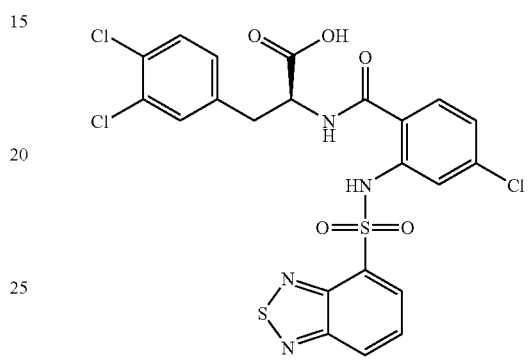

(S)-2-[2-(Benzo[1,2,5]thiadiazole-4-sulfonylamino)-4-chloro-benzoylamino]-3-(3,4-dichloro-phenyl)-propionic acid 2-(Benzo[1,2,5]thiadiazole-4-sulfonylamino)-4-chloro-benzoic acid was coupled to (S)-2-amino-3-(3,4-dichloro-phenyl)-propionic acid methyl ester hydrochloride as in EXAMPLE 1, Part C. The resulting methyl ester was hydrolyzed as in EXAMPLE 2, Part E, to afford the title compound. HPLC: $R_T$=10.98 min. MS (ESI−): mass calcd. for $C_{22}H_{15}Cl_3N_4O_5S_2$, 585.87; m/z found, 583/585 [M−H]−. $^1$H NMR (500 MHz, CDCl$_3$): 11.35 (s, 1H), 8.36 (dd, J=7.0, 0.8, 1H), 8.21 (dd, J=8.8, 0.8, 1H), 7.74-7.69 (m, 1H), 7.34 (d, J=8.2, 1H), 7.21 (d, J=2.0, 1H), 7.15 (d, J=8.4, 1H), 6.97 (dd, J=8.2, 2.0, 1H), 6.93 (dd, J=8.4, 2.0, 1H), 6.44 (d, J=7.0, 1H), 4.95-5.00 (m, 1H), 3.32-3.16 (m, 2H).

Example 118

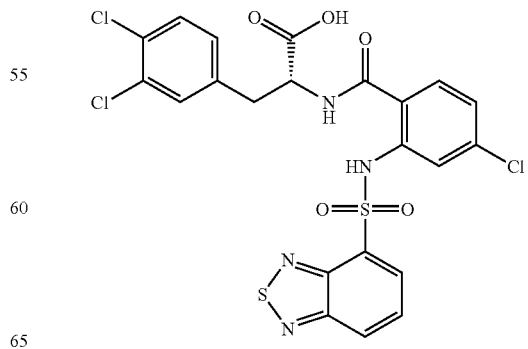

(R)-2-[2-(Benzo[1,2,5]thiadiazole-4-sulfonylamino)-4-chloro-benzoylamino]-3-(3,4-dichloro-phenyl)-propionic acid 2-(Benzo[1,2,5]thiadiazole-4-sulfonylamino)-4-chloro-benzoic acid was coupled to (R)-2-amino-3-(3,4-dichloro-phenyl)-propionic acid methyl ester hydrochloride as in EXAMPLE 1, Part C. The resulting methyl ester was hydrolyzed as in EXAMPLE 2, Part E, to afford the title compound. HPLC: $R_T$=10.97 min. MS (ESI-): mass calcd. for $C_{22}H_{15}Cl_3N_4O_5S_2$, 585.87; m/z found, 583/585 [M-H]$^-$. $^1$H NMR (500 MHz, CDCl$_3$): 11.36 (s, 1H), 8.36 (dd, J=7.0, 0.8, 1H), 8.21 (dd, J=8.8, 0.6, 1H), 7.74-7.70 (m, 2H), 7.34 (d, J=8.2, 1H), 7.21 (d, J=1.9, 1H), 7.15 (d, J=8.4, 1H), 6.97 (dd, J=8.2, 2.0, 1H), 6.93 (dd, J=8.4, 2.0, 1H), 6.44 (d, J=7.0, 1H), 4.98 (q, J=5.7, 1H), 3.32-3.15 (m, 2H).

Example 119

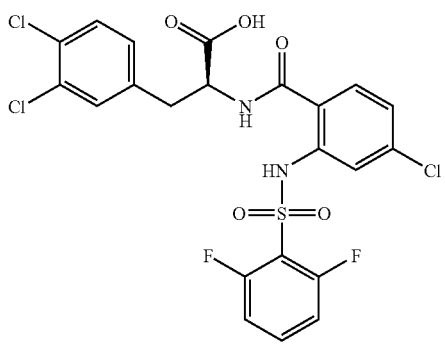

(S)-2-[4-Chloro-2-(2,6-difluoro-benzenesulfonylamino)-benzoylamino]-3-(3,4-dichloro-phenyl)-propionic acid 2-(2,6-Difluoro-benzenesulfonylamino)-4-iodo-benzoic acid was coupled to (S)-2-amino-3-(3,4-dichloro-phenyl)-propionic acid methyl ester hydrochloride as in EXAMPLE 1, Part C. The resulting methyl ester was hydrolyzed as in EXAMPLE 2, Part E, to afford the title compound. HPLC: $R_T$=11.00 min. MS (ESI-): mass calcd. for $C_{22}H_{15}Cl_3F_2N_2O_5S_2$, 563.79; m/z found, 561/563 [M-H]$^-$. $^1$H NMR (500 MHz, CDCl$_3$): 11.45 (s, 1H), 7.75 (d, J=1.9, 1H), 7.56-7.45 (m, 1H), 7.36 (d, J=8.2, 1H), 7.29-7.25 (m, 2H), 7.05-6.97 (m, 4H), 6.62 (d, J=7.0, 1H), 5.03 (q, J=5.5, 1H), 3.39-3.17 (m, 2H).

Example 120

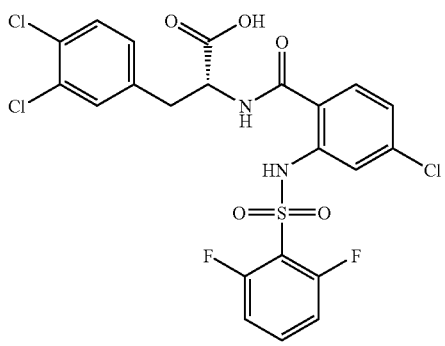

(R)-2-[4-Chloro-2-(2,6-difluoro-benzenesulfonylamino)-benzoylamino]-3-(3,4-dichloro-phenyl)-propionic acid 2-(2,6-Difluoro-benzenesulfonylamino)-4-iodo-benzoic acid was coupled to (R)-2-amino-3-(3,4-dichloro-phenyl)-propionic acid methyl ester hydrochloride as in EXAMPLE 1, Part C. The resulting methyl ester was hydrolyzed as in EXAMPLE 2, Part E, to afford the title compound. HPLC: $R_T$=11.00 min. MS (ESI-): mass calcd. for $C_{22}H_{15}Cl_3F_2N_2O_5S$, 563.79; m/z found, 561/563 [M-H]$^-$. $^1$H NMR (500 MHz, CDCl$_3$): 11.45 (s, 1H), 7.75 (d, J=1.9, 1H), 7.53-7.44 (m, 1H), 7.36 (d, J=8.2, 1H), 7.31-7.25 (m, 2H), 7.06-6.96 (m, 4H), 6.61 (d, J=6.9, 1H), 5.03 (d, J=5.6, 1H), 3.38-3.17 (m, 2H).

Example 121

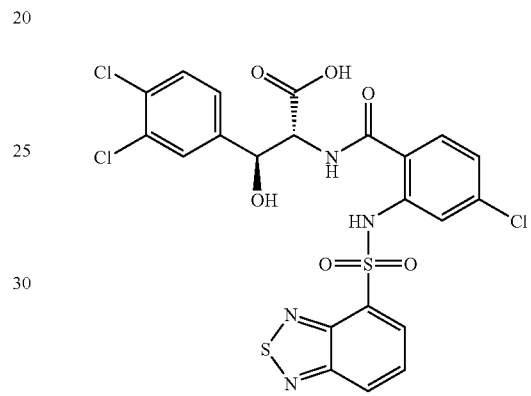

anti-2-[2-(Benzo[1,2,5]thiadiazole-4-sulfonylamino)-4-chloro-benzoylamino]-3-(3,4-dichloro-phenyl)-3-hydroxy-propionic acid A solution of 2-[2-(benzo[1,2,5]thiadiazole-4-sulfonylamino)-4-chloro-benzoylamino]-3-(3,4-dichloro-phenyl)-3-oxo-propionic acid methyl ester (35 mg, 0.057 mmol) in THF (2 mL) was cooled to −78° C. and lithium tri-sec-butyl-borohydride (L-Selectride; 1 M in THF, 86 µL, 0.086 mmol) was added. The mixture was stirred at −78° C. for 1 h and water (0.1 mL), EtOH (0.1 mL), 15% NaOH (0.1 mL), and 30% H$_2$O$_2$ (0.1 mL) were added and the solution was warmed to rt. The mixture was diluted with satd. aq. Na$_2$S$_2$O$_3$ and water and extracted with EtOAc (3×). The combined organic layers were washed with brine, dried (MgSO$_4$), and concentrated. The crude product was purified by reverse phase HPLC to provide 2-[2-(benzo[1,2,5]thiadiazole-4-sulfonylamino)-4-chloro-benzoylamino]-3-(3,4-dichloro-phenyl)-3-hydroxy-propionic acid methyl ester as a single diastereomer (20 mg, 57%). The methyl ester was hydrolyzed as in EXAMPLE 2, Part E, to provide the title compound (73%). HPLC: $R_T$=9.51 min. MS (ESI-): mass calcd. for $C_{22}H_{15}Cl_3N_4O_5S_2$, 601.87; m/z found, 599/601 [M-H]$^-$. $^1$H NMR (400 MHz, CDCl$_3$): 11.31 (s, 1H), 8.34 (dd, J=7.0, 0.6, 1H), 8.19 (dd, J=8.8, 0.6, 1H), 7.71 (dd, J=8.8, 7.1, 1H), 7.64 (d, J=1.9, 1H), 7.43 (d, J=1.7, 1H), 7.36 (d, J=8.3, 1H), 7.23 (d, J=8.5, 1H), 7.18 (dd, J=8.3, 1.8, 1H), 7.01 (d, J=7.3, 1H), 6.86 (dd, J=8.4, 1.9, 1H), 5.37 (d, J=3.7, 1H), 5.10 (dd, J=7.3, 3.9, 1H).

Example 122

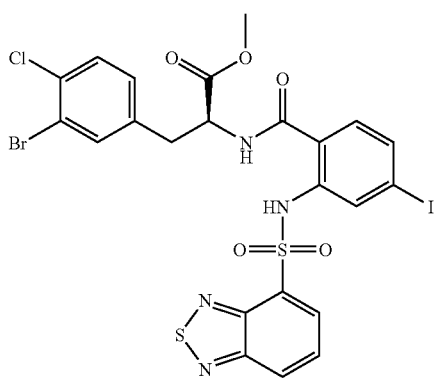

(S)-2-[2-(Benzo[1,2,5]thiadiazole-4-sulfonylamino)-4-iodo-benzoylamino]-3-(3-bromo-4-chloro-phenyl)-propionic acid methyl ester 2-(Benzo[1,2,5]thiadiazole-4-sulfonylamino)-4-iodo-benzoic acid was coupled to (S)-2-amino-3-(3-bromo-4-chloro-phenyl)-propionic acid methyl ester hydrochloride as in EXAMPLE 1, Part C, to afford the title compound. HPLC: $R_T$=10.85 min. MS (ESI+): mass calcd. for $C_{23}H_{17}BrClIN_4O_5S_2$, 735.80; m/z found, 735/737 [M+H]$^+$. $^1$H NMR (500 MHz, CDCl$_3$): 11.31 (s, 1H), 8.36 (d, J=7.1, 1H), 8.22 (d, J=8.7, 1H), 8.08 (d, J=1.4, 1H), 7.72 (dd, J=8.8, 7.1, 1H), 7.36-7.28 (m, 3H), 6.96-6.90 (m, 2H), 6.46 (d, J=7.1, 1H), 4.93 (q, J=5.5, 1H), 3.82 (s, 3H), 3.23-3.10 (m, 2H).

Example 123

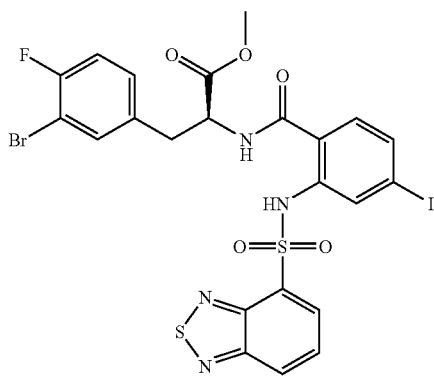

(S)-2-[2-(Benzo[1,2,5]thiadiazole-4-sulfonylamino)-4-iodo-benzoylamino]-3-(3-bromo-4-fluoro-phenyl)-propionic acid methyl ester 2-(Benzo[1,2,5]thiadiazole-4-sulfonylamino)-4-iodo-benzoic acid was coupled to (S)-2-amino-3-(3-bromo-4-fluoro-phenyl)-propionic acid methyl ester hydrochloride as in EXAMPLE 1, Part C, to afford the title compound. HPLC: $R_T$=10.57 min. MS (ESI+): mass calcd. for $C_{23}H_{17}BrFIN_4O_5S_2$, 719.34; m/z found, 719/721 [M+H]$^+$.

$^1$H NMR (500 MHz, CDCl$_3$): 11.31 (s, 1H), 8.36 (dd, J=7.0, 0.7, 1H), 8.22 (dd, J=8.8, 0.7, 1H), 8.08 (d, J=1.5, 1H), 7.72 (dd, J=8.8, 7.1, 1H), 7.32 (dd, J=8.2, 1.5, 1H), 7.23 (dd, J=6.5, 2.1, 1H), 7.06-6.99 (m, 1H), 6.98-6.89 (m, 2H), 6.46 (d, J=6.9, 1H), 4.93 (q, J=5.5, 1H), 3.82 (s, 3H), 3.25-3.08 (m, 2H).

Example 124

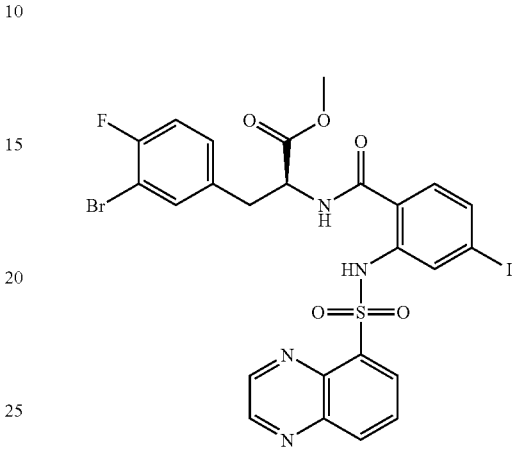

(S)-3-(3-Bromo-4-fluoro-phenyl)-2-[4-iodo-2-(quinoxaline-5-sulfonylamino)-benzoylamino]-propionic acid methyl ester 4-Iodo-2-(quinoxaline-5-sulfonylamino)-benzoic acid was coupled to (S)-2-amino-3-(3-bromo-4-fluoro-phenyl)-propionic acid methyl ester hydrochloride as in EXAMPLE 1, Part C, to afford the title compound. HPLC: $R_T$=10.30 min. MS (ESI+): mass calcd. for $C_{25}H_{19}BrFIN_4O_5S$, 713.32; m/z found, 713/715 [M+H]$^+$. $^1$H NMR (500 MHz, CDCl$_3$): 11.09 (s, 1H), 8.99 (d, J=1.7, 1H), 8.92 (d, J=1.7, 1H), 8.58 (dd, J=7.3, 1.3, 1H), 8.33 (dd, J=8.5, 1.3, 1H), 8.09 (d, J=1.5, 1H), 7.90 (dd, J=8.3, 7.5, 1H), 7.30 (dd, J=8.2, 1.5, 1H), 7.25-7.23 (m, 1H), 7.05-6.98 (m, 1H), 6.98-6.90 (m, 2H), 6.43 (d, J=7.1, 1H), 4.90 (q, J=5.5, 1H), 3.81 (s, 3H), 3.20-3.08 (m, 2H).

Example 125

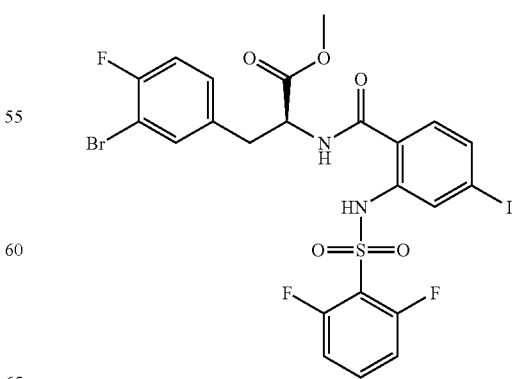

(S)-3-(3-Bromo-4-fluoro-phenyl)-2-[2-(2,6-difluoro-benzenesulfonylamino)-4-iodo-benzoylamino]-propionic acid methyl ester 2-(2,6-Difluoro-benzenesulfonylamino)-4-iodo-benzoic acid was coupled to (S)-2-amino-3-(3-bromo-4-fluoro-phenyl)-propionic acid methyl ester hydrochloride as in EXAMPLE 1, Part C, to afford the title compound. HPLC: $R_T$=10.54 min. MS (ESI+): mass calcd. for $C_{23}H_{17}BrF_3IN_2O_5S$, 697.26; m/z found, 697/699 [M+H]$^+$. $^1$H NMR (500 MHz, CDCl$_3$): 11.37 (s, 1H), 8.11 (d, J=1.4, 1H), 7.55-7.44 (m, 1H), 7.40 (dd, J=8.3, 1.4, 1H), 7.27-7.26 (m, 1H), 7.09-7.04 (m, 2H), 7.02-6.96 (m, 3H), 6.63 (d, J=6.8, 1H), 4.98 (q, J=5.6, 1H), 3.81 (s, 3H), 3.27-3.13 (m, 2H).

Example 126

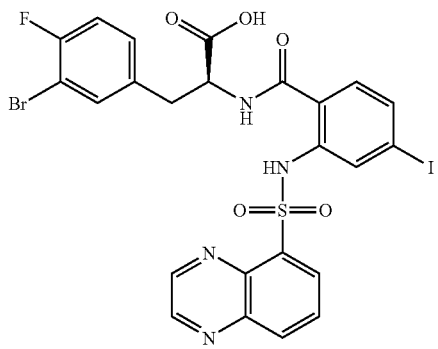

(S)-3-(3-Bromo-4-fluoro-phenyl)-2-[4-iodo-2-(quinoxaline-5-sulfonylamino)-benzoylamino]-propionic acid (S)-3-(3-Bromo-4-fluoro-phenyl)-2-[4-iodo-2-(quinoxaline-5-sulfonylamino)-benzoylamino]-propionic acid methyl ester was hydrolyzed as in EXAMPLE 2, Part E, to afford the title compound. HPLC: $R_T$=9.68 min. MS (ESI-): mass calcd. for $C_{24}H_{17}BrFIN_4O_5S$, 699.29; m/z found, 697/699 [M-H]$^-$. $^1$H NMR (500 MHz, CDCl$_3$): 10.86 (s, 1H), 9.00 (d, J=1.7, 1H), 8.91 (d, J=1.7, 1H), 8.53 (dd, J=7.4, 1.2, 1H), 8.31 (dd, J=8.5, 1.1, 1H), 8.08 (d, J=1.4, 1H), 7.88 (dd, J=8.3, 7.6, 1H), 7.33 (dd, J=6.3, 1.8, 1H), 7.28 (dd, J=8.3, 1.5, 1H), 7.08-6.98 (m, 2H), 6.86 (d, J=8.2, 1H), 6.35 (d, J=7.5, 1H), 4.89 (d, J=5.9, 1H), 3.30-3.07 (m, 2H).

Example 127

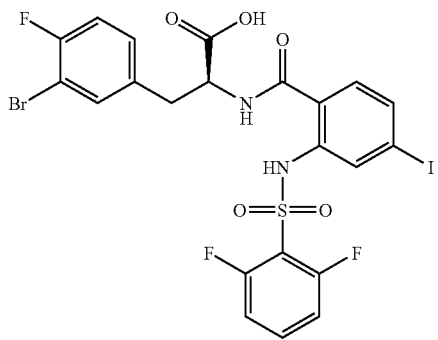

(S)-3-(3-Bromo-4-fluoro-phenyl)-2-[2-(2,6-difluoro-benzenesulfonylamino)-4-iodo-benzoylamino]-propionic acid (S)-3-(3-Bromo-4-fluoro-phenyl)-2-[2-(2,6-difluoro-benzenesulfonylamino)-4-iodo-benzoylamino]-propionic acid methyl ester was hydrolyzed as in EXAMPLE 2, Part E, to afford the title compound. HPLC: $R_T$=9.93 min. MS (ESI-): mass calcd. for $C_{22}H_{15}BrF_3IN_2O_5S$, 683.23; m/z found, 681/683 [M-H]$^-$. $^1$H NMR (500 MHz, CDCl$_3$): 11.27 (s, 1H), 8.07 (d, J=1.4, 1H), 7.54-7.44 (m, 1H), 7.38 (dd, J=8.3, 1.4, 1H), 7.35 (dd, J=6.4, 1.9, 1H), 6.96-7.13 (m, 5H), 6.63 (d, J=6.9, 1H), 5.00 (q, J=5.7, 1H), 3.39-3.14 (m, 2H).

Example 128

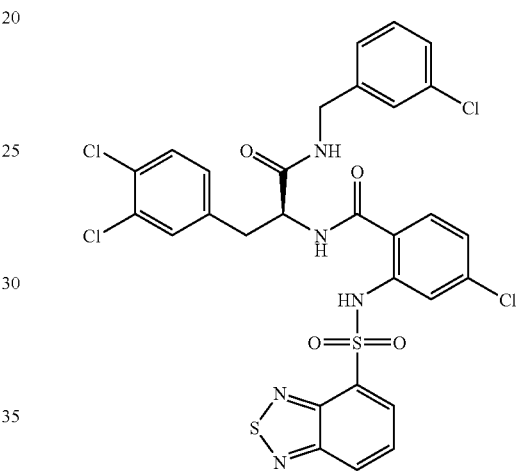

(S)-2-(Benzo[1,2,5]thiadiazole-4-sulfonylamino)-4-chloro-N-[1-(3-chloro-benzylcarbamoyl)-2-(3,4-dichloro-phenyl)-ethyl]-benzamide A. (S)-2-[2-(Benzo[1,2,5]thiadiazole-4-sulfonylamino)-4-chloro-benzoylamino]-3-(3,4-dichloro-phenyl)-propionic acid methyl ester To a solution of 2-(benzo[1,2,5]thiadiazole-4-sulfonylamino)-4-chlorobenzoic acid (300 mg, 0.81 mmol) in 1:4 THF/DMF (5 mL) at rt was added pyridine (0.196 mL, 2.4 mmol) followed by HATU (616 mg, 1.6 mmol). The mixture was stirred for 1 h, and (S)-3,4-dichlorophenylalanine methyl ester hydrochloride (461 mg, 1.6 mmol) and Hünig's base (0.282 mL, 1.6 mmol) were added. After 18 h, the mixture was poured into 1 N HCl and extracted with EtOAc (4×). The combined organic extracts were washed with water (3×), dried (Na$_2$SO$_4$), and concentrated to provide the crude methyl ester, which was used without further purification. $^1$H NMR (400 MHz, CDCl$_3$): 11.48 (br s, 1H), 8.38 (dd, J=7.0, 1.0, 1H), 8.23 (dd, J=8.8, 1.0, 1H), 7.73 (dd, J=8.8, 7.1, 1H), 7.73 (d, J=1.8, 1H), 7.34 (d, J=8.2, 1H), 7.19 (d, J=8.4, 1H), 7.14 (d, J=2.0, 1H), 6.96 (dd, J=8.4, 2.0, 1H), 6.90 (dd, J=8.2, 2.0, 1H), 6.48 (br d, J=7.1, 1H), 5.00-4.93 (m, 1H), 3.82 (s, 3H), 3.22 (dd, J=14.1, 5.9, 1H), 3.16 (dd, J=14.0, 5.1, 1H).

B. (S)-2-[2-(Benzo[1,2,5]thiadiazole-4-sulfonylamino)-4-chloro-benzoylamino]-3-(3,4-dichlorophenyl)-propionic acid A mixture of (S)-2-[2-(benzo[1,2,5]thiadiazole-4-sulfonylamino)-4-chloro-benzoylamino]-3-(3,4-dichloro-phenyl)-propionic acid methyl ester (0.81 mmol), THF (10 mL), and LiOH (2 M in water, 5 mL) was stirred vigorously overnight at rt. The mixture was poured into water, acidified to pH 1 with conc. HCl, and extracted with EtOAc (4×). The combined organic layers were dried ($Na_2SO_4$) and concentrated to provide the desired acid as a tan solid. The acid was purified by preparative reverse phase HPLC to provide 0.44 g (94%, 2 steps) of the acid as a white solid. HPLC: $R_T$=10.08 min. MS (ESI–): mass calcd. for $C_{22}H_{15}Cl_3N_4S_5O_2$, 583.95; m/z found, 583 [M–H]$^-$. $^1$H NMR (400 MHz, $CD_3OD$): 8.34 (dd, J=7.0, 1.0, 1H), 8.25 (dd, J=8.8, 1.0, 1H), 7.77 (dd, J=8.8, 7.0, 1H), 7.66 (d, J=2.0, 1H), 7.45-7.37 (m, 3H), 7.18 (dd, J=8.2, 2.0, 1H), 6.99 (dd, J=8.5, 2.1, 1H), 4.75 (dd, J=9.3, 5.2, 1H), 3.28 (dd, J=14.0, 5.1, 1H), 3.03 (dd, J=14.0, 9.4, 1H).

C. (S)-2-(Benzo[1,2,5]thiadiazole-4-sulfonylamino)-4-chloro-N-[1-(3-chloro-benzylcarbamoyl)-2-(3,4-dichloro-phenyl)-ethyl]-benzamide The title compound (29 mg, 48%) was obtained from (S)-2-[2-(benzo[1,2,5]thiadiazole-4-sulfonylamino)-4-chloro-benzoylamino]-3-(3,4-dichloro-phenyl)-propionic acid and 3-chlorobenzylamine as in Example 1, Part C. HPLC: $R_T$=10.95 min. MS (ESI–): mass calcd. for $C_{29}H_{21}Cl_4N_5O_4S_2$, 709.45; m/z found, 706/708 [M–H]$^-$. $^1$H NMR (500 MHz, $CDCl_3$): 11.55 (s, 1H), 8.39 (dd, J=7.0, 0.9, 1H), 8.22 (dd, J=8.8, 0.8, 1H), 7.73 (dd, J=8.8, 7.1, 1H), 7.70 (d, J=2.0, 1H), 7.38-7.30 (m, 3H), 7.16 (d, J=0.5, 1H), 7.05-6.99 (m, 2H), 6.96 (dd, J=8.5, 2.0, 1H), 6.88-6.81 (m, 1H), 5.87-5.80 (m, 1H), 4.70-4.61 (m, 1H), 4.49-4.41 (m, 1H), 4.34-4.26 (m, 1H), 3.17-3.09 (m, 1H), 3.06-2.96 (m, 1H).

Example 129

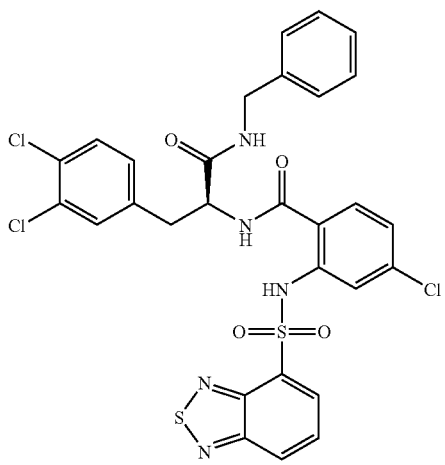

(S)-2-(Benzo[1,2,5]thiadiazole-4-sulfonylamino)-N-[1-benzylcarbamoyl-2-(3,4-dichloro-phenyl)-ethyl]-4-chloro-benzamide The title compound (19 mg, 33%) was obtained from (S)-2-[2-(benzo[1,2,5]thiadiazole-4-sulfonylamino)-4-chlorobenzoylamino]-3-(3,4-dichloro-phenyl)-propionic acid and benzyl amine as in Example 1, Part C. HPLC: $R_T$=10.73 min. MS (ESI–): mass calcd. for $C_{29}H_{22}Cl_3N_5O_4S_2$, 675.01; m/z found, 672/674 [M–H]$^-$. $^1$H NMR (500 MHz, $CDCl_3$): 11.59 (s, 1H), 8.38 (dd, J=7.1, 0.7, 1H), 8.20 (d, J=8.8, 1H), 7.74-7.71 (m, 2H), 7.37-7.25 (m, 5H), 7.13-7.11 (m, 2H), 7.03-6.98 (m, 1H), 6.96-6.87 (m, 2H), 5.79-5.71 (m, 1H), 4.66-4.61 (m, 1H), 4.50-4.45 (m, 1H), 4.33-4.29 (m, 1H), 3.14-3.10 (m, 1H), 3.00-2.96 (m, 1H),

Example 130

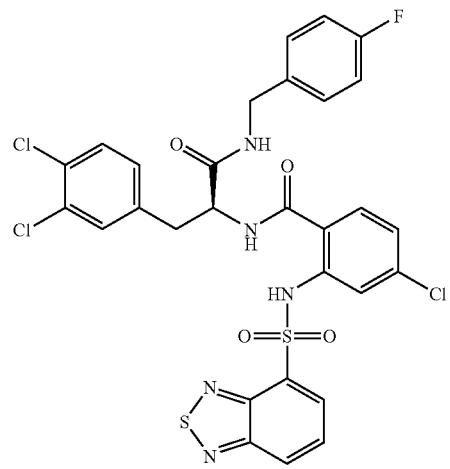

(S)-2-(Benzo[1,2,5]thiadiazole-4-sulfonylamino)-4-chloro-N-[2-(3,4-dichloro-phenyl)-(4-fluoro-benzylcarbamoyl)-ethyl]-benzamide The title compound (27 mg, 46%) was obtained from (S)-2-[2-(benzo[1,2,5]thiadiazole-4-sulfonylamino)-4-chloro-benzoylamino]-3-(3,4-dichloro-phenyl)-propionic acid and 4-fluorobenzyl amine as in Example 1, Part C. HPLC: $R_T$=10.66 min. MS (ESI–): mass calcd. for $C_{29}H_{21}Cl_3FN_5O_4S_2$, 693.00; m/z found, 690/692 [M–H]$^-$. $^1$H NMR (500 MHz, $CDCl_3$): 11.55 (s, 1H), 8.38 (dd, J=7.0, 0.8, 1H), 8.21 (dd, J=8.8, 0.6, 1H), 7.72 (dd, J=8.8, 7.1, 1H), 7.68 (d, J=1.9, 1H), 7.35-7.32 (m, 1H), 7.30-7.25 (m, 2H), 7.12-7.07 (m, 2H), 7.05-6.99 (m, 5H), 6.94 (dd, J=8.4, 1.9, 1H), 6.88-6.81 (m, 1H), 5.79-5.72 (m, 1H), 4.67-4.59 (m, 1H), 4.47-4.40 (m, 1H), 4.29-4.25 (m, 1H), 3.15-3.11 (m, 1H), 3.00-2.96 (m, 1H).

Example 131

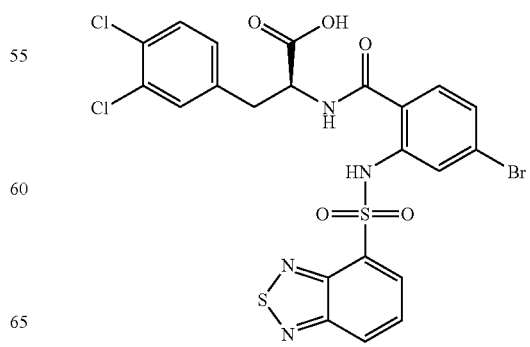

(S)-2-[2-(Benzo[1,2,5]thiadiazole-4-sulfonylamino)-
4-bromo-benzoylamino]-3-(3,4-dichloro-phenyl)-
propionic acid

A. 4-Bromo-2-nitrobenzoic acid

The title compound (1.22 g, 22%) was prepared as in Example 20, Part A. MS (ESI−): mass calcd. for $C_7H_4BrNO_4$, 244.93; m/z found, 244 [M−H]$^-$. $^1$H NMR (400 MHz, CD$_3$OD): 8.07 (d, J=1.9, 1H), 7.85 (dd, J=8.2, 1.9, 1H), 7.65 (d, J=8.2, 1H).

B. Methyl 2-amino-4-bromobenzoate

The title compound (2.89 g, 93%) was prepared as in Example 20, Part B. $^1$H NMR (400 MHz, CDCl$_3$): 7.70 (d, J=8.6, 1H), 6.84 (d, J=1.9, 1H), 6.75 (dd, J=8.6, 1.9, 1H), 5.78 (br s, 2H), 3.86 (s, 3H).

C. 2-(Benzo[1,2,5]thiadiazole-4-sulfonylamino)-4-bromo-benzoic acid methyl ester The title compound (3.95 g, 75%) was prepared as in Example 20, Part C (without DMAP). MS (ESI−): mass calcd. for $C_{14}H_{10}BrN_3O_4S_2$, 429.93; m/z found, 426 [M−H]$^-$. $^1$H NMR (400 MHz, CDCl$_3$): 11.34 (br s, 1H), 8.40 (dd, J=7.0, 0.9, 1H), 8.24 (dd, J=8.8, 0.9, 1H), 7.92 (d, J=1.8, 1H), 7.74 (dd, J=8.8, 7.0, 1H), 7.72 (d, J=8.5, 1H), 7.10 (dd, J=8.5, 1.8, 1H), 3.92 (s, 3H).

D. 2-(Benzo[1,2,5]thiadiazole-4-sulfonylamino)-4-bromobenzoic acid

The title compound (2.76 g, 97%) was prepared as in Example 20, Part D. $^1$H NMR (500 MHz, CDCl$_3$): 11.14 (br s, 1H), 8.42 (dd, J=7.2, 1.1, 1H), 8.26 (dd, J=8.8, 1.1, 1H), 7.98 (d, J=1.6, 1H), 7.82 (d, J=8.5, 1H), 7.75 (dd, J=8.8, 7.2, 1H), 7.16 (dd, J=8.5, 1.6, 1H).

E. (S)-2-[2-(Benzo[1,2,5]thiadiazole-4-sulfonylamino)-4-bromo-benzoylamino]-3-(3,4-dichloro-phenyl)-propionic acid methyl ester The title compound (61 mg, 95%) was prepared from 2-(benzo[1,2,5]thiadiazole-4-sulfonylamino)-4-bromobenzoic acid and (S)-3,4-dichlorophenylalanine methyl ester hydrochloride as in Example 1, Part C. $^1$H NMR (400 MHz, CDCl$_3$): 11.43 (br s, 1H), 8.38 (dd, J=7.0, 1.0, 1H), 8.23 (dd, J=8.8, 1.0, 1H), 7.90 (t, J=1.0, 1H), 7.73 (dd, J=8.8, 7.0, 1H), 7.35 (d, J=8.2, 1H), 7.14 (d, J=2.0, 1H), 7.11 (d, J=1.0, 2H), 6.89 (dd, J=8.2, 2.1, 1H), 6.48 (br d, J=7.1, 1H), 5.00-4.92 (m, 1H), 3.82 (s, 3H), 3.22 (dd, J=14.0, 5.8, 1H), 3.16 (dd, J=14.0, 5.1, 1H).

F. (S)-2-[2-(Benzo[1,2,5]thiadiazole-4-sulfonylamino)-4-bromo-benzoylamino]-3-(3,4-dichloro-phenyl)-propionic acid.

The title compound (43 mg, 72%) was prepared as in Example 94, Part B. HPLC: R$_T$=10.14 min. MS (ESI−): mass calcd. for $C_{22}H_{15}BrCl_2N_4O_5S_2$, 630.32; m/z found, 627/629 [M−H]$^-$. $^1$H NMR (500 MHz, MeOD): 8.32 (dd, J=7.0, 0.8, 1H), 8.24 (dd, J=8.8, 0.9, 1H), 7.81 (d, J=1.8, 1H), 7.76 (dd, J=8.8, 7.1, 1H), 7.44-7.38 (m, 2H), 7.31 (d, J=8.4, 1H), 7.19-7.13 (m, 2H), 4.76-4.70 (m, 1H), 3.29-3.24 (m, 1H), 3.02 (dd, J=14.0, 9.4, 1H).

Example 132

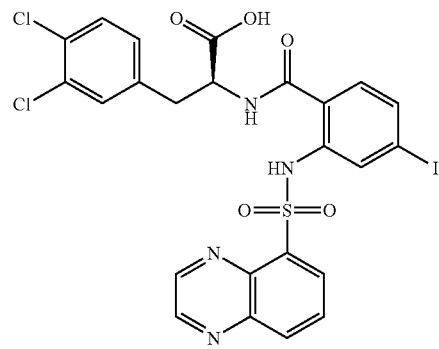

(S)-3-(3,4-Dichloro-phenyl)-2-[4-iodo-2-(quinoxaline-5-sulfonylamino)-benzoylamino]-propionic acid 4-Iodo-2-(quinoxaline-5-sulfonylamino)-benzoic acid was coupled with (S)-2-amino-3-(3,4-dichloro-phenyl)-propionic acid methyl ester hydrochloride as in Example 1, Part C. The resulting methyl ester was hydrolyzed as in EXAMPLE 2, Part E, to afford the title compound. HPLC: R$_T$=10.05 min. MS (ESI−): mass calcd. for $C_{24}H_{17}Cl_2IN_4O_5S$, 671.29; m/z found, 669/671 [M−H]$^-$. $^1$H NMR (500 MHz, CDCl$_3$): 10.86 (s, 1H), 9.01 (d, J=1.6, 1H), 8.92 (d, J=1.6, 1H), 8.55 (dd, J=7.3, 1.0, 1H), 8.32 (dd, J=8.5, 1.0, 1H), 8.08 (d, J=1.3, 1H), 7.91-7.88 (m, 1H), 7.34 (d, J=8.2, 1H), 7.30-7.24 (m, 2H), 6.98 (dd, J=8.2, 1.9, 1H), 6.88 (d, J=8.2, 1H), 6.38 (d, J=7.3, 1H), 4.90 (q, J=5.9, 1H), 3.28-3.12 (m, 2H).

Example 133

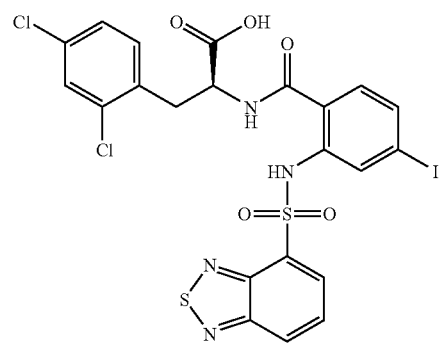

(S)-2-[2-(Benzo[1,2,5]thiadiazole-4-sulfonylamino)-4-iodo-benzoylamino]-3-(2,4-dichloro-phenyl)-propionic acid (S)-2-tert-Butoxycarbonylamino-3-(2,4-dichloro-phenyl)-propionic acid was treated as in EXAMPLE 2, Part A, to produce (S)-2-amino-3-(2,4-dichloro-phenyl)-propionic acid methyl ester hydrochloride as a white solid. This ester was coupled to 2-(benzo[1,2,5]thiadiazole-4-sulfonylamino)-4-iodo-benzoic acid as in EXAMPLE 1, Part C. The resulting methyl ester was hydrolyzed as in EXAMPLE 2, Part E, to afford the title compound. HPLC: $R_T$=10.19 min. MS (ESI−): mass calcd. for $C_{22}H_{15}Cl_2IN_4O_5S_2$, 677.32; m/z found, 675/677 [M−H]−. $^1$H NMR (500 MHz, CDCl$_3$): 11.16 (s, 1H), 8.34 (d, J=7.1, 1H), 8.21 (d, J=8.8, 1H), 8.07-8.05 (m, 1H), 7.71 (dd, J=8.8, 7.1, 1H), 7.40-7.39 (m, 1H), 7.32-7.26 (m, 1H), 7.24-7.22 (m, 2H), 6.94 (d, J=8.3, 1H), 6.53 (d, J=7.5, 1H), 5.02-4.95 (m, 1H), 3.53-3.44 (m, 1H), 3.34-3.24 (m, 1H).

Example 134

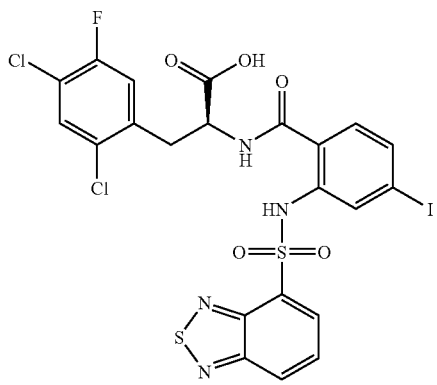

(S)-2-[2-(Benzo[1,2,5]thiadiazole-4-sulfonylamino)-4-iodo-benzoylamino]-3-(2,4-dichloro-5-fluoro-phenyl)-propionic acid The title compound was prepared as in EXAMPLE 4, substituting 2,4-dichloro-5-fluorobenzyl bromide in Part B. HPLC: $R_T$=10.21 min. MS (ESI−): mass calcd. for $C_{22}H_{14}Cl_2FIN_4O_5S_2$, 695.31; m/z found, 693/695 [M−H]−. $^1$H NMR (400 MHz, DMSO-d$_6$): 11.75 (s, 1H), 9.07 (d, J=7.9, 1H), 8.42-8.40 (m, 2H), 7.88 (t, J=7.9, 1H), 7.83-7.81 (m, 2H), 7.46-7.44 (m, 2H), 7.38-7.36 (m, 1H), 4.68-4.65 (m, 1H), 3.40-3.20 (m, 1H), 3.14-3.08 (m, 1H).

Example 135

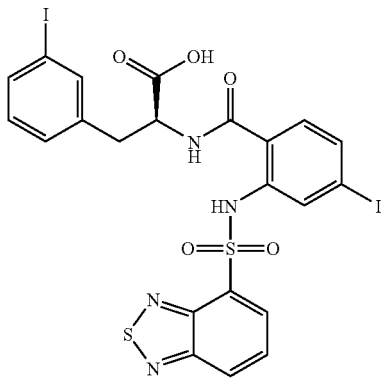

(S)-2-[2-(Benzo[1,2,5]thiadiazole-4-sulfonylamino)-4-iodo-benzoylamino]-3-(3-iodo-phenyl)-propionic acid The title compound was prepared as in EXAMPLE 4, substituting 3-iodobenzyl bromide in Part B. HPLC: $R_T$=10.03 min. MS (ESI−): mass calcd. for $C_{22}H_{16}I_2N_4O_5S_2$, 734.33; m/z found, 733 [M−H]−. $^1$H NMR (400 MHz, DMSO-d$_6$): 11.76 (s, 1H), 9.01 (d, J=7.9, 1H), 8.42-8.40 (m, 2H), 7.88 (t, J=7.9, 1H), 7.82 (d, J=1.5, 1H), 7.68 (s, 1H), 7.57 (d, J=7.9, 1H), 7.43 (d, J=8.2, 1H), 7.36 (d, J=8.3, 1H), 7.29 (d, J=7.6, 1H), 7.08 (t, J=7.7, 1H), 4.59-4.54 (m, 1H), 3.18-3.13 (m, 1H), 2.99-2.93 (m, 1H).

Example 136

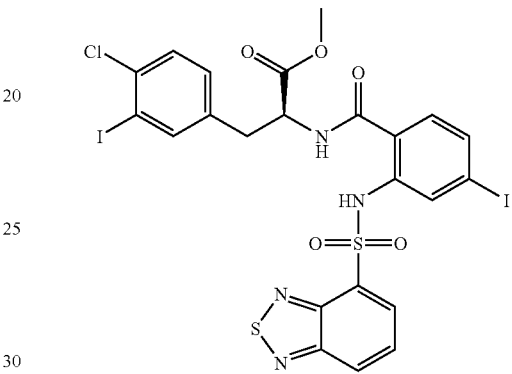

(S)-2-[2-(Benzo[1,2,5]thiadiazole-4-sulfonylamino)-4-iodo-benzoylamino]-3-(4-chloro-3-iodo-phenyl)-propionic acid methyl ester 2-(Benzo[1,2,5]thiadiazole-4-sulfonylamino)-4-iodo-benzoic acid was coupled to (S)-2-amino-3-(4-chloro-3-iodo-phenyl)-propionic acid methyl ester hydrochloride as in EXAMPLE 1, Part C, to afford title compound. HPLC: $R_T$=10.87 min. MS (ESI+): mass calcd. for $C_{23}H_{17}ClI_2N_4O_5S_2$, 782.80; m/z found, 783/785 [M+H]+. $^1$H NMR (400 MHz, CDCl$_3$): 11.31 (s, 1H), 8.37 (dd, J=7.0, 0.9, 1H), 8.23 (dd, J=8.8, 0.9, 1H), 8.09 (d, J=1.5, 1H), 7.73 (dd, J=8.8, 7.1, 1H), 7.55 (d, J=2.0, 1H), 7.35-7.33 (m, 2H), 7.00-6.94 (m, 2H), 6.46 (d, J=7.1, 1H), 4.97-4.91 (m, 1H), 3.82 (s, 3H), 3.21-3.10 (m, 2H).

Example 137

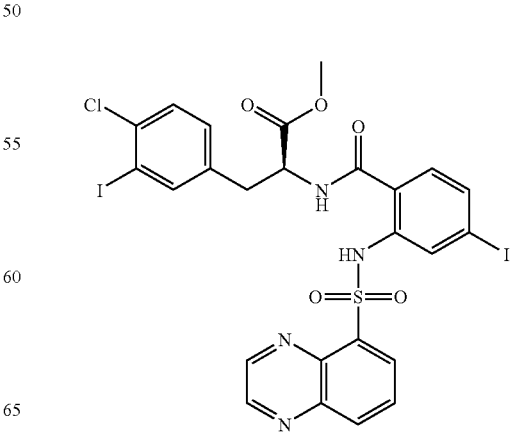

(S)-3-(4-Chloro-3-iodo-phenyl)-2-[4-iodo-2-(quinoxaline-5-sulfonylamino)-benzoylamino]-propionic acid methyl ester 4-Iodo-2-(quinoxaline-5-sulfonylamino)-benzoic acid was coupled to (S)-2-amino-3-(4-chloro-3-iodo-phenyl)-propionic acid methyl ester hydrochloride as in EXAMPLE 1, Part C, to afford title compound. HPLC: $R_T$=10.61 min. MS (ESI+): mass calcd. for $C_{25}H_{19}ClI_2N_4O_5S$, 776.77; m/z found, 777/779 [M+H]⁺. ¹H NMR (400 MHz, CDCl₃): 11.09 (s, 1H), 9.01-8.98 (m, 1H), 8.95-8.92 (m, 1H), 8.58 (d, J=7.3, 1H), 8.34 (d, J=8.5, 1H), 8.11 (d, J=1.5, 1H), 7.94-7.88 (m, 1H), 7.57 (d, J=1.9, 1H), 7.36-7.26 (m, 2H), 7.00-6.94 (m, 2H), 6.42 (d, J=6.3, 1H), 4.95-4.88 (m, 1H), 3.81 (s, 3H), 3.20-3.07 (m, 2H).

Example 138

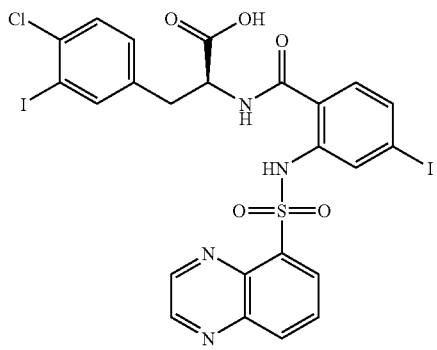

(S)-3-(4-Chloro-3-iodo-phenyl)-2-[4-iodo-2-(quinoxaline-5-sulfonylamino)-benzoylamino]-propionic acid (S)-3-(4-Chloro-3-iodo-phenyl)-2-[4-iodo-2-(quinoxaline-5-sulfonylamino)-benzoylamino]-propionic acid methyl ester was hydrolyzed as in EXAMPLE 2, Part E, to afford the title compound. HPLC: $R_T$=10.01 min. MS (ESI-): mass calcd. for $C_{24}H_{17}ClI_2N_4O_5S_2$, 762.74; m/z found, 761/763 [M-H]⁻. ¹H NMR (500 MHz, CDCl₃): 10.92 (s, 1H), 8.99 (d, J=1.7, 1H), 8.92 (d, J=1.6, 1H), 8.56-8.52 (m, 1H), 8.33-8.29 (m, 1H), 8.10 (d, J=1.3, 1H), 7.88 (m, 1H), 7.62 (d, J=1.8, 1H), 7.35-7.25 (m, 2H), 7.08-7.02 (m, 1H), 6.89 (d, J=8.2, 1H), 6.31 (d, J=7.3, 1H), 4.92-4.86 (m, 1H), 3.24-3.08 (m, 2H).

Example 139

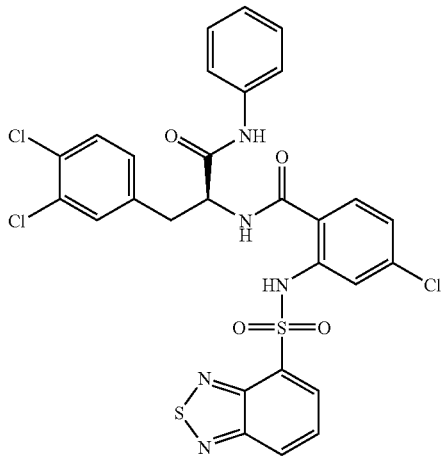

(S)-2-(Benzo[1,2,5]thiadiazole-4-sulfonylamino)-4-chloro-N-[2-(3,4-dichloro-phenyl)-phenylcarbamoyl-ethyl]-benzamide The title compound (25 mg, 45%) was prepared from (S)-2-[2-(benzo[1,2,5]thiadiazole-4-sulfonylamino)-4-chloro-benzoylamino]-3-(3,4-dichloro-phenyl)-propionic acid and aniline as in Example 1, Part C. HPLC: $R_T$=10.81 min. MS (ESI-): mass calcd. for $C_{28}H_{20}Cl_3N_5O_4S_2$, 660.98; m/z found, 658/660 [M-H]⁻. ¹H NMR (400 MHz, CDCl₃): 11.54 (s, 1H), 8.39 (dd, J=7.1, 1.0, 1H), 8.19 (dd, J=8.8, 0.8, 1H), 7.75-7.67 (m, 2H), 7.67-7.62 (m, 1H), 7.47-7.42 (m, 2H), 7.42-7.33 (m, 4H), 7.26-7.23 (m, 1H), 7.11-7.09 (m, 1H), 6.96-6.90 (m, 2H), 4.84-4.77 (m, 1H), 3.23-3.10 (m, 2H).

Example 140

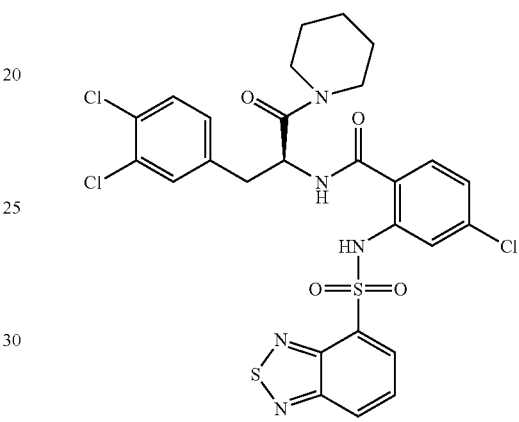

(S)-2-(Benzo[1,2,5]thiadiazole-4-sulfonylamino)-4-chloro-N-[1-(3,4-dichloro-benzyl)-2-oxo-2-piperidin-1-yl-ethyl]-benzamide The title compound (37 mg, 66%) was prepared from (S)-2-[2-(benzo[1,2,5]thiadiazole-4-sulfonylamino)-4-chloro-benzoylamino]-3-(3,4-dichloro-phenyl)-propionic acid and piperidine as in Example 1, Part C. HPLC: $R_T$=11.00 min. MS (ESI-): mass calcd. for $C_{27}H_{24}Cl_3N_5O_4S_2$, 653.00; m/z found, 650/652 [M-H]⁻. ¹H NMR (500 MHz, CDCl₃): 11.70 (m, 1H), 8.38 (d, J=7.0, 1H), 8.21 (d, J=8.8, 1H), 7.72 (dd, J=8.8, 7.1, 1H), 7.69 (d, J=1.9, 1H), 7.35 (d, J=8.2, 1H), 7.28-7.25 (m, 1H), 7.22 (d, J=1.9, 1H), 7.13 (d, J=7.4, 1H), 6.99 (dd, J=8.2, 1.9, 1H), 6.92 (dd, J=8.4, 1.9, 1H), 5.26-5.21 (m, 1H), 3.62-3.49 (m, 2H), 3.43-3.35 (m, 1H), 3.26-3.19 (m, 1H), 3.08-2.95 (m, 2H), 1.70-1.46 (m, 5H), 1.33-1.23 (m, 1H).

Example 141

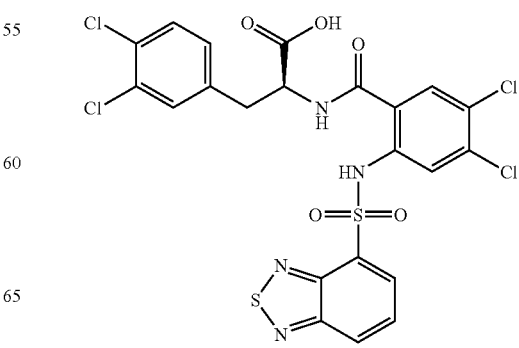

(S)-2-[2-(Benzo[1,2,5]thiadiazole-4-sulfonylamino)-4,5-dichloro-benzoylamino]-3-(3,4-dichloro-phenyl)-propionic acid The title compound was prepared as in EXAMPLE 1, substituting 2-amino-3-(3,4-dichloro-phenyl)-propionic acid methyl ester hydrochloride (prepared as in Example 2, Part A) and 2-(benzo[1,2,5]thiadiazole-4-sulfonylamino)-4,5-dichloro-benzoic acid in Part C. HPLC: $R_T$=10.48 min. MS (ESI–): mass calcd. for $C_{22}H_{14}Cl_4N_4O_5S_2$, 620.31; m/z found, 617/619/621 [M–H]$^-$. $^1$H NMR (400 MHz, acetone-d$_6$): 11.64 (s, 1H), 8.53 (s, 2H), 8.46 (d, J=7.0, 1H), 8.29 (d, J=8.7, 1H), 7.89 (dd, J=8.8, 7.1, 1H), 7.83 (s, 1H), 7.75 (s, 1H), 7.56 (d, J=1.8, 1H), 7.49 (d, J=8.2, 1H), 7.34 (dd, J=8.2, 1.8, 1H), 5.00-4.94 (m, 1H), 3.40-3.36 (m, 1H), 3.25-3.17 (m, 1H).

Example 142

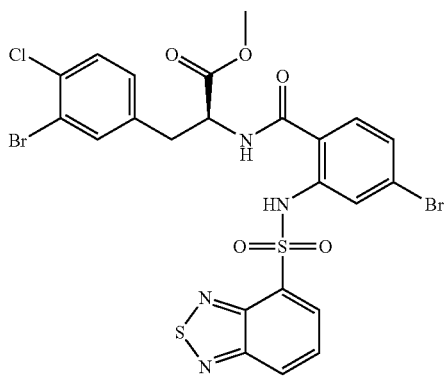

(S)-2-[2-(Benzo[1,2,5]thiadiazole-4-sulfonylamino)-4-bromo-benzoylamino]-3-(3-bromo-4-chloro-phenyl)-propionic acid methyl ester The title compound was prepared as in EXAMPLE 4, substituting 3-bromo-4-chlorobenzyl bromide in Part B, substituting 2-(benzo[1,2,5]thiadiazole-4-sulfonylamino)-4-bromo-benzoic acid in Part E, and eliminating the LiOH hydrolysis step in Part E. HPLC: $R_T$=10.67 min. MS (ESI–): mass calcd. for $C_{23}H_{17}Br_2ClN_4O_5S_2$, 688.80; m/z found, 687/689 [M–H]$^-$. $^1$H NMR (400 MHz, CDCl$_3$): 11.42 (s, 1H), 8.36 (dd, J=7.0, 0.9, 1H), 8.22 (dd, J=8.8, 0.9, 1H), 7.88 (d, J=1.7, 1H), 7.73 (dd, J=8.8, 7.1, 1H), 7.35-7.32 (m, 1H), 7.18-7.05 (m, 2H), 6.96 (dd, J=8.2, 2.0, 1H), 6.57 (d, J=7.0, 1H), 4.97-4.92 (m, 1H), 3.82 (s, 3H), 3.25-3.09 (m, 2H).

Example 143

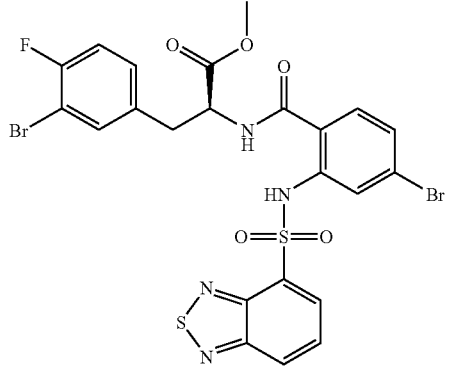

(S)-2-[2-(Benzo[1,2,5]thiadiazole-4-sulfonylamino)-4-bromo-benzoylamino]-3-(3-bromo-4-fluoro-phenyl)-propionic acid methyl ester

A. 2-Acetylamino-3-(3-bromo-4-fluoro-phenyl)-acrylic acid

A mixture of 3-bromo-4-fluorobenzaldehyde (50.0 g, 0.25 mol), N-acetylglycine (26.2 g, 0.22 mol), NaOAc (13.8 g, 0.56 mol), and Ac$_2$O (52 mL) was heated at 130° C. for 10 h in a flask fitted with a reflux condenser. The resulting precipitate was collected by filtration, washed with water, and suspended in AcOH (250 mL). This mixture was heated at 100° C. for 1 h in a flask fitted with a reflux condenser, and then was cooled to 0° C. The solids were collected by filtration, washing with water, to give the product as a yellow solid (53.5 g, 76%). MS (ESI–): mass calcd. for $C_{11}H_9BrFNO_3$, 301.0; m/z found, 299.9 [M–H]$^-$. $^1$H NMR (400 MHz, DMSO-d$_6$): 12.80 (br s, 1H), 9.52 (br s, 1H), 7.93 (dd, J=6.9, 1.9, 1H), 7.66 (ddd, J=8.4, 4.8, 1.9, 1H), 7.42 (t, J=8.7, 1H), 7.19 (s, 1H), 1.98 (s, 3H).

B. (S)-2-Acetylamino-3-(3-bromo-4-fluoro-phenyl)-propionic acid

A mixture of bis(1,5-cyclooctadiene)rhodium(I) trifluoromethanesulfonate (0.11 g, 0.18 mmol) and (R)—N-diphenylphosphino-N-methyl-1-[(S)-2-diphenylphosphino)ferrocenyl]ethylamine [(R)-methyl BoPhoz; 70 mg, 0.15 mmol] in MeOH (150 mL) under N$_2$ was stirred for 30 min. 2-Acetylamino-3-(3-bromo-4-fluoro-phenyl)-acrylic acid (4.5 g, 15 mmol) was added, and the mixture was stirred under H$_2$ (40 psi) on a Parr apparatus for 18 h. The mixture was concentrated to give the title compound as an orange oil (4.5 g, 100%). MS (ESI–): mass calcd. for $C_{11}H_{11}BrFNO_3$, 303.0; m/z found, 301.8 [M–H]$^-$. $^1$H NMR (400 MHz, DMSO-d$_6$): 7.50 (dd, J=6.7, 2.1, 1H), 7.24 (ddd, J=8.4, 4.7, 2.2, 1H), 7.13 (t, J=8.6, 1H), 4.65 (dd, J=9.0, 5.2, 1H), 3.19 (dd, J=14.0, 5.2, 1H), 2.93 (dd, J=14.0, 9.0, 1H), 1.93 (s, 3H).

C. 3-Bromo-4-fluoro-L-phenylalanine hydrochloride

A suspension of (S)-2-acetylamino-3-(3-bromo-4-fluoro-phenyl)-propionic acid (2.5 g, 8.2 mmol) in HCl (6.0 M in water, 5.0 mL) was heated at 100° C. for 2 h and then cooled to 0° C. The resulting solid was collected by filtration to give the title phenylalanine as a light tan solid (2.1 g, 86%). MS (ESI+): mass calcd. for $C_9H_9BrFNO_2$, 261.0; m/z found, 261.8 [M+H]$^+$. $^1$H NMR (400 MHz, D$_2$O): 7.50 (dd, J=6.6, 2.1, 1H), 7.21 (ddd, J=8.4, 4.7, 2.2, 1H), 7.14 (t, J=8.7, 1H), 3.90 (dd, J=7.7, 5.5, 1H), 3.16 (dd, J=14.7, 5.4, 1H), 3.04 (dd, J=14.7, 7.7, 1H).

D. 3-Bromo-4-fluoro-L-phenylalanine methyl ester hydrochloride

3-Bromo-4-fluoro-L-phenylalanine hydrochloride was converted to the methyl ester as described in EXAMPLE 2, Part A.

E. (S)-2-[2-(Benzo[1,2,5]thiadiazole-4-sulfonylamino)-4-bromo-benzoylamino]-3-(3-bromo-4-fluoro-phenyl)-propionic acid methyl ester The title compound was prepared as in EXAMPLE 1, substituting 3-bromo-4-fluoro-L-phenylalanine methyl ester hydrochloride and 2-(benzo[1,2,5]thiadiazole-4-sulfonylamino)-4-bromo-benzoic acid in Part C. HPLC: R$_T$=10.39 min. MS (ESI−): mass calcd. for $C_{23}H_{17}Br_2FN_4O_5S_2$, 672.34; m/z found, 671 [M−H]$^−$. $^1$H NMR (400 MHz, CDCl$_3$): 11.42 (s, 1H), 8.37 (d, J=7.1, 1H), 8.22 (d, J=8.8, 1H), 7.88 (s, 1H), 7.75-7.71 (m, 1H), 7.27-7.25 (m, 1H), 7.11 (q, J=8.4, 2H), 7.09-6.94 (m, 2H), 6.56 (d, J=7.0, 1H), 4.94 (q, J=5.8, 1H), 3.82 (s, 3H), 3.25-3.11 (m, 2H).

Example 144

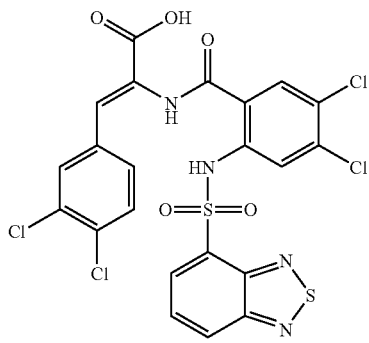

(Z)-2-[2-(Benzo[1,2,5]thiadiazole-4-sulfonylamino)-4,5-dichloro-benzoylamino]-3-(3,4-dichloro-phenyl)-acrylic acid To a solution of 2-[2-(benzo[1,2,5]thiadiazole-4-sulfonylamino)-4-chloro-benzoylamino]-3-(3,4-dichloro-phenyl)-3-hydroxy-propionic acid methyl ester (42 mg, 0.068 mmol) in DCM (1.5 mL) was added Et$_3$N (38 μL, 0.273 mmol) and the mixture was cooled to 0° C. MsCl (8 μL, 0.102 mmol) was added and the mixture was warmed to rt and stirred for 1.5 h. The mixture was heated to 50° C., treated with catalytic DMAP, and stirred overnight. The mixture was diluted with satd. aq. NaHCO$_3$ and extracted with DCM (3×). The combined organic layers were dried (MgSO$_4$) and concentrated to provide 2-[2-(benzo[1,2,5]thiadiazole-4-sulfonylamino)-4,5-dichloro-benzoylamino]-3-(3,4-dichloro-phenyl)-acrylic acid methyl ester. The crude product was hydrolyzed as in EXAMPLE 2, Part E, to provide the title compound (25% for two steps). HPLC: R$_T$=9.97 min. MS (ESI−): mass calcd. for $C_{22}H_{15}Cl_3N_4O_5S_2$, 618.30; m/z found, 581/583 [M−H]$^−$. $^1$H NMR (400 MHz, acetone-d$_6$): 11.82 (s, 1H), 9.37 (d, J=5.1, 1H), 8.48 (d, J=7.1, 1H), 8.34 (dd, J=8.8, 0.9, 1H), 7.96-7.86 (m, 2H), 7.82-7.75 (m, 2H), 7.64-7.55 (m, 3H), 7.11 (dd, J=8.5, 2.0, 1H).

Example 145

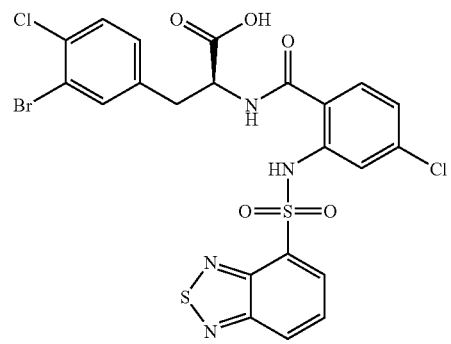

(S)-2-[2-(Benzo[1,2,5]thiadiazole-4-sulfonylamino)-4-chloro-benzoylamino]-3-(3-bromo-4-chloro-phenyl)-propionic acid (S)-2-[2-(Benzo[1,2,5]thiadiazole-4-sulfonylamino)-4-chloro-benzoylamino]-3-(3-bromo-4-chloro-phenyl)-propionic acid was prepared from 3-bromo-4-chloro-L-phenylalanine methyl ester hydrochloride and 2-(benzo[1,2,5]thiadiazole-4-sulfonylamino)-4-chloro-benzoic acid as in EXAMPLE 1, Part C. Hydrolysis of the methyl ester as in EXAMPLE 2, Part E, provided the title compound. HPLC: R$_T$=10.07 min. MS (ESI−): mass calcd. for $C_{22}H_{15}BrCl_2N_4O_5S_2$, 630.32; m/z found, 629/631 [M−H]$^−$. $^1$H NMR (400 MHz, CDCl$_3$): 11.35 (s, 1H), 8.36 (d, J=7.0, 1H), 8.20 (d, J=8.8, 1H), 7.76-7.69 (m, 2H), 7.41 (d, J=1.7, 1H), 7.36 (d, J=8.2, 1H), 7.17 (d, J=8.5, 1H), 7.05 (dd, J=8.2, 1.8, 1H), 6.91 (dd, J=8.4, 1.8, 1H), 6.53 (d, J=7.1, 1H), 5.04-4.95 (m, 1H), 3.36-3.15 (m, 2H).

Example 146

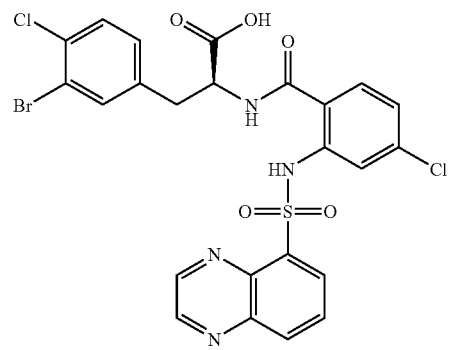

(S)-3-(3-Bromo-4-chloro-phenyl)-2-[4-chloro-2-(quinoxaline-5-sulfonylamino)-benzoylamino]-propionic acid (S)-3-(3-Bromo-4-chloro-phenyl)-2-[4-chloro-2-(quinoxaline-5-sulfonylamino)-benzoylamino]-propionic acid was prepared from 3-bromo-4-chloro-L-phenylalanine methyl ester hydrochloride and 4-chloro-2-(quinoxaline-5-sulfonylamino)-benzoic acid as in Example 1, Part C. Hydrolysis of the methyl ester as in EXAMPLE 2, Part E, provided the title compound. HPLC: $R_T$=9.80 min. MS (ESI–): mass calcd. for $C_{24}H_{17}BrCl_2N_4O_5S$, 624.29; m/z found, 621/623/625 [M–H]⁻. ¹H NMR (400 MHz, CDCl₃): 11.04 (s, 1H), 8.98 (d, J=1.6, 1H), 8.90 (d, J=1.6, 1H), 8.54 (dd, J=7.3, 1.0, 1H), 8.28 (dd, J=8.4, 0.9, 1H), 7.91-7.86 (m, 1H), 7.71 (d, J=1.9, 1H), 7.43 (d, J=1.8, 1H), 7.33 (d, J=8.2, 1H), 7.13 (d, J=8.4, 1H), 7.05 (dd, J=8.2, 1.9, 1H), 6.86 (dd, J=8.4, 1.9, 1H), 6.53 (d, J=7.5, 1H), 4.91 (q, J=6.2, 1H), 3.34-3.09 (m, 2H).

Example 147

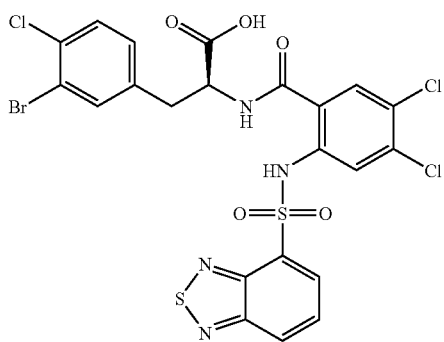

(S)-2-[2-(Benzo[1,2,5]thiadiazole-4-sulfonylamino)-4,5-dichloro-benzoylamino]-3-(3-bromo-4-chloro-phenyl)-propionic acid (S)-2-[2-(Benzo[1,2,5]thiadiazole-4-sulfonylamino)-4,5-dichloro-benzoylamino]-3-(3-bromo-4-chloro-phenyl)-propionic acid was prepared from 3-bromo-4-chloro-L-phenylalanine methyl ester hydrochloride and 4-chloro-2-(quinoxaline-5-sulfonylamino)-benzoic acid as in Example 1, Part C. Hydrolysis of the methyl ester as in EXAMPLE 2, Part E, provided the title compound. HPLC: $R_T$=10.43 min. MS (ESI–): mass calcd. for $C_{22}H_{14}BrCl_3N_4O_5S_2$, 664.76; m/z found, 661/663/665 [M–H]⁻. ¹H NMR (400 MHz, CDCl₃): 11.12 (s, 1H), 8.34 (d, J=7.0, 1H), 8.19 (d, J=8.8, 1H), 7.77 (s, 1H), 7.71 (dd, J=8.6, 7.2, 1H), 7.43 (d, J=1.7, 1H), 7.36-7.31 (m, 2H), 7.07 (dd, J=8.2, 1.6, 1H), 6.78 (d, J=7.3, 1H), 4.97 (q, J=6.3, 1H), 3.32-3.14 (m, 2H).

Example 148

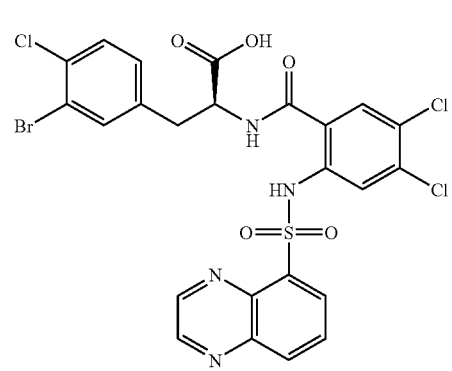

(S)-3-(3-Bromo-4-chloro-phenyl)-2-[4,5-dichloro-2-(quinoxaline-5-sulfonylamino)-benzoylamino]-propionic acid (S)-3-(3-Bromo-4-chloro-phenyl)-2-[4,5-dichloro-2-(quinoxaline-5-sulfonylamino)-benzoylamino]-propionic acid was prepared from 3-bromo-4-chloro-L-phenylalanine methyl ester hydrochloride and 4,5-dichloro-2-(quinoxaline-5-sulfonylamino)-benzoic acid (prepared from quinoxaline-5-sulfonyl chloride as in EXAMPLE 14, Part A) as in Example 1, Part C. Hydrolysis of the methyl ester as in EXAMPLE 2, Part E, provided the title compound. HPLC: $R_T$=10.21 min. MS (ESI–): mass calcd. for $C_{24}H_{16}BrCl_3N_4O_5S$, 658.74; m/z found, 655/657/659 [M–H]⁻. ¹H NMR (400 MHz, CDCl₃): 10.83 (s, 1H), 8.98 (d, J=1.8, 1H), 8.92 (d, J=1.7, 1H), 8.52 (dd, J=7.3, 1.2, 1H), 8.30 (dd, J=8.5, 1.3, 1H), 7.88 (d, J=7.5, 1H), 7.85 (s, 1H), 7.43-7.42 (m, 1H), 7.37-7.34 (m, 1H), 7.07-7.02 (m, 1H), 6.47 (d, J=7.6, 1H), 4.91-4.85 (m, 1H), 3.24-3.09 (m, 2H).

Example 149

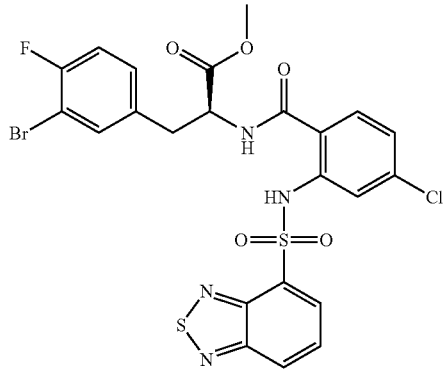

(S)-2-[2-(Benzo[1,2,5]thiadiazole-4-sulfonylamino)-4-chloro-benzoylamino]-3-(3-bromo-4-fluoro-phenyl)-propionic acid methyl ester The title compound was prepared from 3-bromo-4-fluoro-L-phenylalanine methyl ester hydrochloride and 2-(benzo[1,2,5]thiadiazole-4-sulfonylamino)-4-chloro-benzoic acid as in Example 1, Part C. HPLC: $R_T$=10.36 min. MS (ESI−): mass calcd. for $C_{23}H_{17}BrClFN_4O_5S_2$, 627.89; m/z found, 625/627 [M−H]⁻. ¹H NMR (400 MHz, CDCl₃): 11.46 (s, 1H), 8.37 (dd, J=7.0, 0.8, 1H), 8.22 (dd, J=8.8, 0.9, 1H), 7.75-7.68 (m, 2H), 7.32-7.14 (m, 2H), 7.09-6.88 (m, 3H), 6.53 (d, J=6.8, 1H), 4.98-4.90 (m, 1H), 3.82 (s, 3H), 3.24-3.10 (m, 2H).

Example 150

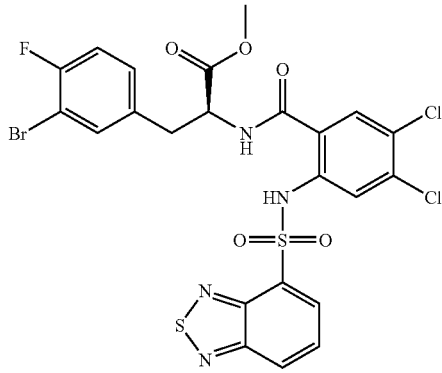

(S)-2-[2-(Benzo[1,2,5]thiadiazole-4-sulfonylamino)-4,5-dichloro-benzoylamino]-3-(3-bromo-4-fluoro-phenyl)-propionic acid methyl ester The title compound was prepared from 3-bromo-4-fluoro-L-phenylalanine methyl ester hydrochloride and 2-(benzo[1,2,5]thiadiazole-4-sulfonylamino)-4,5-dichloro-benzoic acid as in Example 1, Part C. HPLC: $R_T$=10.74 min. MS (ESI−): mass calcd. for $C_{23}H_{16}BrCl_2FN_4O_5S_2$, 662.34; m/z found, 659/661 [M−H]⁻. ¹H NMR (500 MHz, CDCl₃): 11.16 (s, 1H), 8.36 (dd, J=7.1, 0.8, 1H), 8.24 (dd, J=8.8, 0.8, 1H), 7.86 (s, 1H), 7.74 (dd, J=8.8, 7.1, 1H), 7.33 (s, 1H), 7.30-7.27 (m, 1H), 7.06 (t, J=8.3, 1H), 7.03-6.98 (m, 1H), 6.53 (d, J=7.1, 1H), 4.93 (q, J=5.8, 1H), 3.22 (s, 3H), 3.24-3.11 (m, 2H).

Example 151

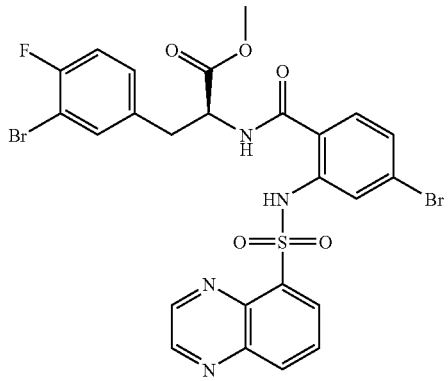

(S)-3-(3-Bromo-4-fluoro-phenyl)-2-[4-bromo-2-(quinoxaline-5-sulfonylamino)-benzoylamino]-propionic acid methyl ester The title compound was prepared from 3-bromo-4-fluoro-L-phenylalanine methyl ester hydrochloride and 4-bromo-2-(quinoxaline-5-sulfonylamino)-benzoic acid (EXAMPLE 8, Parts A-E, substituting 2-amino-4-bromo-benzoic acid methyl ester in Part D) as in Example 1, Part C. HPLC: $R_T$=10.11 min. MS (ESI−): mass calcd. for $C_{25}H_{19}Br_2FN_4O_5S$, 666.31; m/z found, 665/667 [M−H]⁻. ¹H NMR (400 MHz, CDCl₃): 11.19 (s, 1H), 8.98 (d, J=1.5, 1H), 8.92 (d, J=1.4, 1H), 8.58 (d, J=7.3, 1H), 8.33 (d, J=8.5, 1H), 7.94-7.86 (m, 2H), 7.25 (d, J=1.9, 1H), 7.12-6.92 (m, 4H), 6.45 (d, J=7.1, 1H), 4.92 (q, J=5.7, 1H), 3.81 (s, 3H), 3.22-3.09 (m, 2H).

Example 152

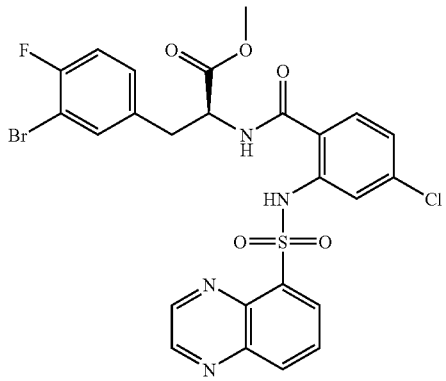

(S)-3-(3-Bromo-4-fluoro-phenyl)-2-[4-chloro-2-(quinoxaline-5-sulfonylamino)-benzoylamino]-propionic acid methyl ester The title compound was prepared from 3-bromo-4-fluoro-L-phenylalanine methyl ester hydrochloride and 4-chloro-2-(quinoxaline-5-sulfonylamino)-benzoic acid as in Example 1, Part C. HPLC: $R_T$=10.09 min. MS (ESI−): mass calcd. for $C_{25}H_{19}BrClFN_4O_5S$, 621.86; m/z found, 619/621 [M−H]⁻. ¹H NMR (400 MHz, CDCl₃): 11.24 (s, 1H), 8.98 (d, J=1.6, 1H), 8.92 (d, J=1.6, 1H), 8.58 (dd, J=7.3, 1.1, 1H), 8.33 (dd, J=8.5, 1.1, 1H), 7.92-7.86 (m, 1H), 7.76 (d, J=1.9, 1H), 7.28-7.25 (m, 1H), 7.19 (d, J=8.4, 1H), 7.06-6.94 (m, 2H), 6.92 (dd, J=8.4, 1.9, 1H), 6.48 (d, J=7.2, 1H), 4.92 (q, J=5.7, 1H), 3.81 (s, 3H), 3.22-3.09 (m, 2H).

Example 153

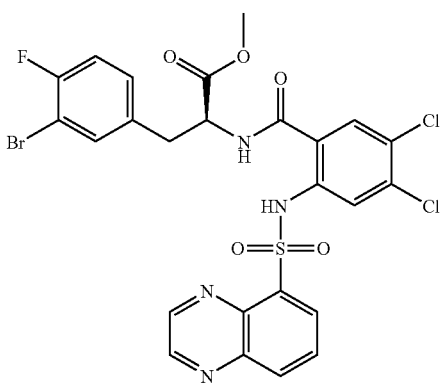

(S)-3-(3-Bromo-4-fluoro-phenyl)-2-[4,5-dichloro-2-(quinoxaline-5-sulfonylamino)-benzoylamino]-propionic acid methyl ester The title compound was prepared from 3-bromo-4-fluoro-L-phenylalanine methyl ester hydrochloride and 4,5-dichloro-2-(quinoxaline-5-sulfonylamino)-benzoic acid (prepared from quinoxaline-5-sulfonyl chloride as in EXAMPLE 14, Part A) as in Example 1, Part C. HPLC: $R_T$=10.50 min. MS (ESI−): mass calcd. for $C_{25}H_{18}BrCl_2FN_4O_5S$, 656.31; m/z found, 653/655/657 [M−H]⁻. ¹H NMR (400 MHz, CDCl₃): 10.99 (s, 1H), 8.96 (d, J=1.7, 1H), 8.93 (d, J=1.7, 1H), 8.55 (dd, J=7.3, 1.1, 1H), 8.33 (dd, J=8.5, 1.1, 1H), 7.91-7.85 (m, 2H), 7.31-7.22 (m, 2H), 7.07-6.94 (m, 2H), 6.52 (d, J=7.3, 1H), 4.89 (q, J=5.8, 1H), 3.81 (s, 3H), 3.21-3.08 (m, 2H).

Example 154

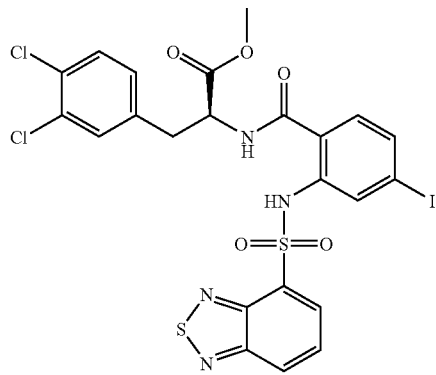

(S)-2-[2-(Benzo[1,2,5]thiadiazole-4-sulfonylamino)-4-iodo-benzoylamino]-3-(3,4-dichloro-phenyl)-propionic acid methyl ester The title compound was prepared from 2-amino-3-(3,4-dichloro-phenyl)-propionic acid methyl ester hydrochloride (prepared as in Example 2, Part A) and 2-(benzo[1,2,5]thiadiazole-4-sulfonylamino)-4-iodo-benzoic acid as in Example 1, Part C. HPLC: $R_T$=10.50 min. MS (ESI−): mass calcd. for $C_{22}H_{15}Cl_3N_4O_5S_2$, 691.35; m/z found, 689/691 [M−H]⁻. ¹H NMR (400 MHz, CDCl₃): 11.34 (s, 1H), 8.36 (dd, J=7.1, 0.9, 1H), 8.23 (dd, J=8.8, 0.9, 1H), 8.08 (d, J=1.5, 1H), 7.73 (dd, J=8.8, 7.1, 1H), 7.36-7.30 (m, 2H), 7.14 (d, J=2.0, 1H), 6.95 (d, J=8.3, 1H), 6.90 (dd, J=8.2, 2.0, 1H), 6.53 (d, J=7.0, 1H), 4.94 (q, J=5.6, 1H), 3.82 (s, 3H), 3.25-3.10 (m, 2H).

Example 155

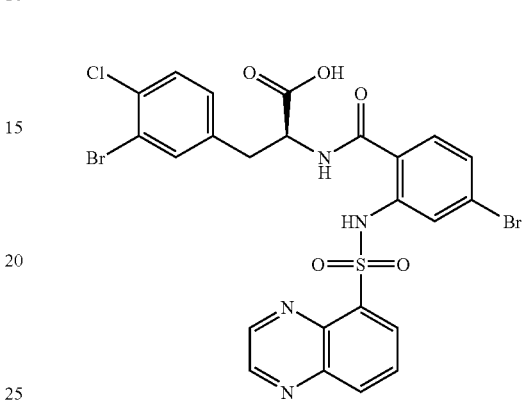

(S)-3-(3-Bromo-4-chloro-phenyl)-2-[4-bromo-2-(quinoxaline-5-sulfonylamino)-benzoylamino]-propionic acid The title compound was prepared from 3-bromo-4-chloro-L-phenylalanine methyl ester hydrochloride and 4-bromo-2-(quinoxaline-5-sulfonylamino)-benzoic acid (EXAMPLE 8, Parts A-E, substituting 2-amino-4-bromo-benzoic acid methyl ester in Part D) as in Example 1, Part C, followed by hydrolysis of the resulting methyl ester as in EXAMPLE 2, Part E. HPLC: $R_T$=9.86 min. MS (ESI−): mass calcd. for $C_{22}H_{15}Cl_3N_4O_5S_2$, 668.74; m/z found, 665/667/669 [M−H]⁻. ¹H NMR (400 MHz, CDCl₃): 11.01 (s, 1H), 9.00 (s, 1H), 8.92 (s, 1H), 8.55 (d, J=7.2, 1H), 8.30 (d, J=8.4, 1H), 7.94-7.85 (m, 2H), 7.42 (s, 1H), 7.34 (d, J=8.1, 1H), 7.10-6.99 (m, 3H), 6.43 (d, J=7.0, 1H), 4.95-4.87 (m, 1H), 3.29-3.10 (m, 2H).

Example 156

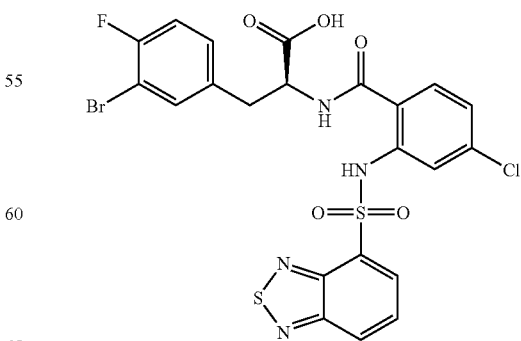

(S)-2-[2-(Benzo[1,2,5]thiadiazole-4-sulfonylamino)-4-chloro-benzoylamino]-3-(3-bromo-4-fluoro-phenyl)-propionic acid The title compound was prepared from 3-bromo-4-fluoro-L-phenylalanine methyl ester hydrochloride and 2-(benzo[1,2,5]thiadiazole-4-sulfonylamino)-4-chloro-benzoic acid as in EXAMPLE 1, Part C, followed by hydrolysis of the resulting methyl ester as in EXAMPLE 2, Part E. HPLC: $R_T$=9.72 min. MS (ESI-): mass calcd. for $C_{22}H_{15}BrClFN_4O_5S_2$, 613.87; m/z found, 611/613 [M-H]$^-$. $^1$H NMR (400 MHz, CDCl$_3$): 11.36 (s, 1H), 8.34 (d, J=6.9, 1H), 8.16 (d, J=8.7, 1H), 7.74-7.67 (m, 1H), 7.66-7.63 (m, 1H), 7.38-7.32 (m, 1H), 7.20-7.15 (m, 1H), 7.12-7.05 (m, 1H), 7.05-6.98 (m, 1H), 6.91-6.84 (m, 1H), 6.68 (d, J=6.7, 1H), 6.09 (s, 2H), 5.04-4.94 (m, 1H), 3.35-3.15 (m, 2H).

Example 157

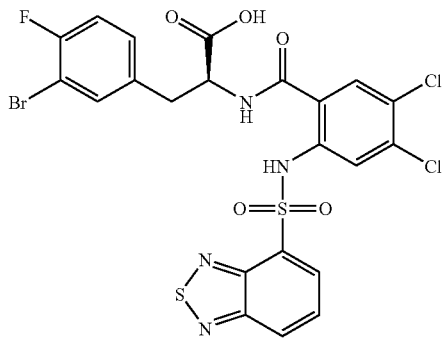

(S)-2-[2-(Benzo[1,2,5]thiadiazole-4-sulfonylamino)-4,5-dichloro-benzoylamino]-3-(3-bromo-4-fluoro-phenyl)-propionic acid The title compound was prepared from 3-bromo-4-fluoro-L-phenylalanine methyl ester hydrochloride and 2-(benzo[1,2,5]thiadiazole-4-sulfonylamino)-4,5-dichloro-benzoic acid as in Example 1, Part C, followed by hydrolysis of the resulting methyl ester as in EXAMPLE 2, Part E. HPLC: $R_T$=10.10 min. MS (ESI-): mass calcd. for $C_{22}H_{14}BrCl_2FN_4O_5S_2$, 648.31; m/z found, 645/647/649 [M-H]$^-$. $^1$H NMR (400 MHz, acetone-d$_6$): 11.58 (s, 1H), 8.47-8.42 (m, 1H), 8.34-8.20 (m, 2H), 7.92-7.85 (m, 1H), 7.85-7.80 (m, 1H), 7.75-7.70 (m, 1H), 7.67-7.60 (m, 1H), 7.42-7.35 (m, 1H), 7.25-7.18 (m, 1H), 4.96-4.87 (m, 1H), 3.40-3.32 (m, 1H), 3.20-3.10 (m, 1H).

Example 158

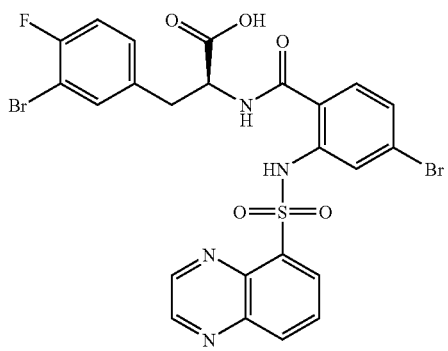

(S)-3-(3-Bromo-4-fluoro-phenyl)-2-[4-bromo-2-(quinoxaline-5-sulfonylamino)-benzoylamino]-propionic acid The title compound was prepared from 3-bromo-4-fluoro-L-phenylalanine methyl ester hydrochloride and 4-bromo-2-(quinoxaline-5-sulfonylamino)-benzoic acid (EXAMPLE 8, Parts A-E, substituting 2-amino-4-bromo-benzoic acid methyl ester in Part D) as in Example 1, Part C, followed by hydrolysis of the resulting methyl ester as in EXAMPLE 2, Part E. HPLC: $R_T$=9.52 min. MS (ESI-): mass calcd. for $C_{24}H_{17}Br_2FN_4O_5S$, 652.29; m/z found, 649/651/653 [M-H]$^-$. $^1$H NMR (400 MHz, acetone-d$_6$): 11.64 (s, 1H), 8.99-8.93 (m, 2H), 8.62-8.57 (m, 1H), 8.37-8.31 (m, 1H), 8.07-7.98 (m, 2H), 7.94-7.90 (m, 1H), 7.65-7.59 (m, 1H), 7.51-7.45 (m, 1H), 7.41-7.34 (m, 1H), 7.23-7.16 (m, 1H), 7.14-7.08 (m, 1H), 5.00-4.90 (m, 1H), 3.37-3.29 (m, 1H), 3.18-3.09 (m, 1H).

Example 59

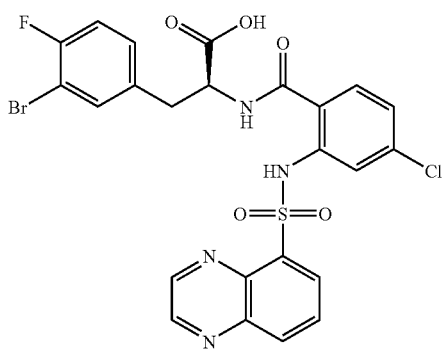

(S)-3-(3-Bromo-4-fluoro-phenyl)-2-[4-chloro-2-(quinoxaline-5-sulfonylamino)-benzoylamino]-propionic acid The title compound was prepared from 3-bromo-4-fluoro-L-phenylalanine methyl ester hydrochloride and 4-chloro-2-(quinoxaline-5-sulfonylamino)-benzoic acid as in Example 1, Part C, followed by hydrolysis of the resulting methyl ester as in EXAMPLE 2, Part E. HPLC: $R_T$=9.46 min. MS (ESI-): mass calcd. for $C_{24}H_{17}BrClFN_4O_5S$, 607.84; m/z found, 605/607 [M-H]$^-$. $^1$H NMR (400 MHz, acetone-d$_6$): 11.66 (s, 1H), 8.99-8.93 (m, 2H), 8.63-8.57 (m, 1H), 8.37-8.31 (m, 1H), 8.02-7.97 (m, 2H), 7.78-7.75 (m, 1H), 7.65-7.60 (m, 1H), 7.58-7.53 (m, 1H), 7.41-7.34 (m, 1H), 7.24-7.17 (m, 1H), 6.97 (dd, J=8.3, 1.6, 1H), 5.00-4.92 (m, 1H), 3.37-3.28 (m, 1H), 3.18-3.10 (m, 1H).

Example 160

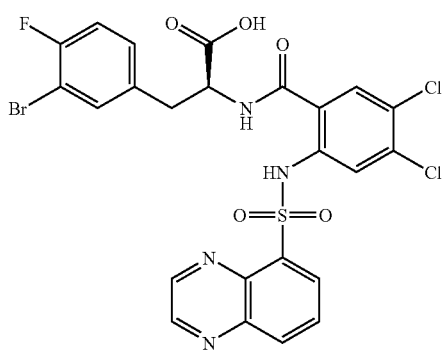

(S)-3-(3-Bromo-4-fluoro-phenyl)-2-[4,5-dichloro-2-(quinoxaline-5-sulfonylamino)-benzoylamino]-propionic acid The title compound was prepared from 3-bromo-4-fluoro-L-phenylalanine methyl ester hydrochloride and 4,5-dichloro-2-(quinoxaline-5-sulfonylamino)-benzoic acid (prepared from quinoxaline-5-sulfonyl chloride as in EXAMPLE 14, Part A) as in Example 1, Part C, followed by hydrolysis of the resulting methyl ester as in EXAMPLE 2, Part E. HPLC: $R_T$=9.91 min. MS (ESI–): mass calcd. for $C_{24}H_{16}BrCl_2FN_4O_5S$, 642.28; m/z found, 639/641/643 [M–H]⁻. ¹H NMR (400 MHz, acetone-$d_6$): 11.49 (s, 1H), 9.00-8.93 (m, 2H), 8.62-8.57 (m, 1H), 8.37-8.32 (m, 1H), 8.20-8.12 (m, 1H), 8.05-7.97 (m, 1H), 7.93-7.88 (m, 1H), 7.73-7.67 (m, 1H), 7.65-7.61 (m, 1H), 7.41-7.33 (m, 1H), 7.25-7.15 (m, 1H), 5.00-4.90 (m, 1H), 3.38-3.28 (m, 1H), 3.18-3.10 (m, 1H).

Example 161

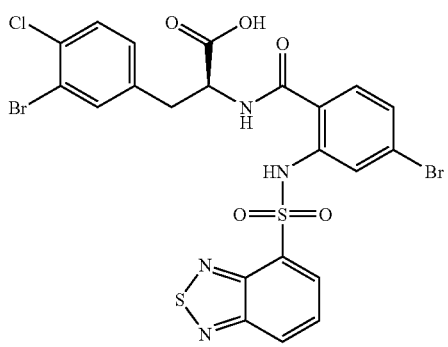

(S)-2-[2-(Benzo[1,2,5]thiadiazole-4-sulfonylamino)-4-bromo-benzoylamino]-3-(3-bromo-4-chloro-phenyl)-propionic acid The title compound was prepared from 3-bromo-4-chloro-L-phenylalanine methyl ester hydrochloride and 2-(benzo[1,2,5]thiadiazole-4-sulfonylamino)-4-bromo-benzoic acid as in Example 1, Part C, followed by hydrolysis of the resulting methyl ester as in EXAMPLE 2, Part E. HPLC: $R_T$=10.05 min. MS (ESI–): mass calcd. for $C_{22}H_{15}Br_2ClN_4O_5S_2$, 674.77; m/z found, 673/675 [M–H]⁻. ¹H NMR (400 MHz, acetone-$d_6$): 11.77 (s, 1H), 8.46-8.42 (m, 1H), 8.34-8.29 (m, 1H), 8.19-8.13 (m, 1H), 7.93-7.87 (m, 1H), 7.87-7.82 (m, 1H), 7.73-7.69 (m, 1H), 7.54-7.46 (m, 2H), 7.40-7.35 (m, 1H), 7.17-7.12 (m, 1H), 4.97-4.88 (m, 1H), 3.40-3.32 (m, 1H), 3.22-3.14 (m, 1H).

Example 162

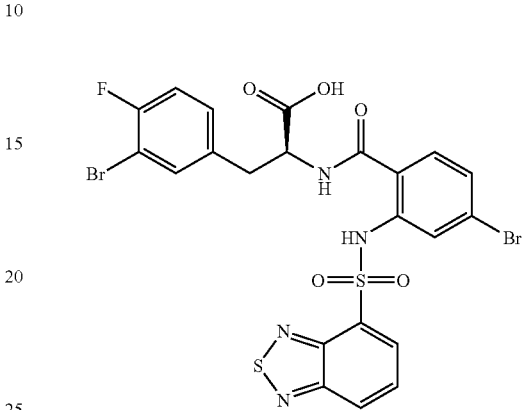

(S)-2-[2-(Benzo[1,2,5]thiadiazole-4-sulfonylamino)-4-bromo-benzoylamino]-3-(3-bromo-4-fluoro-phenyl)-propionic acid The title compound was prepared from 3-bromo-4-fluoro-L-phenylalanine methyl ester hydrochloride and 2-(benzo[1,2,5]thiadiazole-4-sulfonylamino)-4-bromo-benzoic acid as in Example 1, Part C, followed by hydrolysis of the resulting methyl ester as in EXAMPLE 2, Part E. HPLC: $R_T$=9.75 min. MS (ESI–): mass calcd. for $C_{22}H_{15}Br_2FN_4O_5S_2$, 658.32; m/z found, 655/657/659 [M–H]⁻. ¹H NMR (400 MHz, acetone-$d_6$): 11.76 (s, 1H), 8.46-8.41 (m, 1H), 8.32-8.27 (m, 1H), 8.16-8.09 (m, 1H), 7.93-7.82 (m, 2H), 7.66-7.60 (m, 1H), 7.53-7.47 (m, 1H), 7.41-7.34 (m, 1H), 7.24-7.11 (m, 2H), 4.95-4.86 (m, 1H), 3.39-3.31 (m, 1H), 3.21-3.12 (m, 1H).

Example 163

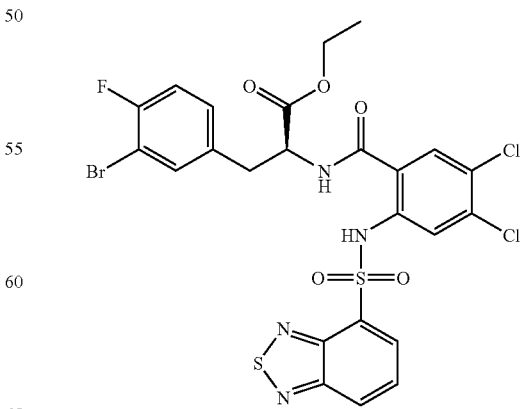

(S)-2-[2-(Benzo[1,2,5]thiadiazole-4-sulfonylamino)-
4,5-dichloro-benzoylamino]-3-(3-bromo-4-fluoro-
phenyl)-propionic acid ethyl ester The title compound was prepared from 3-bromo-4-fluoro-L-phenylalanine ethyl ester hydrochloride and 2-(benzo[1,2,5]thiadiazole-4-sulfonylamino)-4,5-dichloro-benzoic acid as in Example 1, Part C. HPLC: $R_T$=10.96 min. MS (ESI–): mass calcd. for $C_{22}H_{15}Cl_3N_4O_5S_2$, 676.36; m/z found, 673/675 [M–H]⁻. $^1$H NMR (400 MHz, CDCl$_3$): 11.20 (s, 1H), 8.36 (dd, J=7.0, 0.8, 1H), 8.23 (dd, J=8.8, 0.9, 1H), 7.86 (s, 1H), 7.73 (dd, J=8.8, 7.1, 1H), 7.34 (s, 1H), 7.29 (dd, J=6.5, 1.9, 1H), 7.07-6.99 (m, 2H), 6.59 (d, J=7.0, 1H), 4.89 (q, J=5.8, 1H), 4.27 (q, J=7.1, 2H), 3.17 (d, J=5.8, 1H), 1.33 (t, J=7.2, 3H).

The racemic compounds in Examples 164-173 may be prepared according to the methods described above.

Example 164

2-[2-(Benzo[1,2,5]thiadiazole-4-sulfonylamino)-4-iodo-benzoylamino]-3-(3-bromo-4-chloro-phenyl)-propionic acid

Example 165

2-[2-(Benzo[1,2,5]thiadiazole-4-sulfonylamino)-4-iodo-benzoylamino]-3-(4-chloro-3-iodo-phenyl)-propionic acid

Example 166

2-[2-(Benzo[1,2,5]thiadiazole-4-sulfonylamino)-4-iodo-benzoylamino]-3-(3-bromo-4-fluoro-phenyl)-propionic acid

Example 167

2-[2-(Benzo[1,2,5]thiadiazole-4-sulfonylamino)-4-iodo-benzoylamino]-3,3-bis-(4-chloro-phenyl)-propionic acid

Example 168

2-[2-(Benzo[1,2,5]thiadiazole-4-sulfonylamino)-4-iodo-benzoylamino]-3-(4-chloro-phenyl)-3-methyl-butyric acid

Example 169

2-(Benzo[1,2,5]thiadiazole-4-sulfonylamino)-N-[2-(4-chloro-phenyl)-2-hydroxy-1-methyl-ethyl]-4-iodo-benzamide

Example 170

2-(Benzo[1,2,5]thiadiazole-4-sulfonylamino)-N-[2-(3-bromo-phenyl)-2-hydroxy-1-methyl-ethyl]-4-iodo-benzamide

Example 171

2-[2-(Benzo[1,2,5]thiadiazole-4-sulfonylamino)-4-chloro-benzoylamino]-3,3-bis-(4-chloro-phenyl)-propionic acid

Example 172

2-[2-(Benzo[1,2,5]thiadiazole-4-sulfonylamino)-4-chloro-benzoylamino]-3-(4-chloro-phenyl)-3-methyl-butyric acid

Example 173

2-(Benzo[1,2,5]thiadiazole-4-sulfonylamino)-N-[2-(3-bromo-phenyl)-2-hydroxy-1-methyl-ethyl]-4-chloro-benzamide

Example 174

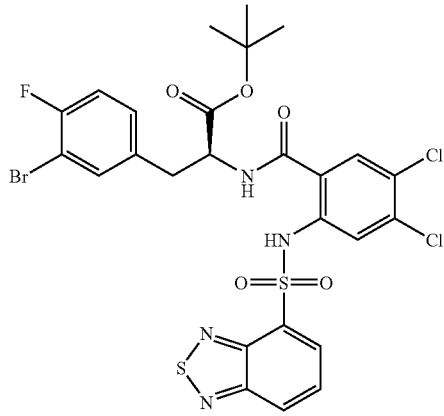

(S)-2-[2-(Benzo[1,2,5]thiadiazole-4-sulfonylamino)-
4,5-dichloro-benzoylamino]-3-(3-bromo-4-fluoro-
phenyl)-propionic acid tert-butyl ester A. (S)-2-(Benzhydrylidene-amino)-3-(3-bromo-4-fluoro-phenyl)-propionic acid tert-butyl ester To a flame-dried flask was added (benzhydrylidene-amino)-acetic acid tert-butyl ester (250 mg, 0.846 mmol), O-allyl-N-(9-anthracenylmethyl)-cinchonidinium bromide (51 mg, 0.085 mmol), and DCM (5 mL). The flask was cooled to –55° C. and CsOH.H$_2$O (1.4 g, 8.46 mmol) was added. The mixture was stirred for 30 min, treated with 3-bromo-4-fluorobenzyl bromide (1.1 g, 4.23 mmol), and stirred at –55° C. overnight. The mixture was diluted with Et$_2$O (5 mL) and water (10 mL), warmed to rt, and washed with water and brine. The organic layer was dried (MgSO$_4$) and concentrated. The residue was purified by column chromatography to provide the title compound (300 mg, 74%, er=97:3). MS (ESI+): mass calcd. for $C_{26}H_{25}BrFNO_2$, 482.4; m/z found, 483.4 [M+H]⁺. $^1$H NMR (400 MHz, CDCl$_3$): 7.59-7.54 (m, 2H), 7.41-7.20 (m, 7H), 7.02-6.91 (m, 2H), 6.72 (d, J=6.5 Hz, 2H), 4.11-4.07 (m, 1H), 3.19-3.08 (m, 2H), 1.45 (s, 9H).

B. (S)-2-Amino-3-(3-bromo-4-fluoro-phenyl)-propionic acid tert-butyl ester

A solution of (S)-2-(benzhydrylidene-amino)-3-(3-bromo-4-fluoro-phenyl)-propionic acid tert-butyl ester (300 mg, 0.622 mmol) in THF (3 mL) was treated with 10% citric acid (3 mL). The mixture was stirred overnight, diluted with water, and extracted with Et$_2$O (2x). The aqueous layer was basified to pH=10 with satd. aq. K$_2$CO$_3$ and extracted with EtOAc (3x). The combined organic layers were dried (MgSO$_4$) and concentrated to give the title compound (247 mg, 64%). MS (ESI+): mass calcd. for C$_{13}$H$_{17}$BrFNO$_2$, 318.18; m/z found, 262.2 [M-t-Bu]$^+$. $^1$H NMR (400 MHz, CDCl$_3$): 7.42 (dd, J=6.6, 2.1 Hz, 1H), 7.16-7.11 (m, 1H), 7.08-7.02 (m, 1H), 3.56 (dd, J=7.3, 5.9 Hz, 1H), 2.85-2.78 (m, 1H), 2.99-2.92 (m, 1H), 1.43 (m, 9H).

C. (S)-2-[2-(Benzo[1,2,5]thiadiazole-4-sulfonylamino)-4,5-dichloro-benzoylamino]-3-(3-bromo-4-fluoro-phenyl)-propionic acid tert-butyl ester The title compound may be prepared as described in Example 1, Part C.

The compounds in Examples 175-176 may be prepared according to the methods described above.

Example 175

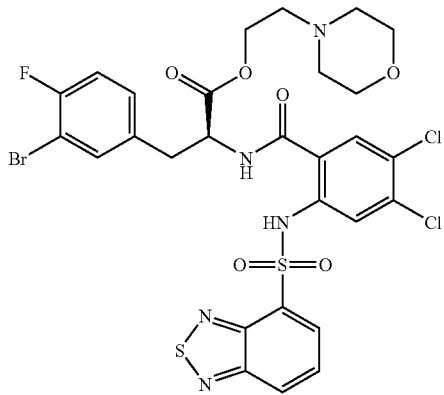

(S)-2-[2-(Benzo[1,2,5]thiadiazole-4-sulfonylamino)-4,5-dichloro-benzoylamino]-3-(3-bromo-4-fluoro-phenyl)-propionic acid 2-morpholin-4-yl-ethyl ester Example 176

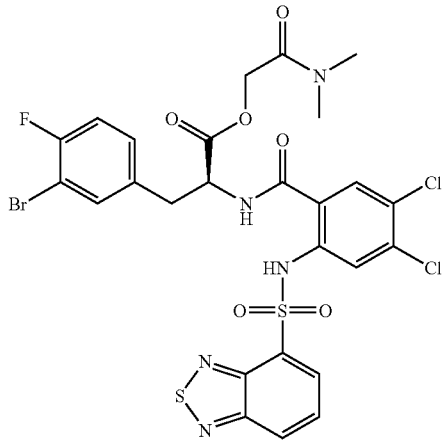

(S)-2-[2-(Benzo[1,2,5]thiadiazole-4-sulfonylamino)-4,5-dichloro-benzoylamino]-3-(3-bromo-4-fluoro-phenyl)-propionic acid dimethylcarbamoylmethyl ester

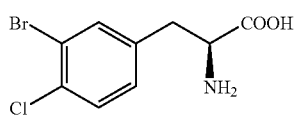

INTERMEDIATE 1

Preparation of 3-bromo-4-chloro-L-phenylalanine

A. 3-Bromo-4-chlorobenzyl chloride

To a solution of 3-bromo-4-chlorobenzyl alcohol (9.6 g, 43 mmol) in CH$_2$Cl$_2$ (100 mL) was added Ph$_3$P (17.1 g, 1.5 mmol) and CCl$_4$ (6.3 mL, 65 mmol). After 18 h, the solution was washed with brine (3×100 mL) and passed through a short silica gel column to afford the product as colorless oil (9.14 g, 88%). $^1$H NMR (400 MHz, CDCl$_3$): 7.65 (d, J=2.1 Hz, 1H), 7.43 (d, J=8.2 Hz, 1H), 7.27 (dd, J=8.3, 2.1 Hz, 1H), 4.51 (s, 3H).

B. 3-Bromo-4-chloro-L-phenylalanine

To a solution of 2-acetylamino-malonic acid diethyl ester (15.1 g, 70 mmol) and 3-bromo-4-chlorobenzyl chloride (16.7 g, 70 mmol) in EtOH (110 mL) was added a solution of NaOEt (20% in EtOH, 28.7 mL, 73 mmol). The mixture was heated at reflux for 3 h in a flask fitted with a reflux condenser, then was treated with additional 2-acetylamino-malonic acid diethyl ester (3.0 g, 14 mmol) and NaOEt (20% in EtOH, 2.0 mL, 5.1 mmol). The mixture was heated at reflux for an additional 3 h. The mixture was cooled to rt and treated with water (200 mL). The resulting white precipitate was collected by filtration, washed with water, and suspended in a mixture of water (60 mL) and EtOH (60 mL). This mixture was heated to reflux temperature in a flask fitted with a reflux condenser. A solution of KOH (3.3 g, 59 mmol) in water (10 mL) was added dropwise. After 2 h at reflux, more KOH (5.9 g, 105 mmol) in water (20 mL) was added dropwise, and the mixture was heated at reflux for 3 h. The mixture was cooled to 0° C., diluted with water (120 mL), and treated with 50% aq. HCl until pH~1. The resulting white precipitate was collected by filtration and washed with 0.1 M HCl. The solid was suspended in water (80 mL) and treated with 2 M aq. KOH until pH~8.0. The solution was filtered. The filtrate was warmed to 40° C., treated with Acylase "Amano" (0.19 g, Amano Enzyme Inc., Japan) and CoCl$_2$ (10 mg), and 2 M aq. KOH was added to keep the pH of solution at 8.0. After 4 d at 40° C., 2 M HCl was added until pH=1. The suspension was filtered and the filtrate was concentrated to 20 mL. The pH was adjusted to 6.0 with 2.0 M KOH. The mixture was kept at 0° C. overnight and the solid was collected by filtration to obtain the title compound as a light tan solid (7.67 g, 40% overall). $^1$H NMR (400 MHz, DMSO-d$_6$): 7.66 (br s, 1H), 7.51 (d, J=8.2 Hz, 1H), 7.29 (d, J=8.2 Hz, 1H), 3.39 (dd, J=7.1, 5.3 Hz, 1H), 3.08 (dd, J=14.2, 4.6 Hz, 1H), 2.86 (dd, J=14.0, 7.7 Hz, 1H). To determine the enantiomeric ratio, the product was transformed to the corresponding methyl ester (SOCl$_2$, MeOH, rt) and then to the Mosher's amide (Mosher's acid chloride, iPr$_2$NEt, CH$_2$Cl$_2$). The analysis of $^1$H-NMR data of the amide showed that the product was a single enantiomer (e.e. >99.5%).

C.

The product from Step B may be used to prepare compounds of the invention according to the methods described in the preceding examples.

Assay Methods

A. Binding Assays

1. CCK1 Assay Development and Data Generation

Cell Culture

CHO-K1 cells that had undergone stable transfection with the CCK-1 receptor were grown in DMEM supplemented with L-glutamine (2 mM), penicillin (50 units/mL) and streptomycin (50 μg/mL). Cells were cultured under continuous G418 selection (2 mM) and were harvested using a rubber cell scraper. CHO-K1 cells were sub-cultured a maximum of ten times before being reseeded from the original stocks.

Membrane Preparation

Membranes were prepared from the stably transfected CHO-K1 cells. Frozen cell pellets (−40° C.) were thawed in 14 mL of buffer A (10 mM HEPES, 130 mM NaCl, 4.7 mM KCl, 5 mM MgCl, 1 mM EGTA and 15.4 mg/100 mL bacitracin at pH 7.2), adapted from Harper et al. (Br. J. Pharmacol. 1996, 118:1717-1726). The thawed pellets were homogenized using a Polytron PT-10 (7×1 s). The homogenates were centrifuged for 5 min at 1500 rpm (600×g), and the resulting pellets were discarded. The supernatants were re-centrifuged in order to collect the receptor-membrane pellets (25 min 15,000 rpm; 39,800×g), which were re-suspended in buffer A.

Incubation Conditions

All assays were conducted in 96-well plates (GF/B millipore filter plates) using buffer A, with 0.3 μM PD-134,308, for the dilutions. The CCK-2 receptor ligand was included to eliminate the contribution of this receptor subtype to the binding. For the optimal cell number determination experiments 20 pM [$^{125}$I]-BH-CCK-8S (50 μL 60 μM solution) was incubated with a range of cell concentrations (2.5×105 to 12.5×105 cells/well) in a total volume of 150 μL. Total binding of [$^{125}$I]-BH-CCK-8S was determined in the presence of 15 μL of buffer A. Non-specific binding of [$^{125}$I]-BH-CCK-8S was determined in the presence of 15 μL of 100 μM 2-naphthalenesulphonyl L-aspartyl-(2-phenethyl)amide (2-NAP: see R. A. Hull et al. Br. J. Pharmacol. 1993, 108: 734-740), a CCK-1 receptor selective antagonist that is structurally unrelated to the radioligand [$^{125}$I]-BH-CCK-8S. The assay preparation was incubated for 1 h at 21±3° C., and then the assay was terminated upon rapid filtration of the preparation under reduced pressure. The loaded filters were washed three times using undiluted PBS (100 EL), and then the residues were transferred to 5 mL scintillation tubes. Bound radioactivity was determined using a gamma counter (count time=1 min). From these experiments a cell concentration of 1 pellet in 40 mL of buffer (2.5×106 cells/mL) was chosen for use in other assays (below). To validate the radioligand concentration and incubation time for the assay, saturation and kinetic binding studies were also conducted (see M. F. Morton, The Pharmacological Characterization of Cholecystokinin Receptors in the Human Gastrointestinal Tract. PhD Thesis, University of London, 2000). The affinity of novel compounds was estimated by incubating membrane preparations with 15 μL of competing ligand (0.1 pM-1 mM) for 60 min at 21±3° C. The assay was then terminated according to the procedure outlined above.

2. CCK2 Assay Development and Data Generation

Zinc Finger Proteins (ZFP) specific for the CCK2R gene were identified by Sangamo Biosciences. The ZFP domain was fused with the herpes simplex virus VP16 activation domain, and the fusion protein was subsequently cloned into the pcDNA3 mammalian expression vector (Invitrogen, San Diego, Calif.). Tet-inducible cell lines expressing the coding region from the ZFP vector were created using the T-REx-293™ cell line (Invitrogen). After 2 weeks of selection in culture medium containing 400 mg/mL Zeocin (Invitrogen), sixty drug-resistant stable clones were isolated and analyzed for ZFP expression as well as CCK2R induction upon addition of doxycycline to the culture medium. The cell line with the most appropriate CCK2R ZFP construct was used in all further assays and was termed the HEKZFP cell line.

Cell Culture

HEKZFP cells were grown in DMEM supplemented with L-glutamine (2 mM), penicillin (50 units/mL) and streptomycin (50 μg/mL) and 10% FBS (v/v). HEKZFP cells were treated with 2 mM doxycycline (Sigma-Aldrich, Mo.; USA) for 2 days to de-repress the tet-regulated expression of the CCK2 receptor selective zinc finger proteins and were harvested using a rubber cell scraper.

Membrane Preparation

Membranes were prepared from the HEKZFP cells after induction. Frozen cell pellets (−40° C.) were thawed in 14 mL of buffer A (10 mM HEPES, 130 mM NaCl, 4.7 mM KCl, 5 mM MgCl, 1 mM EGTA and 15.4 mg/100 mL bacitracin at pH 7.2), adapted from E. A. Harper et al. (Br. J. Pharmacol. (1996) 118(7):1717-1726). The thawed pellets were homogenized using a Polytron PT-10 (7×1 s). The homogenates were centrifuged for 5 min at 1500 rpm (600×g), and the resulting pellets were discarded. The supernatants were re-centrifuged in order to collect the receptor-membrane pellets (25 min 15,000 rpm; 39,800×g), which were re-suspended in buffer A.

Incubation Conditions

All assays were conducted in 96-well plates (GF/B millipore filter plates) using buffer A. For the optimal cell number determination experiments, cells in concentrations ranging from 2.5×10$^5$ to 12.5×10$^5$ cells/well were incubated with 20 pM [$^{125}$I]-BH-CCK-8S (50 μL 60 μM solution) in a total volume of 150 μL. Total binding of [$^{125}$I]-BH-CCK-8S was determined in the presence of 15 μL of buffer A. Non-specific binding of [$^{125}$I]-BH-CCK-8S was determined in the presence of 15 μL of 10 μM YF476, a CCK-2 receptor selective antagonist that is structurally unrelated to the radioligand [$^{125}$I]-BH-CCK-8S. The assay preparation was incubated for 1 h at 21±3° C., and then the assay was terminated by rapid filtration of the preparation under reduced pressure. The loaded filters were washed three times using undiluted PBS (100 μL), and then 100 μL of scintillation fluid was added to the filter plate. Bound radioactivity was determined using a Topcount (Packard BioScience, Meriden, Conn.) with a count time of 1 min. From these experiments a cell concentration of 1 pellet in 15 mL of buffer was chosen for use in other assays. To validate the radioligand concentration and incubation time for the assay, saturation and kinetic binding studies were also conducted (see M. F. Morton, The Pharmacological Characterization of Cholecystokinin Receptors in the Human Gastrointestinal Tract. PhD Thesis, University of London, 2000). The affinity of novel compounds was estimated by incubating membrane preparations with 15 μL of competing ligand (0.1 pM-1 mM) for 60 min at 21±3° C. The assay was then terminated according to the procedure outlined above.

3. Data Analysis for CCK1 and CCK2 Binding Assays

The pKi values were determined using the equation of Y.-C. Cheng and W. H. Prusoff (Biochem. Pharmacol., 1973, 22(23):3099-3108):

$$K_i = \frac{IC_{50}}{1 + \frac{[L]}{K_D}}$$

To circumvent problems associated with computer-assisted data analysis of compounds with low affinity, the data obtained in the current study were weighted according to a method described by Morton. In brief, 100% and 0% specific binding were defined independently using total binding and binding obtained in the presence of a high concentration of the reference antagonist, 2-NAP. Data for compounds tested are presented in Table 1.

TABLE 1

| EX | CCK1 p$K_i$ | CCK2 p$K_i$ |
|---|---|---|
| 1 | 6.9 | 6.4 |
| 2 | 6.7 | 7.5 |
| 3 | 6.0 | 7.4 |
| 4 | 6.2 | 8.3 |
| 5 | 7.8 | 6.5 |
| 6 | 7.5 | 5.0 |
| 7 | 7.3 | 5.1 |
| 8 | 5.5 | 6.3 |
| 9 | 6.8 | 6.4 |
| 10 | 7.7 | 5.1 |
| 11 | 6.4 | 6.5 |
| 12 | 5.9 | 7.2 |
| 13 | 5.9 | 6.2 |
| 14 | 7.9 | 6.5 |
| 15 | 7.4 | 6.7 |
| 16 | 7.2 | 6.2 |
| 17 | 7.1 | 5.6 |
| 18 | 6.5 | 5.8 |
| 19 | 6.7 | 6.6 |
| 20 | 5.7 | 7.0 |
| 21 | 6.9 | 6.0 |
| 22 | 6.3 | 6.2 |
| 23 | 6.0 | 6.2 |
| 24 | 7.0 | 5.9 |
| 25 | 5.0 | 7.4 |
| 26 | 5.6 | 7.4 |
| 27 | 5.0 | 7.5 |
| 28 | 5.0 | 7.1 |
| 29 | 5.2 | 7.1 |
| 30 | 7.2 | 5.6 |
| 31 | 7.1 | 6.2 |
| 32 | 6.4 | 7.0 |
| 33 | 6.8 | 7.4 |
| 34 | 6.4 | 7.0 |
| 35 | 7.2 | 6.3 |
| 36 | 7.1 | 5.8 |
| 37 | 6.4 | 5.4 |
| 38 | 6.5 | 5.7 |
| 39 | 7.6 | 6.6 |
| 40 | 6.9 | 6.5 |
| 41 | 6.2 | 7.3 |
| 42 | 7.5 | 5.5 |
| 43 | 6.9 | 6.6 |
| 44 | 7.0 | 5.4 |
| 45 | 6.6 | 5.8 |
| 46 | 5.8 | 7.2 |
| 47 | 7.0 | 5.3 |
| 48 | 7.3 | 5.7 |
| 49 | 6.7 | 5.7 |
| 50 | 6.2 | 5.2 |
| 51 | 5.0 | 6.1 |
| 52 | 6.3 | 7.0 |
| 53 | 6.9 | 5.6 |
| 54 | 6.1 | 6.5 |
| 55 | 7.4 | 6.0 |
| 56 | 6.3 | 6.8 |
| 57 | 7.9 | 6.3 |
| 58 | 7.5 | 6.3 |
| 59 | 7.1 | 6.1 |
| 60 | 7.1 | 6.4 |
| 61 | 6.9 | 6.4 |
| 62 | 6.5 | 5.5 |
| 63 | 5.0 | 7.5 |
| 64 | 5.8 | 7.0 |
| 65 | 6.5 | 6.1 |
| 66 | 5.7 | 6.3 |
| 67 | 6.7 | 6.6 |
| 68 | 6.5 | 7.5 |
| 69 | 7.2 | 5.1 |
| 70 | 6.7 | 5.2 |
| 71 | 6.9 | 5.6 |
| 72 | 7.1 | 6.3 |
| 73 | 6.8 | 5.0 |
| 74 | 6.5 | 5.1 |
| 75 | 6.0 | 5.4 |
| 76 | 5.5 | 7.4 |
| 77 | 5.0 | 7.5 |
| 78 | 5.4 | 7.5 |
| 79 | 7.2 | 5.9 |
| 80 | 7.0 | 5.8 |
| 81 | 6.1 | 5.7 |
| 82 | 6.1 | 5.1 |
| 83 | 5.8 | 6.6 |
| 84 | 5.0 | 7.5 |
| 85 | 5.0 | 7.2 |
| 86 | 5.0 | 7.5 |
| 87 | 5.0 | 6.8 |
| 88 | 5.2 | 6.2 |
| 89 | 5.1 | 7.2 |
| 90 | 5.9 | 7.5 |
| 91 | 7.1 | 7.8 |
| 92 | 7.2 | 7.5 |
| 93 | 6.8 | 8.3 |
| 94 | 5.2 | 6.0 |
| 95 | 5.5 | 6.1 |
| 99 | 7.1 | 6.1 |
| 101 | 7.4 | 6.1 |
| 106 | 5.0 | 5.9 |
| 107 | 5.4 | 6.1 |
| 108 | 7.6 | 5.9 |
| 115 | 6.4 | 7.1 |
| 116 | 6.9 | 5.7 |
| 117 | 6.6 | 7.8 |
| 118 | 7.1 | 6.3 |
| 119 | 6.3 | 6.7 |
| 120 | 7.1 | 6.0 |
| 121 | 6.9 | 6.3 |
| 122 | 6.8 | 6.4 |
| 123 | 7.0 | 6.8 |
| 124 | 6.5 | 7.3 |
| 125 | 6.5 | 6.2 |
| 126 | 6.6 | 8.3 |
| 127 | 6.7 | 7.1 |
| 128 | 7.0 | 6.2 |
| 129 | 7.0 | 6.2 |
| 130 | 6.4 | 6.5 |
| 131 | 6.8 | 7.8 |
| 132 | 6.6 | 7.8 |
| 133 | 6.4 | 7.5 |
| 134 | 6.3 | 7.7 |
| 135 | 6.3 | 8.1 |
| 136 | 7.4 | 6.5 |
| 137 | 7.1 | 6.7 |

TABLE 1-continued

| EX | CCK1 pK$_i$ | CCK2 pK$_i$ |
|---|---|---|
| 138 | 7.0 | 7.3 |
| 139 | 7.1 | 6.2 |
| 140 | 6.9 | 6.5 |
| 141 | 7.0 | 7.2 |
| 142 | 6.8 | 6.2 |
| 143 | 6.8 | 6.7 |
| 144 | 6.3 | 7.3 |
| 145 | 6.7 | 7.4 |
| 146 | 6.6 | 7.6 |
| 147 | 6.8 | 7.4 |
| 148 | 6.6 | 7.2 |
| 149 | 6.7 | 6.7 |
| 150 | 7.1 | 6.6 |
| 151 | 6.1 | 6.9 |
| 152 | 6 | 6.8 |
| 153 | 6.7 | 6.6 |
| 154 | 6.8 | 6.6 |
| 155 | 7.0 | 8.0 |
| 156 | 6.6 | 8.0 |
| 157 | 6.8 | 8.0 |
| 158 | 6.5 | 8.3 |
| 159 | 6.4 | 8.0 |
| 160 | 6.8 | 8.2 |
| 161 | 6.9 | 7.9 |
| 162 | 6.6 | 8.2 |
| 163 | 6.9 | 6.4 |

B. Guinea-Pig Gastric Corpeal Muscle Assay

CCK2 receptor-mediated muscle contraction was measured in an isolated muscle-strip assay of guinea-pig gastric corpeal muscle according to the methods described by Roberts et al. (S. P. Roberts, E. A. Harper, G. F. Watt, V. P. Gerskowitch, R. A. Hull, N. P. Shankley, and J. W. Black, Br. J. Pharmacol., 1996, 118(7):1779-1789). In brief, strips of muscle were dissected and suspended in isolated tissue organ baths for isotonic muscle contraction recording. The baths, containing Krebs-Henseleit solution, were maintained at 24° C. and gassed continuously with 95% $O_2$ and 5% $CO_2$. CCK1 receptors known to be present in this assay were blocked using a selective concentration of a suitable CCK1 receptor antagonist (e.g. 2-NAP). The effectiveness of the test compounds was assessed by measuring their effect on contractile concentration-response curves obtained using a well-characterized surrogate for the hormone gastrin (pentagastrin). The title compound of Example 2 behaved as a competitive antagonist in this assay with a pK$_B$ value of 8.8.

What is claimed is:
1. A compound of formula (I):

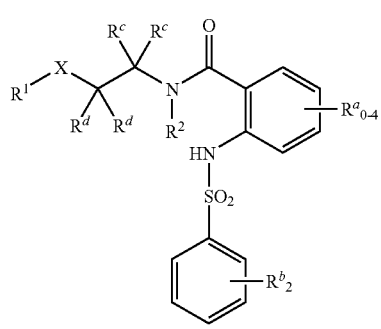

(I)

wherein
X is $C_{1-2}$alkyl or a bond;
R$^1$ is Ar$^5$—, where Ar$^5$ is a 5-membered heteroaryl having carbon as a point of attachment, having 1 heteroatom member selected from the group consisting of O, S, >NH, and >N$C_{1-4}$alkyl, having 0 or 1 additional heteroatom member which is —N= and optionally benzo or pyrido fused,
and Ar$^5$ is substituted with 0, 1, 2, or 3 of R$^q$,
R$^q$ is independently selected from the group consisting of —$C_{1-4}$alkyl, hydroxy, fluoro, chloro, bromo, iodo, trifluoromethyl, nitro, cyano, amino$C_{1-4}$alkyl, $C_{1-4}$alkylamino$C_{1-4}$alkyl, di$C_{1-4}$alkylamino$C_{1-4}$alkyl, HO—$C_{1-4}$alkyl, $C_{1-4}$alkylO—$C_{1-4}$alkyl, HS—$C_{1-4}$alkyl, $C_{1-4}$alkylS—$C_{1-4}$alkyl, $C_{1-4}$alkoxy, and $C_{1-4}$alkylS—;
R$^2$ is selected from the group consisting of —H, —$C_{1-6}$alkyl, —$C_{2-6}$alkenyl, —$C_{2-6}$alkynyl, —$C_{3-7}$cycloalkyl, and —$C_{3-7}$cycloalkenyl;
R$^a$ is, independently, selected from the group consisting of —$C_{1-6}$alkyl, —$C_{2-6}$alkenyl, —$C_{3-6}$cycloalkyl, phenyl, furanyl, thiophenyl, benzyl, pyrrol-1-yl, —OH, —O$C_{1-6}$ alkyl, —O$C_{3-6}$cycloalkyl, —Ophenyl, —Obenzyl, —SH, —S$C_{1-6}$alkyl, —S$C_{3-6}$cycloalkyl, —Sphenyl, —Sbenzyl, cyano, nitro, —N(R$^y$)R$^z$ (wherein R$^y$ and R$^z$ are independently —H, —$C_{1-4}$alkyl, or $C_{1-6}$cycloalkyl$C_{1-4}$alkyl), —(C=O)$C_{1-4}$alkyl, —SCF$_3$, halo, trifluoromethyl, —OCF$_3$, and —COO$C_{1-4}$ alkyl, —COOH, or, alternatively, two adjacent R$^a$, may be taken together with the carbons of attachment to form a fused ring selected from the group consisting of phenyl, pyridyl, and pyrimidinyl;
alternatively, R$^2$ and one of R$^a$ may be taken together as —CH$_2$— or >C=O to form a fused ring to the phenyl;
R$^b$ is two adjacent R$^b$ substituents at 2- and 3-positions taken together to form a five- or six-membered heterocyclic ring selected from the group consisting of oxazole, thiazole, thiadiazole, [1,3]dioxole, and pyrazine;
R$^c$ is independently selected from the group consisting of hydrogen, —$C_{1-4}$alkyl, perhalo$C_{1-4}$alkyl, mono- or di-halo$C_{1-4}$alkyl, amino$C_{1-4}$alkyl, $C_{1-4}$alkylamino$C_{1-4}$alkyl, di$C_{1-4}$alkylamino$C_{1-4}$alkyl, HO—$C_{1-4}$alkyl, HS—$C_{1-4}$alkyl, $C_{1-4}$alkylS—$C_{1-4}$alkyl, —$C_{0-2}$alkyl-COO$C_{1-4}$alkyl, —$C_{0-2}$alkylCOOH, —$C_{0-2}$alkylCON(R$^s$)R$^t$, —COO—$C_{0-2}$alkyl-ringA, and —COO—$C_{1-2}$alkyl-CON(R$^s$)R$^t$;
R$^s$ and R$^t$ are independently selected from the group consisting of —H, —$C_{1-4}$alkyl, $C_{1-6}$cycloalkyl$C_{1-4}$alkyl, phenyl, phenyl substituted with halo, benzyl, benzyl substituted with halo,
or alternatively, R$^s$ and R$^t$ taken together with their nitrogen of attachment form pyrrolidine, piperidine, or morpholine;
ringA is selected from the group consisting of
i) a 6-membered heteroaryl having carbon as a point of attachment and having 1 or 2 heteroatom members which are —N=;
ii) a 5-membered heteroaryl having carbon as a point of attachment, having 1 heteroatom member selected from the group consisting of O, S, >NH, and >N$C_{1-4}$alkyl, and having 0 or 1 additional heteroatom member which is —N=; and
iii) a 5- or 6-membered non-aromatic heterocycle having a carbon or nitrogen as a point of attachment, having 1 or 2 heteroatoms selected from the group consisting of O, S, and N, having 0 or 1 double bonds, having 0 or 1 carbon member replaced by a carbonyl, and optionally substituted with —$C_{1-4}$alkyl, —OH, or halo;

$R^d$ is independently selected from the group consisting of hydrogen, —$C_{1-4}$alkyl, —OH, —$OC_{1-6}$alkyl, HO—$C_{1-4}$ alkyl, perhalo$C_{1-4}$alkyl, mono- or di-halo$C_{1-4}$ alkyl, amino$C_{1-4}$alkyl, $C_{1-4}$alkylamino$C_{1-4}$alkyl, di$C_{1-4}$alkylamino$C_{1-4}$alkyl, HS—$C_{1-4}$alkyl, $C_{1-4}$alkylS—$C_{1-4}$alkyl, and optionally substituted phenyl; or two $R^d$ together can be =O where at least one $R^c$ is selected from the group consisting of —$COOC_{1-4}$ alkyl, —COO-ringA, —COOH, —CON($R^s$)$R^t$, and —$COOC_{1-2}$alkylCON($R^s$)$R^t$;

alternatively, one $R^c$ and one $R^d$ may be taken together to form a double bond;

and enantiomers, diastereomers and pharmaceutically acceptable salts thereof.

2. The compound of claim 1 wherein X is a bond.

3. The compound of claim 1 wherein $R^1$ is selected from the group consisting of furanyl, thiophenyl, 1-(H or $C_{1-4}$alkyl)pyrrolyl, oxazolyl, thiazolyl, pyrazolyl, imidazolyl, isoxazolyl, isothiazolyl, benzofuran-2 or 3-yl, benzothiophen-2 or 3-yl, 1-(H or $C_{1-4}$alkyl)-1H-indol-2 or 3-yl, 1-(H or $C_{1-4}$alkyl)-1H-benzimidazol-2-yl, benzooxazol-2-yl, benzothiazol-2-yl, 1H-pyrrolopyridin-2 or 3-yl is substituted with 0, 1, 2, or 3 of $R^q$.

4. The compound of claim 1 wherein $R^1$ is selected from the group consisting of furanyl, thiophenyl, and benzothiophenyl, where each member is substituted with 0, 1, 2, or 3 of $R^q$.

5. The compound of claim 1 wherein $R^1$ is selected from the group consisting of thiophen-3-yl, 5-bromothiophen-3-yl, and benzothiophen-3-yl.

6. The compound of claim 1 wherein $R^q$ is selected from the group consisting of methyl, ethyl, propyl, t-butyl, hydroxy, fluoro, chloro, bromo, iodo, trifluoromethyl, nitro, cyano, aminomethyl, methylaminomethyl, dimethylaminomethyl, hydroxymethyl, methoxymethyl, methylsulfanyl, methylsulfanylmethyl, methoxy, ethoxy, mercaptomethyl, and mercaptoethyl.

7. The compound of claim 1 wherein $R^q$ is selected from the group consisting of methyl, fluoro, chloro, bromo, iodo, trifluoromethyl, nitro, and cyano.

8. The compound of claim 1 wherein $R^2$ is selected from the group consisting of —H, methyl, ethyl, i-propyl, t-butyl, allyl, propargyl, cyclopropyl, cyclohexyl, and cyclopentenyl.

9. The compound of claim 1 wherein $R^2$ and one of $R^a$ are taken together as —$CH_2$— or >C=O to form a fused ring to the phenyl.

10. The compound of claim 1 wherein $R^2$ is —H or methyl.

11. The compound of claim 1 wherein $R^a$ is selected from the group consisting of methyl, ethyl, propyl, i-propyl, ethenyl, propenyl, cyclopropyl, cyclobutyl, phenyl, furanyl, thiophenyl, pyrrol-1-yl, benzyl, methoxy, ethoxy, propoxy, cyclopropoxy, cyclobutoxy, cyclopentoxy, phenoxy, benzoxy, mercapto, methylsulfanyl, ethylsulfanyl, t-butylsulfanyl, cyclopropylsulfanyl, phenylsulfanyl, nitro, cyano, amino, dimethylamino, (cyclohexylmethyl)amino, acetyl, —$SCF_3$, iodo, fluoro, chloro, bromo, trifluoromethyl, —$OCF_3$, and methoxycarbonyl.

12. The compound of claim 1 wherein there is one $R^a$.

13. The compound of claim 1 wherein there is one $R^a$ positioned on the ring para to the amide substituent.

14. The compound of claim 1 wherein two adjacent $R^a$ are taken together with the carbons of attachment to form a fused phenyl ring.

15. The compound of claim 1 wherein there are two $R^a$ substituents.

16. The compound of claim 1 wherein each $R^a$ is independently selected from the group consisting of methyl, i-propyl, ethenyl, 2-propenyl, cyclopropyl, phenyl, thiophenyl, methoxy, ethoxy, propoxy, i-propoxy, nitro, cyano, dimethylamino, (cyclohexylmethyl)amino, acetyl, fluoro, chloro, bromo, iodo, —$CF_3$, and fused phenyl.

17. The compound of claim 1 wherein two $R^b$ are 2,6-difluoro or 2,4-difluoro.

18. The compound of claim 1 wherein two adjacent $R^b$ substituents at 2- and 3-positions are taken with the benzene ring of attachment to form benzothiazole, benzothiadiazole, or quinoxaline.

19. The compound of claim 1 wherein $R^c$ is selected from the group consisting of hydrogen, methyl, ethyl, i-propyl, hydroxymethyl, methoxymethyl, dimethylaminomethyl, methylsulfanylmethyl, methoxycarbonyl, ethoxycarbonyl, tert-butoxycarbonyl, methoxycarbonylmethyl, carboxy, carboxymethyl, carbamoyl, carbamoylmethyl, dimethylcarbamoyl, piperidine-1-carbonyl, 5-methyl-2-oxo-[1,3]dioxol-4-yl-methoxycarbonyl, 3-pyridylmethoxycarbonyl, 3-chlorobenzylcarbamoyl, 4-fluorobenzylcarbamoyl, benzylcarbamoyl, phenylcarbamoyl, dimethylcarbamoylmethoxycarbonyl, and 2-morpholin-4-ylethoxycarbonyl.

20. The compound of claim 1 wherein the carbon to which the two $R^c$ groups are attached is in the (S) configuration.

21. The compound of claim 1 wherein $R^d$ is selected from the group consisting of hydrogen, methyl, ethyl, i-propyl, hydroxy, hydroxymethyl, methoxymethyl, dimethylaminomethyl, phenyl, 4-chlorophenyl, and methylsulfanylmethyl.

22. The compound of claim 1 wherein two $R^d$ together form =O.

23. The compound of claim 1 wherein $R^d$ is selected from the group consisting of hydrogen, methyl, phenyl, and hydroxy.

24. The compound of claim 1 wherein said pharmaceutically acceptable salt is an amino addition salt.

25. The compound of claim 1 wherein said pharmaceutically acceptable salt is an acid addition salt.

26. The compound of claim 1 wherein said pharmaceutically acceptable salt is selected from the group consisting of hydrobromide, hydrochloride, sulfate, bisulfate, nitrate, acetate, oxalate, valerate, oleate, palmitate, stearate, laurate, borate, benzoate, lactate, phosphate, tosylate, citrate, maleate, fumarate, succinate, tartrate, naphthylate, mesylate, glucoheptonate, lactiobionate, and laurylsulfonate.

27. The compound of claim 1 wherein said pharmaceutically acceptable salt is selected from the group consisting of sodium, potassium, calcium, magnesium, ammonium, quaternary ammonium, tetramethyl ammonium, methylammonium, trimethylammonium, and ethylammonium.

28. The compound of claim 1 selected from the group consisting of:
(S)-3-(5-Bromo-thiophen-2-yl)-2-[4-chloro-2-(quinoxaline-5-sulfonylamino)-benzoylamino]-propionic acid methyl ester;
(S)-3-Benzo[b]thiophen-3-yl-2-[4-chloro-2-(quinoxaline-5-sulfonylamino)-benzoylamino]-propionic acid methyl ester;
(S)-3-Benzo[b]thiophen-3-yl-2-[4-chloro-2-(quinoxaline-5-sulfonylamino)-benzoylamino]-propionic acid;
(S)-2-[2-(Benzo[1,2,5]thiadiazole-4-sulfonylamino)-4-chloro-benzoylamino]-3-thiophen-3-yl-propionic acid; and
(S)-2-[4-Chloro-2-(quinoxaline-5-sulfonylamino)-benzoylamino]-3-thiophen-3-yl-propionic acid.

29. A pharmaceutical composition comprising a pharmaceutically acceptable carrier and an effective amount of at least one compound of formula (I):

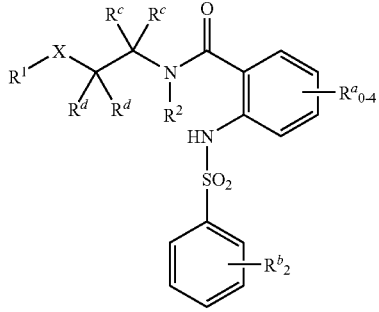

wherein
X is $C_{1-2}$alkyl or a bond;
$R^1$ is $Ar^5$—, where $Ar^5$ is a 5-membered heteroaryl having carbon as a point of attachment, having 1 heteroatom member selected from the group consisting of O, S, >NH, and >N$C_{1-4}$alkyl, having 0 or 1 additional heteroatom member which is —N= and optionally benzo or pyrido fused,
and $Ar^5$ is substituted with 0, 1, 2, or 3 of $R^q$,
$R^q$ is independently selected from the group consisting of —$C_{1-4}$alkyl, hydroxy, fluoro, chloro, bromo, iodo, trifluoromethyl, nitro, cyano, amino$C_{1-4}$alkyl, $C_{1-4}$alkoxy, and $C_{1-4}$alkylS—;
$R^2$ is selected from the group consisting of —H, —$C_{2-6}$alkenyl, —$C_{2-6}$alkynyl, —$C_{3-7}$cycloalkyl, and —$C_{3-7}$cycloalkenyl;
$R^a$ is, independently, selected from the group consisting of —$C_{1-6}$alkyl, —$C_{2-6}$alkenyl, —$C_{3-6}$cycloalkyl, phenyl, furanyl, thiophenyl, benzyl, pyrrol-1-yl, —OH, —O$C_{3-6}$ cycloalkyl, —Ophenyl, —Obenzyl, —SH, —S$C_{3-6}$cycloalkyl, —Sphenyl, —Sbenzyl, cyano, nitro, —N($R^y$)$R^z$ (wherein $R^y$ and $R^z$ are independently —H, —$C_{1-4}$alkyl, or $C_{1-6}$cycloalkyl$C_{1-4}$alkyl), —(C=O)$C_{1-4}$ alkyl, —SCF$_3$, halo, trifluoromethyl, —OCF$_3$, and —COO$C_{1-4}$alkyl, —COOH, or, alternatively, two adjacent $R^a$, may be taken together with the carbons of attachment to form a fused ring selected from the group consisting of phenyl, pyridyl, and pyrimidinyl;
alternatively, $R^2$ and one of $R^a$ may be taken together as —CH$_2$— or >C=O to form a fused ring to the phenyl;
$R^b$ is two adjacent $R^b$ substituents at 2- and 3-positions taken together to form a five- or six-membered heterocyclic ring selected from the group consisting of oxazole, thiazole, thiadiazole, [1,3]dioxole, and pyrazine;
$R^c$ is independently selected from the group consisting of hydrogen, —$C_{1-4}$alkyl, perhalo$C_{1-4}$alkyl, mono- or di-halo$C_{1-4}$alkyl, amino$C_{1-4}$alkyl, $C_{1-4}$alkylamino$C_{1-4}$alkyl, di$C_{1-4}$alkylamino$C_{1-4}$alkyl, HO—$C_{1-4}$alkyl, HS—$C_{1-4}$alkyl, $C_{1-4}$alkylS—$C_{1-4}$alkyl, —$C_{0-2}$alkyl-COO$C_{1-4}$alkyl, —$C_{0-2}$alkylCOOH, —$C_{0-2}$alkylCON($R^s$)$R^t$, —COO—$C_{0-2}$alkyl-ringA, and —COO—$C_{1-2}$alkyl-CON($R^s$)$R^t$;
$R^s$ and $R^t$ are independently selected from the group consisting of —H, —$C_{1-4}$alkyl, $C_{1-6}$cycloalkyl$C_{1-4}$alkyl, phenyl, phenyl substituted with halo, benzyl, benzyl substituted with halo,
or alternatively, $R^s$ and $R^t$ taken together with their nitrogen of attachment form pyrrolidine, piperidine, or morpholine;
ringA is selected from the group consisting of
i) a 6-membered heteroaryl having carbon as a point of attachment and having 1 or 2 heteroatom members which are —N=;
ii) a 5-membered heteroaryl having carbon as a point of attachment, having 1 heteroatom member selected from the group consisting of O, S, >NH, and >N$C_{1-4}$alkyl, and having 0 or 1 additional heteroatom member which is —N=; and
iii) a 5- or 6-membered non-aromatic heterocycle having a carbon or nitrogen as a point of attachment, having 1 or 2 heteroatoms selected from the group consisting of 0, S, and N, having 0 or 1 double bonds, having 0 or 1 carbon member replaced by a carbonyl, and optionally substituted with —$C_{1-4}$alkyl, —OH, or halo;
$R^d$ is independently selected from the group consisting of hydrogen, —$C_{1-4}$alkyl, —OH, —O$C_{1-6}$alkyl, HO—$C_{1-4}$ alkyl, perhalo$C_{1-4}$alkyl, mono- or di-halo$C_{1-4}$ alkyl, amino$C_{1-4}$alkyl, $C_{1-4}$alkylamino$C_{1-4}$alkyl, di$C_{1-4}$alkylamino$C_{1-4}$alkyl, HS—$C_{1-4}$alkyl, $C_{1-4}$alkylS—$C_{1-4}$alkyl, and optionally substituted phenyl; or two $R^d$ together can be =O where at least one $R^c$ is selected from the group consisting of —COO$C_{1-4}$ alkyl, —COO-ringA, —COOH, —CON($R^s$)$R^t$, and —COO$C_{1-2}$alkylCON($R^s$)$R^t$;
alternatively, one $R^c$ and one $R^d$ may be taken together to form a double bond;
and enantiomers, diastereomers and pharmaceutically acceptable salts thereof.

* * * * *